(12) United States Patent
Bruce

(10) Patent No.: US 11,534,457 B2
(45) Date of Patent: Dec. 27, 2022

(54) USE OF DEXTRAN SULFATE

(71) Applicant: TX MEDIC AB, Viken (SE)

(72) Inventor: Lars Bruce, Viken (SE)

(73) Assignee: TX MEDIC AB, Viken (SE)

( * ) Notice: Subject to any disclaimer, the term of this patent is extended or adjusted under 35 U.S.C. 154(b) by 0 days.

(21) Appl. No.: 16/644,575

(22) PCT Filed: Sep. 7, 2018

(86) PCT No.: PCT/SE2018/050898
§ 371 (c)(1),
(2) Date: Mar. 5, 2020

(87) PCT Pub. No.: WO2019/050460
PCT Pub. Date: Mar. 14, 2019

(65) Prior Publication Data
US 2021/0060057 A1    Mar. 4, 2021

Related U.S. Application Data

(60) Provisional application No. 62/555,848, filed on Sep. 8, 2017.

(51) Int. Cl.
*A61K 31/737* (2006.01)
*A61P 25/28* (2006.01)

(52) U.S. Cl.
CPC ............ *A61K 31/737* (2013.01); *A61P 25/28* (2018.01)

(58) Field of Classification Search
None
See application file for complete search history.

(56) References Cited

U.S. PATENT DOCUMENTS

| 5,705,178 A | 1/1998 | Roufa et al. |
| 6,756,362 B2 | 6/2004 | Roufa et al. |
| 2019/0381090 A1 | 12/2019 | Waas et al. |

FOREIGN PATENT DOCUMENTS

| JP | 2016-132619 A | 7/2016 |
| JP | 2017-518322 A | 7/2017 |
| WO | 99/26633 A1 | 6/1999 |
| WO | 2008/134430 A1 | 11/2008 |
| WO | 2015/190989 A1 | 12/2015 |
| WO | 2016/076780 A1 | 5/2016 |
| WO | 2017/018922 A1 | 2/2017 |

OTHER PUBLICATIONS

Abrams, Ann Intern Med. Feb. 1, 1989; 110(3):183-8, abstract only. (Year: 1989).*
Toru, JP2016132619A, Jul. 25, 2016, machine translation. (Year: 2016).*
Inhibit Definition & Meaning—Merriam-Webster, internet article, https://www.merriam-webster.com/dictionary/inhibit, downloaded from the internet Dec. 26, 2021. (Year: 2021).*
Klebe, Robert J. et al., Effect of Glycosaminoglycans on Fibronectin-Medicated Cell Attachment, Journal of Cellular Physiology, vol. 112, pp. 5-9 (1982).
Aimi, Takahiro et al., Dextran sulfate sodium inhibits amyloid-B oligomer binding to cellular prion protein, J. Neurochem, vol. 134, pp. 611-617 (2015).
Chicoine, Linda M. et al., Excitotoxic Protection by Polyanionic Polysaccharide: Evidence of a Cell Survival Pathway Involving AMPA Receptor-MAPK Interactions, Journal of Neuroscience Research, vol. 85, pp. 294-302 (2007).
Klegeris, Andis et al., Effects of C-reactive protein and pentosan polysulphate on human complement activation, Immunology, vol. 106, pp. 381-388 (2002).
Tradtrantip, Lukmanee et al., Potential Therapeutic Benefit of C1-Esterase Inhibitor in Neuromyelitis Optica Evaluated In Vitro and in an Experimental Rat Model, Plos One, vol. 9, No. 9, e106824, pp. 1-8 (Sep. 2014).
Yarchoan, Mark et al., Association of Plasma C-Reactive Protein Levels with Diagnosis of Alzheimer's Disease, J. Neurol Sci., vol. 333, No. 0, .doi:10.1016/j.jns.2013.05.028, pp. 1-12 (Oct. 15, 2013).
Ishikawa et al, "Constant blood flow reduction in premotor frontal lobe regions in ALS with dementia—a SPECT study with 3D-SSP," Acta Neurol. Scand. 116: 340-344 (2007).
Office Action from corresponding Japanese Patent Application No. 2020-511484 dated Oct. 11, 2022, with English Translation.

* cited by examiner

*Primary Examiner* — Layla D Berry
(74) *Attorney, Agent, or Firm* — Porter Wright Morris & Arthur LLP

(57) ABSTRACT

Dextran sulfate, or a pharmaceutically acceptable derivative thereof, is used to induce differentiation of glial cells and neurons. The cell differentiation induction of dextran sulfate has positive effects in subjects suffering from neurological diseases, including neurodegenerative diseases, demyelinating diseases, neuro ischemic diseases and neuromuscular diseases.

17 Claims, 38 Drawing Sheets

USE OF DEXTRAN SULFATE

TECHNICAL FIELD

The present embodiments generally relate to neurological and fibrotic conditions, and in particular to the use of dextran sulfate in combating such conditions.

BACKGROUND

In neurological diseases, such as Alzheimer's disease (AD), Parkinson's disease (PD), Huntington's disease (HD), amyotrophic lateral sclerosis (ALS) and multiple sclerosis (MS), and damages to the central nervous system (CNS) or peripheral nervous system (PNS), such as traumatic brain injury (TBI), stroke and sub-arachnoid hemorrhage (SAH), loss of differentiation of neurons and glial cells, such as oligodendrocytes and Schwann cells, is one of the first disease stages, followed by cell death. The function of the cells is also compromised as seen in impaired metabolic function and mitochondrial energy metabolism and elevated oxygen stress. Damaged neurons furthermore release glutamate having an excitotoxicity effect on nearby neurons, in turn causing further cell damage and cell death.

Accordingly, there are a multitude of deleterious mechanisms taking place in neurological diseases, disorders and conditions. There is therefore a general need for drugs that are effective in combating such deleterious mechanisms and therefore could be of benefit for patients suffering from such neurological diseases, disorders and conditions.

US 2011/0014701 relates to the use of polysulfated polysaccharides to improve the viability of progenitor cells. The U.S. patent application also discloses the use of polysulfated polysaccharides to regulate differentiation of progenitor cells. Various polysulfated polysaccharides were tested. It was concluded that the polysulfated polysaccharide dextran polysulfate ($M_w$=5,000 Da) downregulated or repressed differentiation of progenitor cells.

SUMMARY

It is a general objective to provide a drug useful for patients suffering from neurological and/or fibrotic conditions.

This and other objectives are met by embodiments as defined herein.

The present invention is defined in the independent claims. Further embodiments of the present invention are defined in the dependent claims.

The present embodiments are directed towards dextran sulfate, or a pharmaceutically acceptable derivative thereof, having several advantageous effects to patients suffering from neurological and/or fibrotic diseases, disorders or conditions.

Dextran sulfate, or the pharmaceutically acceptable derivative thereof, is, among others, capable of inducing differentiation of glial cells and neurons, reducing oxidative stress in neurons and glial cells, reducing glutamate excitotoxicity, improving metabolic function and energy metabolism in mitochondria of neurons and glial cells, and activating the intrinsic repair mechanism of the body. Dextran sulfate, or the pharmaceutically acceptable derivative thereof, is also capable preventing fibrogenesis by inhibiting fibrogenic factors like TGF-β and activating fibrolysis, thereby dissolving existing scar tissue, inducing a tissue remodeling and a viable healing of tissue. Dextran sulfate, or the pharmaceutically acceptable derivative thereof, also had effect in various inflammatory and auto-immune conditions, including neuroinflammatory conditions by resolving the immune or inflammatory response.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
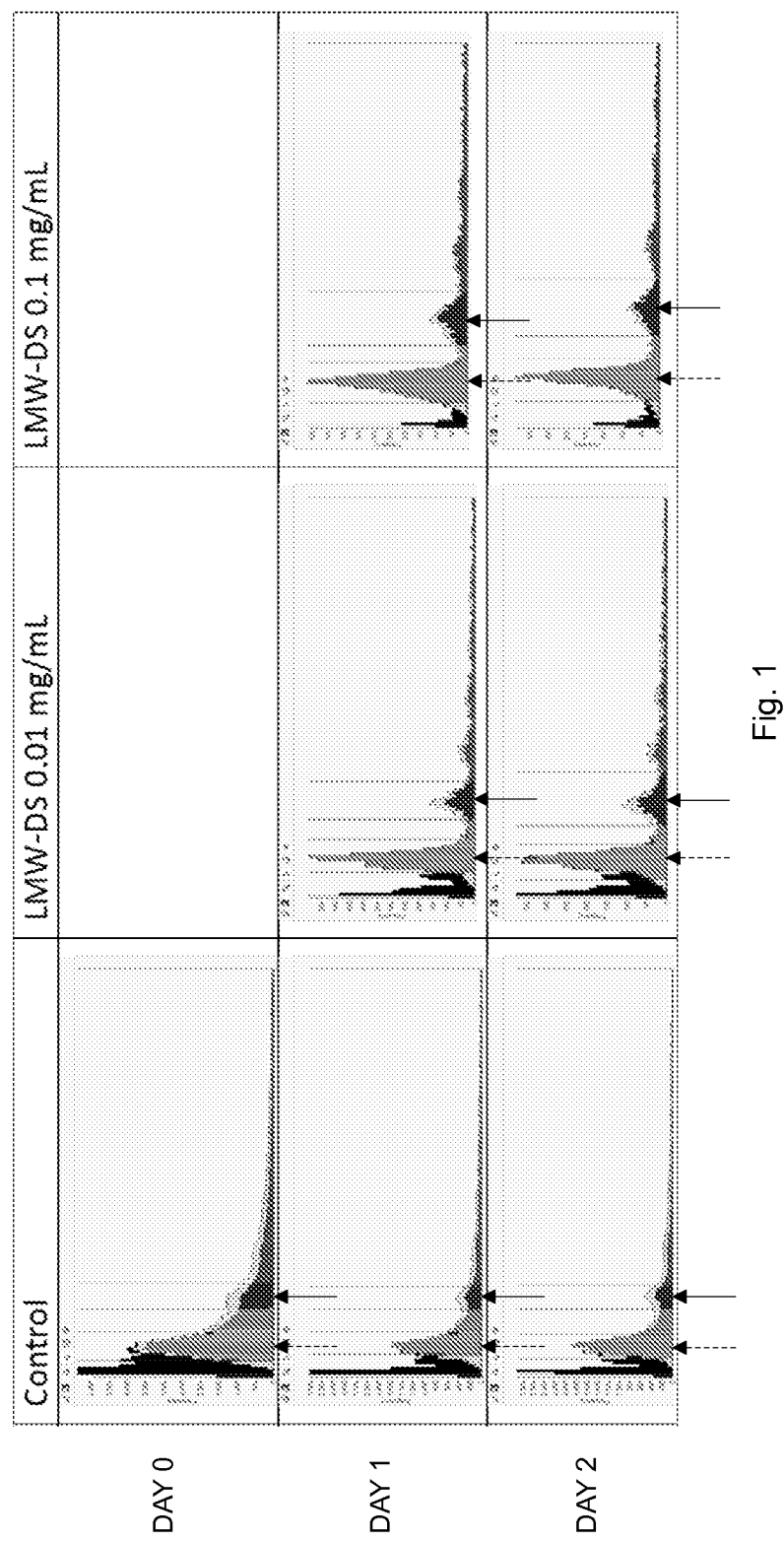
FIG. 1 illustrates propidium iodine (PI) content of mouse cortical neurons. The cells were stained with PI, which binds to DNA. Based on DNA content, the cells can be grouped into different phases of the cell cycle. As DNA content varies during the cell cycle, PI staining can be indicative of cell cycle progression. Data indicated that most cells remained in the G1 phase of the cell cycle (dashed arrows), although low molecular weight dextran sulfate (LMW-DS) appeared to increase the number of cells in the G2/M phase (full arrows).

The present embodiments generally relate to neurological and fibrotic conditions, and in particular to the use of dextran sulfate in combating such conditions.

A neurological disorder is any disorder of the body nervous system, i.e., the brain, spine and the nerves that connect them. Structural, biochemical or electrical abnormalities in the brain, spinal cord or other nerves can result in a range of symptoms. Although the brain and spinal cord are surrounded by tough membranes, enclosed in the bones of the skull and spinal vertebrae, and chemically isolated by the blood-brain barrier, they are very susceptible if compromised. Nerves tend to lie deep under the skin but can still become exposed to damage. Individual neurons, and the neural networks and nerves into which they form, are susceptible to electrochemical and structural disruption. Neuroregeneration may occur in the peripheral nervous system and, thus, overcome or work around injuries to some extent, but it is thought to be rare in the brain and spinal cord.

The specific causes of neurological problems vary, but can include genetic disorders, congenital abnormalities or disorders, infections, lifestyle or environmental health problems including malnutrition, and brain injury, spinal cord injury or nerve injury. The problem may start in another body system that interacts with the nervous system. For example, cerebrovascular disorders involve brain injury due to problems with the blood vessels, i.e., the cardiovascular system, supplying the brain; autoimmune disorders involve damage caused by the body's own immune system; lysosomal storage diseases, such as Niemann-Pick disease, can lead to neurological deterioration.

A neurodegenerative disease, disorder or condition is a disease, disorder or condition causing progressive loss of structure and/or function of neurons, including death of neurons.

Non-limiting examples of such neurodegenerative diseases, disorders or conditions include Alzheimer's disease (AD), Parkinson's disease (PD), Huntington's disease (HD) and amyotrophic lateral sclerosis (ALS).

AD is characterized by loss of neurons and synapses in the cerebral cortex and subcortical regions. The classic neuropathologic findings in AD include amyloid plaques, neurofibrillary tangles, and synaptic and neuronal cell death. White matter disease (WMD) is frequently seen in AD at neuropathological examination. It is defined as a subtotal tissue loss with a reduction of myelin, axons and oligodendrocytes as well as astrocytosis.

PD is a neurodegenerative disorder of the CNS. The motor symptoms of PD result from the death of dopamine-generating cells in the substantia nigra. In a diseased nerve, the myelin sheath surrounding the axon begins to erode. Neuroinflammation is a pathological hallmark in PD and is characterized by activated microglia and infiltrating T cells at sites of neuronal injury.

HD is a neurodegenerative disorder that affects muscle coordination and leads to cognitive decline and psychiatric problems. The disease is caused by an autosomal dominant mutation in a gene called Huntingtin. Part of this gene is a repeated section called trinucleotide repeat, which varies in length between individuals. When the length of this repeated section reaches a certain threshold, it produces an altered form of the protein. The protein (Htt) encoded by the Huntingtin gene interacts with over 100 other proteins and has multiple biological functions. The mutated form of Htt is toxic to certain cell types, particularly in the brain. HD is characterized by damages to the myelin sheath on the nerves. Increased activated T cells in the peripheral blood have been identified in HD patients.

ALS, also referred to as Lou Gehrig's disease, is a debilitating disease with varied etiology characterized by rapidly progressive weakness, muscle atrophy and fasciculations, muscle spasticity, dysarthria, dysphagia and dyspnea. ALS is the most common of the motor neuron diseases (ALS, hereditary spastic paraplegia (HSP), primary lateral sclerosis (PLS), progressive muscular atrophy (PMA), progressive bulbar palsy (PBP) and pseudobulbar palsy). The principle characteristic in the pathology of ALS is loss of motor nerve cells in the anterior horns of the spinal cord and in the motor nuclei of the brain stem. This results in secondary atrophy of the corresponding muscles (amyotrophy). Neuroinflammation is a pathological hallmark of ALS and is characterized by activated microglia and infiltrating T cells at sites of neuronal injury. "Lateral sclerosis" refers to corticospinal tract degeneration (lateral in location in the spinal cord). In fact, myelin loss occurs in the corticospinal tract. The sclerosis of ALS, the hardening, involves the lateral columns, or corticospinal tracts and is a secondary phenomenon.

A neurological disease, disorder or condition may be a demyelinating disease, disorder or condition. A demyelinating disease, disorder or condition is a disease of the nervous system in which the myelin sheath of neurons is damaged. Such damage impairs the conduction of signals in the affected nerves and thereby causing deficiency in sensation, movement, cognition and other functions depending on the nerves involved in the damage.

Non-limiting examples of such demyelinating diseases, disorders or conditions include multiple sclerosis (MS), acute disseminated encephalomyelitis (ADEM), central nervous system (CNS) neuropathies, central pontine myelinolysis (CPM), myelopathies, leukoencephalopathies and leukodystrophies (all affecting the CNS), and Guillain-Barré syndrome (GBS), peripheral neuropathies and Charcot-Marie-Tooth (CMT) disease (all affecting the peripheral nervous system (PNS)).

MS is an inflammatory disease in which the fatty myelin sheaths around axons of the brain and the spinal cord are damaged, leading to demyelination and scarring as well as a broad spectrum of signs and symptoms. MS involves T cells that induce an immune response against the white matter of the brain and spinal cord. MS is a disease of myelin, not primarily of nerve cells. Since myelin occurs throughout the nervous system, lesions can be and typically are at multiple sites. The disease, however, affects only central myelin, not the myelin of peripheral nerves. Therefore, the symptoms are specifically of a CNS disorder.

ADEM is an immune mediated disease of the brain. It usually occurs following a viral, bacterial or parasitic infection, or even appears spontaneously. ADEM attacks the nerves of the CNS and damages their myelin insulation, which, as a result, destroys the white matter. As it involves autoimmune demyelination, it is similar to MS, and is considered part of the MS borderline diseases. ADEM produces multiple inflammatory lesions in the brain and spinal cord, particularly in the white matter. ADEM involves cytokines secreted by myelin-reactive T cells.

Neuropathies, including CNS neuropathies and peripheral neuropathies, is a group of damages to or diseases affecting nerves, which may impair sensation, movement, gland or organ function, or other aspects of health, depending on the type of nerve affected. Common causes include systemic diseases, such as diabetes or leprosy; vitamin deficiency; medication, e.g., chemotherapy, or commonly prescribed antibiotics; traumatic injury; ischemia; radiation therapy; excessive alcohol consumption; immune system disease; Coeliac disease; or viral infection. Neuropathy may be or acute. Acute neuropathies demand urgent diagnosis. Motor nerves that control muscles, sensory nerves, or autonomic nerves that control automatic functions, such as heart rate, body temperature, and breathing, may be affected. More than one type of nerve may be affected at the same time.

CPM is a neurological disease caused by severe damage of the myelin sheath of nerve cells in the brainstem, more precisely in the area termed the pons, predominately of iatrogenic etiology. It is characterized by acute paralysis, dysphagia, and dysarthria, and other neurological symptoms.

Myelopathy describes any neurologic deficit related to the spinal cord. When due to trauma, it is generally known as spinal cord injury (SCI), when inflammatory, it is generally known as myelitis, and when the disease that is vascular in nature it is known as vascular myelopathy. The most common form of myelopathy in human, cervical spondylotic myelopathy (CSM) is caused by arthritic changes (spondylosis) of the cervical spine, which result in narrowing of the spinal canal (spinal stenosis) ultimately causing compression of the spinal cord.

Leukoencephalopathy is a broad term for leukodystrophy-like diseases. It is applied to all brain white matter diseases, whether their molecular cause is known or not. Leukoencephalopathy can refer specifically to any of these diseases progressive multifocal leukoencephalopathy, toxic leukoencephalopathy, leukoencephalopathy with vanishing white matter, leukoencephalopathy with neuroaxonal spheroids, reversible posterior leukoencephalopathy syndrome, megalencephalic leukoencephalopathy with subcortical cysts.

Leukodystrophy is one of a group of disorders characterized by degeneration of the white matter in the brain. The leukodystrophies are caused by imperfect growth or development of the myelin sheath, the fatty covering that acts as an insulator around nerve fibers. When damage occurs to white matter, immune responses can lead to inflammation in the CNS, along with loss of myelin. Leukodystrophy is characterized by specific symptoms including decreased motor function, muscle rigidity, and eventually degeneration of sight and hearing. Specific types of leukodystrophies include adrenomyeloneuropathy, Alexander disease, cerebrotendineous xanthomatosis, hereditary CNS demyelinating disease, Krabbe disease, metachromatic leukodystrophy, Pelizaeus-Merzbacher disease, Canavan disease, leukoencephalopathy with vanishing white matter, adrenoleukodystrophy and Refsum disease.

GBS, also referred to as Landry's paralysis or Guillan-Barré-Strohl syndrome, is an acute polyneuropathy affecting the PNS. In GBS, immune cells attack the myelin sheath—the fatty substance covering nerve fibers. Ascending paralysis is a common symptom. GBS is thought to be an immune-mediated disease involving an abnormal T cell response precipitated by an infection. Cellular and humoral immune mechanisms probably play a role in its development. Most patients report an infectious illness in the weeks prior to the onset of GBS. Many of the identified infectious agents are thought to induce production of antibodies that cross-react with specific gangliosides and glycolipids, such as GM1 and GD1b, which are distributed throughout the myelin in the peripheral nervous system.

CMT is one of the hereditary motor and sensory neuropathies, a group of varied inherited disorders of the peripheral nervous system characterized by progressive loss of muscle tissue and touch sensation across various parts of the body. CMT was previously classified as a subtype of muscular dystrophy.

In neurological disorders loss of differentiation of neurons and glial cells, such as oligodendrocytes and Schwann cells, is one of the first stages in the disease progress. Generally, the disorders subsequently progress with cell death of such neurons and glial cells.

Accordingly, a drug that is capable of promoting differentiation of neuronal and glial cells would be beneficial to patients suffering from neurological diseases, disorders or conditions. Such a differentiation-inducing drug could be neuroprotective and may, for instance, be useful in the treatment of neurological diseases, disorders or conditions.

Experimental data as presented herein indicates that dextran sulfate of the embodiments is capable of inducing differentiation of neurons and glial cells. This effect of dextran sulfate is seen both for cortical neurons and motor neurons and for neurons from both mouse and human origin. Correspondingly, dextran sulfate is capable of inducing differentiation of Schwann cells that constitute a type of glial cells.

Dextran sulfate of the embodiments additionally showed positive effects in an in vivo model of inflammatory demyelinating disease of the CNS, which is the currently most widely accepted animal model of MS and ADEM.

These results with regard to induction of cells differentiation in neurons and glial cells by dextran sulfate of the embodiments were highly surprising in the light of US 2011/0014701 stating that dextran sulfate ($M_w$=5,000 Da) did not induce, but rather downregulated or repressed, differentiation of progenitor cells. Thus, it seems that the cell differentiating capability of dextran sulfate of the embodiments might be cell type specific and thereby, potentially, limited to neurons and glial cells. The prior art data shows that dextran sulfate in fact had the opposite effect for other cell types, represented by progenitor cells in the above mentioned U.S. patent application.

Neurons, also referred to as nerve cells, are electrically excitable cells that process and transmit information through electrical and chemical signals. These signals between neurons occur via synapses, specialized connections with other cells. Neurons can connect to each other to form neural networks. Neurons are the core components of the brain and spinal cord of the CNS, and of the ganglia of the PNS. Specialized types of neurons include: sensory neurons which respond to touch, sound, light and all other stimuli affecting the cells of the sensory organs that then send signals to the spinal cord and brain, motor neurons that receive signals from the brain and spinal cord to cause muscle contractions and affect glandular outputs, and interneurons which connect neurons to other neurons within the same region of the brain, or spinal cord in neural networks.

A typical neuron consists of a cell body (soma), dendrites, and an axon. The term neurite is used to describe either a dendrite or an axon, particularly in its undifferentiated stage. Dendrites are thin structures that arise from the cell body, often extending for hundreds of micrometers and branching multiple times, giving rise to a complex "dendritic tree". An axon, also called a nerve fiber when myelinated, is a special cellular extension that arises from the cell body at a site called the axon hillock and travels for a distance. Nerve fibers are often bundled into fascicles, and in the PNS, bundles of fascicles make up nerves. At the majority of synapses, signals are sent from the axon of one neuron to a dendrite of another.

Neurons do not undergo cell division. In most cases, neurons are generated by special types of stem cells. Astrocytes are star-shaped glial cells that have also been observed to turn into neurons by virtue of the stem cell characteristic pluripotency. In humans, neurogenesis largely ceases during adulthood; but in two brain areas, the hippocampus and olfactory bulb, there is strong evidence for generation of substantial numbers of new neurons.

Dextran sulfate of the embodiments is capable of inducing an increase in beta-tubulin, in particular βIII-tubulin, expression in the neurons.

βIII-tubulin, also referred to as class III β-tubulin, is a microtubule element expressed exclusively in neurons. The microtubule cytoskeleton is essential for the development and survival of neurons. Microtubules are assembled from tubulin heterodimers, which contain different tubulin isotypes. Microtubules are polarized and, in neurons, their 'minus-ends' are usually oriented towards the centrosome in the cell body, whereas their 'plus-ends' project towards the tips of axons. Microtubule polarity serves important functions in both differentiating and adult neurons. During differentiation, tubulin is increased in the cell and builds up microtubule which allow the differentiating neurons to extend or retract growing axons in response to guidance cues in order to maintain directional growth towards post-synaptic targets. Their activities are essential for cell migration, axon development and guidance, and are also required for the function and viability of adult neurons (Bioscience Reports (2010), 30: 319-330).

The increased expression of the βIII-tubulin in neurons indicates that dextran sulfate of the embodiments acts as a differentiation factor for these cells.

In an embodiment, the neurons are selected from a group consisting of cortical neurons and motor neurons.

A motor neuron is a nerve cell whose cell body is located in the spinal cord and whose axon projects outside the spinal cord to directly or indirectly control effector organs, mainly muscles and glands. The axons of motor neurons are efferent nerve fibers that carry signals from the spinal cord to the effectors to produce effects.

A motor neuron disease (MND) is a neurological disorder that selectively affects motor neurons. These MNDs are ALS, HSP, PLS, PMA, PBP, pseudobulbar palsy, spinal muscular atrophy (SMA) and post-polio syndrome (PPS). They are neurodegenerative in nature and cause increasing disability and, eventually, death.

HSP, also referred to as hereditary spastic paraparesis, familial spastic paraplegia, French settlement disease, or Strumpell-Lorrain disease, is a group of inherited diseases whose main feature is a progressive gait disorder. The disease presents with progressive stiffness (spasticity) and contraction in the lower limbs. The symptoms are a result of dysfunction of long axons in the spinal cord. The affected cells are the primary motor neurons, therefore the disease is an upper motor neuron disease. HSP is caused by defects in transport of proteins, structural proteins, cell maintaining proteins, lipids, and other substances through the cell.

PLS is a rare neuromuscular disease characterized by progressive muscle weakness in the voluntary muscles. PLS only affects upper motor neurons.

PMA, also known as Duchenne-Aran muscular atrophy, is a rare subtype of MND that affects only the lower motor neurons.

PBP is a disease that attacks the nerves supplying the bulbar muscles. These disorders are characterized by the degeneration of motor neurons in the cerebral cortex, spinal cord, brain stem, and pyramidal tracts. This specifically involves the glossopharyngeal nerve (IX), vagus nerve (X), and hypoglossal nerve (XII).

Pseudobulbar palsy is a medical condition characterized by the inability to control facial movements, such as chewing and speaking, and caused by a variety of neurological disorders. Patients experience difficulty chewing and swallowing, have increased reflexes and spasticity in tongue and the bulbar region, and demonstrate slurred speech, sometimes also demonstrating uncontrolled emotional outbursts. The condition is usually caused by the damage, bilateral degeneration, to the neurons of the brain stem, specifically to the corticobulbar tract (upper motor neuron tract to cranial nerve motor nuclei).

SMA, also called autosomal recessive proximal spinal muscular atrophy and 5q spinal muscular atrophy, is a rare neuromuscular disorder characterized by loss of motor neurons and progressive muscle wasting, often leading to early death. The disorder is caused by a genetic defect in the SMN1 gene, which encodes SMN, a protein widely expressed in all eukaryotic cells and necessary for survival of motor neurons. Lower levels of the protein results in loss of function of neuronal cells in the anterior horn of the spinal cord and subsequent system-wide atrophy of skeletal muscles.

PPS, also referred to as post-poliomyelitis syndrome or post-polio sequelae, is a condition that affects approximately 25 to 40% of people who have previously survived an acute attack of poliomyelitis—a viral infection of the nervous system—after the initial infection. Symptoms include acute or increased muscular weakness, pain in the muscles, and fatigue. The same symptoms may also occur years after a nonparalytic polio (NPP) infection. The precise mechanism that causes PPS is unknown. It shares many features with chronic fatigue syndrome, but unlike that disorder, it tends to be progressive, and can cause loss of muscle strength.

Cortical neurons are the cells of the cerebral cortex in the brain. Most of the complex activity of the brain enabling thought, perception, and voluntary movement is connected to the activity of cortical neurons.

Cortical neuron loss occurs in several neurodegenerative diseases, such as AD.

Glial cells, sometimes referred to as neuroglia, are non-neuronal cells that maintain homeostasis, form myelin, and provide support and protection for neurons in the CNS and the PNS. Glial cells have four key functions; surrounding neurons and hold them in place, supplying nutrients and oxygen to neurons, insulating neurons from each other and destroying pathogens and removing dead neurons.

There are many types of glial cells present either in the CNS or in the PNS. Glial cell types present in the CNS include astrocytes, oligodendrocytes, ependymal cells, radial glia and microglia. Glial cell types present in the PNS include Schwann cells, satellite cells and enteric glial cells.

Astrocytes, also referred to as astroglia, are the most abundant type of macroglial cell in the CNS. Astrocytes have numerous projections that anchor neurons to their blood supply. They regulate the external chemical environment of neurons by removing excess ions and recycling neurotransmitters released during synaptic transmission. Astrocytes may regulate vasoconstriction and vasodilation by producing substances, such as arachidonic acid, whose metabolites are vasoactive.

Oligodendrocytes are cells that coat axons in the CNS with their cell membrane, forming a specialized membrane differentiation called myelin, producing the so-called myelin sheath. The myelin sheath provides insulation to the axon that allows electrical signals to propagate more efficiently.

Ependymal cells, also referred to as ependymocytes, line the spinal cord and the ventricular system of the brain. These cells are involved in the creation and secretion of cerebrospinal fluid (CSF) and beat their cilia to help circulate the CSF and make up the blood-CSF barrier. They are also thought to act as neural stem cells.

Radial glia cells arise from neuroepithelial cells after the onset of neurogenesis. Their differentiation abilities are more restricted than those of neuroepithelial cells. In the developing nervous system, radial glia function both as neuronal progenitors and as a scaffold upon which new born neurons migrate. In the mature brain, the cerebellum and retina retain characteristic radial glial cells. In the cerebellum, these are Bergmann glia, which regulate synaptic plasticity. In the retina, the radial Müller cell is the principal glial cell, and participates in a bidirectional communication with neurons.

Microglia are a type of neuroglia located throughout the brain and spinal cord. As the resident macrophage cells, they act as the first and main form of active immune defense in the CNS. Microglia are key cells in overall brain maintenance, they are constantly scavenging the CNS for plaques, damaged or unnecessary neurons and synapses, and infectious agents.

Schwann cells are similar in function to oligodendrocytes but are present in the PNS instead of the CNS. Thus, Schwann cells provide myelination to axons in the PNS. They also have phagocytotic activity and clear cellular debris that allows for regrowth of PNS neurons.

Satellite glial cells are small cells that surround neurons in sensory, sympathetic, and parasympathetic ganglia. These cells help regulate the external chemical environment. They are highly sensitive to injury and inflammation, and appear to contribute to pathological states, such as chronic pain.

Enteric glial cells are found in the intrinsic ganglia of the digestive system. They are thought to have many roles in the enteric system, some related to homeostasis and muscular digestive processes.

Dextran sulfate of the embodiments further induces an increase in myelin basic protein (MBP) expression in the glial cells.

MBP is a protein that is important in the process of myelination of nerves in the nervous system and is a major constituent of the myelin sheath of oligodendrocytes and Schwann cells. MBP maintains the correct structure of myelin, interacting with the lipids in the myelin membrane. Interest in MBP has centered on its role in demyelinating diseases, in particular MS.

Axonal myelination is an essential process for normal functioning of vertebrate CNS. In the PNS, myelin is formed by the differentiation of the plasma membrane of Schwann cells. Loss of axonal contact, as occurs after nerve injury, leads to the down-regulation of myelin gene expression (*Progress in Neurobiology* (2000), 61: 267-304). The differentiation of Schwann cells and increase in MBP in injured peripheral nerves is critical for regeneration after injury (*Frontiers in Neuroscience* (2015), 9: Article 298, 1-13).

The increased expression of MBP in glial cells indicates that dextran sulfate of the embodiments acts as a differentiation factor for these cells (*Physiological Reviews* (2001), 81(2): 871-927, *Journal of Neurochemistry* (2013), 125(3): 334-361).

In an embodiment, the glial cells are myelinating cells, i.e., cells creating a myelin sheath that is wrapped around one or more axons of adjacent neurons. Thus, in a particular embodiment the glial cells are selected from a group consisting of Schwann cells and oligodendrocytes.

Dextran sulfate of the embodiment does not only induce differentiation of cells of the CNS and PNS, which is beneficial in neurological diseases, disorders and conditions. Experimental data as presented herein indicates that dextran sulfate of the embodiments has positive effect in combating metabolic modifications that are seen in neurological diseases, disorders and conditions, such as traumatic brain injury (TBI). Thus, many neurological diseases, disorders and conditions are characterized by modifications of various metabolites connected to the cell energy state and mitochondrial functions. Furthermore, modifications in amino acid metabolisms are seen in many neurological diseases, disorders and conditions. These metabolic modifications are early cellular signals that influence changes in enzymatic activities and gene and protein expressions indicative of a pathological tissue response. Dextran sulfate of the embodiments acts to positively regulate cellular metabolism in the compromised tissues, thereby inhibiting or at least suppressing any subsequent modifications in enzyme activity and gene and protein expression that contribute to adverse outcomes.

In more detail, dextran sulfate of the embodiments was capable of reducing levels of glutamate excitotoxicity and ameliorated adverse changes in metabolic hemostastis, thereby efficiently protecting mitochondrial function and providing a neuroprotective effect. Dextran sulfate of the embodiments positively affected various compounds related to energy metabolism and mitochondrial functions. Particularly interesting are the concentrations of adenine nucleotides and ATP/ADP ratio as measurement of mitochondrial phosphorylating capacity.

Dextran sulfate of the embodiments also led to a significant reduction in oxidative stress. In particular, the levels of ascorbic acid, as the main water-soluble brain antioxidant, and glutathione (GSH), as the major intracellular-sulfhydryl group (SH) donor, were significantly improved. In addition, malondialdehyde (MDA) levels, as end product of polyunsaturated fatty acids of membrane phospholipids and therefore taken as a marker of reactive oxygen species (ROS) mediated lipid peroxidation, showed a significant reduction after dextran sulfate administration. The oxidative stress markers described above all indicated an improvement in the recovery of antioxidant status after dextran sulfate treatment.

Dextran sulfate administration also significantly decreased the nitrate concentrations in both acute and chronic phases of neurological diseases, disorders and conditions. Accordingly, dextran sulfate of the embodiments has a positive effect on NO-mediated nitrosative stress.

N-acetylaspartate (NAA) is a brain specific metabolite and a valuable biochemical marker for monitoring deterioration or recovery after neurological diseases, disorders and conditions, such as TBI. NAA is synthesized in neurons from aspartate and acetyl-CoA by aspartate N-acetyltransferase. Dextran sulfate of the embodiment showed significant improvements in NAA levels.

Experimental data as presented herein thereby indicates that dextran sulfate of the embodiments can thereby protect against the cell loss that occurs due to oxidative stress and/or glutamate excitotoxicity in the diseased and damaged nervous system. By protecting cell metabolism, dextran sulfate of the embodiments may be a useful protective treatment in many degenerative conditions where cells are progressively lost due to ischemic, oxidative or traumatic damage, such as stroke, ALS, MND, MS, dementia, TBI, SCI, retinal damage, etc. These neurological diseases, disorders and conditions have a common link in terms of death and compromise of neuronal function of neurons that occurs in all conditions. There are commonalities in the causes of this of neuronal death. Of particular relevance is the toxicity caused by the high levels of the neurotransmitter glutamate that is released from dying neurons. Dextran sulfate of the embodiments induces scavenging of released glutamate in glial cells and thereby prevent accumulation of toxic amounts of glutamate in the neuronal clefts. This will be useful in all neurodegenerative diseases, disorders and conditions, both acute and chronic, where neurons are dying.

Excitotoxicity is the pathological process by which nerve cells are damaged or killed by excessive stimulation by neurotransmitters, in particular glutamate. This occurs when receptors for the excitatory neurotransmitter glutamate, such as the N-methyl-D-aspartate (NMDA) receptor and α-amino-3-hydroxy-5-methyl-4-isoxazolepropionic acid (AMPA) receptor are overactivated by glutamatergic storm or when neurons are damaged or dies, releasing their content of glutamate.

Excitotoxicity may be involved in SCI, stroke, TBI, hearing loss (through noise overexposure or ototoxicity), and in neurodegenerative diseases of the CNS, such as MS, AD, ALS, PD, alcoholism or alcohol withdrawal and especially over-rapid benzodiazepine withdrawal, and also HS. Other common conditions that cause excessive glutamate concentrations around neurons are hypoglycemia.

During normal conditions, glutamate concentration can be increased up to 1 mM in the synaptic cleft, which is rapidly decreased in the lapse of milliseconds. When the glutamate concentration around the synaptic cleft cannot be decreased or reaches higher levels, the neuron kills itself by a process called apoptosis. This pathologic phenomenon can also occur after brain injury, such as in TBI, and SCI. Within minutes after the injury, damaged neural cells within the lesion site spill glutamate into the extracellular space where glutamate can stimulate presynaptic glutamate receptors to enhance the release of additional glutamate. Brain trauma or stroke can cause ischemia, in which blood flow is reduced to inadequate levels. Ischemia is followed by accumulation of glutamate in the extracellular fluid, causing cell death, which is aggravated by lack of oxygen and glucose. The biochemical cascade resulting from ischemia and involving excitotoxicity is called the ischemic cascade. Because of the events resulting from ischemia and glutamate receptor activation, a deep chemical coma may be induced in patients with brain injury to reduce the metabolic rate of the brain, its need for oxygen and glucose, and save energy to be used to remove glutamate actively.

Furthermore, increased extracellular glutamate levels leads to the activation of $Ca^{2+}$ permeable N-methyl-D-aspartate (NMDA) receptors on myelin sheaths and oligodendrocytes, leaving oligodendrocytes susceptible to $Ca^{2+}$ influxes and subsequent excitotoxicity. One of the damaging results of excess calcium in the cytosol is initiating apoptosis through cleaved caspase processing. Another damaging result of excess calcium in the cytosol is the opening of the mitochondrial permeability transition pore, a pore in the membranes of mitochondria that opens when the organelles absorb too much calcium. Opening of the pore may cause mitochondria to swell and release reactive oxygen species and various proteins that can lead to apoptosis. The pore can also cause mitochondria to release more calcium. In addition, production of adenosine triphosphate (ATP) may be stopped, and ATP synthase may in fact begin hydrolyzing ATP instead of producing it.

Inadequate ATP production resulting from brain trauma can eliminate electrochemical gradients of certain ions. Glutamate transporters require the maintenance of these ion gradients to remove glutamate from the extracellular space. The loss of ion gradients results in not only the halting of glutamate uptake, but also the reversal of the transporters. The $Na^+$-glutamate transporters on neurons and astrocytes can reverse their glutamate transport and start secreting glutamate at a concentration capable of inducing excitotoxicity. This results in a buildup of glutamate and further damaging activation of glutamate receptors.

On the molecular level, calcium influx is not the only factor responsible for apoptosis induced by excitotoxicity. Recently, it has been noted that extrasynaptic NMDA receptor activation, triggered by both glutamate exposure or hypoxic/ischemic conditions, activate a cAMP response element binding (CREB) protein shut-off, which in turn caused loss of mitochondrial membrane potential and apoptosis.

Thus, the activation of glutamate transporter in glial cells by dextran sulfate of the embodiments to prevent or at least inhibit accumulation of toxic levels of glutamate will effectively protect surrounding neurons from glutamate excitotoxicity. As a result, dextran sulfate of the embodiments protect neurons from damages and cell death that is otherwise the result of this glutamate excitotoxicity.

Also, when any tissue, including the CNS and PNS, and the brain, which is particularly sensitive to changes in oxygen/energy supply, is damaged or diseased, the energy supply to cells is compromised. As a result the cells in the tissue, such as CNS, PNS or brain, cannot function efficiently. Accordingly, the reduction in oxidative stress by dextran sulfate of the embodiments, i.e., the protection of the mitochondrial energy supply, allows surviving cells to function more efficiently and will also protect compromised neurons from dying by apoptosis.

Thus, dextran sulfate of the embodiments was effective in restoring mitochondrial related energy metabolism, profoundly imbalanced in subject suffering from brain damages, such as severe TBI (sTBI), with positive effects on the concentration of triphosphates purine and pyrimidine nucleotides. Particularly, ATP levels were only 16% lower than the value of healthy control subjects, whilst in untreated sTBI subjects a 35% decrease was found. Remarkably, NAA concentration in sTBI subjects treated with dextran sulfate was only 16% lower than the value of healthy control subjects, whilst sTBI subjects showed 48% lower values of this compound. This finding once again strongly confirms the strict connection between the homeostasis of NAA and correct mitochondrial energy metabolism, and underlines the importance of pharmacological interventions capable to act positively on mitochondrial functioning.

The general amelioration of brain metabolism produced by dextran sulfate administration also involved nicotinic coenzymes and metabolism of free CoA-SH and CoA-SH derivatives. This implies that dextran sulfate treated subjects, notwithstanding submitted to sTBI, had quasi-normal coenzymes to ensure correct oxido-reductive reactions and to allow a good functioning of the TCA cycle.

The aforementioned improvement of brain metabolism further contributed to the other remarkable dextran sulfate effects, i.e., the abolishment of glutamate excitotoxicity. Additionally, dextran sulfate affected sulfur-containing amino acids. Possibly, this effect might be related to the dextran sulfate molecule that contains S atoms. Increasing the bioavailability of this atom might have produced a net increase in the biosynthesis of these amino acids, one of them (MET) is crucial in the methylation reaction and in the so called methyl cycle.

Further positive effects recorded were the increase in antioxidants and the decrease of biochemical signatures of oxidative/nitrosative stress in sTBI subjects receiving administration of dextran sulfate. Of relevance is that the effects of dextran sulfate were more evident at 7 days post sTBI than at 2 days post sTBI. This strongly suggest that the general amelioration of brain metabolism caused by the dextran sulfate administration was not a transitory phenomenon.

Dextran sulfate of the embodiments further has an affinity to compete for the protein-protein interaction between oligomeric amyloid-β and $PrP^c$, which will have a beneficial effect in subjects suffering from AD, prion diseases or amyloidosis.

Gene-expression data as presented herein indicates that dextran sulfate of the embodiments has a role in Schwann cells, neurons and in human umbilical vein endothelial cells (HUVECs) in protection against apoptosis; induction of angiogenesis (in HUVECs); increased migration and movement of cells; increased cell viability and survival; and induction of cellular differentiation.

The results from the HUVEC cell model indicates that dextran sulfate of the embodiments can protect against cell damage and promotes the development of new blood vessels in injured or diseased tissue, such as following stroke or other ischemic conditions.

Figure 19:
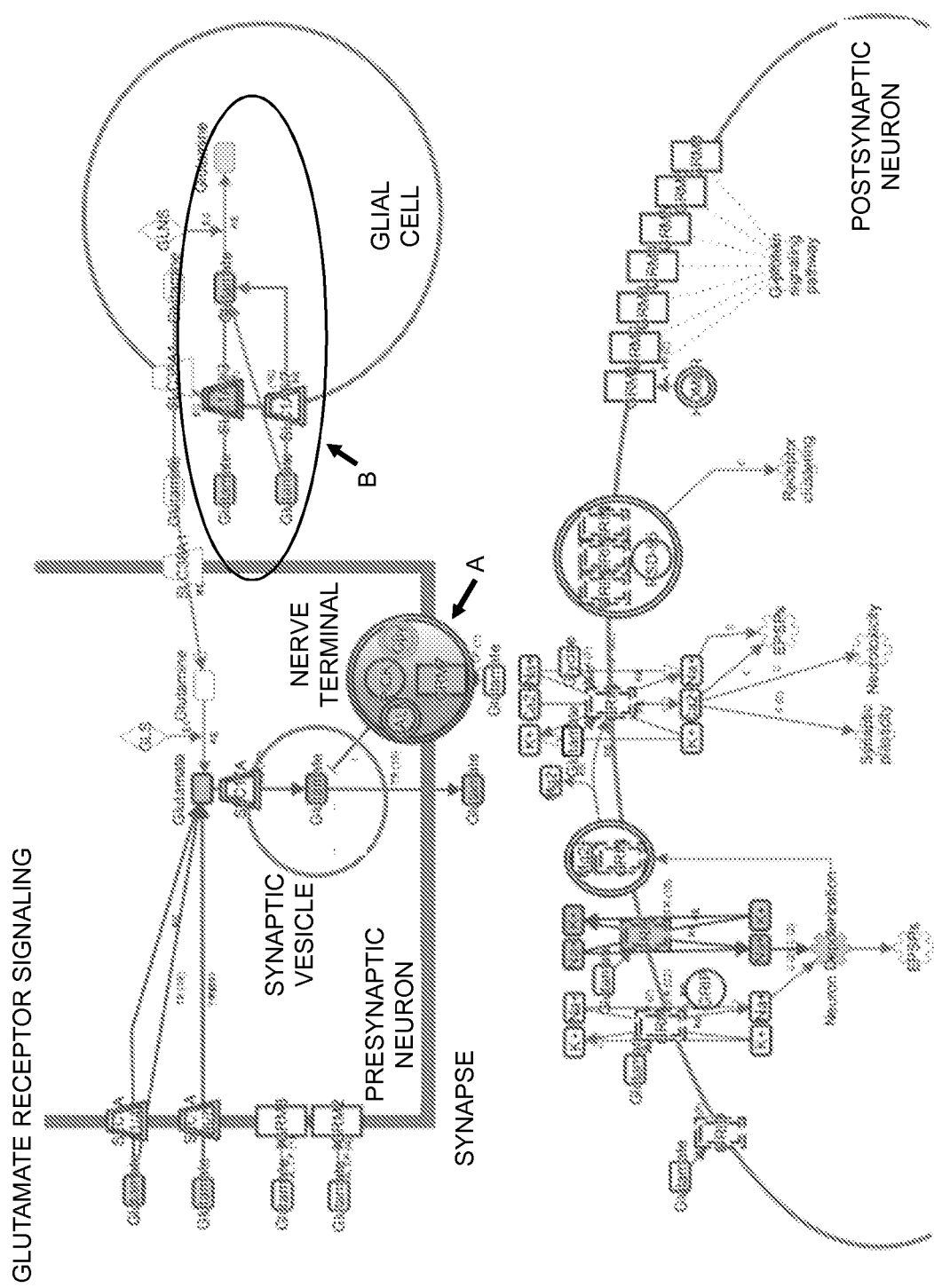
FIG. 19 schematically illustrates molecules involved in the glutamate signaling pathway.

The analysis of pivotal molecular pathways indicated that dextran sulfate reduced the effect of oxidative stress on mitochondria and increased uptake of damaging glutamate in Schwann cells. The gene expression data thereby confirmed the results seen in the animal model of TBI. Of particular interest was the finding that dextran sulfate of the embodiments inhibited Complex III. Inhibition of Complex III in turn leads to a reduction in mitochondrial oxidative stress. Furthermore, dextran sulfate of the embodiments also induced expression of a protein complex of calmodulin (CALM), which is a multifunctional intermediate calcium-binding messenger protein; G beta-gamma complex (Gβγ), which is a tightly bound dimeric G protein complex composed of one Gβ and one Gγ subunit; metabotropic glutamate receptor 7 (GRM7); and protein interacting with C kinase-1 (PICK1). This protein complex in turn inhibits glutamate release from presynaptic neurons as schematically shown in FIG. 19.

The results in Schwann cells indicate that dextran sulfate of the embodiment can protect against cell loss that occurs due to oxidative stress and glutamate excitotoxicity in the diseased or damaged nervous system, which is of relevance in, for instance, neurodegenerative diseases and TBI.

The results from the neurons indicate that dextran sulfate of the embodiment is capable of preventing and inhibiting apoptosis, preventing amyloid-β and Lewy body pathology and its negative effects on mitochondrial fragmentation and dysfunction, and subsequent damage and inhibiting fatty acid oxidation. Dextran sulfate of the embodiments also improved mitochondrial function, reduced the mitochondrial level of $H_2O_2$ and reactive oxygen species.

The analysis of the upstream regulators of the genes regulated by dextran sulfate indicated that dextran sulfate of the embodiments enhanced the effect of existing growth factors on cells. As shown in Table 12-14, dextran sulfate of the embodiments was capable of modulating the effect of several growth factors by either increasing their activation or by reducing their inhibition. This means that dextran sulfate of the embodiments has potential use in diseases, disorders and conditions in which an increase of the activity or a reduction of the inhibition of these growth factors would be beneficial to the patient. Non-limiting examples of such diseases, disorders and conditions include ALS; stroke; SCI; depression and other psychiatric disorders, such as mood disorders and bipolar disease; and metabolic disorders.

A hypothesis is that dextran sulfate binds to the growth factor molecules and facilitates binding to their receptors. This hypothesis is also supported by the observation that the dextran sulfate-induced differential gene expression in HUVECs, where the normal control medium already contained heparin, was relatively smaller than in the Schwann cells where the normal control medium did not contain heparin. This mechanism of action also explains why dextran sulfate is mainly effective in the acute stage of TBI, when growth factors are present, but less effective at later stage when the initial repair attempt has already diminished.

Thus, it could be possible that at least some of the therapeutic effects of dextran sulfate of the embodiments depends on existing repair mechanisms, which are amplified by it. In such a case, it is generally recommended that in any neurodegenerative disease, disorder or condition dextran sulfate is given in the early stage of the disease, disorder or condition when there is enough repair potential in the tissue.

By protecting cell metabolism, dextran sulfate may be a useful protective treatment in many degenerative conditions where cells are progressively lost due to ischemic, oxidative or traumatic damage. Non-limiting, but illustrative, examples of such degenerative conditions include stroke, ALS, MS, dementia, TBI, SCI, retinal damage, AD, etc. Dextran sulfate of the embodiments may help the damaged tissues to recover some lost function as it enhances the residual intrinsic repair mechanisms.

The gene-expression data therefore confirms the potential therapeutic usefulness of dextran sulfate of the embodiments in compromised states of the CNS and PNS, by promoting revascularisation, reducing secondary tissue damage, and promoting repair, and for neurodegenerative diseases, disorders and conditions, where it could promote neuronal survival, differentiation and ultimately repair.

A further interesting effect of dextran sulfate of the embodiments is that it affects cell adhesion. Cell adhesion was affected mainly in neurons and Schwann cells, where dextran sulfate of the embodiments promoted cell detachment and movement. The effect on cell adhesion was mainly due to the expression of metalloproteinase-type enzymes. This finding would also explain an anti-scarring effect of dextran sulfate of the embodiments. The results suggest that an anti-scarring effect mediated by dextran sulfate of the embodiments by activating degrading enzymes that help tissue remodeling and block the fibrogenic (scarring) signals in damaged tissues.

The metalloproteinase-type enzymes that are activated by dextran sulfate of the embodiments specifically act by dissolving the fibrous molecules that make up the scar, see Table 10-11. These enzymes are released by cells that migrate into damaged tissues. Accordingly, by allowing these cells to be more mobile, reducing their adhesion, dextran sulfate of the embodiments is permitting them to migrate better, release scar dissolving enzymes and remodel the tissue for better repair.

Thus, the anti-scarring actions of dextran sulfate of the embodiments indicate a potential use to treat fibroproliferative (scarring) conditions. These include, for instance, glaucoma, proliferative vitreoretinopathy, brain and spinal trauma injuries, sub-arachnoid hemorrhage in the brain, invasive surgical procedures, surgical adhesions, rotator cuff injuries, burns, reconstructive surgery, ulcerative conditions (diabetes), etc. Other fibrotic diseases and conditions include fibrosis in the lungs, such as pulmonary fibrosis, cystic fibrosis, idiopathic pulmonary fibrosis, progressive massive fibrosis and radiation-induced lung injury following treatment for cancer; in the liver, such as cirrhosis and biliary atresia; fibrosis in the heart, such as atrial fibrosis, endomyocardial fibrosis, old myocardial infarction; fibrosis in the brain, such as glial scar; pancreatitis; arthrofibrosis; Crohn's disease; Dupuytren's contracture; keloid; mediastinal fibrosis; myelofibrosis; Peyronie's disease; nephrogenic systemic fibrosis; retroperitoneal fibrosis; scleroderma or systemic sclerosis.

Fibrosis may also occur in connection with organ transplantation, such as of kidneys, lungs, livers, hearts, etc., and in connection with cell therapies and cell transplantation, such as of islet of Langerhans, hepatocytes, insulin producing cells, stem cells, progenitor cells, etc.

Interestingly, the gene expression data also shows that dextran sulfate of the embodiments activates the production of a natural scar reducing molecule called decorin, which further blocks scar production by 'mopping up' the growth factors that stimulate scar production by fibroblasts.

Decorin is a glycoprotein of on average 90-140 kD molecular weight. It belongs to the small-leucine rich proteoglycan (SLRP) family and consists of a protein core containing leucine repeats with a glucosaminoglycan (GAG) chain consisting of either chondroitin sulphate or dermatan sulphate. It binds to type I collagen fibrils through the decorin type I collagen binding region.

Decorin acts as a transforming growth factor beta 1 or 2 (TGF-β1/2) antagonist and reduces scarring. Reports show that in acute scarring the dominant effect of decorin is anti-fibrogenic through suppression of inflammatory fibrosis by neutralization of TGF-β1/2. Decorin also binds directly to collagen and one of its functions is to influence on the organization of collagen during wound healing.

Decorin has previously been described in inhibition of scarring in a model of cerebral lesion, hydrocephalus, and chronic spinal cord wounds. Decorin also induces fibrolysis of existing trabecular meshwork scars in a glaucoma model.

Taken together the anti-scarring actions of dextran sulfate of the embodiments indicate the potential for use to treat all clinical conditions where scarring is a problem. Dextran sulfate should work on both old and new scars. This is confirmed in the experimental data showing that dextran sulfate of the embodiments was capable of inducing dissolution of already established scar elements in the trabecular meshwork in glaucomatous eyes. This is a significant advantage of dextran sulfate of the embodiments since it cannot only be used to inhibit or at least suppress fibrosis and deleterious scar formation but also dissolve already established scars. This means that dextran sulfate of the embodiments allows for a scar dissolving and tissue remodeling for a better repair.

Dextran sulfate was assessed in a panel of human primary cell-based assays modeling complex tissue and disease biology and general tissue biology. The results from the assay indicate that dextran sulfate plays a role in regulating immune activation and/or immune resolution responses in the context of inflammation and wound healing biology.

The modulations of the inflammatory markers indicate utility of dextran sulfate in treating multiple chronic and acute inflammatory conditions and diseases including inflammatory components, such as ALS.

Initially after injury, the innate/proinflammatory response and selected components of the acquired immune response are up-regulated to maintain a defense against foreign pathogens, clear tissue debris present at the injury site, and orchestrate tissue remodeling, cell proliferation and angiogenic processes associated with the wound response. However, for proper wound healing to progress, this initial inflammatory response has to be regulated or shut down so as to allow for the reestablishment of matrix, recellularization and tissue remodeling. Such immune resolving activities were induced by dextran sulfate, including activation of MMP-1, PAR-1 and uPAR, indicating an induced immune resolution having utility in treating tissue damaged by trauma, including neurotrauma, which otherwise would result in deleterious fibrosis formation.

The effect in inflammation resolution of dextran sulfate as shown in the experimental data indicates that dextran sulfate would be useful in preventing, treating or at least inhibiting auto-immune diseases, and in particular auto-immune diseases effecting the central and/or peripheral nervous system. The inflammation resolution of dextran sulfate is also important in terms of blocking fibrogenesis. Furthermore, resolution of inflammation and suppression of microglial responses as seen from the experimental data are also important in neurodegenerative diseases, disorders and conditions.

Accordingly, the dextran sulfate, or the pharmacologically acceptable derivative thereof, would be useful preventing, treating or at least inhibiting neuroinflammation and neuroinflammatory conditions. Examples of such neuroinflammatory conditions include PD, ALS, MS, ADEM, myelitis and GDS.

In conclusion, dextran sulfate seemed to normalize and resolve the inflammation present in tissue after trauma or a disease and these results are thereby consistent with the effects of dextran sulfate seen in gene array and animal studies.

Generally, the function of the nervous system depends on the number of nerve cells, a healthy energy metabolism of the nerve cells and healthy connections between the nerve cells. Neurodegenerative diseases and disorders, and injuries causing neurodegeneration, typically have different triggers and causes but all lead to the same end-results, i.e., neurodegeneration. The functional effects of such diseases, disorders or injuries are often seen only after a comparatively large number of nerve cells are dead, whereas the triggers of the diseases or disorders may be present years before the symptoms occur.

Accordingly, a new approach is needed to treat or inhibit neurodegeneration. Such an approach should involve enhancing viable functions of the nervous system including a healthy energy metabolism of the nerve cells and healthy connections between the nerve cells. Furthermore, further neurodegeneration should be prevented or at least slowed down by reducing the triggers that lead to neuronal death and prevent further pathology even if triggers are present. In addition, the regenerative potential of the nervous system should be enhanced.

There are, thus, multiple triggers of neuron apoptosis that all contribute to neuronal loss during neurodegeneration and damage. These triggers include dysregulation of neurotransmitters leading to glutamate excitotoxicity and oxidative stress leading to mitochondrial dysfunction, thereby limiting the energy supply to neurons. Also, dysregulated neurofilaments lead to reduced motility and restricted supply of factors needed for neuron survival. Further triggers include release of inflammatory mediators causing secondary cell damage and scarring. Furthermore, vascular defects are common in neurodegenerative conditions.

Glutamate is produced in neurons and is pivotal for signaling mechanisms that support learning and memory in neurons. Excess glutamate released is in healthy brain tissue mopped up by glial cells to prevent toxic levels. Dextran sulfate induces an increased glutamate uptake by glia cells, whereas the glutamate production in neurons is not altered by dextran sulfate. Hence, the glutamate needed for learning and memory is not affected by dextran sulfate administrations, whereas harmful toxic amounts of glutamate is mopped up by glial cells. Accordingly, dextran sulfate attenuates the dysregulation of neurotransmitters leading to glutamate excitotoxicity.

Oxidative stress in neurodegeneration leads to mitochondrial dysfunction, thereby limiting the energy supply to neurons. Dextran sulfate reduced production of molecules that induce oxidative stress, including amyloid-β and Lewy bodies, and reduced oxidative stress. Hence, dextran sulfate prevents neuronal death induced by oxidative stress and prevents mitochondrial dysfunction in neurons. This means that dextran sulfate promotes a normalization of mitochondrial function in presence of oxidative stress and prevents energy crisis in neurons in presence of such oxidative stress. Accordingly, dextran sulfate attenuates oxidative stress in neurodegeneration that otherwise would lead to mitochondrial dysfunction.

A further trigger in neurodegeneration is dysregulated neurofilaments, which lead to reduced motility and restricted supply of survival factors. Dextran sulfate enhances the effect of growth factors present in neurons, increases migration and movement of nerve cells, reduces the production of degeneration-related protein products and induces cellular differentiation. Accordingly, dextran sulfate attenuates dysregulated neurofilaments.

Neurodegeneration also induces release of inflammatory mediators causing secondary cell damage and scarring. Such scarring is driven by inflammatory cytokines, in particular TGF-β. Dextran sulfate induces metallopeptidase expression, induces expression of the natural anti-scarring molecule decorin and inhibits TGF-β activity. Furthermore, dextran sulfate inhibits immune cell adhesion, cell aggregation, cell activation and fibrosis even in the presence of excessive TGF-β. Accordingly, dextran sulfate attenuates the negative effects, including scarring, caused by release inflammatory mediators. Dextran sulfate also acts to inhibit fibrogenesis as well as activating fibrolysis, which in combination leads to the beneficial effects seen by dextran sulfate in attenuating or even dissolving scarring.

Dextran sulfate protects HUVECs against apoptosis, induced angiogenesis and increased migration and movement of the endothelial cells. Accordingly, dextran sulfate enhances the physiological repair response in hypoxic tissues caused by neurodegenerative diseases, disorders or injuries but does not affect the normal healthy vasculature.

Accordingly, an aspect of the embodiments relates to a method of inducing differentiation of cells selected from a group consisting of glial cells and neurons. The method comprises contacting the cells with dextran sulfate, or a pharmaceutically acceptable derivative thereof, in order to induce differentiation of the cells.

In an embodiment, the method is an in vitro method. In such a case, contacting the cells comprises contacting the cells in vitro with the dextran sulfate, or the pharmaceutically acceptable derivative thereof. Thus, the cells are treated with and interacts in vitro with dextran sulfate, or the pharmaceutically acceptable derivative thereof.

In an embodiment, the neurons are obtained from stem cells, i.e., by differentiating stem cells into neurons that may be treated and further differentiated by the dextran sulfate, or the pharmaceutically acceptable derivative thereof.

Such an in vitro method may have important uses within research and diagnostics, in which fields neurons and/or glial cells are cultured in vitro. The dextran sulfate, or the pharmaceutically acceptable derivative thereof, may be added to such neuron or glial cell cultures, for instance added to the culture medium, in order to induce a differentiation of the cells as described herein.

The method may also be an ex vivo method, in which the neurons and/or glial cells have been extracted from a subject and is to be contacted with the dextran sulfate, or the pharmaceutically acceptable derivative thereof, outside of the subject's body.

The neurons and/or glial cells treated by the dextran sulfate, or the pharmaceutically acceptable derivative thereof, in the above described in vitro or ex vivo method to induce differentiation may be transplanted into a subject. The differentiated neurons and/or glial cells should then exert their desired function in the subject's body. In this approach, the subject may be suffering from a neurological disease as is further described herein.

The dextran sulfate, or the pharmaceutically acceptable derivative thereof, is, in an alternative embodiment, administered to a subject, such as a subject suffering from a neurological disease, disorder or condition. The dextran sulfate, of the pharmaceutically acceptable derivative thereof, will then contact neurons and/or glial cells inside the subject's body to induce cell differentiation. In this embodiment, the method is an in vivo method.

Another aspect of the embodiments relates to dextran sulfate, or a pharmaceutically acceptable derivative thereof, for use in inducing differentiation of cells selected from a group consisting of glial cells and neurons.

In an embodiment, the dextran sulfate, of the pharmaceutically acceptable derivative thereof, is for use in inducing differentiation of the cells in a subject suffering from a neurological disease, disorder or condition.

In a particular embodiment, the dextran sulfate, of the pharmaceutically acceptable derivative thereof, is for use in inducing differentiation of the cells in a subject suffering from a neurological disease, disorder or condition selected from a group consisting of a neurodegenerative disease, disorder or condition; a demyelinating disease, disorder or condition; a neuro ischemic disease, disorder or condition; a neuromuscular disease, disorder or condition; a traumatic nerve injury and a post-operative neurological condition.

In an embodiment, the subject is a human subject suffering from a neurodegenerative disease, disorder or condition selected from a group consisting of AD, PD, HD and ALS.

In an embodiment, the subject is a human subject suffering from a demyelinating disease, disorder or condition selected from a group consisting of MS, ADEM, a CNS neuropathy, CPM, a myelopathy, a leukoencephalopathy, a leukodystrophy, GBS, a peripheral neuropathy and Charcot-Marie-Tooth disease, preferably selected from a group consisting of MS, ADEM, CPM and GBS.

The dextran sulfate, or the pharmaceutically acceptable derivative thereof, may also, or alternatively, be used in inducing differentiation of the cells in other types of neurological diseases, disorders or conditions. Non-limiting examples of such other types of neurological diseases, disorders or conditions include neuro ischemic diseases, such as stroke, cerebral ischemic conditions and critical limb ischemia (CLI); neuromuscular disorders, such as ALS, botulism, congenital myasthenic syndromes, congenital myopathies, cramp-fasciculation syndrome, cerebral palsy, elevated creatine kinase, fasciculations, inclusion-body myositis, Lambert-Eaton syndrome, mitochondrial myopathy, motor neuron disease, muscle disorders, muscular dystrophy, myasthenia gravis, myotonic dystrophy, neuromuscular junction disorders, neuromyotonia, peripheral neuropathy and polymyositis; traumatic nerve injuries and post-operative neurological conditions.

A further aspect of the embodiments relates to dextran sulfate, or a pharmaceutically acceptable derivative, for use in treating, inhibiting or preventing glutamate excitotoxicity in a subject.

In an embodiment, dextran sulfate, or the pharmaceutically acceptable derivative thereof, is effective in treating, inhibiting or preventing glutamate excitotoxicity in neurons of the subjects.

In a particular embodiment, the subject is suffering from a neurological disease, disorder or condition causing cell damage and/or cell death to neurons as previously described herein.

This aspect also relates to a method of treating, inhibiting or preventing glutamate excitotoxicity. The method comprises administering dextran sulfate, or a pharmaceutically acceptable derivative thereof, to a subject in order to treat, inhibit or prevent glutamate excitotoxicity Other aspects of the embodiments relates to dextran sulfate, or a pharmaceutically acceptable derivative thereof, for use in protecting neurons from oxidative stress induced by a neurological disease, disorder or condition, for use in ameliorating adverse changes in metabolic hemostasis in neurons induced by a neurological disease, disorder or condition, protecting mitochondrial function and mitochondrial energy metabolism in neurons in a subject suffering from a neurological disease, disorder or condition.

Dextran sulfate, or the pharmaceutically acceptable derivative thereof, can thereby be used to treat, inhibit or prevent a neurological disease, disorder or condition as described herein.

Dextran sulfate, or the pharmaceutically acceptable derivative thereof, can also be used to treat, inhibit or prevent ischemic, oxidative or traumatic damage to neurons and the CNS, or PNS, such as stroke, ALS, MND, MS, dementia, TBI, SCI, retinal damage, etc.

A further aspect relates to dextran sulfate, or a pharmaceutically acceptable derivative thereof, for use in treating, inhibiting or preventing fibrosis in a subject, and in particular for use in treating or inhibiting, such as by dissolving, established scars in a subject suffering from fibrosis or a fibrotic disease, disorder or condition.

Thus, dextran sulfate of the embodiments having an anti-scarring effect would be effective in wound treatment and tissue remodeling, in which there is a need for dissolving already established scars in order to enable a correct wound healing. This anti-scarring effect of dextran sulfate of the embodiments is thought to be a consequence of the previously described mechanisms of action of dextran sulfate including, for instance, inhibition of cell adhesion, induction of cell mobilization, induction of metalloproteases and scar dissolving enzymes, and inhibition of TGFβ, in particular TGFβ1, through the induction of decorin. This latter effect obtained with dextran sulfate of the embodiments is further of relevance in preventing or at least inhibiting fibrosis and scar formation through the induction of decorin.

Another aspect relates to dextran sulfate, or a pharmaceutically acceptable derivative thereof, for use in treating, inhibiting or prevent neuroinflammation in a subject, in particular in a subject suffering from a neurological disease, disorder or condition causing neuroinflammation.

Relates aspect of the embodiments define use of dextran sulfate, or a pharmaceutically acceptable derivative thereof, for the manufacture of a medicament for the various medical applications as disclosed herein, e.g., for treating, inhibiting or prevent any of the diseases, disorders or conditions as disclosed herein.

Further aspects relates to methods of treating, inhibiting or preventing the various diseases, disorders or conditions described above for the various uses of dextran sulfate, or the pharmaceutically acceptable derivative thereof. In such methods, dextran sulfate, or the pharmaceutically acceptable derivative thereof, is administered to the subject to treat, inhibit or prevent the disease, disorder or condition as disclosed herein.

In the following, reference to (average) molecular weight and sulfur content of dextran sulfate applies also to any pharmaceutically acceptable derivative of dextran sulfate. Hence, the pharmaceutically acceptable derivative of dextran sulfate preferably has the average molecular weight and sulfur content as discussed in the following embodiments.

Dextran sulfate outside of the preferred ranges of the embodiments are believed to have inferior effect and/or causing negative side effects to the cells or subject.

For instance, dextran sulfate of a molecular weight exceeding 10,000 Da (10 kDa) generally has a lower effect vs. side effect profile as compared to dextran sulfate having a lower average molecular weight. This means that the maximum dose of dextran sulfate that can be safely administered to a subject is lower for larger dextran sulfate molecules (>10,000 Da) as compared to dextran sulfate molecules having an average molecular weight within the preferred ranges. As a consequence, such larger dextran sulfate molecules are less appropriate in clinical uses when the dextran sulfate is to be administered to subjects in vivo.

Dextran sulfate is a sulfated polysaccharide and in particular a sulfated glucan, i.e., polysaccharide made of many glucose molecules. Average molecular weight as defined herein indicates that individual sulfated polysaccharides may have a molecular weight different from this average molecular weight but that the average molecular weight represents the mean molecular weight of the sulfated polysaccharides. This further implies that there will be a natural distribution of molecular weights around this average molecular weight for a dextran sulfate sample.

Average molecular weight, or more correctly weight average molecular weight ($M_w$), of dextran sulfate is typically determined using indirect methods such as gel exclusion/penetration chromatography, light scattering or viscosity. Determination of average molecular weight using such indirect methods will depend on a number of factors, including choice of column and eluent, flow rate, calibration procedures, etc.

$$\text{Weight average molecular weight } (M_w): \frac{\Sigma M_i^2 N_i}{\Sigma M_i N_i},$$

typical for methods sensitive to molecular size rather than numerical value, e.g., light scattering and size exclusion chromatography (SEC) methods. If a normal distribution is assumed, then a same weight on each side of $M_w$, i.e., the total weight of dextran sulfate molecules in the sample having a molecular weight below $M_w$ is equal to the total weight of dextran sulfate molecules in the sample having a molecular weight above $M_w$. The parameter $N_i$ indicates the number of dextran sulfate molecules having a molecular weight of $M_i$ in a sample or batch.

In an embodiment, the dextran sulfate or the pharmaceutically acceptable derivative thereof has a $M_w$ equal to or below 10,000 Da. In a particular embodiment, the dextran sulfate or the pharmaceutically acceptable derivative thereof has a $M_w$ within an interval of from 2,000 Da to 10,000 Da.

In another embodiment, the dextran sulfate or the pharmaceutically acceptable derivative thereof has a $M_w$ within an interval of from 2,500 Da to 10,000 Da, preferably within an interval of from 3,000 Da to 10,000 Da. In a particular embodiment, the dextran sulfate or the pharmaceutically acceptable derivative thereof has a $M_w$ within an interval of from 3,500 Da to 9,500 Da, such as within an interval of from 3,500 Da to 8,000 Da.

In another particular embodiment, the dextran sulfate or the pharmaceutically acceptable derivative thereof has a $M_w$ within an interval of from 4,500 Da to 7,500 Da, such as within an interval of from 4,500 Da and 5,500 Da.

Thus, in some embodiments, the dextran sulfate or the pharmaceutically acceptable derivative thereof has a $M_w$ equal to or below 10,000 Da, equal to or below 9,500 Da, equal to or below 9,000 Da, equal to or below 8,500 Da, equal to or below 8,000 Da, equal to or below 7,500 Da, equal to or below 7,000 Da, equal to or below 6,500 Da, equal to or below 6,000 Da, or equal to or below 5,500 Da.

In some embodiments, the dextran sulfate or the pharmaceutically acceptable derivative thereof has a $M_w$ equal to or above 1,000 Da, equal to or above 1,500 Da, equal to or above 2,000 Da, equal to or above 2,500 Da, equal to or above 3,000 Da, equal to or above 3,500 Da, equal to or above 4,000 Da. or equal to or above 4,500 Da. Any of these embodiments may be combined with any of the above presented embodiments defining upper limits of the $M_w$, such combined with the upper limit of equal to or below 10,000 Da.

In a particular embodiment, the $M_w$ of dextran sulfate, or the pharmaceutically acceptable derivative thereof, as presented above is average $M_w$, and preferably determined by gel exclusion/penetration chromatography, size exclusion chromatography, light scattering or viscosity-based methods.

$$\text{Number average molecular weight } (M_n): \frac{\Sigma M_i N_i}{\Sigma N_i},$$

typically derived by end group assays, e.g., nuclear magnetic resonance (NMR) spectroscopy or chromatography. If a normal distribution is assumed, then a same number of dextran sulfate molecules can be found on each side of $M_n$, i.e., the number of dextran sulfate molecules in the sample having a molecular weight below $M_n$ is equal to the number of dextran sulfate molecules in the sample having a molecular weight above $M_n$.

In an embodiment, the dextran sulfate, of the pharmaceutically acceptable derivative thereof, has a $M_n$ as measured by NMR spectroscopy within an interval of from 1,850 to 3,500 Da.

In a particular embodiment, the dextran sulfate, of the pharmaceutically acceptable derivative thereof, has a $M_n$ as measured by NMR spectroscopy within an interval of from 1,850 Da to 2,500 Da, preferably within an interval of from 1,850 Da to 2,300 Da, such as within an interval of from 1,850 Da to 2,000 Da.

Thus, in some embodiments, the dextran sulfate or the pharmaceutically acceptable derivative thereof has a $M_n$ equal to or below 3,500 Da, equal to or below 3,250 Da, equal to or below 3,000 Da, equal to or below 2,750 Da, equal to or below 2,500 Da, equal to or below 2,250 Da, or equal to or below 2,000 Da. In addition, the dextran sulfate or the pharmaceutically acceptable derivative thereof has a $M_n$ equal to or above 1,850 Da.

In an embodiment, the dextran sulfate, or the pharmaceutically acceptable derivative thereof, has an average sulfate number per glucose unit within an interval of from 2.5 to 3.0.

In a particular embodiment, the dextran sulfate, or the pharmaceutically acceptable derivative thereof, has an average sulfate number per glucose unit within an interval of from 2.5 to 2.8, preferably within an interval of from 2.6 to 2.7.

In an embodiment, the dextran sulfate, or the pharmaceutically acceptable derivative thereof, has an average number of glucose units within an interval of from 4.0 to 6.0.

In a particular embodiment, the dextran sulfate, or the pharmaceutically acceptable derivative thereof, has an average number of glucose units within an interval of from 4.5 to 5.5, preferably within an interval of from 5.0 to 5.2.

In an embodiment, the dextran sulfate, or the pharmaceutically acceptable derivative thereof, has a $M_n$ as measured by NMR spectroscopy within an interval of from 1,850 to 3,500 Da, an average sulfate number per glucose unit within an interval of from 2.5 to 3.0, and an average sulfation of C2 position in the glucose units of the dextran sulfate is at least 90%.

In an embodiment, the dextran sulfate has an average number of glucose units of about 5.1, an average sulfate number per glucose unit within an interval of from 2.6 to 2.7 and a $M_n$ within an interval of from 1,850 Da and 2,000 Da.

In an embodiment, the pharmaceutically acceptable derivative of dextran sulfate is a sodium salt of dextran sulfate. In a particular embodiment, the sodium salt of dextran sulfate has an average number of glucose units of about 5.1, an average sulfate number per glucose unit within an interval of from 2.6 to 2.7 and a $M_n$ including the Na$^+$ counter ion within an interval of from 2,100 Da to 2,300 Da.

In an embodiment, the dextran sulfate has an average number of glucose units of 5.1, an average sulfate number per glucose unit of 2.7, an average $M_n$ without Na$^+$ as measured by NMR spectroscopy of about 1,900-1,950 Da and an average $M_n$ with Na$^+$ as measured by NMR spectroscopy of about 2,200-2,250 Da.

The dextran sulfate according to the embodiments can be provided as a pharmaceutically acceptable derivative of dextran sulfate, such as a pharmaceutically active derivative of dextran sulfate. Such pharmaceutically acceptable derivatives include pharmaceutically acceptable salts and pharmaceutically acceptable solvates of dextran sulfate, e.g., a sodium or potassium salt.

The subject is preferably a mammalian subject, more preferably a primate and in particular a human subject. The dextran sulfate, or the pharmaceutically acceptable derivative thereof, can, however, be used also in veterinary applications. Non-limiting example of animal subjects include primate, cat, dog, pig, horse, mouse, rat.

The dextran sulfate, or the pharmaceutically acceptable derivative thereof, is preferably administered by injection to the subject and in particular by intravenous (i.v.) injection, subcutaneous (s.c.) injection or (i.p.) intraperitoneal injection, preferably i.v. or s.c. injection. Other parenteral administration routes that can be used include intramuscular and intraarticular injection. Injection of the dextran sulfate, or the pharmaceutically acceptable derivative thereof, could alternatively, or in addition, take place directly in, for instance, a tissue or organ or other site in the subject body, at which the target effects are to take place.

The dextran sulfate, or the pharmaceutically acceptable derivative thereof, may alternatively, or in addition, be administered intrathecally. For instance, the dextran sulfate, or the pharmaceutically acceptable derivative thereof, can be injected together with a suitable aqueous carrier or solution into the spinal canal, or into the subarachnoid space so that it reaches the cerebrospinal fluid (CSF). A further administration route is intraocular administration.

The dextran sulfate, or the pharmaceutically acceptable derivative thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer. For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline, i.e., NaCl (aq). Furthermore, other buffer systems than CAM could be used if a buffered solution are desired.

The embodiments are not limited to injections and other administration routes can alternatively be used including orally, nasally, bucally, rectally, dermally, tracheally, bronchially, or topically. The active compound, dextran sulfate, is then formulated with a suitable excipient or carrier that is selected based on the particular administration route.

Suitable dose ranges for the dextran sulfate, or the pharmaceutically acceptable derivative thereof, may vary according to the application, such as in vitro versus in vivo, the size and weight of the subject, the condition for which the subject is treated, and other considerations. In particular for human subjects, a possible dosage range could be from 1 µg/kg to 100 mg/kg of body weight, preferably from 10 µg/kg to 50 mg/kg of body weight.

In preferred embodiments, the dextran sulfate, or the pharmaceutically acceptable derivative thereof, is formulated to be administered at a dosage in a range from 0.05 to 50 mg/kg of body weight of the subject, preferably from 0.05 or 0.1 to 40 mg/kg of body weight of the subject, and more preferably from 0.05 or 0.1 to 30 mg/kg, or 0.1 to 25 mg/kg or from 0.1 to 15 mg/kg or 0.1 to 10 mg/kg body weight of the subject.

Administration of the dextran sulfate, or the pharmaceutically acceptable derivative thereof, does not necessarily have to be limited to treatment or inhibition of a present disease, disorder or condition but could alternatively, or in addition, be used for prophylaxis. In other words, the dextran sulfate, or the pharmaceutically acceptable derivative thereof, could be administered to a subject that will undergo a medical procedure, such as surgery, that may cause nerve injuries or damage and/or fibrosis. The dextran sulfate, or the pharmaceutically acceptable derivative thereof, may also be used to prevent, inhibit or alleviate post-operative neurological complications and conditions in a subject that is about to undergo a medical procedure, such as surgery, and/or fibrosis.

The dextran sulfate, or the pharmaceutically acceptable derivative thereof, can be administered at a single administration occasion, such as in the form of a single bolus injection. This bolus dose can be injected quite quickly to the subject but is advantageously infused over time so that the dextran sulfate solution is infused over a few minutes of time to the patient, such as during 5 to 10 minutes.

Alternatively, the dextran sulfate, or the pharmaceutically acceptable derivative thereof, can be administered at multiple, i.e., at least two, occasions during a treatment period.

The dextran sulfate, or the pharmaceutically acceptable derivative thereof, can be administered together with other active agents, either sequentially, simultaneously or in the form of a composition comprising the dextran sulfate, or the pharmaceutically acceptable derivative thereof, and at least one other active agent. The at least one active agent can be selected among any agent useful in any of the above mentioned diseases, disorders or conditions. The at least one active agent could also be in the form of cells in cell therapy, such as stem cells including, but not limited to, embryonic stem cells (ESCs) and mesenchymal stromal cells (MSCs).

For instance, research has been conducted on the effects of stem cells on animal models of brain degeneration, such as in Parkinson's disease, MS, ALS, and Alzheimer's disease. Furthermore clinical and animal studies have been conducted into the use of stem cells in cases of TBI.

The dextran sulfate, or the pharmaceutically acceptable derivative thereof, has beneficial effects to cells in vitro as shown in the experimental data. For instance, the dextran sulfate, or the pharmaceutically acceptable derivative thereof, protects the cells from oxidative stress, restores metabolic hemostasis in the cells, which is beneficial for the energy metabolism in the cells, and may act as a differentiation factor for the cells. These beneficial effects of the dextran sulfate, or the pharmaceutically acceptable derivative thereof, may also find uses in other types of cell therapy, i.e., not necessarily limited to stem cell therapy. Non-limiting, but illustrative, examples of such other types of cell therapy include myocardial cells, liver cells, connective tissue cells, optic nerve cells, lymphocytes, macrophages, glial cells, Schwann cells, neurons, etc. In such a case, the cells may be treated with the dextran sulfate, or the pharmaceutically acceptable derivative thereof, in vitro prior to administration into a subject. Alternatively, or in addition, the cells may be administered together with the dextran sulfate, or the pharmaceutically acceptable derivative thereof. Also treatment of tissue and organs in vitro or ex vivo with the dextran sulfate, or the pharmaceutically acceptable derivative thereof, could be useful to benefit from the positive effects of dextran sulfate of the embodiment, for instance protection against oxidative stress and restoration of metabolic hemostasis. Furthermore, treatment of cells, tissue and organs, in addition or as an alternative, following transplantation with the dextran sulfate, or the pharmaceutically acceptable derivative thereof, would be possible.

In an embodiment, dextran sulfate, or the pharmaceutically acceptable derivative thereof, is advantageously administered to the subject at an early or acute state following a damage causing the disease, disorder or conditions, such as TBI, or at an early or acute state following diagnosis of the disease, disorder or condition. This is in particular advantageous since some of the beneficial effects as seen by dextran sulfate of the embodiments is its capability of boosting and amplifying the intrinsic repair mechanism in the CNS and PNS. This is in particular relevant for treatment or inhibition of neurological diseases. However, the anti-scarring effect as seen by dextran sulfate of the embodiments indicates that the dextran sulfate will be effective also in dissolving already existing scar tissue and elements. Hence, for fibrosis and fibrotic conditions, dextran sulfate of the embodiments will have a therapeutic effect also during a late or chronic state.

EXAMPLES

In the following examples, a sodium salt of dextran sulfate, denoted low molecular weight dextran sulfate (LMW-DS) herein, was used (Tikomed AB, Sweden, WO 2016/076780).

Example 1

The study aims were to evaluate the effect of LMW-DS on cell survival and expression of differentiation proteins in three cell types, cerebral cortical neurons, motor neurons and Schwann cells, using two concentrations 0.01 and 0.1 mg/ml of LMW-DS.

Material and Methods

Cell Culture

All cells were cultured in specialized medium suited for that cell type. Plastic ware was treated with specific adhesion factors to improve adhesion of cells.

TABLE 1

| Cell specifications | | | |
|---|---|---|---|
| Cell type | Species | Origin | Manufacturer |
| Cortical neurons | Mouse | Embryonic brain | Lonza M-CX-400 |
| Motor neurons | Human | Embryonic stem cells | Lonza FP-6051 |
| Schwann cells | Human | Tumor | ATCC-CRL-2884 |

Neurons were cultured as 40,000 cells per well and Schwann cells 3,000 cells per. Cells were treated after 24 hours. The number of cells per well depended on the growth phenotype, proliferative capacity, etc.

Coating of Tissue Culture Plates 96-well plates were coated by adding 100 µl per well of a solution of 50 µg/ml poly-d-lysine (Sigma) in Hanks' Balanced Salt Solution (HBSS, Sigma) and incubating overnight at 37° C. in the dark. Plates were washed with cell culture water (Fisher) and air-dried for 30 min in the dark. Plates were coated by adding 75 µl per well of a solution of 15 µg/ml laminin (Sigma) in media for the different cell types—PNGM™ (Primary Neuron Basal Medium, Lonza) for cortical neurons (Lonza), NeuroBlast (Lonza) for motor neurons (Lonza) and high glucose Dulbecco's Modified Eagle's medium (DMEM) (Sigma) for Schwann cells (ATCC)—and incubating for 1 hour at 37° C. in the dark. Laminin as removed from the plates right before seeding the cells.

Cortical Neurons

PNGM was prepared by adding PNGM Singlequots (Lonza) to PNBM medium and pre-warmed to 37° C. Cells were thawed in a 37° C. water bath for no longer than 2 min and gently transferred into a 15 ml tube. 5 ml of medium was gently added drop-wise. Cell suspension was mixed by inverting the tube carefully twice. Cells were counted with a Cellometer AUTO T4 (Nexcelom Bioscience). 40,000 cells per well were seeded in previously coated 96-well plates. Cells were incubated at 37° C. with 5% $CO_2$. After at 2-hour incubation 80 µl of medium was removed and replaced with 80 µl of fresh medium and cells were allowed to settle for 24 hours before drug treatment.

Motor Neurons

NeuroBlast was pre-warmed to 37° C. Cells were thawed in a 37° C. water bath for no longer than 2 min. 1 ml of media was gently added drop-wise. Cells were resuspended and transferred to a 15 ml tube containing 9 ml of medium. Cells were centrifuged at 200 relative centrifugal force (RCF) for 5 min. Pellet was resuspended in 5 ml of medium and cells were counted with the Cellometer. 40,000 cells per well were seeded in previously coated 96-well plates. Cells were incubated at 37° C. with 5% $CO_2$. Cells were allowed to settle for 24 hours before drug treatment. After 24 hours NeuroBlast medium was replaced with MotorBlast medium (Lonzo).

Schwann Cells

Schwann cells growth medium was prepared by adding 10% of fetal bovine serum (FBS, PAA) to high-glucose DMEM and pre-warmed to 37° C. Cells were thawed in a 37° C. water bath for no longer than 2 min. Cells were gently transferred to a tube containing 10 ml of medium and centrifuged at 200 RCF for 5 min. Pellet was resuspended in 5 ml of medium and cells were counted with the Cellometer. 3,000 cells per well were seeded in previously coated 96-well plates. Cells were incubated at 37° C. with 5% $CO_2$. Cells were allowed to settle for 24 hours before drug treatment.

Drug Treatment and Plate Setup

LMW-DS was prepared in the culture media of choice for each cell line and added to the respective wells in the doses 0.01 and 0.1 mg/ml. For cell survival assays cells were analyzed after 24 and 48 hours in eight identical wells/dose/time point. Differentiation and protein expression assay was analyzed after 48 hours, also in octuplicates.

PI and Immuno-Staining No Adjustment for PI Histogram Shift

Cells were fixated in the wells. Propidium iodine was used for viability assay. For immunohistochemical analysis, neurons were stained with βIII-tubulin, which is a tubulin specific for neurons. Schwann cells were stained for Myelin Basic Protein (MBP). For the negative controls PBST (0.1% Triton-X-100 in PBS) was applied instead of primary antibodies.

Acumen Cytometry

The Acumen cytometer allows the direct cytometric analysis of attached cells without prior detachment. Therefore cells were imaged in situ and based on DNA content (PI) categorized in different phases of cell cycle or deemed apoptotic or polyploid. The protein content of the cells can also be directly measured and expressed as either 'total protein content' or 'mean protein content'.

Statistics

Data are expressed as mean values plus standard deviation of octuplicates (SD). Comparison between groups was performed using Student's t-test (two-tailed, equal variance; excel software). A p-value less than 0.05 was considered to be statistically significant (*$p<0.05$, $p<0.01$, *$p<0.001$).

Results

Mouse Cortical Neurons

The DNA histograms in FIG. 1 showed that the PI uptake of the cells were altered, shift of histograms to the right, which indicated that LMW-DS treatment had an effect on the cortical neurons. The cell population (G2/M phase) that started to divide is indicated in the figure.

The cell numbers were significantly reduced after treatment with LMW-DS. Although the fraction of apoptotic cells increased slightly, this was not the explanation for all cell loss but more likely due to cell detachment.

Human Motor Neurons

Figure 2:
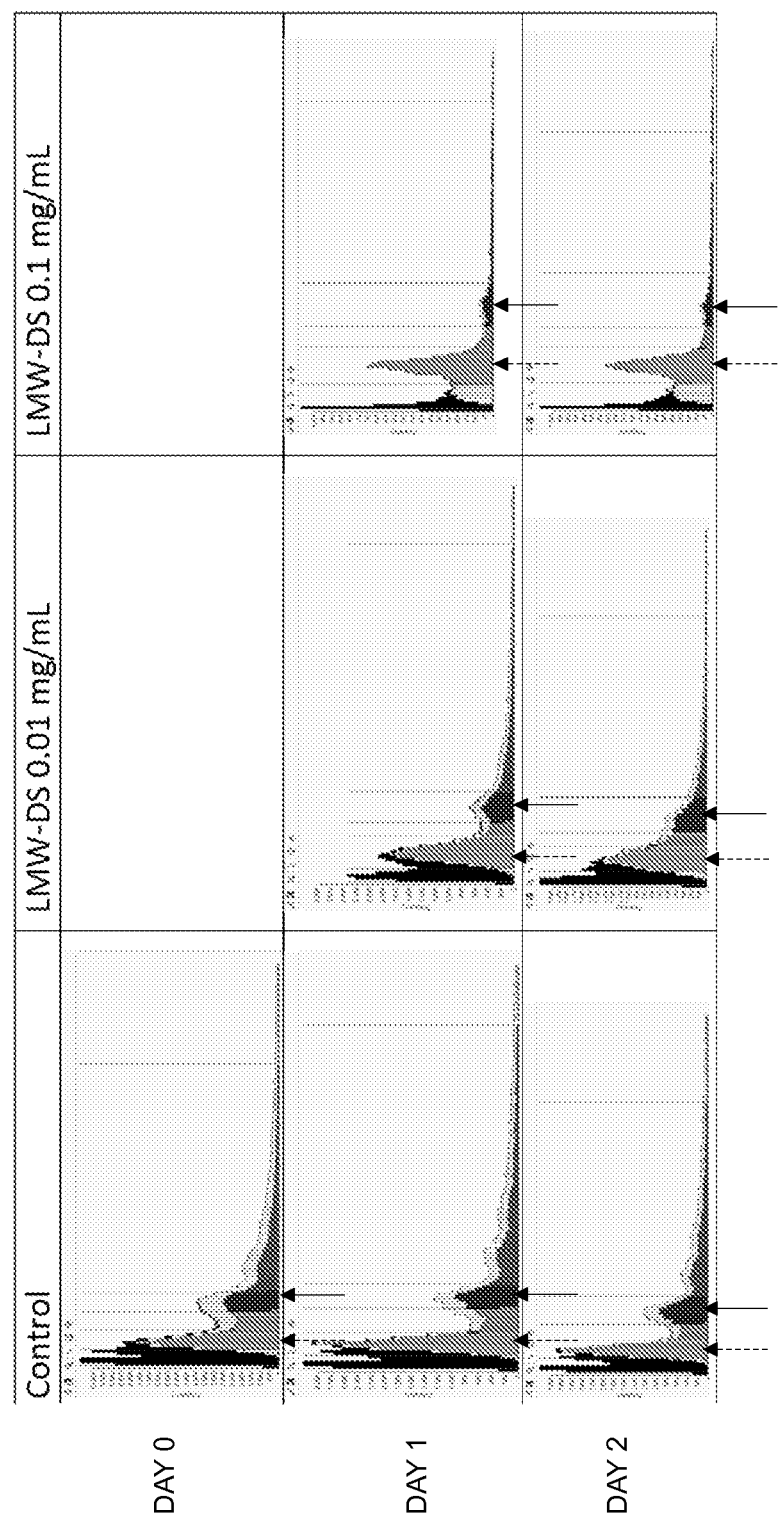
FIG. 2 illustrates PI content of human motor neurons. Data indicated that most cells remained in the G1 phase of the cell cycle (dashed arrows), although LMW-DS appeared to increase the number of cells in the G2/M phase (full arrows).

The data for motor neurons was similar to the cortical neurons, with a shift in PI uptake (FIG. 2) and a small increase in proliferation within a population of very small cells.

There was a major cell loss in these cultures as well. The explanation to this is likely the same as for the cortical neurons.

Schwann Cells

Figure 3:
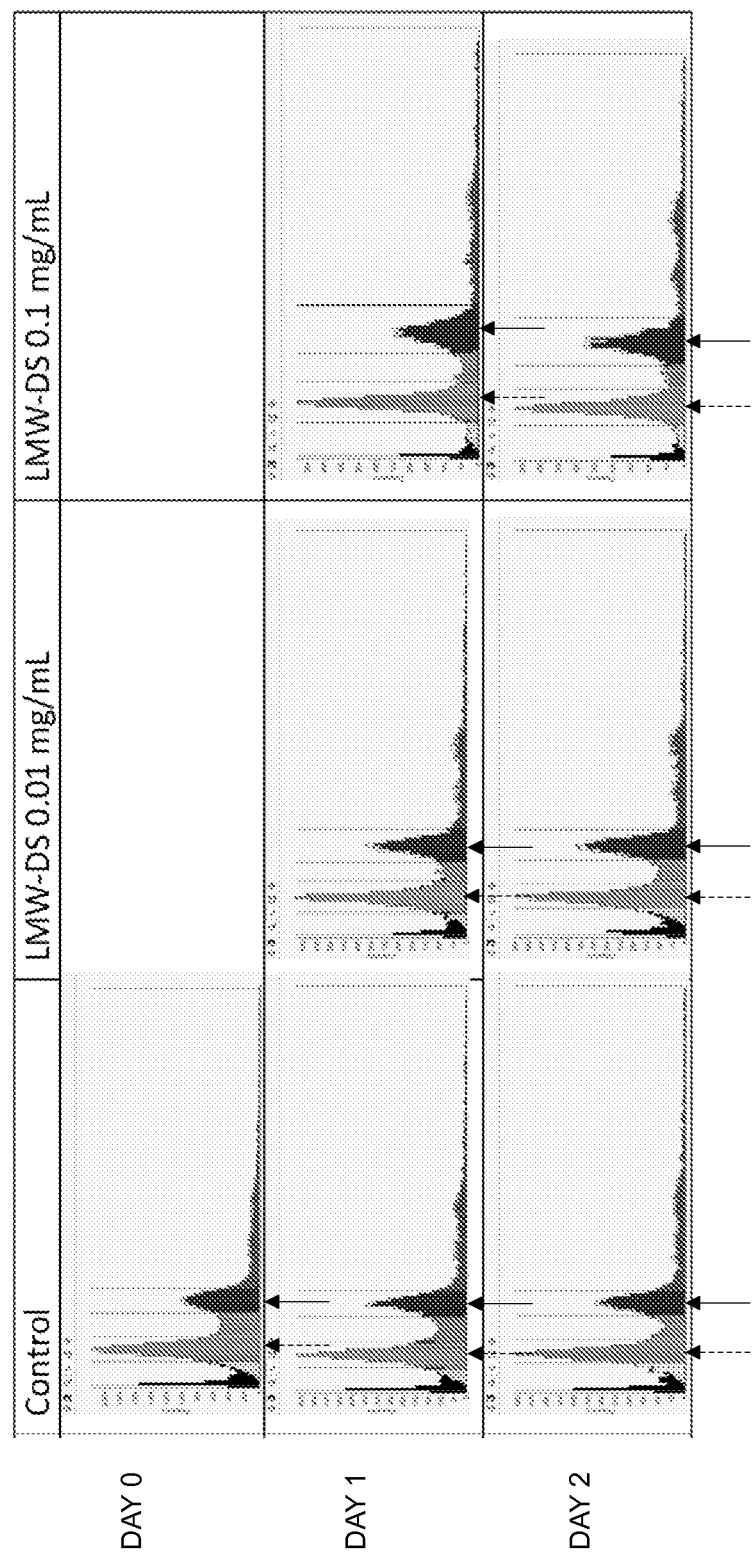
FIG. 3 illustrates PI content of human Schwann cells. Data indicated that most cells remained in the G1 phase of the cell cycle (dashed arrows), although LMW-DS appeared to increase the number of cells in the G2/M phase (full arrows).

Schwann cells did not appear as affected by LMW-DS as the neurons were. There was a similar PI shift (FIG. 3).

The effect on cell numbers and cell detachment was not as evident with Schwann cells as compared to the neurons. In contrast to neurons, the fraction of apoptotic cells reduced upon treatment with LMW-DS.

Differentiation-Related Protein Expression

Tubulin Expression in Mouse Cortical Neurons

Figure 4:
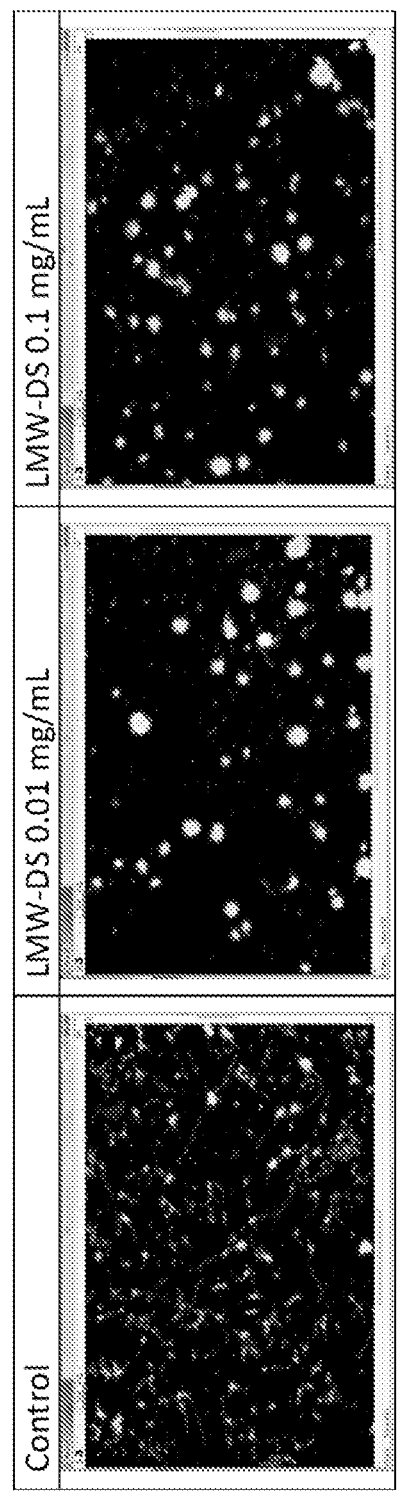
FIG. 4 are representative pictures of βIII-tubulin expression in mouse cortical neurons.

The morphology of the cells changed in the treated cultures and cells were more rounded and larger (FIG. 4).

Figure 5B:
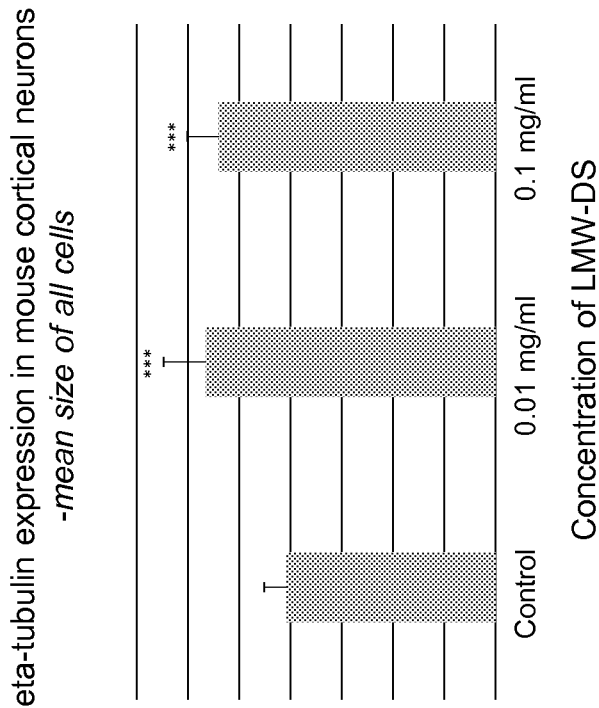
FIGS. 5A and 5B illustrate the effects of LMW-DS on βIII-tubulin expression in mouse cortical neurons. The graphs show total intensity (FIG. 5A) and mean size of the positive cells (FIG. 5B).
Figure 5A:
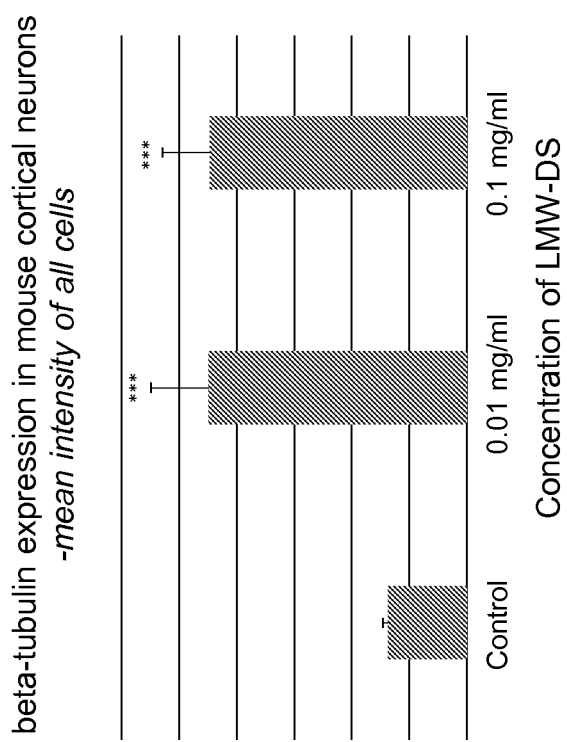

Tubulin is a family of proteins that are important building blocks in the cytoskeleton of cells. The βIII-tubulin is expressed solely by neurons. The intensity of tubulin was significantly increased in the cells treated with LMW-DS (FIG. 5A). Analysis of the positive cells showed that these cells were larger than the positive cells in the control culture (FIG. 5B).

Tubulin Expression in Human Motor Neurons

Figure 6A:
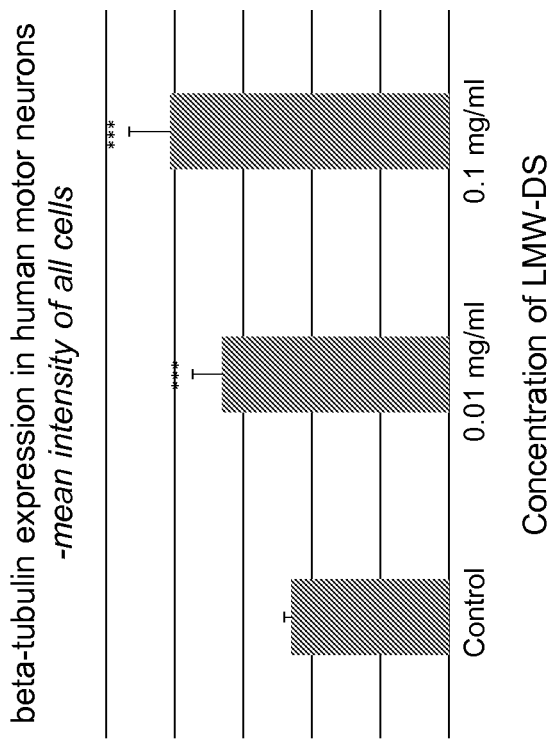
FIGS. 6A and 6B illustrate the effects of LMW-DS on βIII-tubulin expression in human motor neurons. The graphs show total intensity (FIG. 6A) and mean size of the positive cells (FIG. 6B).
Figure 6B:
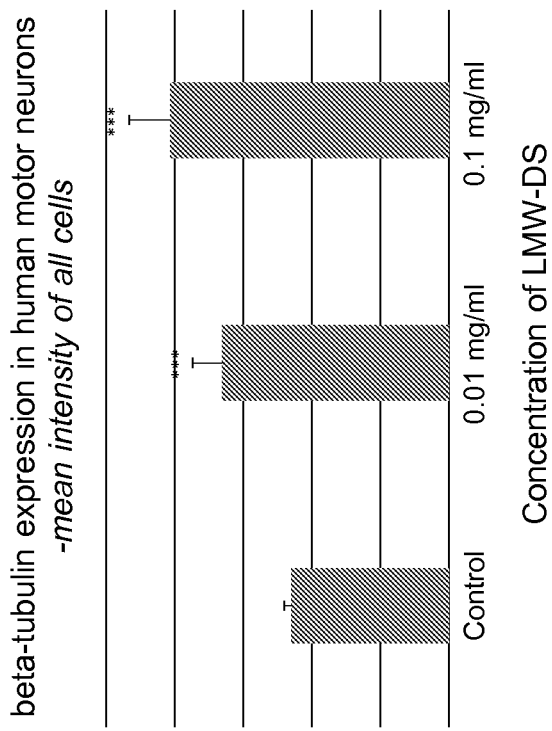
Figure 7:
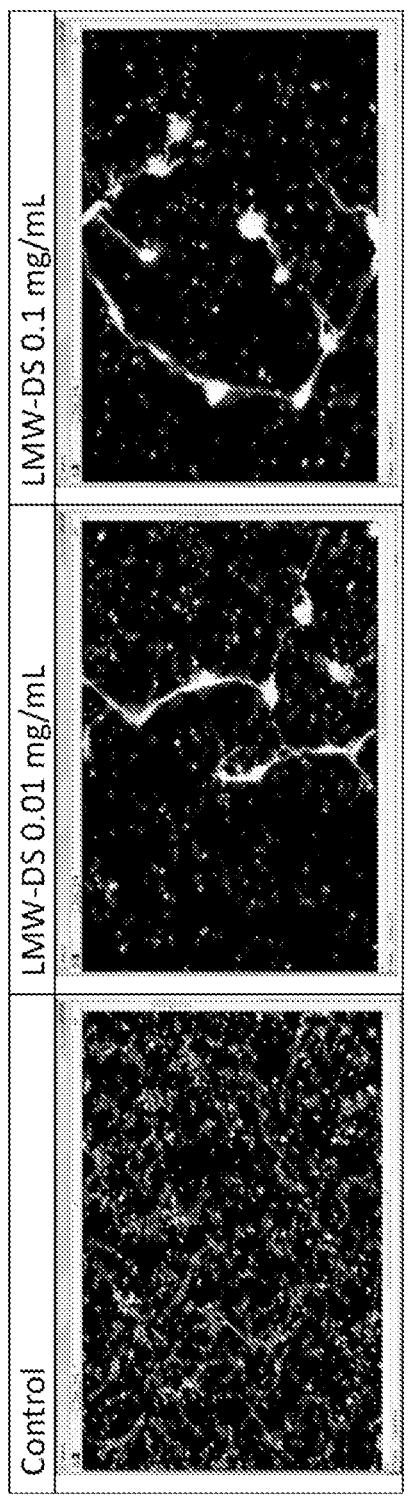
FIG. 7 are representative pictures of βIII-tubulin expression in human motor neurons.

The expression of βIII-tubulin was significantly increased by LMW-DS (FIG. 6A). Cell morphology was dramatically altered by LMW-DS. The majority of the positive cells were smaller than the control cultures (FIG. 6B) although some cells became very large with extensive neurites (FIG. 7).

MBP Expression in Human Schwann Cells

Figure 8B:
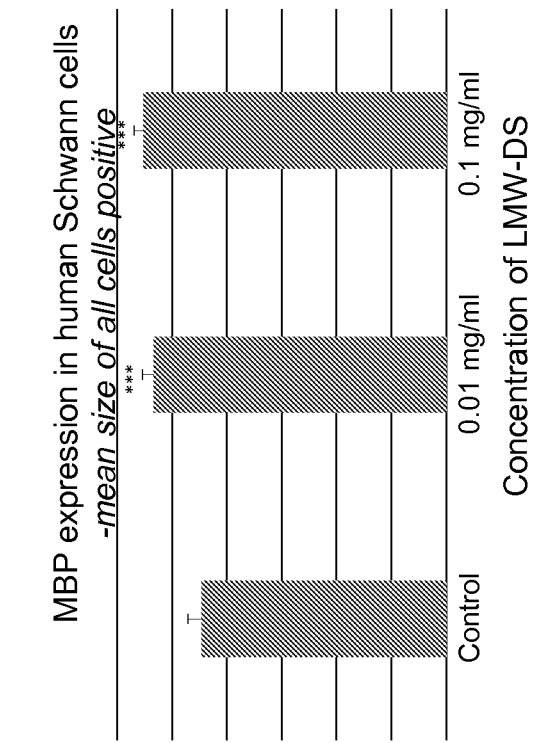
FIGS. 8A and 8B illustrate the effects of LMW-DS on myelin basic protein (MBP) expression in human Schwann cells. The graphs show total intensity (FIG. 8A) and mean size of the positive cells (FIG. 8B).
Figure 8A:
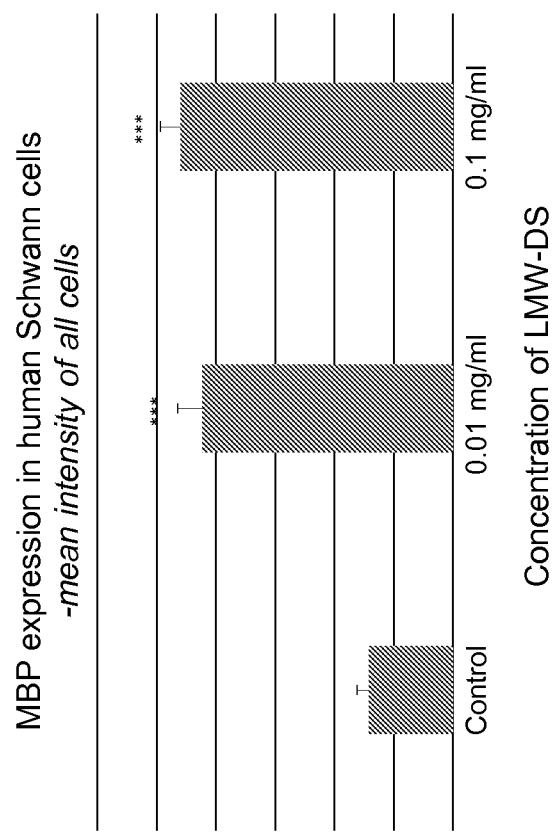
Figure 9:
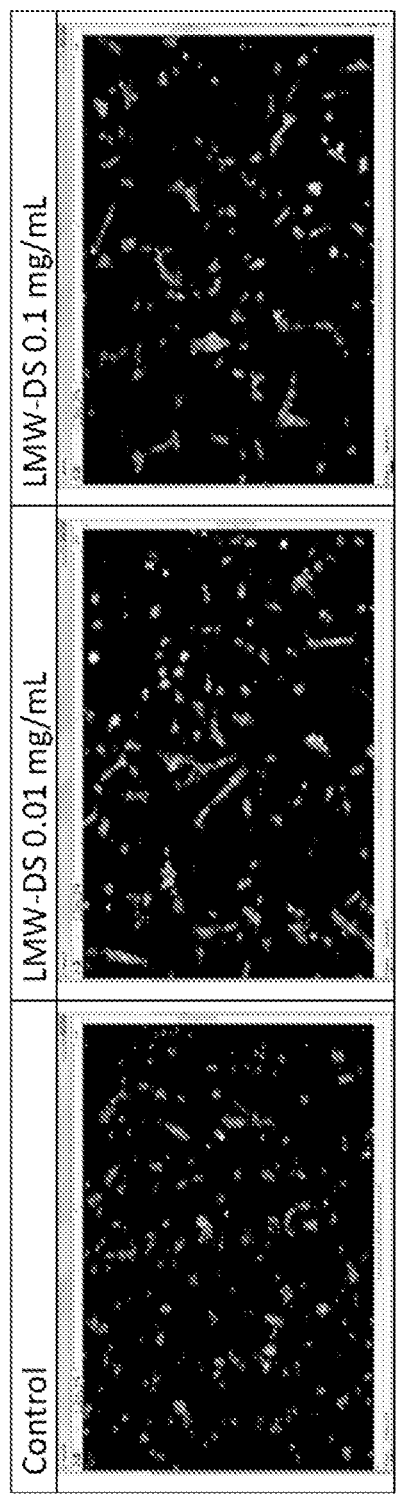
FIG. 9 are representative pictures of MBP expression in human Schwann cells.

The expression of MBP was significantly increased in LMW-DS treated cultures of Schwann cells (FIG. 8A). Analysis of cell size showed that the MBP-positive cells were larger after LMW-DS treatment compared to control (FIGS. 8B and 9).

Conclusions

Mouse Cortical Neurons and Human Motor Neurons

The increased expression of the βIII-tubulin and the morphological changes in the cells indicated that LMW-DS acted as a differentiation factor. The effect on motor neurons was particularly striking.

The changes induced by LMW-DS were evident in both mouse and human cells indicating that this effect was independent of species.

LMW-DS treatment led to an apparent cell loss in the cultures. It is believed that this effect of LMW-DS treatment was not due to a toxic effect. It is more likely that LMW-DS affected neuronal attachment. For instance, even the maximum measurements of apoptotic fraction (after the adjustment for the PI shift) did not explain by far the loss of cells in the cultures and the apparent cell loss was much greater in the immunostained preparations (more washes) than in the PI preparations.

Human Schwann Cells

The increased expression of MBP and the morphological changes in the cells indicated that LMW-DS acted as a differentiation factor in glial cells.

In the dividing Schwann cells, the signs of cell detachment due to LMW-DS treatment were not as dramatic as in the neuronal cultures but they were visible Accordingly, LMW-DS appeared to promote the differentiation of both neuronal and Schwann cells within a very short period of time (48 hours).

It is becoming widely accepted that neurodegenerative diseases, including trauma-related neurodegeneration, AD, post-stroke dementia, are associated with the reactivation of cell cycle related phenomena in neurons. In this context differentiation-inducing drugs have been proposed to be neuroprotective. Drugs supporting differentiation of Schwann cells would also be good candidates for the treatment of diseases associated with demyelination.

Example 2

The present study was performed to investigate the in vivo effect of LMW-DS in a mouse Experimental Autoimmune Encephalomyelitis (EAE) model.

EAE, sometimes denoted Experimental Allergic Encephalomyelitis, is an inflammatory demyelinating disease of the CNS and is CD4+ T-cell mediated. An EAE model in mice is the currently most widely accepted animal model of MS and ADEM in humans (*Annals of Neurology*, 60: 12-21, 2006). Generally, EAE is induced in mice with a single injection of peptides and proteins, including Myelin Oligodendrocyte Glycoprotein$_{35-55}$ (MOG$_{35-55}$) emulsified with adjuvant, which triggers an immune reaction against myelin. The injection results in a highly reproducible onset of EAE at about one week after injection. Inflammatory lesions of the CNS causing peripheral paralysis are characteristics of EAE in mice. Disease progression in the mice is followed by daily evaluation of disease symptoms using a well-recognized and evaluated scoring system (*International Immunology*, 10: 333-340, 1998).

Materials and Methods
Incomplete Freund's Adjuvant (IFA) (Difco)
*M. tuberculosis* H37RA (Difco)
MOG$_{35-55}$ rodent (MDBioproducts)
Pertussis toxin (Sigma Aldrich)
Hank's Balanced Salt Solution (HBSS) (Gibco/Invitrogen)
Dulbecco's Phosphate-Buffered Saline (D-PBS) (Life Technologies)
Hydroxypropylmethylcellulosa (HPMC) (Sigma Aldrich)
0.9% saline solution (9 mg/ml NaCl, autoclaved) (Scharlau)
Cyclosporine A (Sigma Aldrich)
LMW-DS dissolved in 0.9% saline solution
Hepatocyte growth factor (HGF) recombinant mouse (R&D Systems)
Isoba vet 3.5% (Schering Plough Animal Health)
Methyl butane (Sigma Aldrich)

C57B1.6 mice (females, 8-10 weeks) were obtained from Harlan Europe. Mice were housed in the conventional animal facility, Lund University, Sweden, and kept at 12 h light/dark cycles in polystyrene cages (type IIL cages, max 7 mice per cage) containing wood shavings and fed with standard rodent chow and water ad libitum.

Disease Induction and Boost
EAE was induced day 0 by a s.c. injection at the flank of an emulsion containing 150 μg MOG$_{35-55}$ and 300 μg H37RA in a volume of 100 μl per mouse. The emulsion was prepared by mixing complete Freund's adjuvant (CFA) (H37RA in IFA at a concentration of 6 mg/ml) and MOG$_{35-55}$ (dissolved in PBS to a concentration of 3 mg/ml) on ice. Mice were anesthetized during immunization to ascertain correct location of the injection. Pertussis toxin (PTX) was re-suspended in mqH$_2$O at a concentration of 50 μg/ml and diluted to a final concentration of 1 μg/ml in PBS. Mice received a booster injection of 200 ng PTX i.p. on day 0 and day 2.

Dose Preparation
LMW-DS dilutions were prepared on day 0 and 14 for group 3. LMW-DS was diluted in 0.9% saline solution and sterile filtered through a 0.2 μM filter, according to doses described in Table 2 below. Vehicle given was 0.9% saline solution. Recombinant HGF was reconstituted in 1 ml 0.1% bovine serum albumin (BSA) in PBS at a concentration of 25 μg/ml and further diluted in PBS to 1 μg/ml. Cyclosporine A was prepared by dissolving 50 mg in 1 ml 70% ethanol and diluted in HPMC to final concentration of 0.98 mg/ml.

TABLE 2

Dose preparation

| Group | Substance | Dose | Prepared | Weight/ dose | Saline solution/dose |
|---|---|---|---|---|---|
| 1 | Vehicle | N/A | Day 0 | N/A | 200 μl |
| 2 | Cyclosporine A | 10 mg/kg | Day 0 | 0.195 mg | 200 μl |
| 3 | LMW-DS | 10 mg/kg | Day 9, 14 | 0.195 mg | 200 μl |
| 4 | HGF | 100 ng | Day 16 | 100 ng | 100 μl |

Experimental Groups and Administration of LMW-DS
Treatment was initiated day 0 for group 2-3, which was administered i.p. in group 2 and s.c. in group 3 three times weekly. Treatment was initiated day 18 for remaining groups. Animals in group 4 were administered every other day i.v., with a total of three injections. The treatment groups were mixed within cages to avoid cage effects and systemic errors caused by unequal housing.

Disease Evaluation
Disease progression was followed through the experiment. Plasma was collected at the end of the experiment, i.e., day 28 after disease induction.

Clinical disease was monitored daily where the disease is graded according to a scale ranging from 0-8.
0=healthy
1=tail weakness
2=tail paralysis
3=tail paralysis and mild waddle
4=tail paralysis and severe waddle
5=tail paralysis and paralysis of one limb
6=tail paralysis and paralysis of a pair of limbs
7=tetraparesis or paralysis of three limbs
8=premorbid or dead Graphs and Statistics
Graphs and statistical analysis were performed using Prism 5 for Mac OS X (GraphPad Software, San Diego, Calif., USA). All statistics were calculated using a one-tailed non parametric Mann-Whitney test where p<0.05 was considered significant*, # and **, ## represent a p-value<0.01.

Figure 10:
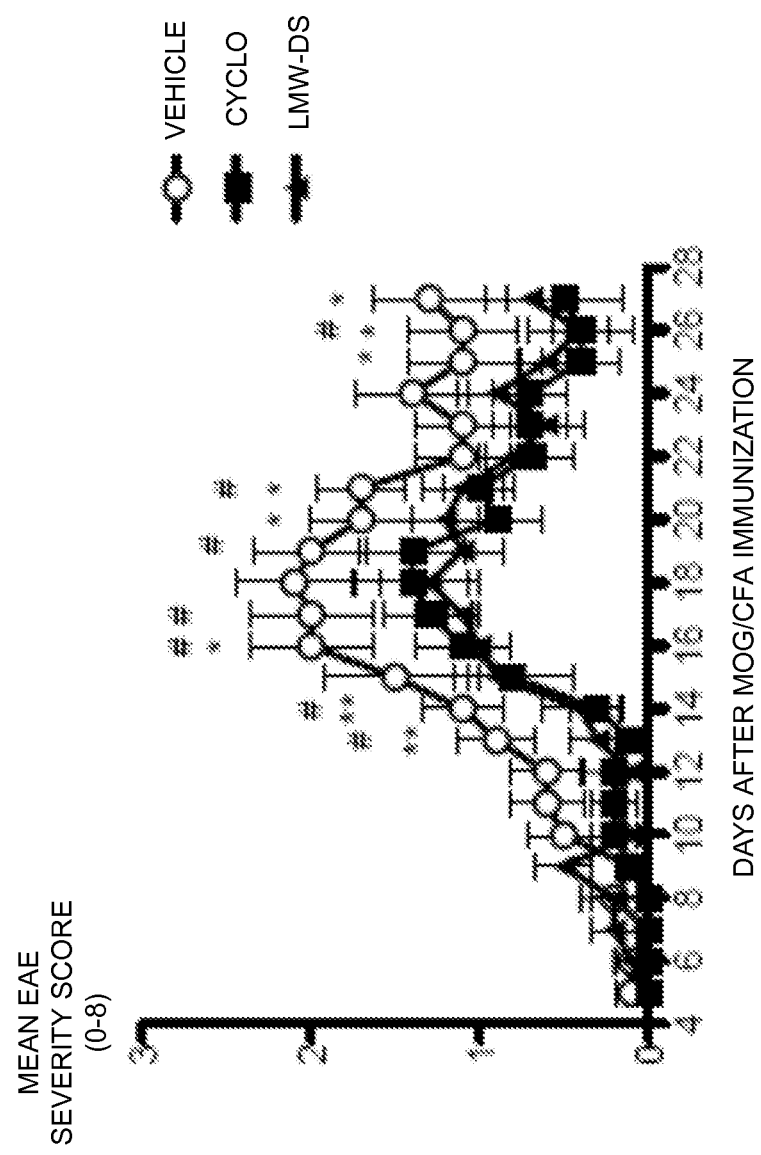
FIG. 10 is a diagram illustrating mean experimental autoimmune encephalomyelitis (EAE) severity scores following EAE induction in mice for negative control (vehicle), positive control cyclosporine A (cyclo) and LMW-DS.

Results and Discussion
FIG. 10 illustrates the EAE development in mice in control groups (vehicle and Cyclosporine A) and a group treated with LMW-DS s.c. three times weekly, where Cyclosporine A had significantly (*) lower mean score on day 13, 14, 16, 20, 21 and 25-27 compared with vehicle control. Animals treated with 10 mg/kg dextran sulfate s.c. three times weekly had significantly (#) lower mean score on day 13, 14, 16, 17, 19, 21 and 26 compared with vehicle control.

Figure 11:
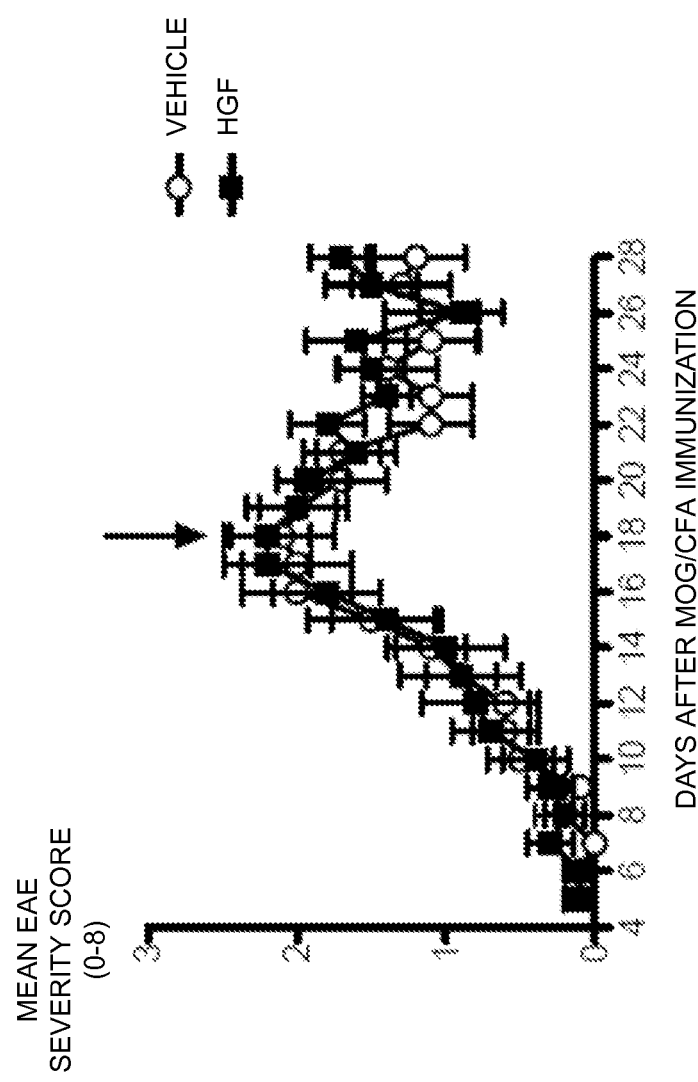
FIG. 11 is a diagram illustrating mean EAE severity scores following EAE induction in mice for negative control (vehicle) and HGF. The arrow indicates the start of the treatment.

FIG. 11 illustrates vehicle and mice treated with 100 ng/dose HGF i.v. every other day for five days stating at day 18 (see arrow). HGF did not result in any significant difference as compared to vehicle.

LMW-DS, thus, resulted in a significantly lower mean score compared with vehicle control in the EAE model. Accordingly, the results indicate that LMW-DS has positive effects in neurodegenerative and demyelinating diseases of the CNS, such as MS and ADEM.

Example 3

The effects of daily sub-cutaneous injections of LMW-DS on glutamate excitotoxicity and mitochondrial function after severe traumatic brain injury (sTBI) in rats were evaluated by high-performance liquid chromatography (HPLC) analysis of frozen brain samples. The results suggest that LMW-DS interferes with mitochondrial function to improve energy metabolism and also decreases glutamate excitotoxicity.

Materials and Methods

Induction of sTBI and Drug Administration Protocol

The experimental protocol used in this study was approved by the Ethical Committee of the Catholic University of Rome, according to international standards and guidelines for animal care. Male Wistar rats of 300-350 g body weight (b.w.) were fed with standard laboratory diet and water ad libitum in a controlled environment.

They were divided into three groups:

1) n=6 animals subjected to sTBI, with drug administration after 30 minutes and sacrifice at 2 days post-TBI (Acute phase 1)

2) n=6 animals subjected to severe-TBI, with drug administration after 30 minutes and sacrifice at 7 days post-TBI (Acute phase 2).

3) n=6 animals subjected to severe-TBI, with drug administration after 3 days and sacrifice at 7 days post-TBI (Chronic phase).

As the anesthetic mixture, animals received 35 mg/kg b.w. ketamine and 0.25 mg/kg b.w. midazolam by i.p. injection. sTBI was induced by dropping a 450 g weight from 2 m height on to the rat head that had been protected by a metal disk previously fixed on the skull, according to the "weight drop" impact acceleration model (Marmarou et al., A new model of diffuse brain injury in rats. Part I: Pathophysiology and biomechanics. *J Neurosurg.* 1994; 80: 291-300). Rats that suffered from skull fracture, seizures, nasal bleeding, or did not survive the impacts, were excluded from the study. At the end of each period of treatment, rats were anesthetized again and then immediately sacrificed.

The drug treatment was a subcutaneous injection of 0.5 ml of LMW-DS (15 mg/kg) and administered according to the aforementioned schematic protocol.

Cerebral Tissue Processing

An in vivo craniectomy was performed in all animals during anesthesia, after carefully removing the rat's skull, the brain was exposed and removed with a surgical spatula and quickly dropped in liquid nitrogen. After the wet weight (w.w.) determination, tissue preparation was affected as previously disclosed (Tavazzi et al., Cerebral oxidative stress and depression of energy metabolism correlate with severity of diffuse brain injury in rats. *Neurosurgery.* 2005; 56: 582-589; Vagnozzi et al., Temporal window of metabolic brain vulnerability to concussions: mitochondrial-related impairment-part I. *Neurosurgery.* 2007; 61: 379-388; Tavazzi et al., Temporal window of metabolic brain vulnerability to concussions: oxidative and nitrosative stresses-part II. *Neurosurgery.* 2007; 61: 390-395; Amorini et al., Severity of experimental traumatic brain injury modulates changes in concentrations of cerebral free amino acids. *J Cell Mol Med.* 2017; 21: 530-542.). Briefly, whole brain homogenization was performed with 7 ml of ice-cold, nitrogen-saturated, precipitating solution composed by $CH_3CN$+10 mM $KH_2PO_4$, pH 7.40, (3:1; v:v), and using an Ultra-Turrax set at 24,000 rpm/min (Janke & Kunkel, Staufen, Germany). After centrifugation at 20,690×g, for 10 min at 4° C., the clear supernatants were saved, pellets were supplemented with 3 ml of the precipitating solution and homogenized again as described above. A second centrifugation was performed (20,690×g, for 10 min at 4° C.), pellets were saved, supernatants combined with those previously obtained, extracted by vigorous agitation with a double volume of HPLC-grade $CHCl_3$ and centrifuged as above. The upper aqueous phases containing water-soluble low-molecular weight compounds were collected, subjected to chloroform washings for two more times (this procedure allowed the removal of all the organic solvent and of any lipid soluble compound from the buffered tissue extracts), adjusted in volumes with 10 mM $KH_2PO_4$, pH 7.40, to have ultimately aqueous 10% tissue homogenates and saved at −80° C. until assayed.

HPLC Analyses of Purine-Pyrimidine Metabolites

Aliquots of each deproteinized tissue samples were filtered through a 0.45 µm HV Millipore filter and loaded (200 µl) onto a Hypersil C-18, 250×4.6 mm, 5 µm particle size column, provided with its own guard column (Thermo Fisher Scientific, Rodano, Milan, Italy) and connected to an HPLC apparatus consisting of a Surveyor System (Thermo Fisher Scientific, Rodano, Milan, Italy) with a highly sensitive diode array detector (equipped with a 5 cm light path flow cell) and set up between 200 and 300 nm wavelength. Data acquisition and analysis were performed by a PC using the ChromQuest® software package provided by the HPLC manufacturer.

Metabolites belonging to the purine-pyrimidine profiles (listed below) and related to tissue energy state, mitochondrial function and relative to oxidative-nitrosative stresses were separated, in a single chromatographic run, according to slight modifications of existing ion-pairing HPLC methods (Lazzarino et al., Single-sample preparation for simultaneous cellular redox and energy state determination. *Anal Biochem.* 2003; 322: 51-59; Tavazzi et al., Simultaneous high performance liquid chromatographic separation of purines, pyrimidines, N-acetylated amino acids, and dicarboxylic acids for the chemical diagnosis of inborn errors of metabolism. *Clin Biochem.* 2005; 38: 997-1008). Assignment and calculation of the compounds of interest in chromatographic runs of tissue extracts were carried out at the proper wavelengths (206, 234 and 260 nm) by comparing retention times, absorption spectra and areas of peaks with those of peaks of chromatographic runs of freshly-prepared ultra-pure standard mixtures with known concentrations.

List of compounds: Cytosine, Creatinine, Uracil, Beta-Pseudouridine, Cytidine, Hypoxanthine, Guanine, Xanthine, Cytidine diphosphate-Choline (CDP-Choline), Ascorbic Acid, Uridine, Adenine, Nitrite ($-NO_2^-$), reduced glutathione (GSH), Inosine, Uric Acid, Guanosine, Cytidine monophosphate (CMP), malondialdehyde (MDA), Thyimidine, Orotic Acid, Nitrate ($-NO_3^-$), Uridine monophosphate (UMP), Nicotinamide adenine dinucleotide, oxidized ($NAD^+$), Adenosine (ADO), I nosine monophosphate (IMP), Guanosine monophosphate (GMP), Uridine diphosphate-glucose (UDP-Glc), UDP-galactose (UDP-Gal), oxidized glutathione (GSSG), UDP-N-acetyl-glucosamine (UDP-GlcNac), UDP-N-acetyl-galactosamine (UDP-GalNac), Adenosine monophosphate (AMP), Guanosine diphosphate-glucose (GDP-glucose), Cytidine diphosphate (CDP), UDP, GDP, Nicotinamide adenine dinucleotide phosphate, oxidized (NADP+), Adenosine diphosphate-Ribose (ADP-Ribose), Cytidine triphosphate (CTP), ADP, Uridine triphosphate (UTP), Guanosine triphosphate (GTP), Nicotinamide adenine dinucleotide, reduced (NADH), Adenosine triphosphate (ATP), Nicotinamide adenine dinucleotide phosphate, reduced (NADPH), Malonyl-CoA, Coenzyme A (CoA-SH), Acetyl-CoA, N-acetylaspartate (NAA).

HPLC Analyses of Free Amino Acids and Amino Group Containing Compounds

The simultaneous determination of primary free amino acids (FAA) and amino group containing compounds (AGCC) (listed below) was performed using the precolumn derivatization of the sample with a mixture of Ortho-phthalaldehyde (OPA) and 3-Mercaptopropionic acid (MPA), as described in detail elsewhere (Amorini et al., Severity of experimental traumatic brain injury modulates changes in concentrations of cerebral free amino acids. *J Cell Mol Med.* 2017; 21: 530-542; Amorini et al., Metabolic profile of amniotic fluid as a biochemical tool to screen for inborn errors of metabolism and fetal anomalies. *Mol Cell Biochem.* 2012; 359: 205-216). Briefly, the derivatization mixture composed by 25 mmol/l OPA, 1% MPA, 237.5 mmol/l sodium borate, pH 9.8 was prepared daily and placed in the autosampler. The automated precolumn derivatization of the samples (15 µl) with OPA-MPA was carried out at 24° C. and 25 µl of the derivatized mixture were loaded onto the HPLC column (Hypersil C-18, 250×4.6 mm, 5 µm particle size, thermostated at 21° C.) for the subsequent chromatographic separation. In the case of glutamate, deproteinized brain extracts were diluted 20 times with HPLC-grade $H_2O$ prior to the derivatization procedure and subsequent injection. Separation of OPA-AA and OPA-AGCC was carried out at a flow rate of 1.2 ml/min using two mobile phases (mobile phase A=24 mmol/l $CH_3COONa$+24 mmol/l $Na_2HPO_4$+1% tetrahydrofurane+0.1% trifluoroacetic acid, pH 6.5; mobile phase B=40% $CH_3OH$+30% $CH_3CN$+30% $H_2O$), using an appropriate step gradient (Amorini et al., Severity of experimental traumatic brain injury modulates changes in concentrations of cerebral free amino acids. *J Cell Mol Med.* 2017; 21: 530-542; Amorini et al., Metabolic profile of amniotic fluid as a biochemical tool to screen for inborn errors of metabolism and fetal anomalies. *Mol Cell Biochem.* 2012; 359: 205-216).

Assignment and calculation of the OPA-AA and OPA-AGCC in chromatographic runs of whole brain extracts were carried out at 338 nm wavelengths by comparing retention times and areas of peaks with those of peaks of chromatographic runs of freshly-prepared ultra-pure standard mixtures with known concentrations.

List of FAA and ACGC compounds: aspartate (ASP), glutamate (GLU), asparagine (ASN), serine (SER), glutamine (GLN), histidine (HIS), glycine (GLY), threonine (THR), citrulline (CITR), arginine (ARG), alanine (ALA), taurine (TAU), gamma-aminobutyrric acid (GABA), tyrosine (TYR), S-adenosylhomocysteine (SAH), L-cystathionine (L-Cystat), valine (VAL), methionine (MET), tryptophane (TRP), phenylalanine (PHE), isoleucine (ILE), leucine (LEU), ornithine (ORN), lysine (LYS).

Statistical Analysis

Figure 12:
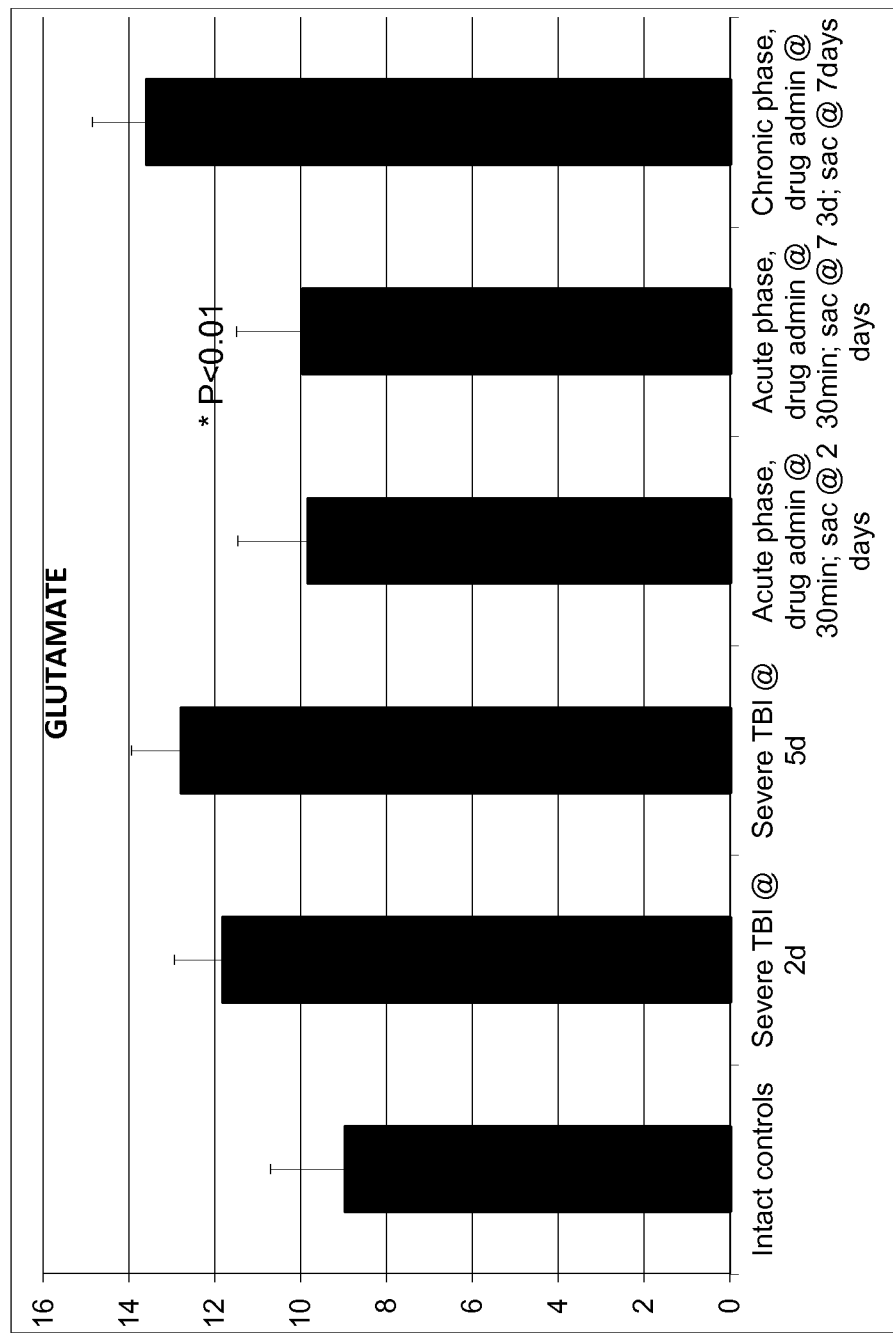
FIG. 12 is a diagram illustrating changes in brain glutamate levels.
Figure 13A:
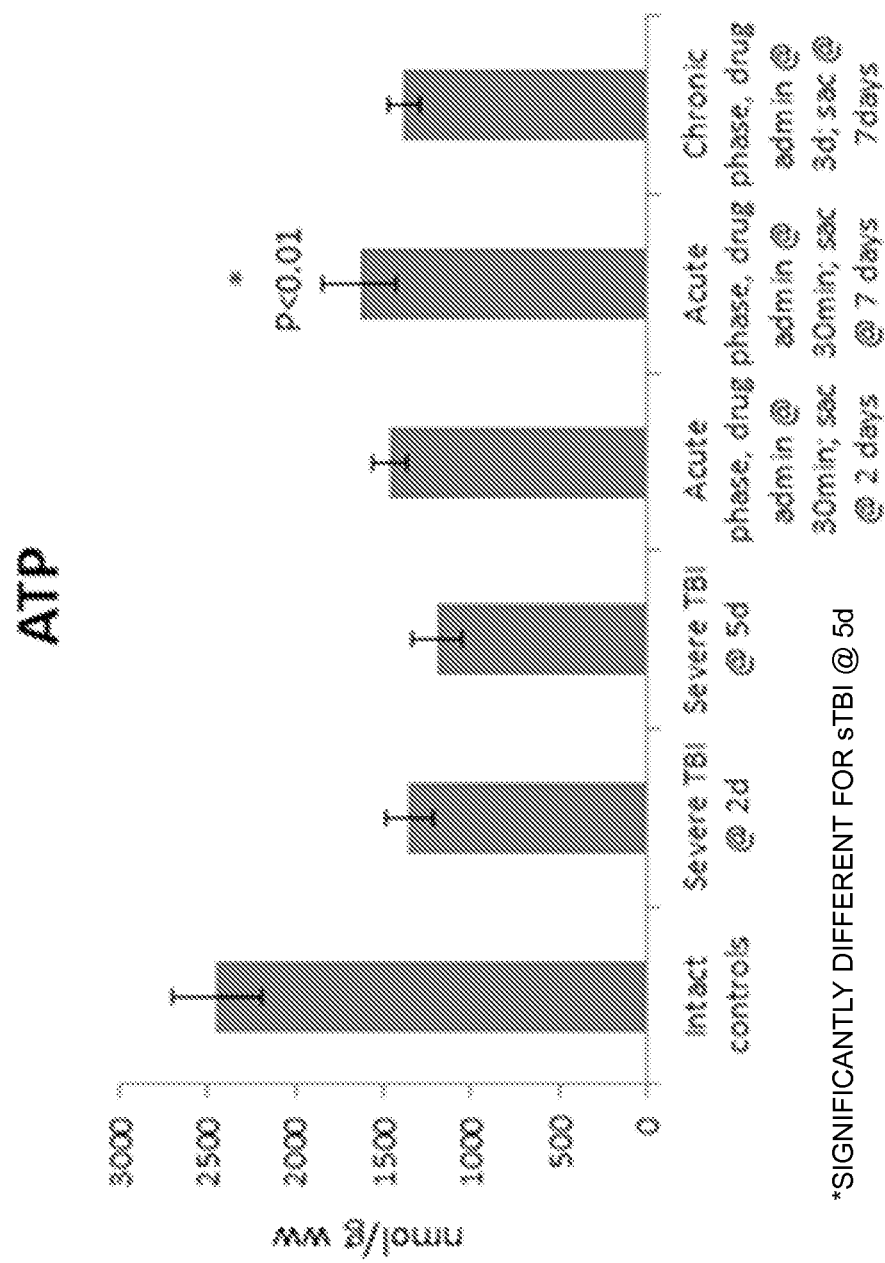
FIGS. 13A-13D are diagrams illustrating changed levels of adenine nucleotides (ATP, ADP, AMP) and ATP/ADP ratio as a measurement of mitochondrial phosphorylating capacity.
Figure 13B:
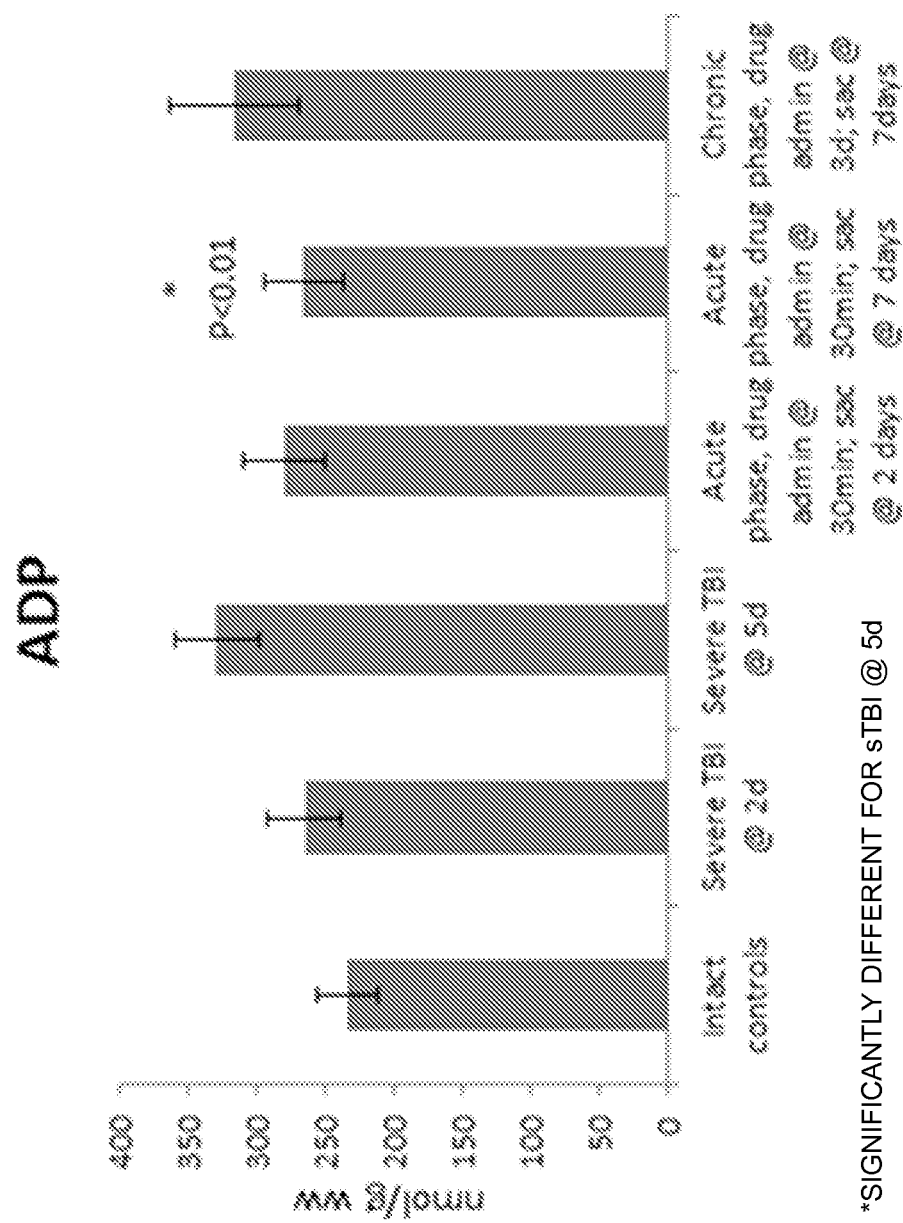
Figure 13C:
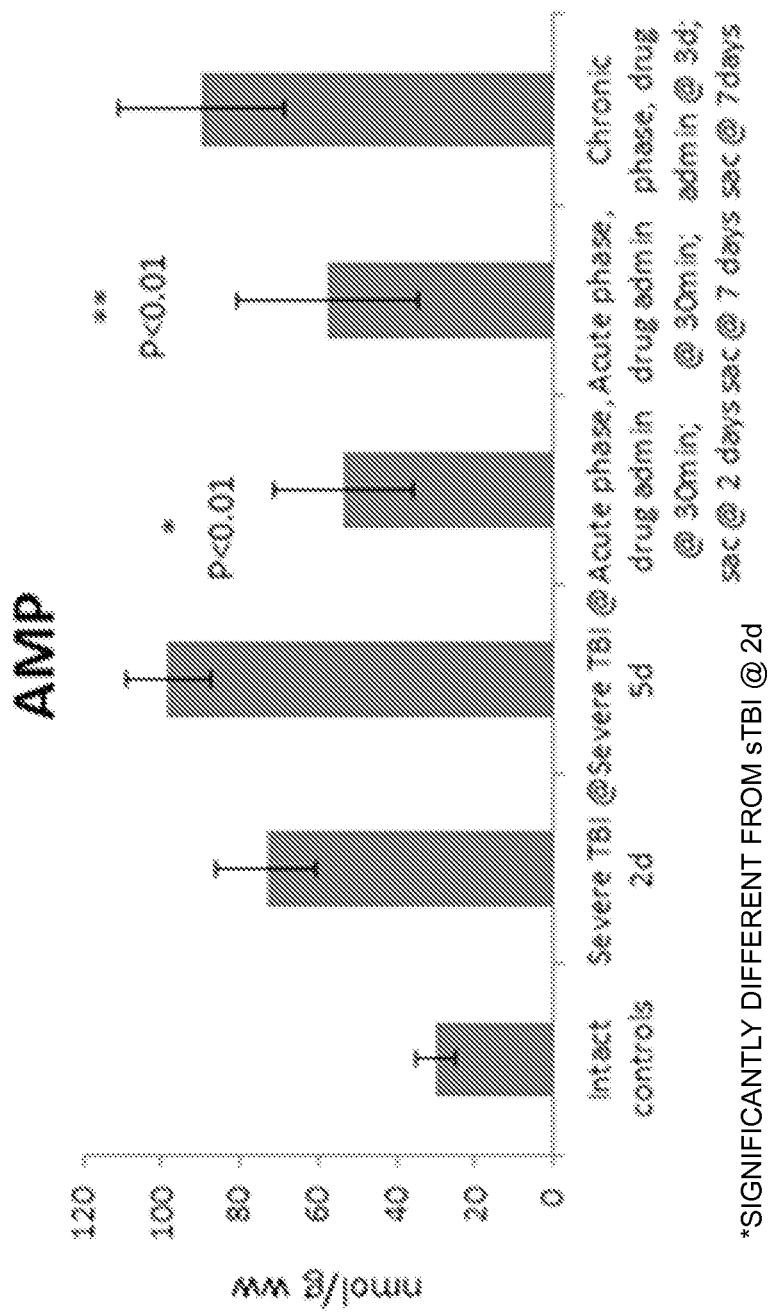
Figure 13D:
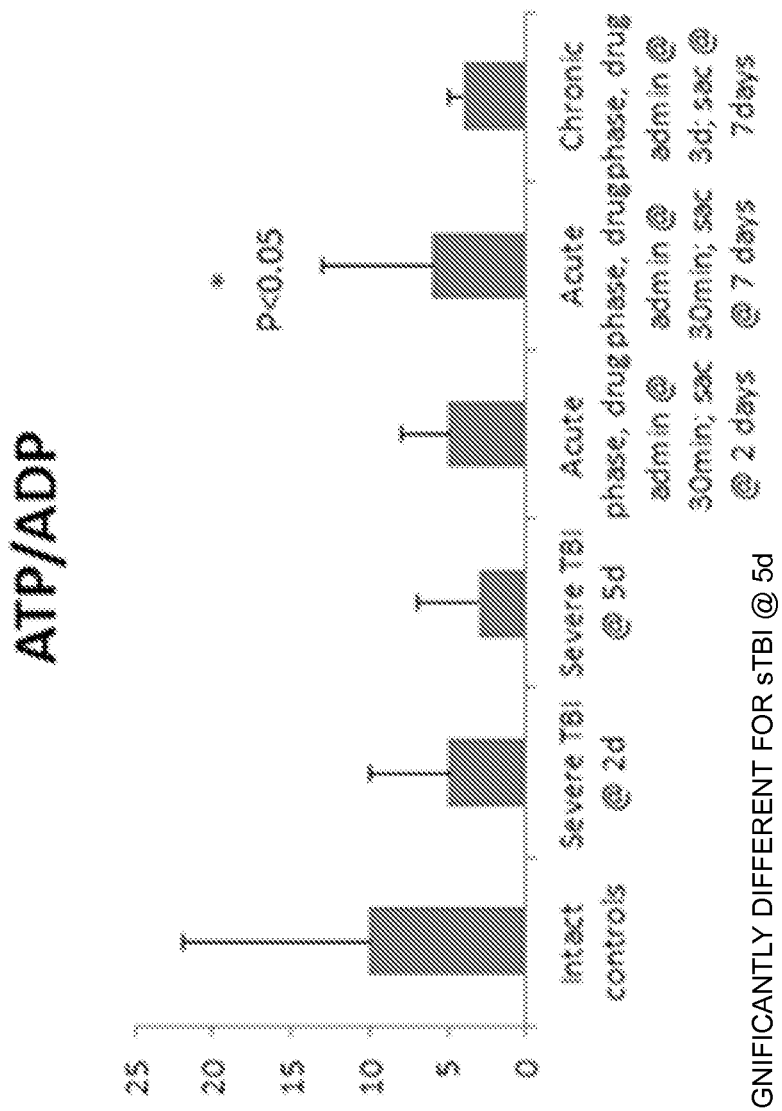
Figure 14A:
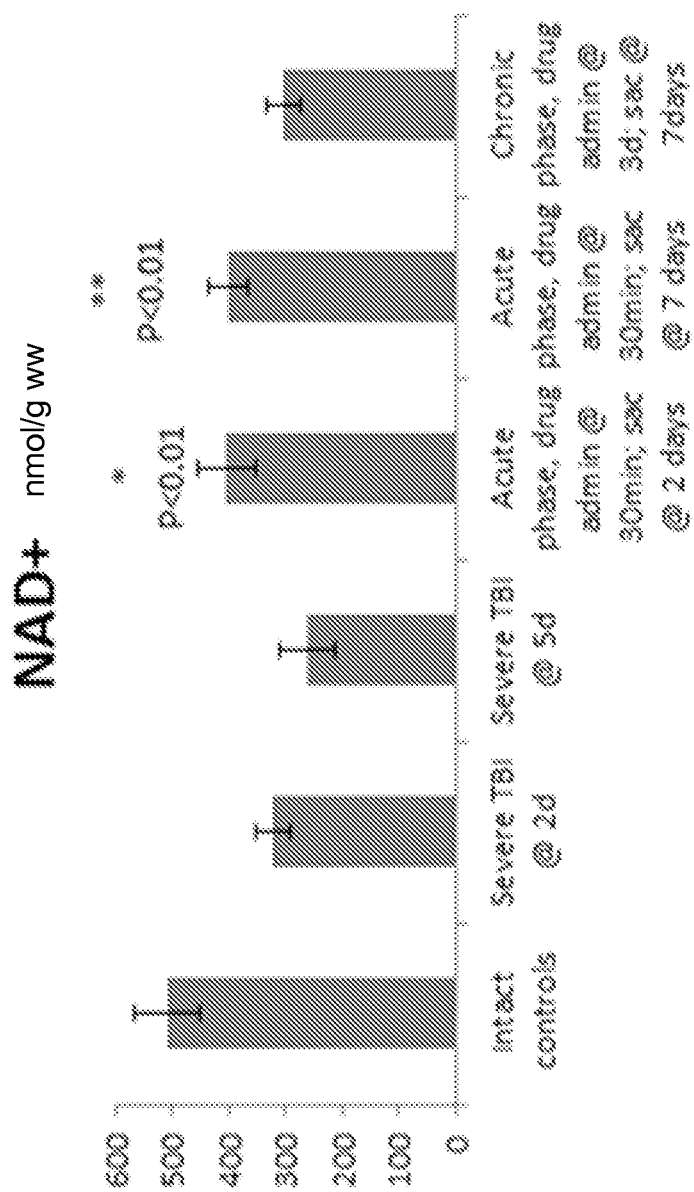
FIGS. 14A-14D are diagrams illustrating changed levels of oxidative and reduced nicotinic coenzymes.
Figure 14B:
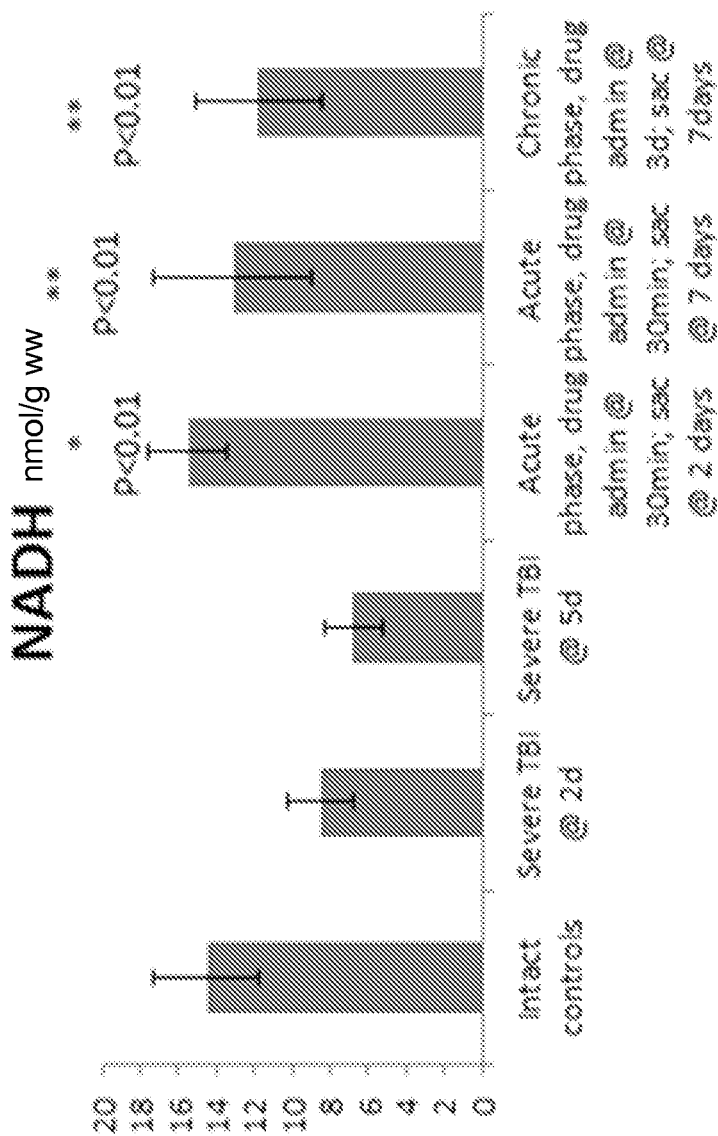
Figure 14C:
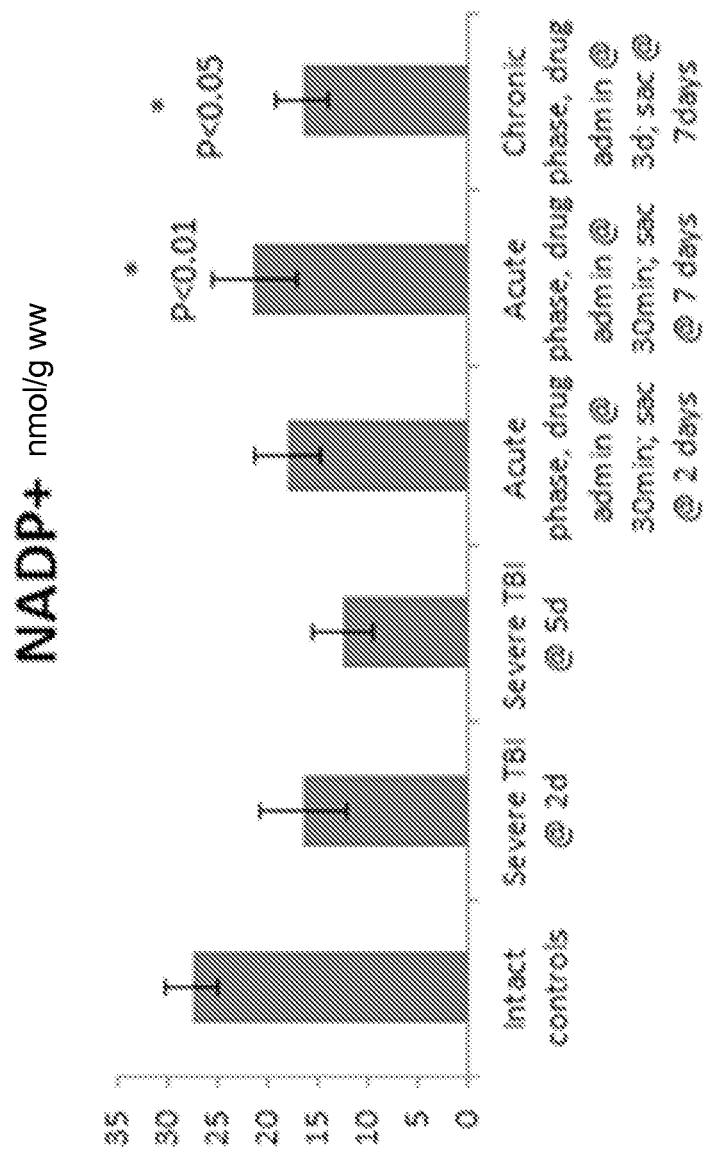
Figure 14D:
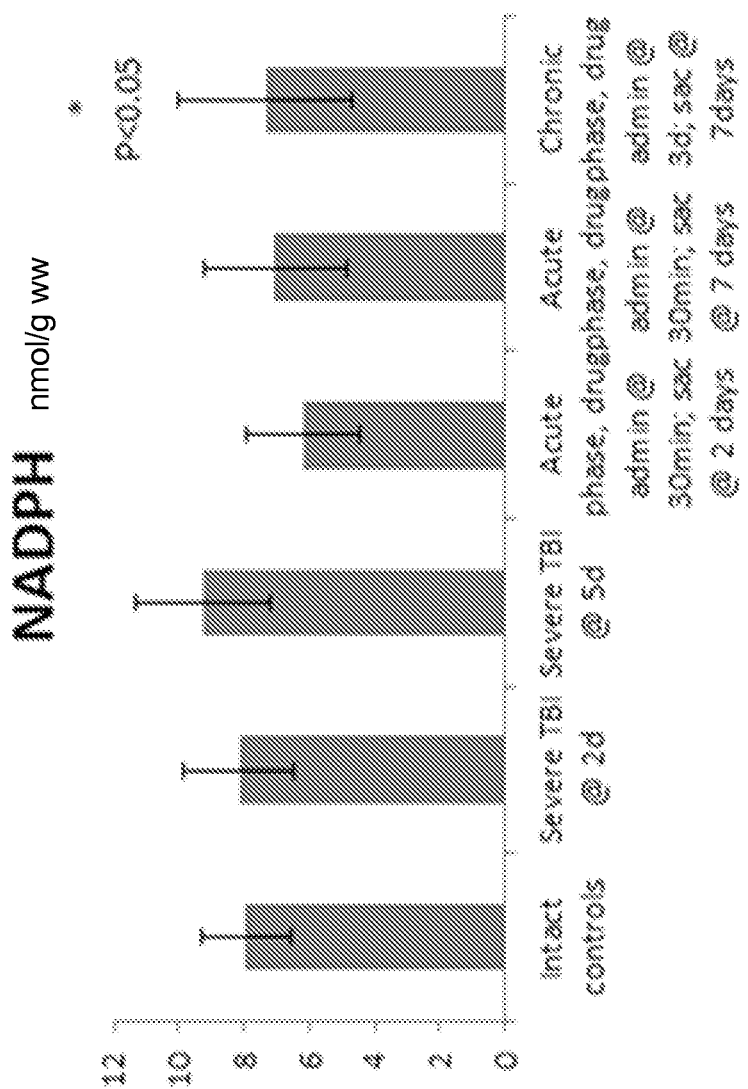

Normal data distribution was tested using the Kolmogorov-Smirnov test. Differences across groups were estimated by the two-way ANOVA for repeated measures. Fisher's protected least square was used as the post hoc test. Only two-tailed p-values of less than 0.05 were considered statistically significant Results The most evident result among the cerebral values of the 24 standard and non-standard amino acids and primary amino-group containing compounds was that LMW-DS treatment had a remarkable inhibition of the increase in glutamate (GLU) induced by sTBI (FIG. 12), thus certainly causing a decrease of excitotocity consequent to excess of this compound.

This effect was, however, visible only if the drug was administered early post-injury (30 min following sTBI), with no efficacy on this excitotoxicity marker when LMW-DS was injected at 3 days after sTBI. It is also worth underlining that LMW-DS had significant beneficial effects on compounds involved in the so-called methyl cycle (Met, L-Cystat, SAH), see Table 3.

TABLE 3

| concentrations of cerebral compounds | | | | | |
|---|---|---|---|---|---|
| | ASP | GLU | ASN | SER | GLN | HIS |
| Control | 2.67 ± 0.45 | 8.95 ± 1.76 | 0.11 ± 0.02 | 0.56 ± 0.14 | 3.70 ± 0.72 | 0.045 ± 0.01 |
| TBI 2 days | 3.86 ± 0.80 | 11.8 ± 1.15 | 0.12 ± 0.02 | 0.85 ± 0.17 | 4.81 ± 0.78 | 0.060 ± 0.01 |
| TBI 5 days | 3.85 ± 0.91 | 12.77 ± 1.17 | 0.09 ± 0.03 | 0.69 ± 0.19 | 3.57 ± 0.62 | 0.046 ± 0.008 |
| Acute phase 1 | 2.40 ± 0.56$^{d,i}$ | 9.81 ± 1.66$^i$ | 0.12 ± 0.02$^i$ | 0.88 ± 0.25$^a$ | 4.78 ± 1.09$^a$ | 0.068 ± 0.015$^b$ |
| Acute phase 2 | 2.94 ± 0.98$^{f,j}$ | 9.93 ± 1.56$^{e,i}$ | 0.13 ± 0.03$^i$ | 0.71 ± 0.28$^b$ | 3.66 ± 0.41 | 0.055 ± 0.019 |
| Chronic phase | 4.46 ± 0.70$^{a,f}$ | 13.58 ± 1.28$^a$ | 0.18 ± 0.02$^a$ | 0.93 ± 0.27$^{a,e}$ | 3.98 ± 0.34 | 0.047 ± 0.021 |

| | GLY | THR | CITR | ARG | ALA | TAU |
|---|---|---|---|---|---|---|
| Control | 0.65 ± 0.10 | 0.58 ± 0.15 | 0.018 ± 0.002 | 0.16 ± 0.034 | 0.30 ± 0.067 | 3.60 ± 0.89 |
| TBI 2 days | 1.54 ± 0.16 | 0.78 ± 0.17 | 0.017 ± 0.006 | 0.098 ± 0.029 | 0.66 ± 0.17 | 4.93 ± 0.79 |
| TBI 5 days | 0.84 ± 0.13 | 0.60 ± 0.12 | 0.017 ± 0.007 | 0.13 ± 0.52 | 0.35 ± 0.047 | 4.00 ± 0.97 |
| Acute phase 1 | 0.83 ± 0.25$^{a,c}$ | 0.92 ± 0.29$^a$ | 0.018 ± 0.004 | 0.13 ± 0.02$^{b,d}$ | 0.50 ± 0.12$^a$ | 4.86 ± 0.85$^b$ |
| Acute phase 2 | 0.71 ± 0.16$^{f,i}$ | 0.66 ± 0.23 | 0.018 ± 0.008 | 0.16 ± 0.03 | 0.52 ± 0.24$^{a,e}$ | 3.80 ± 1.19 |
| Chronic phase | 1.05 ± 0.13$^{a,f}$ | 0.75 ± 0.24$^{a,e}$ | 0.020 ± 0.006 | 0.14 ± 0.02 | 0.57 ± 0.28$^{a,e}$ | 4.49 ± 0.43$^a$ |

TABLE 3-continued concentrations of cerebral compounds

| | GABA | TYR | SAH | L-Cystat | VAL | MET |
|---|---|---|---|---|---|---|
| Control | 1.15 ± 0.40 | 0.120 ± 0.022 | 0.26 ± 0.010 | 0.147 ± 0.080 | 0.049 ± 0.005 | 0.015 ± 0.002 |
| TBI 2 days | 1.74 ± 0.35 | 0.160 ± 0.023 | 0.077 ± 0.009 | 0.337 ± 0.011 | 0.057 ± 0.005 | 0.011 ± 0.001 |
| TBI 5 days | 1.50 ± 0.30 | 0.123 ± 0.013 | 0.043 ± 0.013 | 0.202 ± 0.061 | 0.042 ± 0.014 | 0.010 ± 0.001 |
| Acute phase 1 | 1.43 ± 0.25$^a$ | 0.15 ± 0.03 | 0.033 ± 0.008$^{b,c,j}$ | 0.185 ± 0.031$^{b,c,i}$ | 0.042 ± 0.011 | 0.016 ± 0.005$^{d,j}$ |
| Acute phase 2 | 1.60 ± 0.24$^a$ | 0.172 ± 0.046$^{b,f}$ | 0.026 ± 0.010$^{f,i}$ | 0.173 ± 0.038$^{b,f,i}$ | 0.057 ± 0.017 | 0.022 ± 0.006$^{b,e,i}$ |
| Chronic phase | 1.85 ± 0.65$^a$ | 0.21 ± 0.05$^f$ | 0.050 ± 0.013$^a$ | 0.26 ± 0.05$^{a,f}$ | 0.040 ± 0.016$^b$ | 0.009 ± 0.004$^b$ |

| | TRP | PHE | ILE | LEU | ORN | LYS |
|---|---|---|---|---|---|---|
| Control | 0.013 ± 0.002 | 0.023 ± 0.001 | 0.030 ± 0.010 | 0.015 ± 0.002 | 0.012 ± 0.003 | 0.206 ± 0.042 |
| TBI 2 days | 0.023 ± 0.004 | 0.046 ± 0.011 | 0.043 ± 0.005 | 0.014 ± 0.007 | 0.013 ± 0.015 | 0.202 ± 0.023 |
| TBI 5 days | 0.012 ± 0.003 | 0.033 ± 0.006 | 0.038 ± 0.010 | 0.014 ± 0.005 | 0.009 ± 0.002 | 0.19 ± 0.092 |
| Acute phase 1 | 0.030 ± 0.007$^{b,d,g,i}$ | 0.031 ± 0.011$^{b,d}$ | 0.038 ± 0.007 | 0.021 ± 0.005$^{a,c}$ | 0.014 ± 0.007 | 0.236 ± 0.057$^{b,d,h}$ |
| Acute phase 2 | 0.015 ± 0.006 | 0.028 ± 0.010 | 0.048 ± 0.017$^a$ | 0.018 ± 0.004 | 0.011 ± 0.005 | 0.32 ± 0.04$^{a,e,i}$ |
| Chronic phase | 0.012 ± 0.007 | 0.033 ± 0.011$^b$ | 0.041 ± 0.016$^b$ | 0.024 ± 0.032$^{b,f}$ | 0.017 ± 0.009$^{a,e}$ | 0.179 ± 0.036 |

$^a$p < 0.01 (comparison with control),
$^b$p < 0.05 (comparison with control),
$^c$p < 0.01 (comparison with TBI 2 days),
$^d$p < 0.05 (comparison with TBI 2 days),
$^e$p < 0.01 (comparison with TBI 5 days),
$^f$p < 0.05 (comparison with TBI 5 days),
$^g$p < 0.01 (comparison with Acute phase 2),
$^h$p < 0.05 (comparison with Acute phase 2),
$^i$p < 0.01 (comparison with Chronic phase),
$^j$p < 0.05 (comparison with Chronic phase)
Table 3 lists the compounds in µmol/g (w.w.)

As is seen in Table 4, LMW-DS positively affected various compounds related to energy metabolism and mitochondrial functions. Particularly interesting are the concentrations of adenine nucleotides and ATP/ADP ratio as measurement of mitochondrial phosphorylating capacity (FIG. 13).

TABLE 4 concentrations of energy metabolites

| | cytosine | creatinine | uracil | β-pseudouridine | cytidine |
|---|---|---|---|---|---|
| Control | 12.89 ± 1.77 | 18.77 ± 2.09 | 10.65 ± 1.11 | 6.32 ± 1.11 | 12.54 ± 1.84 |
| TBI 2 days | 23.58 ± 5.62 | 28.61 ± 3.33 | 17.32 ± 1.54 | 8.45 ± 0.98 | 11.33 ± 1.23 |
| TBI 5 days | 21.56 ± 2.88 | 76.03 ± 8.19 | 24.31 ± 2.60 | 18.66 ± 1.29 | 26.12 ± 2.37 |
| Acute phase 1 | 17.69 ± 2.50$^{b,d}$ | 24.55 ± 3.20$^{b,g,i}$ | 14.56 ± 5.44 | 6.65 ± 1.30$^{g,i}$ | 15.40 ± 3.04 |
| Acute phase 2 | 15.70 ± 4.10$^f$ | 37.27 ± 5.82$^{a,e,j}$ | 19.40 ± 7.52$^{a,e}$ | 13.26 ± 3.16$^{a,e,j}$ | 16.18 ± 4.21$^e$ |
| Chronic phase | 15.58 ± 2.50$^{b,f}$ | 51.25 ± 10.17$^{a,f}$ | 16.57 ± 2.99$^{a,f}$ | 18.62 ± 2.80$^a$ | 14.71 ± 2.83$^e$ |

| | hypoxanthine | guanine | xanthine | CDP choline | ascorbic acid |
|---|---|---|---|---|---|
| Control | 7.21 ± 1.22 | 3.12 ± 0.78 | 8.09 ± 1.48 | 7.50 ± 1.01 | 4954.36 ± 212.43 |
| TBI 2 days | 11.36 ± 1.52 | 5.42 ± 0.87 | 13.15 ± 2.88 | 9.83 ± 1.71 | 3186.09 ± 287.87 |
| TBI 5 days | 16.83 ± 2.13 | 4.56 ± 1.29 | 14.14 ± 2.11 | 8.12 ± 1.55 | 2234.51 ± 198.62 |
| Acute phase 1 | 14.47 ± 2.87$^a$ | 4.80 ± 1.24$^b$ | 9.46 ± 2.34$^d$ | 10.93 ± 3.22$^{b,h}$ | 3733.10 ± 277.88$^{a,d}$ |
| Acute phase 2 | 12.90 ± 2.58$^{a,j}$ | 4.73 ± 1.07 | 10.41 ± 2.11$^f$ | 6.91 ± 1.86 | 3512.58 ± 224.62$^{a,e}$ |
| Chronic phase | 17.97 ± 4.49$^a$ | 5.31 ± 1.04$^b$ | 9.35 ± 0.83$^f$ | 8.37 ± 2.19 | 3375.03 ± 856.41$^{a,e}$ |

| | uridine | adenine | NO$_2$ | GSH | inosine |
|---|---|---|---|---|---|
| Control | 56.17 ± 3.88 | 23.14 ± 2.16 | 151.21 ± 16.79 | 3810.29 ± 200.65 | 94.33 ± 17.48 |
| TBI 2 days | 112.09 ± 15.65 | 54.85 ± 8.88 | 233.14 ± 25.48 | 2109.89 ± 156.71 | 126.36 ± 14.06 |
| TBI 5 days | 94.8 ± 10.75 | 76.55 ± 6.33 | 256.28 ± 28.07 | 1902.56 ± 183.42 | 137.73 ± 24.82 |
| Acute phase 1 | 76.35 ± 12.85$^{a,c}$ | 44.82 ± 6.31$^{b,d,g}$ | 216.03 ± 41.74$^a$ | 2649.50 ± 397.31$^{a,d}$ | 92.55 ± 31.20$^c$ |

TABLE 4-continued concentrations of energy metabolites

| | | | | | |
|---|---|---|---|---|---|
| Acute phase 2 | 63.02 ± 9.66$^{b,e}$ | 58.16 ± 6.36$^{a,f}$ | 226.40 ± 30.95$^b$ | 2821.50 ± 242.82$^{a,e}$ | 85.52 ± 20.36$^e$ |
| Chronic phase | 63.28 ± 3.37$^f$ | 52.94 ± 8.59$^{a,f}$ | 217.67 ± 55.04$^a$ | 2608.67 ± 358.07$^{a,e}$ | 105.81 ± 25.57$^f$ |

| | uric acid | guanosine | CMP | MDA | thymidine |
|---|---|---|---|---|---|
| Control | 2.75 ± 0.35 | 18.96 ± 2.90 | 12.16 ± 1.61 | 1.13 ± 0.25 | 0.54 ± 0.16 |
| TBI 2 days | 30.84 ± 5.13 | 17.52 ± 2.44 | 30.83 ± 4.81 | 28.37 ± 3.37 | 0.67 ± 0.19 |
| TBI 5 days | 23.63 ± 3.40 | 21.32 ± 3.04 | 27.20 ± 3.76 | 7.69 ± 2.18 | 0.97 ± 0.32 |
| Acute phase 1 | 23.62 ± 3.77$^{a,d,h}$ | 20.71 ± 5.66 | 30.12 ± 9.97$^{a,h}$ | 12.47 ± 2.09$^{a,c,g}$ | 0.69 ± 0.11 |
| Acute phase 2 | 19.17 ± 2.15$^{a,h,i}$ | 17.90 ± 3.24$^j$ | 15.68 ± 2.12$^{f,j}$ | 4.82 ± 1.73$^{a,e,i}$ | 0.49 ± 0.20$^f$ |
| Chronic phase | 27.77 ± 3.60$^a$ | 28.87 ± 7.60$^{a,f}$ | 20.51 ± 3.73$^{a,f}$ | 11.62 ± 3.90$^{a,e}$ | 0.71 ± 0.11 |

| | orotic acid | NO$_3$ | UMP | NAD$^+$ | ADO |
|---|---|---|---|---|---|
| Control | 5.67 ± 0.85 | 178.66 ± 37.75 | 96.21 ± 10.51 | 506.88 ± 59.15 | 50.73 ± 8.29 |
| TBI 2 days | 10.09 ± 1.54 | 265.31 ± 47.68 | 116.06 ± 13.55 | 322.37 ± 30.87 | 66.19 ± 11.06 |
| TBI 5 days | 14.27 ± 1.67 | 325.19 ± 60.08 | 128.70 ± 28.28 | 261.67 ± 49.97 | 78.91 ± 20.42 |
| Acute phase 1 | 8.80 ± 2.45$^{b,h,j}$ | 210.64 ± 91.95$^d$ | 107.80 ± 21.62 | 404.63 ± 51.10$^{a,c,i}$ | 71.67 ± 15.87 |
| Acute phase 2 | 13.34 ± 3.65$^a$ | 198.56 ± 25.93$^{e,i}$ | 138.73 ± 32.01$^b$ | 401.18 ± 34.53$^{a,e,i}$ | 82.11 ± 16.51$^a$ |
| Chronic phase | 12.05 ± 1.50$^a$ | 241.27 ± 18.84$^e$ | 103.11 ± 29.79 | 301.13 ± 29.90$^a$ | 89.97 ± 12.98$^a$ |

| | IMP | GMP | UDP-Glc | UDP-Gal | GSSG |
|---|---|---|---|---|---|
| Control | 54.09 ± 12.15 | 98.93 ± 10.42 | 47.23 ± 3.14 | 120.18 ± 10.99 | 189.21 ± 20.19 |
| TBI 2 days | 50.82 ± 10.45 | 181.94 ± 27.20 | 45.17 ± 6.67 | 131.19 ± 18.49 | 179.51 ± 29.17 |
| TBI 5 days | 124.46 ± 18.97 | 158.35 ± 40.43 | 41.43 ± 5.14 | 112.26 ± 17.36 | 196.65 ± 33.48 |
| Acute phase 1 | 67.71 ± 10.63$^{g,i}$ | 177.00 ± 32.39$^{a,g}$ | 32.14 ± 4.59$^g$ | 119.45 ± 12.50 | 185.21 ± 48.10 |
| Acute phase 2 | 102.63 ± 22.09$^a$ | 91.47 ± 12.35$^{e,j}$ | 44.44 ± 7.59$^j$ | 145.14 ± 27.76 | 219.54 ± 53.36 |
| Chronic phase | 99.29 ± 13.82$^a$ | 148.56 ± 31.21$^a$ | 35.79 ± 3.45$^b$ | 122.29 ± 12.15 | 231.08 ± 44.34$^{b,f}$ |

| | UDP-GlcNac | UDP-GalNac | AMP | GDP glucose | CDP |
|---|---|---|---|---|---|
| Control | 93.71 ± 14.16 | 35.09 ± 3.07 | 30.31 ± 5.12 | 34.89 ± 8.18 | 14.08 ± 1.14 |
| TBI 2 days | 93.71 ± 14.16 | 20.17 ± 3.33 | 73.32 ± 12.88 | 39.16 ± 6.87 | 18.31 ± 2.15 |
| TBI 5 days | 129.54 ± 21.21 | 10.56 ± 2.89 | 98.32 ± 10.99 | 59.88 ± 12.54 | 19.03 ± 6.45 |
| Acute phase 1 | 95.85 ± 19.73$^{h,i}$ | 19.17 ± 4.01$^a$ | 53.61 ± 17.91$^{a,c,j}$ | 38.71 ± 6.86 | 25.53 ± 6.83$^{a,c}$ |
| Acute phase 2 | 130.65 ± 28.41$^a$ | 19.90 ± 3.12$^{a,e}$ | 57.70 ± 23.01$^{a,e,j}$ | 49.25 ± 10.33$^a$ | 24.29 ± 6.76$^a$ |
| Chronic phase | 129.42 ± 15.88$^b$ | 21.84 ± 2.80$^{a,e}$ | 90.01 ± 21.24$^a$ | 43.85 ± 5.06$^b$ | 23.55 ± 6.45$^a$ |

| | UDP | GDP | NADP$^+$ | ADP-ribose | CTP |
|---|---|---|---|---|---|
| Control | 26.06 ± 7.32 | 61.78 ± 17.09 | 27.52 ± 2.58 | 48.88 ± 5.61 | 38.90 ± 4.64 |
| TBI 2 days | 55.47 ± 6.70 | 149.02 ± 19.09 | 16.36 ± 4.41 | 133.31 ± 30.02 | 21.57 ± 3.19 |
| TBI 5 days | 43.71 ± 8.81 | 113.11 ± 28.34 | 12.50 ± 2.97 | 221.80 ± 36.72 | 18.79 ± 3.69 |
| Acute phase 1 | 61.83 ± 10.23$^{a,g}$ | 158.72 ± 24.57$^a$ | 17.95 ± 3.28$^a$ | 137.87 ± 43.18$^a$ | 18.98 ± 6.58$^{a,g}$ |
| Acute phase 2 | 40.38 ± 8.50$^{a,i}$ | 126.70 ± 31.35$^{a,j}$ | 21.27 ± 4.19$^{b,e,j}$ | 141.96 ± 23.56$^{a,e,j}$ | 32.63 ± 3.99$^{e,i}$ |
| Chronic phase | 57.40 ± 5.88$^{a,f}$ | 173.05 ± 28.68$^{a,e}$ | 16.44 ± 2.66$^{a,f}$ | 173.94 ± 8.45$^a$ | 25.23 ± 2.93$^{a,f}$ |

| | ADP | UTP | GTP | NADH | ATP |
|---|---|---|---|---|---|
| Control | 233.19 ± 21.33 | 138.95 ± 28.89 | 567.33 ± 54.79 | 14.50 ± 2.75 | 2441.66 ± 257.71 |
| TBI 2 days | 264.71 ± 26.31 | 107.77 ± 12.83 | 208.13 ± 28.36 | 8.54 ± 1.73 | 1350.25 ± 140.87 |
| TBI 5 days | 328.26 ± 31.30 | 90.50 ± 18.69 | 191.81 ± 37.56 | 6.77 ± 1.58 | 1195.81 ± 137.82 |
| Acute phase 1 | 279.34 ± 29.59$^b$ | 123.46 ± 15.42$^d$ | 255.29 ± 45.21$^{a,g}$ | 15.49 ± 2.05$^{c,j}$ | 1464.25 ± 99.09$^{a,h}$ |
| Acute phase 2 | 264.07 ± 28.29$^{b,e,j}$ | 146.71 ± 32.68$^e$ | 336.65 ± 35.18$^{a,e,j}$ | 13.12 ± 4.19$^e$ | 1632.23 ± 90.07$^{a,e,j}$ |
| Chronic phase | 315.53 ± 46.53$^a$ | 136.80 ± 33.25$^f$ | 290.92 ± 34.68$^{a,f}$ | 11.78 ± 3.32$^e$ | 1381.03 ± 212.64$^a$ |

| | NADPH | malonyl-CoA | CoA-SH | acetyl-CoA | NM |
|---|---|---|---|---|---|
| Control | 7.95 ± 1.38 | 15.83 ± 1.31 | 28.91 ± 3.19 | 38.97 ± 5.79 | 9141.22 ± 366.64 |
| TBI 2 days | 8.14 ± 1.69 | 10.46 ± 2.56 | 19.64 ± 2.37 | 21.76 ± 4.49 | 5570.00 ± 912.08 |
| TBI 5 days | 9.24 ± 2.07 | 11.89 ± 1.96 | 21.77 ± 1.44 | 18.94 ± 3.75 | 4300.00 ± 480.84 |
| Acute phase 1 | 6.22 ± 1.73 | 12.33 ± 1.82$^b$ | 21.61 ± 3.42$^{a,h}$ | 21.56 ± 6.22$^{a,g,j}$ | 6147.91 ± 989.12$^a$ |
| Acute phase 2 | 7.05 ± 2.21 | 11.29 ± 2.27$^b$ | 30.57 ± 6.02$^f$ | 36.86 ± 4.11$^e$ | 7262.84 ± 749.73$^{a,e}$ |
| Chronic phase | 7.34 ± 2.65$^f$ | 10.00 ± 1.95$^b$ | 27.58 ± 6.24$^f$ | 35.68 ± 6.55$^e$ | 6375.36 ± 974.12$^{a,e}$ |

$^a$p < 0.01 (comparison with control),
$^b$p < 0.05 (comparison with control),
$^c$p < 0.01 (comparison with TBI 2 days),
$^d$p < 0.05 (comparison with TBI 2 days),
$^e$p < 0.01 (comparison with TBI 5 days),
$^f$p < 0.05 (comparison with TBI 5 days),
$^g$p < 0.01 (comparison with Acute phase 2),
$^h$p < 0.05 (comparison with Acute phase 2),
$^i$p < 0.01 (comparison with Chronic phase),
$^j$p < 0.05 (comparison with Chronic phase)
Table 4 lists the compounds in nmol/g (w.w.)

Remarkable changes of oxidative and reduced nicotinic coenzymes were also observed (FIG. 14).

Parameters related to oxidative stress were also measured and a significant reduction of oxidative stress was detected after administration of LMW-DS. In particular, ascorbic acid, as the main water-soluble brain antioxidant, and GSH, as the major intracellular-SH donor, were measured. Results showed a significant improvement in their levels after administration of LMW-DS as shown in Table 4 and FIG. 15.

Figure 15A:
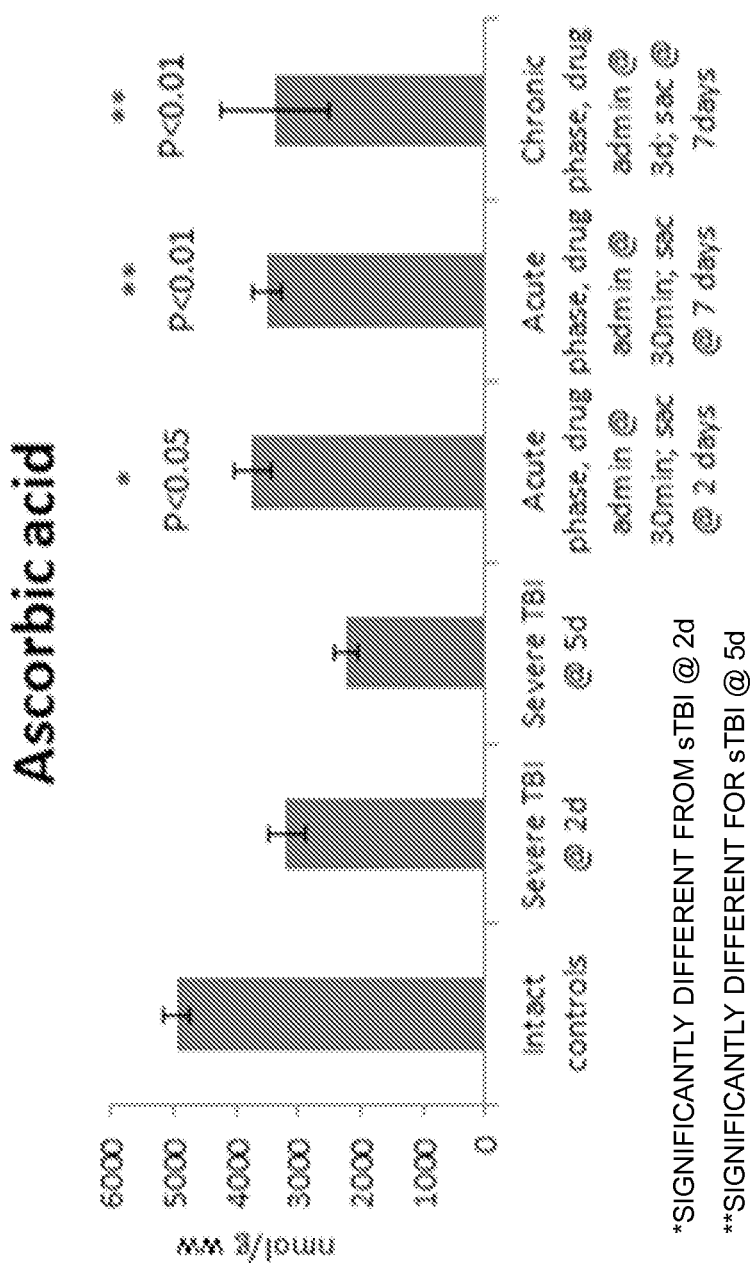
FIGS. 15A-15O are diagrams illustrating changed levels of biomarkers representative of oxidative stress.
Figure 15B:
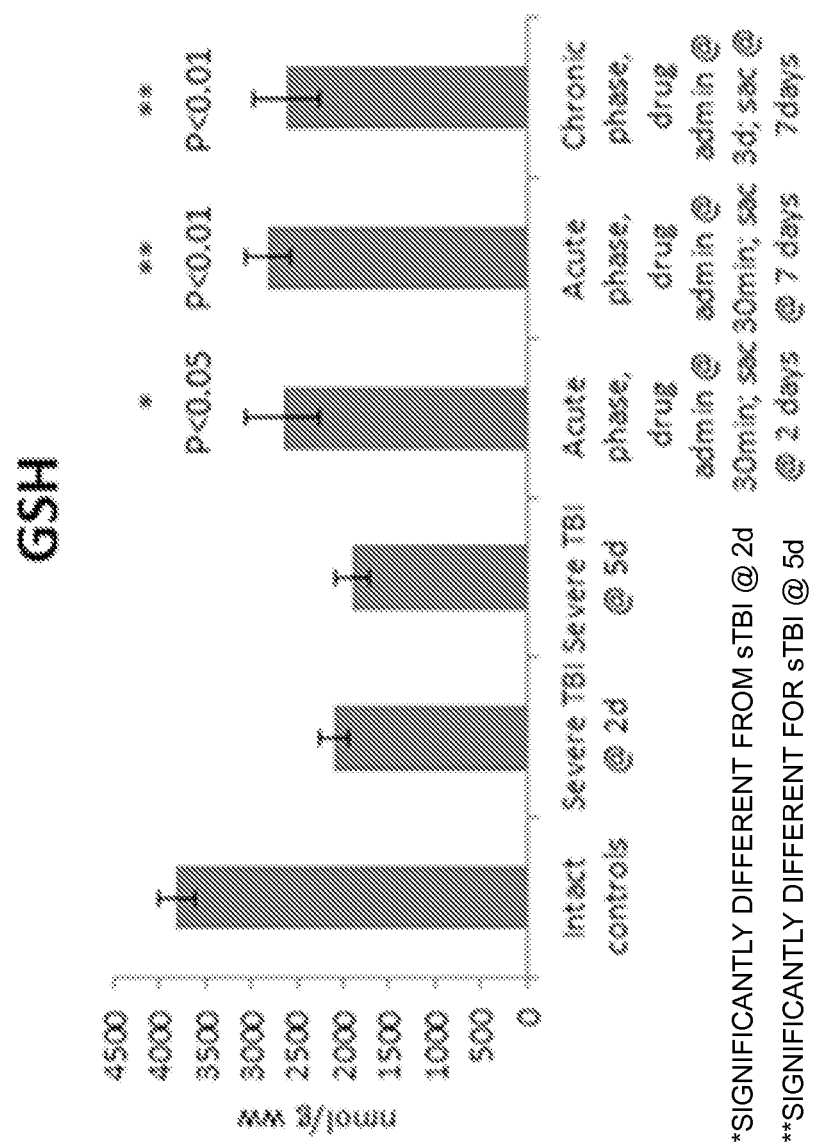
Figure 15C:
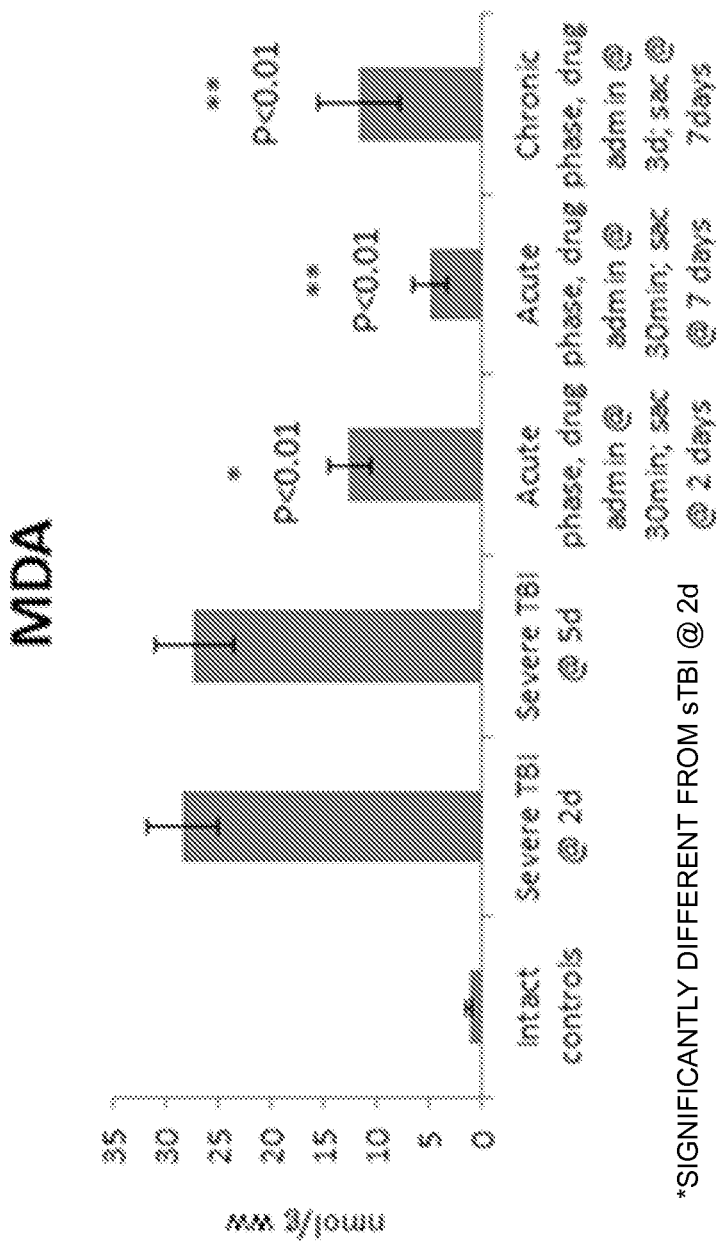

In addition, MDA, as end product of polyunsaturated fatty acids of membrane phospholipids and therefore taken as a marker of ROS-mediated lipid peroxidation, was also measured. MDA levels showed a significant reduction after administration of LMW-DS. The oxidative stress markers described above all indicated an improvement in the recovery of antioxidant status after treatment with LMW-DS (FIG. 15).

Figure 16:
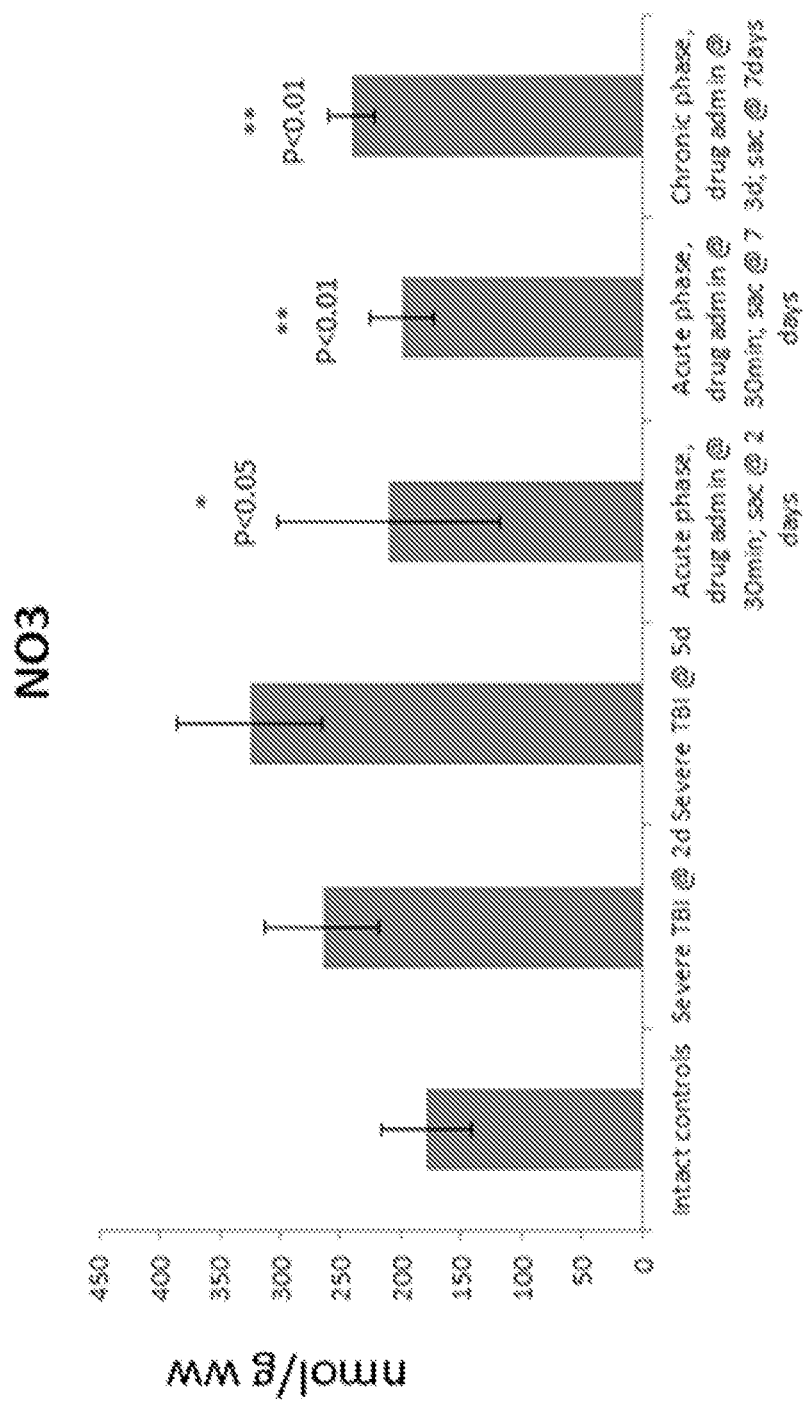
FIG. 16 is a diagram illustrating changed levels of nitrate as a measurement of NO-mediated nitrosative stress.

Indices of representative of NO-mediated nitrosative stress (nitrite and nitrate) were also analyzed. LMW-DS administration significantly decreased the nitrate concentrations in both the acute and chronic phases of sTBI (FIG. 16).

Figure 17A:
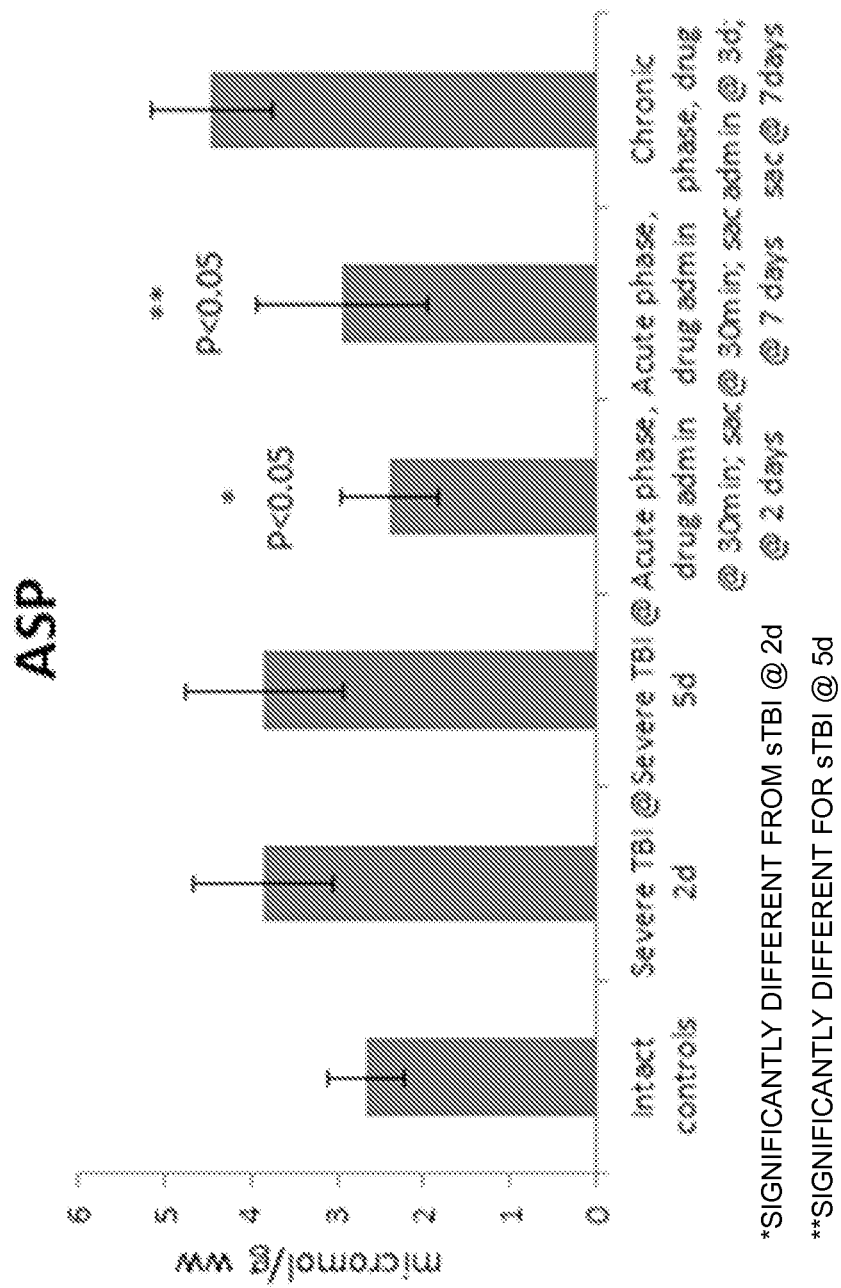
FIGS. 17A-17O are diagrams illustrating changed levels of N-acetylaspartate (NAA) and its substrates.
Figure 17B:
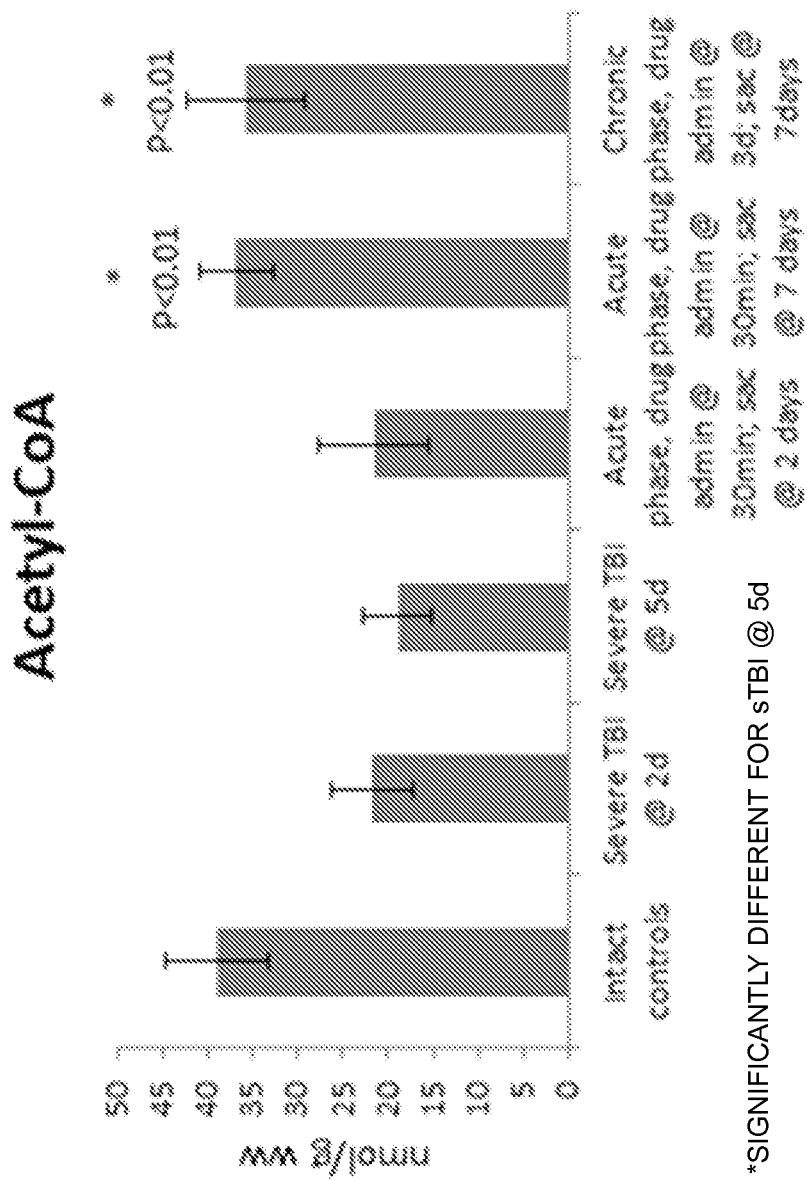
Figure 17C:
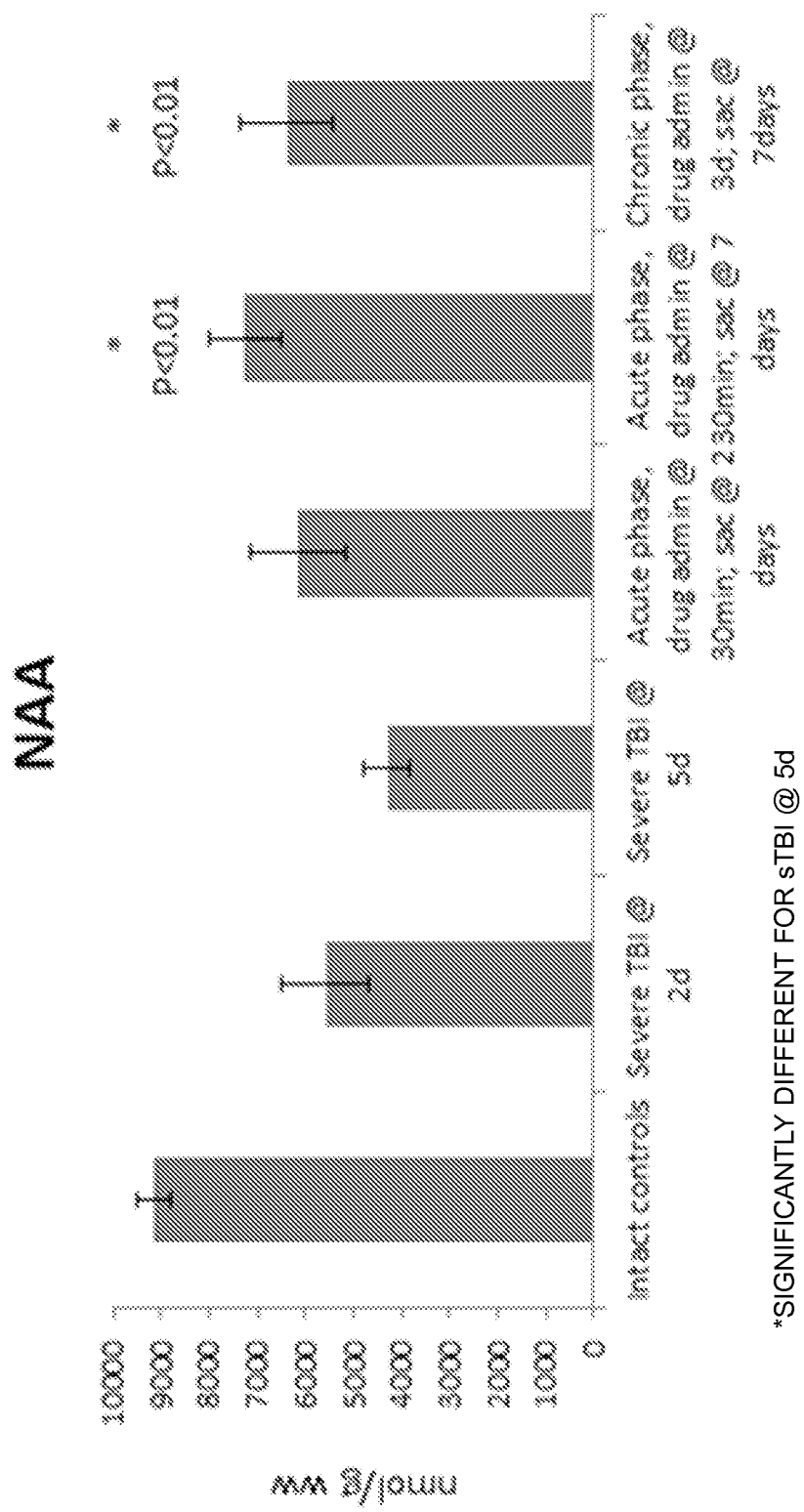

NAA is a brain specific metabolite and a valuable biochemical marker for monitoring deterioration or recovery after TBI. NM is synthesized in neurons from aspartate and acetyl-CoA by aspartate N-acetyltransferase. To ensure NAA turnover, the molecule must move between cellular compartments to reach oligodendrocytes where it is degraded into acetate and aspartate by aspartoacylase (ASPA). An upregulation of the catabolic enzyme ASPA and an NAA decrease in order to supply the availability of the substrates asparate and acetyl-CoA are an indication of the status of metabolic impairment. In this study NAA and its substrates were measured after sTBI and showed significant improvements in levels after LMW-DS administration (FIG. 17).

These effects on energy metabolites were particularly evident when animals received the LMW-DS administration early post-injury (30 mins). It is important to note that the overall beneficial effects of LMW-DS were observed either when the animals were sacrificed 2 days after sTBI or when sacrifice occurred 7 days post sTBI. In these groups of animals, the general amelioration of metabolism connected to AGCC and energy metabolites was more evident, suggesting a long-lasting positive effect of the LMW-DS administration on brain metabolism.

Discussion

TBI is the leading cause of death and disability in the first four decades of life. The cost to the UK economy alone is estimated to be £8 billion per year, for comparison this is a greater cost to the economy than stroke. In the USA, the combined healthcare and socioeconomic costs of TBI are estimated to exceed $60 billion per year, not including military expenditure. In addition, the last few years have seen a massive surge of interest in sport concussion on both sides of the Atlantic.

Despite the obvious clinical need, there are currently no approved pharmacological treatments for TBI. Whilst the primary insult (contusion) associated with TBI may be amenable to surgical treatment, reduction in the subsequent secondary non-mechanical damage of surrounding brain tissue (penumbra) offers greater potential therapeutic opportunities.

Using a well-established rodent model of severe traumatic brain injury (sTBI), characterized by diffuse axonal damage of TBI, it has previously been shown that severely injured animals have long-lasting modifications of various metabolites connected to the cell energy state and mitochondrial functions (Vagnozzi et al., Changes of cerebral energy metabolism and lipid peroxidation in rats leading to mitochondrial dysfunction after diffuse brain injury. *J Neurotrauma.* 1999; 16: 903-913; Signoretti et al., N-Acetylaspartate reduction as a measure of injury severity and mitochondrial dysfunction following diffuse traumatic brain injury. *J Neurotrauma.* 2001; 18: 977-993; Tavazzi et al., Cerebral oxidative stress and depression of energy metabolism correlate with severity of diffuse brain injury in rats. *Neurosurgery.* 2005; 56: 582-589; Vagnozzi et al., Temporal window of metabolic brain vulnerability to concussions: mitochondrial-related impairment-part I. *Neurosurgery.* 2007; 61: 379-388; Tavazzi et al., Temporal window of metabolic brain vulnerability to concussions: oxidative and nitrosative stresses-part II. *Neurosurgery.* 2007; 61: 390-395), as well as to amino acidic metabolism (Amorini et al., Severity of experimental traumatic brain injury modulates changes in concentrations of cerebral free amino acids. *J Cell Mol Med.* 2017; 21: 530-542). In the complex molecular mechanisms causing TBI-induced cerebral damages, it appears that metabolic modifications are early cellular signals that influence the changes in enzymatic activities and gene and protein expression indicative of the pathological tissue response (Di Pietro et al., Potentially neuroprotective gene modulation in an in vitro model of mild traumatic brain injury. *Mol Cell Biochem.* 2013; 375: 185-198; Di Pietro et al., The molecular mechanisms affecting N-acetylaspartate homeostasis following experimental graded traumatic brain injury. *Mol Med.* 2014; 20: 147-157; Di Pietro et al., Neuroglobin expression and oxidant/antioxidant balance after graded traumatic brain injury in the rat. *Free Radic Biol Med.* 2014; 69: 258-264; Amorini et al., Metabolic, enzymatic and gene involvement in cerebral glucose dysmetabolism after traumatic brain injury. *Biochim Biophys Acta Mol Basis of Dis.* 2016; 1862: 679-687). This implies that agents that act to positively regulate cellular metabolism in the compromised tissues might decrease the subsequent TBI-associated modifications in enzyme activity and gene and protein expression that contribute to adverse outcomes.

The data presented herein suggests that early administration of LMW-DS reduced levels of glutamate excitotoxicity and ameliorated adverse changes in metabolic homeostasis by protecting mitochondrial function, indicating a neuroprotective effect of the compound after severe TBI. Accordingly, LMW-DS has a potential to be used in the treatment or inhibition of TBI, including STBI.

Example 4

An analysis of changes in gene-expression induced by LMW-DS was investigated in cell lines.

Materials and Methods

Experimental Design

For each cell line, n=8×25 cm$^2$ culture flasks were set up. Two flasks were harvested for each cell type on the day of treatment (24 hours after seeding). This represents the Day0 time point. From the remaining flasks, three flasks were treated with Control Medium and three were treated with Culture Medium (CM) containing LMW-DS to give a final concentration of 0.01 mg/ml. Cells from the treated flasks were collected after 48 hours. Therefore the collected data represent (a) untreated cells (Day0 Controls and Day2 Controls) and (b) cells treated with LMW-DS for 48 hours (Day2 LMW-DS treated).

Coating of Tissue Culture Plates for all Cells 25 cm$^2$ flasks were coated by adding 2 ml per flask of a solution of 50 µg/ml poly-d-lysine in Hank's balanced salt solution (HBSS) and incubating overnight at 37° C. in the dark. Flasks were washed with cell culture water and air-dried for 30 min in the dark. Flasks were coated by adding 1 ml per flask of a solution of 25 µg/ml laminin in phosphate-buffered saline (PBS) and incubating for 2 hour at 37° C. in the dark. The laminin flasks were washed with PBS three times before plating cells.

Human Umbilical Vein Endothelial Cells (HUVECs)

Medium 200+Large Vessel Endothelial Supplement (M200+LVES) additive (1:50) was prepared and pre-warmed to 37° C. Cells were thawed in a 37° C. water bath for no longer than 2 min and gently transferred into a 50 ml tube containing 20 ml Dulbecco's Modified Eagle Medium, Nutrient Mixture F-12 (DMEM-F12). The cell suspension was mixed by inverting the tube carefully twice. Cells were spun at 400×g for 10 minutes. Supernatant removed and cells were resuspended in 10 ml of culture media (M200+LVES additive).

Cells were counted with the Cellometer. 1,000,000 cells/flask were seeded in 25 cm$^2$ flasks (n=8) and medium was topped up to a total of 5 ml per flask. Cells were incubated at 37° C. with 5% $CO_2$. Cells were allowed to settle for 24 hours before LMW-DS treatment.

Human Schwann Cells

Schwann cells growth medium was prepared by adding 10% of fetal bovine serum (FBS) to high-glucose DMEM and pre-warmed to 37° C. Cells were thawed in a 37° C. water bath for no longer than 2 min.

Cells from 12 vials were each gently transferred to a tube containing 10 ml of high-glucose DMEM medium and centrifuged at 400 relative centrifugal field (RCF) for 10 min. Pellet was resuspended in culture medium. The cells from the 12 vials were mixed and distributed equally into the previously coated 25 cm$^2$ flasks (n=8). Cells were incubated at 37° C. with 5% $CO_2$. Cells were allowed to settle for 24 hours before LMW-DS treatment.

Mouse Cortical Neurons (Lonza)

Medium was prepared by adding 10 ml B-27 Serum-Free Supplement and 2.5 ml GlutaMAX™-1 Supplement to 500 ml of Neurobasal medium. The medium was pre-warmed to 37° C. Cells from 12 vials were thawed sequentially in a 37° C. water bath for no longer than 2 min and gently transferred into a 15 ml tube. 9 ml of medium was gently added drop-wise to each. The cell suspension was mixed by inverting the tubes carefully twice.

The cells were centrifuged for 5 minutes at 200×g. Supernatant was removed (to the last 0.5 ml) and cells were gently resuspended by trituration. The cells from the 12 vials were mixed and distributed equally into the previously coated 25 cm$^2$ flasks (n=8). Cells were incubated at 37° C. with 5% $CO_2$ for 24 hours.

Mouse Motor Neurons (Aruna)

The culture medium was prepared according to Table 5.

TABLE 5

Preparation of culture medium

| Component | Stock concentration | Final concentration | For 50 ml |
|---|---|---|---|
| Advanced DMEM/F12 | | | 25 ml |
| AB2 ™ Basal Neural Medium | | | 25 ml |
| Knockout Serum Replacement | | | 5 ml |
| L-Glutamate | 100X | 1X | 0.5 ml |
| Penicillin/Streptomycin | 100X | 1X | 0.5 ml |
| B-mercaptoethanol | 1 M (diluted in PBS) | 0.1 mM | 5 µl |
| Glial cell-derived neurotrophic factor (GDNF) | 100 µg/ml in $H_2O$ | 10 ng/ml | 5 µl |
| Ciliary neurotrophic factor (CNTF) | 100 µg/ml in PBS with 0.1% BSA | 10 ng/ml | 5 µl |

Medium (see Table 5) was pre-warmed to 37° C. Cells were thawed in a 37° C. water bath for no longer than 2 min. 9 ml of media was gently added drop-wise. The cell suspension was mixed by inverting the tube carefully twice. The cells were counted with a Cellometer. The cells were centrifuged for 5 minutes at 200×g. Supernatant was removed (to the last 0.5 ml) and cells were gently resuspended by trituration. The cells from the 8 vials were mixed and distributed equally into the previously coated 25 cm$^2$ flasks (n=8). Cells were incubated at 37° C. with 5% $CO_2$ for 24 hours before treatment.

Drug Treatment

LMW-DS was provided at a stock concentration of 20 mg/ml and was kept in a temperature monitored refrigerator at 4° C. A fresh 100×LMW-DS stock (1.0 mg/ml) was prepared in sterile DMEM-F12. The concentrated drug stock was sterile filtered and added to the respective culture media (19.6 ml CM and 0.4 ml LMW-DS stock solution). The Control was made using 19.6 ml CM and 0.4 ml of DMEM-F12. LMW-DS and CM were added to the respective flasks (5 ml each) to reach the 0.01 mg/ml concentration of LMW-DS in each dish with a total of 10 ml CM each.

Culture Collection and Cell Lysis.

CM was aspirated into a clean and labelled 15 ml Falcon tube. The flasks (without culture medium) were placed into the −80° C. freezer for 30 minutes. The CM in the Falcon tubes were spun at 3000×g for 5 minutes. Supernatant was removed and the small pellet was re-suspended in 2.5 ml Trizol:Water (4:1) solution at room temperature (RT, −22° C.).

The frozen flasks were removed one-by one from the freezer and the Trizol-Water from the appropriate tubes was moved to the flask. Flasks were left at RT for 5 minutes before the content was aspirated back into the 15 ml Falcon tube (after washing the bottom of the flask with the solution thoroughly). The flasks were inspected under the microscope to ensure full removal of cells. The collected lysates in the 15 ml Falcon tubes were placed into the −80° C. freezer.

RNA Extraction

Falcon tubes containing the homogenates were removed from the freezer and stored for 5 minutes at RT to permit the complete dissociation of nucleoprotein complexes.

Two aliquots of 1 ml lysate was removed from each sample and 200 µl of chloroform was added to each (0.2 ml of chloroform per 1 ml of TRIzol Reagent used during the cell lysis step) and the tube was shaken vigorously. Samples were stored at RT for 2-3 minutes and subsequently centrifuged at 12,000×g for 15 minutes at 4° C.

The mixture separated into three layers: a lower red phenol-chloroform phase, an interphase and a colorless upper aqueous phase. The RNA remained in the top aqueous phase, DNA in the white middle (interphase) phase and protein in the pink bottom (organic) phase. The top ¾ of the aqueous phase was transferred to a new clean Eppendorf tube.

The RNA was precipitated from the aqueous phase by adding an equal amount of 100% ethanol. The precipitated RNA was fixed onto a Spin Cartridge, washed twice and dried. The RNA was eluted in 50 µl warm RNase-Free Water. The amount and quality of the purified RNA was measured by Nanodrop. The RNA was stored at −80° C. before transfer to Source Bioscience for Array analysis.

Analysis Plan for Expression Data

The expression data were downloaded into separate files for each cell line. The 'Background corrected' expression is the data from the "gProcessedSignal" of the arrays that is the result of the background signal extracted from the actual signal of the relevant probe. This is the most often used variable in array analysis. The background corrected signal was log 2 transformed for all samples for statistical analysis. To reduce the false discovery rate in the samples, the signals that were below 'expression level' were removed. The 'below expression' level was set at 5 for the log 2 transformed expression values.

Statistical Analysis

Based on the expression pattern of the Control probes on each array it was decided to carry out Median Centering for all arrays before analysis to reduce the variability of the results. Data were grouped by cell type and each cell type was analyzed using the following algorithms:

Comparison of D0 control to D2 control samples— expression changes seen in the cells in normal cultures Comparison of D0 control to D2 LMW-DS treated samples—expression changes seen in the cells in the LMD-DS treated cultures Comparison of D2 control to D2 LMD-DS treated samples—differential expression induced by LMW-DS in the culture.

A preliminary analysis was carried out to screen out genes that were not differentially expressed between any combination of the three datasets. Simple, non-stringent ANOVA ($p<0.05$) was carried out to look for patterns of expression. Probes with no changes across the three datasets were eliminated. The remaining probe sets were analyzed for fold change and significance using Volcano plots. More than 20% change in the expression of a probe (FC 1.2 or FC 0.84) was regarded as significant in the first instance to allow the detection of expression patterns.

Quality Parameters

Seeding densities were calculated from the cell counts retrieved from the cell stocks for the Schwann cells. The HUVECS were seeded at their optimum density.

The additional quality control from the Array service provider indicated that the RNA was high quality (no degradation) and the amounts were within the parameters of the Low input RNA microarray from Agilent.

The analysis of the raw data indicated that, as expected, there were significant differences between arrays. These differences (reflected by differences in the same control samples included on all arrays), were, however, easily eliminated by normalization techniques. The chosen median centering of the data that eliminates the array-to-array variation did not affect the overall differences expected to be seen between the controls representing different concentrations of RNA.

Expression Analysis of Schwann Cells

As described in the foregoing, genes not expressed in the Schwann cells were removed prior to data analysis. The 'below expression' level was set at 5 for the log 2 transformed expression values. This left 15,842 unique probes to analyze in the Schwann cell cultures. In the next step of the analysis, three sets of data (comparison of D0 control to D2 control samples; comparison of D0 control to D2 LMW-DS treated samples; comparison of D2 control to D2 LMD-DS treated samples) were analyzed to establish the effect of the CM on the cells and the relative changes induced by LMW-DS.

585 genes were differentially expressed in Schwann cell cultures when comparing the D0 control to the D2 control samples. The molecular functions influenced by these genes relate to cellular movement (1.14E-07-2.49E-03); cell morphology (5.56E-07-2.36E-03); cellular development (7.3E-06-2.48E-03); cellular growth and proliferation (7.3E-06-2.48E-03); cellular assembly and organization (1.23E-05-2.36E-03); cellular function and maintenance (1.23E-05-2.47E-03); cell death and survival (1.53E-05-2.51E-03); lipid metabolism (8.14E-05-1.6E-03); small molecule biochemistry (8.14E-05-1.6E-03); molecular transport (1.18E-04-2.29E-03); protein trafficking (1.62E-04-1.6E-03); carbohydrate metabolism (3.22E-04-1.78E-03); gene expression (3.98E-04-2.2E-03); cell signaling (4.39E-04-2.25E-03); cell-to-cell signaling and interaction (5.05E-04-2.48E-03); cellular compromise (7.69E-04-1.58E-03); cell Cycle (1.12E-03-1.8E-03); amino acid metabolism (1.6E-03-1.6E-03); and nucleic acid metabolism (1.6E-03-1.6E-03).

The values presented above are p-values representing the statistical significance of the association of these genes with the different pathways. The two p values represent the lower and upper limits of the statistical significance observed ($p<0.05$ is significant).

LMW-DS induced differential expression in Schwann cell culture of 1244 genes as assessed when comparing the D0 control to the D2 LMW-DS treated samples. The molecular functions influenced by these genes relate to cell morphology (1.43E-08-8.39E-04); cellular movement (1.4E-07-9.6E-04); post-translational modification (3.93E-07-6.71E-05); protein synthesis (3.93E-07-1.08E-04); protein trafficking (3.93E-07-1.26E-06); cell death and survival (2.13E-06-8.65E-04); cellular assembly and organization (7.46E-06-8.24E-04); DNA replication, recombination, and repair (7.46E-06-7.46E-06); cellular function and maintenance (9.53E-06-6.46E-04); gene expression (1.27E-05-4.92E-04); cellular development (1.29E-05-9.06E-04); cellular growth and proliferation (1.29E-05-9.06E-04); cell-to-cell signaling and interaction (1.97E-05-8.81E-04); amino acid metabolism (4.22E-05-8.24E-04); small molecule biochemistry (4.22E-05-8.24E-04); lipid metabolism (4.81E-05-3.64E-04); molecular transport (3.64E-04-3.64E-04); and cell cycle (4.53E-04-4.86E-04).

LMW-DS induced differential expression in Schwann cell culture of 700 genes as assessed when comparing the D2 control to the D2 LMW-DS treated samples. The molecular functions influenced by these genes relate to cell morphology (1.49E-07-5.62E-03); cellular assembly and organization (1.49E-07-5.95E-03); cellular movement (7.24E-07-6.06E-03); cell death and survival (9.41E-06-5.95E-03); amino acid metabolism (2.56E-05-3.7E-03); post-translational modification (2.56E-05-1.05E-03); small molecule biochemistry (2.56E-05-3.7E-03); cell-to-cell signaling and interaction (5.05E-05-5.76E-03); gene expression (7.18E-05-4.94E-03); cell cycle (1.06E-04-5.95E-03); cellular development (1.06E-04-5.95E-03); cellular function and maintenance (1.96E-04-5.95E-03); cellular growth and proliferation (2.35E-04-5.95E-03); DNA replication, recombination and repair (2.75E-04-5.95E-03); cell signaling (5.92E-04-2.54E-03); cellular comprise (6.26E-04-6.26E-04); lipid metabolism (6.26E-04-1.85E-03); molecular transport (6.26E-04-5.95E-03); protein synthesis (1.05E-03-1.93E-03); cellular response to therapeutics (1.85E-03-1.85E-03); protein trafficking (2.66E-03-5.95E-03); and RNA post-transcriptional modification (4.32E-03-4.32E-03).

The mechanistic molecular network model simulates the effect of the differentially regulated molecules by LMW-DS enabling the functional consequences of these changes to be evaluated. The in silico model indicated that LMW-DS inhibits neuronal cell death; apoptosis; and synthesis of protein and activates angiogenesis; migration of cells; cell viability; cell survival; cell movement; proliferation of cells;

differentiation of cells; cellular homeostasis; cell cycle progression; cell transformation; and expression of RNA.

Table 6 summarizes the results of the gene expression changes in the cultured Schwann cells.

TABLE 6

Overall pattern of gene expression changes in Schwann cells

|  | abolished nutrient effect | enhanced response to nutrients | new effect induced by LMW-DS | not different from control | total |
|---|---|---|---|---|---|
| no effect | 21 |  |  |  | 21 |
| significant downregulation | 1 | 122 | 352 | 42 | 517 |
| significant upregulation | 13 | 441 | 74 | 373 | 901 |
| total | 35 | 563 | 426 | 415 | 1439 |

21 genes that have altered expression in the Control cultures in the two days did not show any changes at all in the LMW-DS treated cultures during the same two days. 1 gene that had increased expression in the control cultures was downregulated in the LMW-DS treated cultures during the same two days. 13 genes that were downregulated in the control cultures were upregulated in the LMW-DS treated cultures during the two days. 122 genes were significantly downregulated by growth factors in the culture medium and this downregulation was even stronger in the LMW-DS treated cultures. 441 genes were upregulated in the Control cultures and the addition of LMW-DS made this upregulation significantly stronger.

Expression Analysis of HUVECs

As described in the foregoing, genes that are not expressed in the HUVECs have been removed before attempting any analysis. The 'below expression' level was set at 5 for the log 2 transformed expression values. This left 15,239 unique probes to analyze in HUVEC cultures. In the next step, the three sets of data were analyzed to establish the effect of the CM on gene expression in the cells and the differences induced by LMW-DS. A preliminary analysis was carried out to screen out genes that were not differentially expressed between any combination of the three datasets. Simple, non-stringent ANOVA ($p<0.05$) was carried out to look for patterns of expression. Genes with no changes across the three datasets were eliminated, leaving a total of 12,313 probes (10,368 genes) to analyze.

1551 genes were differentially expressed in HUVEC cultures when comparing the D0 control to the D2 control samples. The molecular functions influenced by these genes relate to cellular assembly and organization (2.55E-15-1.29E-03); cellular function and maintenance (2.55E-15-1.29E-03); cell cycle (1.98E-11-1.32E-03); cell morphology (3.18E-10-1.29E-03); gene expression (1.05E-08-2.01E-04); cellular development (1.66E-07-1.37E-03); cellular growth and proliferation (1.66E-07-1.37E-03); DNA replication, recombination, and repair (2.04E-07-9.84E-04); cell death and survival (2.09E-07-1.3E-03); RNA post-transcriptional modification (4.86E-06-6.53E-04); cellular movement (9.9E-06-1.18E-03); post-translational modification (1.92E-05-1.34E-03); cell-to-cell signaling and interaction (2.19E-05-9.1E-04); protein synthesis (5.49E-05-1.14E-03); cellular compromise (8.16E-05-8.16E-05); molecular transport (6.27E-04-6.27E-04); protein trafficking (6.27E-04-6.27E-04); cell signaling (8.86E-04-8.86E-04); cellular response to therapeutics (9.84E-04-9.84E-04); and protein degradation (1.14E-03-1.14E-03)

LMW-DS induced differential expression in HUVEC culture of 1779 genes as assessed when comparing the D0 control to the D2 LMW-DS treated samples. The molecular functions influenced by these genes relate to cellular assembly and organization (4.14E-17-9.7E-04); cellular function and maintenance (4.14E-17-8.05E-04); cell cycle (5.83E-14-9.85E-04); cell morphology (1.69E-10-7.48E-04); gene expression (7.99E-09-8.62E-04); cell death and survival (2E-08-8.4E-04); cellular development (1.28E-07-8.88E-04); cellular growth and proliferation (1.28E-07-8.88E-04); DNA replication, recombination, and repair (3.07E-07-9.7E-04); RNA post-transcriptional modification (1.13E-06-6.31E-04); cellular movement (1.42E-06-8.34E-04); post-translational modification (3.4E-05-9.17E-04); cell-to-cell signaling and interaction (6.97E-05-9.56E-04); molecular transport (7.43E-05-9.7E-04); protein trafficking (7.43E-05-7.43E-05); RNA trafficking (1.57E-04-5.72E-04); protein synthesis (1.92E-04-9.02E-04); cellular compromise (2.47E-04-6.28E-04); and cell signaling (4.64E-04-9.02E-04).

LMW-DS induced differential expression in HUVEC culture of 76 genes as assessed when comparing the D2 control to the D2 LMW-DS treated samples. The molecular functions influenced by these genes relate to DNA replication, recombination, and repair (9.62E-05-2.57E-02); cell cycle (1.22E-04-2.4E-02); cellular development (1.59E-04-2.67E-02); cell morphology (4.64E-04-2.42E-02); cellular function and maintenance (4.64E-04-2.57E-02); lipid metabolism (9.49E-04-1.07E-02); molecular transport (9.49E-04-1.61E-02); small molecule biochemistry (9.49E-04-1.87E-02); cellular compromise (1.6E-03-2.62E-02); cell death and survival (2.06E-03-2.67E-02); amino acid metabolism (2.7E-03-2.7E-03); carbohydrate metabolism (2.7E-03-1.07E-02); cell-to-cell signaling and interaction (2.7E-03-2.4E-02); cellular assembly and organization (2.7E-03-2.57E-02); cellular growth and proliferation (2.7E-03-2.4E-02); cellular movement (2.7E-03-2.4E-02); energy production (2.7E-03-2.7E-03); nucleic acid metabolism (2.7E-03-1.07E-02); post-translational modification (2.7E-03-1.61E-02); gene expression (5.39E-03-2.36E-02); RNA post-transcriptional modification (5.39E-03-2.4E-02); drug metabolism (8.07E-03-1.61E-02); vitamin and mineral metabolism (8.07E-03-8.07E-03); protein synthesis (1.07E-02-1.07E-02); RNA trafficking (1.07E-02-1.07E-02); cellular response to therapeutics (1.24E-02-1.24E-02); and free radical scavenging (1.43E-02-1.43E-02).

Although the overall difference between Control and LMW-DS-treated cultures after 2 days of treatment at first hand does not appear to be large, the effects of LMW-DS on gene expression changes were significant, in particular when considering the modulation of growth factor induced gene expression by LMW-DS.

Using the mechanistic molecular network model it is possible to simulate the effect of the genes differentially regulated by LMW-DS to look for the functional consequences of these changes. The in silico model indicated that LMW-DS inhibits neuronal cell death; apoptosis; and synthesis of protein and activates angiogenesis; migration of cells; cell viability; cell survival; cell movement; proliferation of cells; differentiation of cells; cellular homeostasis; cell cycle progression; cell transformation; and expression of RNA.

The HUVEC control cultures comprise growth factors. In the treated cultures, LMW-DS was added to the culture medium that already contained growth factors.

Table 7 summarizes the results of the gene expression changes in the cultured HUVECs. 67 genes that have altered expression in the Control cultures in the two days (under the effect of the growth factors) did not show any changes at all in the LMW-DS treated cultures during the same two days. 4 genes that had increased expression in the control cultures with the growth factors were downregulated in the LMW-DS treated cultures during the same two days. 11 genes that were downregulated by the growth factors in the control cultures were upregulated in the LMW-DS treated cultures during the two days. 120 genes were significantly downregulated by growth factors and this downregulation was even stronger in the LMW-DS treated cultures. 229 genes were upregulated in the Control cultures and the addition of LMW-DS made this upregulation significantly stronger.

TABLE 7

Overall pattern of gene expression changes in HUVECs

|  | abolished nutrient effect | enhanced response to nutrients | not different from control | total |
|---|---|---|---|---|
| no effect | 67 |  |  | 67 |
| significant downregulation | 4 | 120 | 167 | 291 |
| significant upregulation | 11 | 229 | 1326 | 1566 |
| total | 82 | 349 | 1493 | 1924 |

The effect of LMW-DS on several molecular pathways that are important for different disease conditions and therapeutic applications were analyzed. For the analysis, the effects of adding LMW-DS on gene expression was compared to that seen in cells in CM and the functional effects were predicted based on the observed changes in the expression patterns.

Expression Analysis of Motor Neurons

As described in the foregoing, genes that are not expressed in the motor neurons have been removed before attempting any analysis. The 'below expression' level was set at 5 for the log 2 transformed expression values. This left 12,240 unique probes where the expression threshold was met by at least three samples in the series. In the next step, the three sets of data were analyzed to establish the effect of the CM on the cells and the differences induced by the LMW-DS.

The changes in gene expression under normal culture conditions mimic the normal developmental processes of the motor neurons, when from a dissociated set of cells they develop a motor neuron phenotype. The growth factors in the normal culture medium are those necessary for these cells to differentiate. The stress factor present in these cultures is the oxidative stress (normal for tissue culture conditions).

485 genes were differentially expressed in motor neuron cultures when comparing the D0 control to the D2 control samples. The molecular functions influenced by these genes relate to cell death and survival (1.99E-17-1.98E-04); cellular movement (1.14E-16-1.91E-04); cellular assembly and organization (1.22E-16-1.93E-04); cellular function and maintenance (1.22E-16-1.95E-04); cell morphology (6.46E-16-1.74E-04); cell-to-cell signaling and interaction (3.16E-12-1.95E-04); cellular development (1.59E-10-1.93E-04); cellular growth and proliferation (1.59E-10-1.9E-04); molecular transport (4.27E-10-1.89E-04); protein synthesis (9.85E-09-5.03E-05); lipid metabolism (1.08E-08-1.61E-04); small molecule biochemistry (1.08E-08-1.89E-04); gene expression (8.45E-08-3.8E-05); cell cycle (4.55E-07-1.09E-04); free radical scavenging (7.12E-07-1.65E-04); cell signaling (1.23E-05-1.89E-04); vitamin and mineral metabolism (1.23E-05-1.89E-04); protein degradation (3.07E-05-1.31E-04); carbohydrate metabolism (3.32E-05-1.61E-04); drug metabolism (4.16E-05-4.16E-05); post-translational modification (7.1E-05-1.31E-04); and protein folding (7.1E-05-7.1E-05).

LMW-DS induced differential expression in motor neurons of 315 genes as assessed when comparing the D0 control to the D2 LMW-DS treated samples. The molecular functions influenced by these genes relate to cell death and survival (6.54E-08-9.06E-03), cellular movement (8.21E-08-5.42E-03); cellular assembly and organization (8.36E-08-9.01E-03); cellular function and maintenance (8.36E-08-9.01E-03); cell morphology (2.9E-06-8.75E-03); cellular development (1.04E-05-9.01E-03); cellular growth and proliferation (1.04E-05-7.83E-03); DNA replication, recombination, and repair (2.79E-05-8.01E-03); cell-to-cell signaling and interaction (8.18E-05-7.11E-03); post-translational modification (1.32E-04-7.56E-03); protein degradation (1.32E-04-4.35E-03); protein synthesis (1.32E-04-5.09E-03); gene expression (1.9E-04-9.01E-03); cellular compromise (3.58E-04-9.01E-03); cell cycle (6.08E-04-9.01E-03); free radical scavenging (7.41E-04-7.31E-03); amino acid metabolism (7.67E-04-6.61E-03); small molecule biochemistry (7.67E-04-9.01E-03); vitamin and mineral metabolism (7.67E-04-1.13E-03); lipid metabolism (1.05E-03-9.01E-03); molecular transport (1.05E-03-9.01E-03); cell signaling (1.13E-03-5.09E-03); and carbohydrate metabolism (4.71E-03-4.71E-03).

LMW-DS induced differential expression in motor neurons of 425 genes as assessed when comparing the D0 control to the D2 LMW-DS treated samples. The molecular functions influenced by these genes relate to cell death and survival (2.87E-08-6.27E-03); cellular movement (4.73E-07-6.47E-03); cell morphology (4.95E-07-7.47E-03); cellular development (1.02E-06-7.13E-03); cellular growth and proliferation (1.02E-06-7.48E-03); cellular assembly and organization (7.03E-06-7.47E-03); cellular function and maintenance (7.03E-06-7.47E-03); gene expression (1.95E-05-6.18E-03); cell cycle (2.88E-05-7.48E-03); DNA replication, recombination, and repair (3.39E-05-5.16E-03); amino acid metabolism (7.75E-05-4.68E-03); small molecule biochemistry (7.75E-05-4.68E-03); cellular compromise (8.23E-05-4.61E-03); cell-to-cell signaling and interaction (3.27E-04-7.48E-03); vitamin and mineral metabolism (3.27E-04-3.27E-04); protein synthesis (8.94E-04-5.29E-03); post-translational modification (9.67E-04-9.67E-04); molecular transport (9.7E-04-4.68E-03); protein trafficking (9.7E-04-9.7E-04); carbohydrate metabolism (1.44E-03-1.92E-03); cellular response to therapeutics (1.92E-03-1.92E-03); and lipid metabolism (4.68E-03-4.68E-03).

TABLE 8

Overall pattern of gene expression changes in motor neurons

|  | abolished nutrient effect | enhanced response to nutrients | new effect induced by LMW-DS | not different from control | total |
|---|---|---|---|---|---|
| no effect | 177 |  | 108 |  | 285 |
| significant downregulation | 47 | 36 | 375 | 104 | 562 |
| significant upregulation | 40 | 103 | 71 | 75 | 289 |
| total | 264 | 139 | 554 | 179 | 1136 |

Expression Analysis of Cortical Neurons

As described in the foregoing, genes that are not expressed in the motor neurons have been removed before attempting any analysis. The 'below expression' level was set at 5 for the log 2 transformed expression values. This left 10,653 unique probes where the expression threshold was met by at least three samples in the series. In the next step, the three sets of data were analyzed to establish the effect of the CM on the cells and the differences induced by the LMW-DS.

The changes in gene expression under normal culture conditions mimic the normal developmental processes of the cortical neurons, when from a dissociated set of cells they develop a cortical neuron phenotype. The growth factors in the normal culture medium are those necessary for these cells to differentiate. The stress factor present in these cultures is the oxidative stress (normal for tissue culture conditions).

1101 genes were differentially expressed in motor neuron cultures when comparing the D0 control to the D2 control samples. The molecular functions influenced by these genes relate to cellular assembly and organization (3.57E-25-6.65E-04); cellular function and maintenance (3.57E-25-6.65E-04); cell morphology (4.28E-22-6.36E-04); cellular development (4.28E-22-6.53E-04); cellular growth and proliferation (4.28E-22-6.6E-04); cell-to-cell signaling and interaction (2.16E-13-6.65E-04); molecular transport (5.18E-12-4.95E-04); cellular movement (1.86E-11-6.65E-04); cell death and survival (3.37E-11-6.41E-04); gene expression (1.27E-08-8.96E-05); protein synthesis (3.84E-07-8.69E-05); small molecule biochemistry (6.65E-07-5.18E-04); cellular compromise (7.12E-06-4.54E-04); protein degradation (1.62E-05-1.62E-05); amino acid metabolism (2.11E-05-4.25E-04); protein trafficking (3.4E-05-3.4E-05); cell signaling (8.69E-05-3E-04); post-translational modification (8.69E-05-2.15E-04); protein folding (2.15E-04-2.15E-04); cell cycle (2.69E-04-3.07E-04); DNA replication, recombination, and repair (2.69E-04-4.77E-04); nucleic acid metabolism (2.69E-04-2.69E-04); lipid metabolism (3.12E-04-5.18E-04); and carbohydrate metabolism (5.18E-04-5.18E-04).

LMW-DS induced differential expression in motor neurons of 609 genes as assessed when comparing the D0 control to the D2 LMW-DS treated samples. The molecular functions influenced by these genes relate to cellular assembly and organization (3.91E-15-1.83E-03); cellular function and maintenance (3.91E-15-1.83E-03); cell morphology (2.53E-13-1.43E-03); cellular development (2.53E-13-1.81E-03); cellular growth and proliferation (2.53E-13-1.83E-03); cellular movement (4.95E-09-1.2E-03); cell-to-cell signaling and interaction (5.96E-09-1.47E-03); cell death and survival (2.25E-08-1.77E-03); molecular transport (7.08E-08-1.79E-03); DNA replication, recombination, and repair (3.03E-06-1.71E-03); cellular compromise (9.23E-06-7.65E-04); amino acid metabolism (1.75E-05-1.64E-03); cell cycle (1.75E-05-1.77E-03); small molecule biochemistry (1.75E-05-1.79E-03); protein synthesis (2.77E-05-1.5E-03); protein trafficking (2.77E-05-1.9E-04); cell signaling (7.65E-05-1.73E-03); post-translational modification (3.01E-04-1.4E-03); gene expression (3.65E-04-1.15E-03); drug metabolism (6.49E-04-6.49E-04); carbohydrate metabolism (6.95E-04-7.69E-04); vitamin and mineral metabolism (1.09E-03-1.09E-03); and nucleic acid metabolism (1.44E-03-1.73E-03).

LMW-DS induced differential expression in motor neurons of 247 genes as assessed when comparing the D0 control to the D2 LMW-DS treated samples. The molecular functions influenced by these genes relate to cell morphology (6.01E-08-1.01E-02); cellular development (7.46E-08-1.01E-02); cellular growth and proliferation (7.46E-08-1.01E-02); cell death and survival (4.23E-07-1.01E-02); cellular movement (2.69E-06-9.91E-03); cellular assembly and organization (1.57E-05-1.01E-02); cellular function and maintenance (1.57E-05-1.01E-02); cell cycle (1.01E-04-1.01E-02); cell-to-cell signaling and interaction (1.01E-04-1.01E-02); lipid metabolism (1.56E-04-1.01E-02); small molecule biochemistry (1.56E-04-1.01E-02); gene expression (2.28E-04-3.38E-03); RNA damage and repair (2.28E-04-2.28E-04); RNA post-transcriptional modification (2.28E-04-2.28E-04); molecular transport (4.18E-04-8.32E-03); cellular compromise (4.47E-04-2.2E-03); protein synthesis (2.66E-03-7.29E-03); protein trafficking (4.11E-03-8.32E-03); protein degradation (5.64E-03-7.29E-03); and DNA replication, recombination, and repair (7.31E-03-1.01E-02).

TABLE 9

Overall pattern of gene expression changes in cortical neurons

| | abolished nutrient effect | enhanced response to nutrients | new effect induced by LMW-DS | not different from control | total |
|---|---|---|---|---|---|
| no effect | 572 | | 19 | | 591 |
| significant downregulation | 7 | 158 | 22 | 95 | 282 |
| significant upregulation | 33 | 43 | 7 | 221 | 304 |
| total | 612 | 612 | 48 | 316 | 1177 |

The Effect of LMW-DS on Oxidative Stress Pathways in Mitochondria

The oxidative stress pathways occurring in mitochondria are important not just for cancer but also for ageing and age-related degenerative diseases. Normal growth conditions trigger a certain amount of oxidative stress in cells, which contributes to both the in vivo and the in vitro ageing process.

Figure 18:
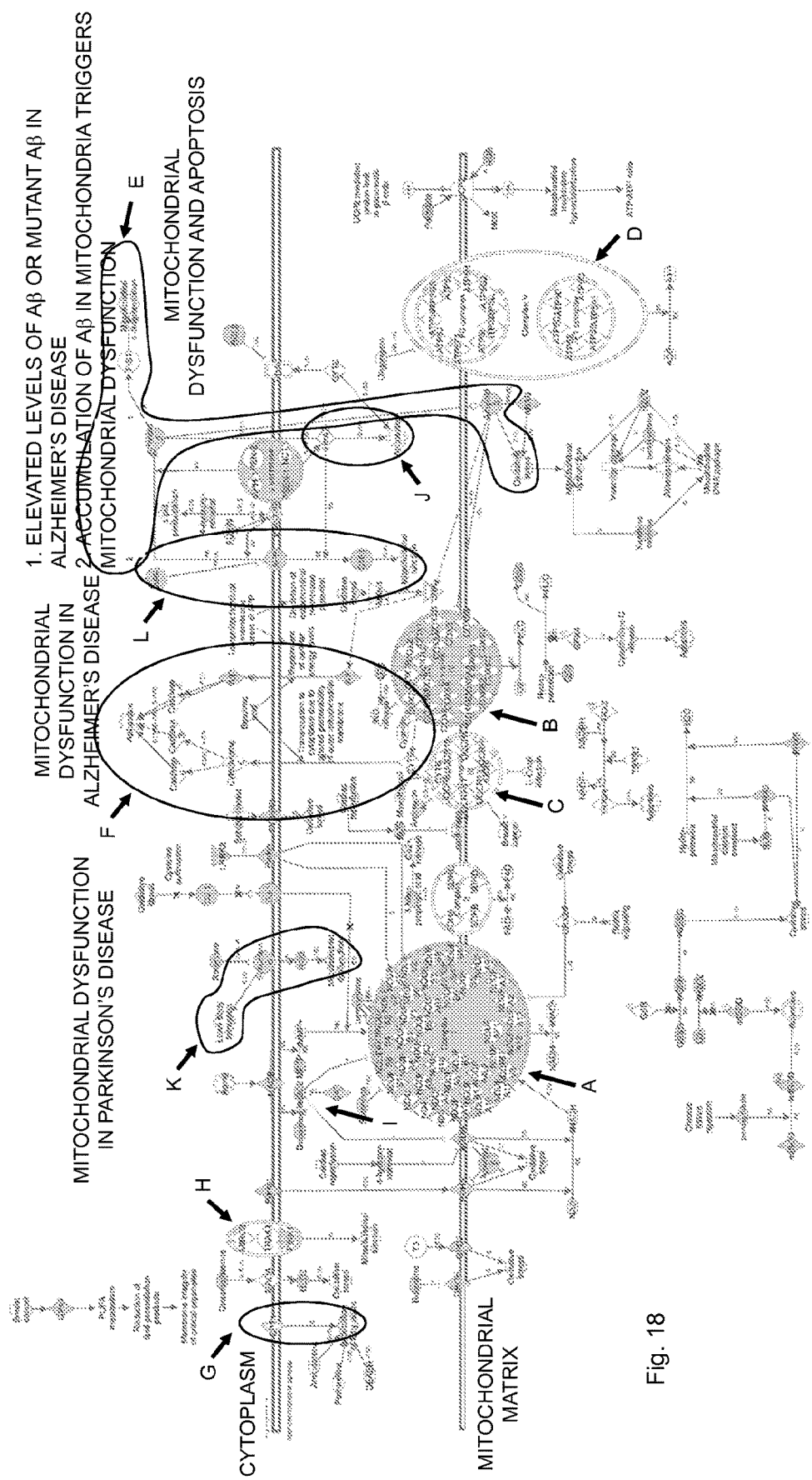
FIG. 18 schematically illustrates the effect on oxidative stress on mitochondrial (dys)function.

In Schwann cells cultured in normal conditions Complex I (NADH dehydrogenase), marked as A in FIG. 18, was inhibited while Complex IV (cytochrome c oxidase), marked as B in FIG. 18, was activated. When LMW-DS was added to the cultures Complex III (cytochrome bc1), marked as C in FIG. 18), was inhibited. The inhibition of Complex III inhibits the oxidative stress phenomena that are involved in the pathogenesis of cancer and neurological diseases.

Complex III, sometimes referred to as coenzyme Q: cytochrome c—oxidoreductase or the cytochrome bc1 complex, is the third complex in the electron transport chain (EC 1.10.2.2), playing a critical role in biochemical generation of ATP (oxidative phosphorylation). Complex III is a multi-subunit transmembrane protein encoded by both the mitochondrial (cytochrome b) and the nuclear genomes (all other subunits). Complex III is present in the mitochondria of all animals and all aerobic eukaryotes and the inner membranes of most eubacteria. Mutations in Complex III cause exercise intolerance as well as multisystem disorders. The bc1 complex contains 11 subunits, 3 respiratory subunits (cytochrome B, cytochrome C1, Rieske protein), 2 core proteins and 6 low-molecular weight proteins.

In HUVECs no significant modulation of the effects of oxidative stress on mitochondria was detected following treatment with LMW-DS.

In normal culture conditions the motor neurons appear to suffer from significant oxidative stress. This leads to the activation of some apoptotic mechanisms, marked as F in FIG. 18 and involving activation of cytochrome C, AIF, Caspase 3, 8 and 9. In addition, the motor neurons are characterized by production of amyloid-β in the cells, marked as E in FIG. 18, further exacerbating oxidative stress and mitochondrial fragmentation, via FIAS1, as well as the oxidation of fatty acids, marked as G in FIG. 18. Furthermore, Complex V, marked as D in FIG. 18, was activated.

The addition of LMW-DS to the cultures ameliorated these negative effects by preventing and inhibiting apoptosis by shutting down the reaction path marked as F in FIG. 18, preventing amyloid-β production and its negative effects on mitochondrial fragmentation and dysfunction, marked as E in FIG. 18, and subsequent damage and by inhibiting fatty acid oxidation, marked as G in FIG. 18. LMD-DS also inhibited the reaction path marked as H in FIG. 18 involving TRAK1 and PINK1, thereby contributing to improved mitochondrial function. LMW-DS further reduced the level of $H_2O_2$ indicated by I in FIG. 18. A further effect was the inhibition of HtrA2, marked as J in FIG. 18, contributing to inhibition of apoptosis.

In normal culture conditions the cortical neurons are exposed to significant oxidative stress leading to the production of amyloid-β and Lewy body formation, marked as K in FIG. 18 and involving activation of Synuclein α and increased levels of ROS; apoptosis, marked as F in FIG. 18; mitochondrial fragmentation, marked as E in FIG. 18; and reduction of mitochondrial function, marked as L in FIG. 18 and involving C161. The addition of LMW-DS to the cultures was able to prevent and reverse most of these deleterious effects, such as the accumulation of the amyloid-β and Lewy body pathology (marked as E, K in FIG. 18), mitochondrial dysfunction (marked as L in FIG. 18). Some apoptosis (marked as F in FIG. 18) inducing mechanisms remain active probably due to strong activation in the cultures.

The Effect of LMW-DS on Glutamate Excitotoxicity

Glutamate is an essential excitatory amino acid involved in long-term potentiation (LTP), i.e., learning and memory functions. However, too much glutamate is also associated with excitotoxicity, leading to neuronal death. This later phenomenon is hypothesized to be involved in the neuronal death triggered in chronic neurodegenerative conditions but also in TBI. The genes involved in glutamate signaling are not expressed in HUVECs but are present in the Schwann and neuron cell lines used in this study, see FIG. 19.

Glutamate production was inhibited by the baseline conditions in the motor neuron cultures. The inhibition was not affected by LMW-DS. Glutamate production was elevated in the cortical neurons at baseline. The addition of LMW-DS dis not alter the glutamate production in these cells.

The addition of LMW-DS to the CM of the Schwan cells induced the expression of a protein complex (CALM, Gβγ, GRM7, PICK1), marked as A in FIG. 19. More importantly, LMW-DS increased activity and/or levels of glutamate transporters in the Schwann cells, and in particular of SLC1A2/3, thereby leading to a scavenging of glutamate produced by and released from the presynaptic neuron. Accordingly, LMW-DS induced the Schwann cells to remove the toxic glutamate from the synaptic cleft, thereby preventing it from exerting its excitotoxicity.

SLC1A3, solute carrier family 1 (glial high-affinity glutamate transporter), member 3, is a protein that, in humans, is encoded by the SLC1A3 gene. SLC1A3 is also often called the GLutamate ASpartate Transporter (GLAST) or Excitatory Amino Acid Transporter 1 (EAAT1). SLC1A3 is predominantly expressed in the plasma membrane, allowing it to remove glutamate from the extracellular space. It has also been localized in the inner mitochondrial membrane as part of the malate-aspartate shuttle. SLC1A3 functions in vivo as a homotrimer. SLC1A3 mediates the transport of glutamic and aspartic acid with the cotransport of three $Na^+$ and one $H^+$ cations and counter transport of one $K^+$ cation. This co-transport coupling (or symport) allows the transport of glutamate into cells against a concentration gradient. SLC1A3 is expressed throughout the CNS, and is highly expressed in astrocytes and Bergmann glia in the cerebellum. In the retina, SLC1A3 is expressed in Muller cells. SLC1A3 is also expressed in a number of other tissues including cardiac myocytes.

SLC1A2, solute carrier family 1 member 2, also known as excitatory amino acid transporter 2 (EAAT2) and glutamate transporter 1 (GLT-1), is a protein that in humans is encoded by the SLC1A2 gene. SLC1A2 is a member of a family of the solute carrier family of proteins. The membrane-bound protein is the principal transporter that clears the excitatory neurotransmitter glutamate from the extracellular space at synapses in the CNS. Glutamate clearance is necessary for proper synaptic activation and to prevent neuronal damage from excessive activation of glutamate receptors. SLC1A2 is responsible for over 90% of glutamate reuptake within the brain.

These findings indicate that LMW-DS may be useful for the prevention of glutamate excitotoxicity in conditions where its high extracellular levels is harmful, like after TBI.

The Effect of LMW-DS on Cell Adhesion

One of the strong noticeable phenotypic effects of LMW-DS was the effect on cell adhesion, which was cell type specific. Cell adhesion was affected in neurons most strongly, then in Schwann cells, while HUVECs were not affected.

The analysis of gene expression indicated that this is due to the effect of LMW-DS on the expression of enzymes that regulate cell attachment including metallopeptidases, also referred to as matrix metalloproteinases (MMPs), see Table 10.

The aggregate effect of these molecules on the pathways regulating cell movement and attachment in Schwann cells (17 molecules, see Table 10) was such that cell adhesion would be inhibited while cell movement would be activated, while in HUVECs (1 molecule, ADAM11) adhesion would not be affected but angiogenesis would be activated.

TABLE 10

Molecules of the pathway regulating cell movement and attachment in Schwann cells

| Symbol | Entrez gene name | Location | Type(s) |
|---|---|---|---|
| A2M | alpha-2-macroglobulin | Extracellular Space | transporter |
| ADAM10 | ADAM metallopeptidase domain 10 | Plasma Membrane | peptidase |
| ADAM23 | ADAM metallopeptidase domain 23 | Plasma Membrane | peptidase |
| ADAMTS9 | ADAM metallopeptidase with thrombospondin type 1 motif 9 | Extracellular Space | peptidase |

TABLE 10-continued

Molecules of the pathway regulating cell movement and attachment in Schwann cells

| Symbol | Entrez gene name | Location | Type(s) |
| --- | --- | --- | --- |
| CDH11 | cadherin 11 | Plasma Membrane | other |
| CSF3 | colony stimulating factor 3 | Extracellular Space | cytokine |
| FAS | Fas cell surface death receptor | Plasma Membrane | transmembrane receptor |
| HIF1A | hypoxia inducible factor 1 alpha subunit | Nucleus | transcription regulator |
| IL6 | interleukin 6 | Extracellular Space | cytokine |
| IL15 | interleukin 15 | Extracellular Space | cytokine |
| LUM | lumican | Extracellular Space | other |
| MMP3 | matrix metallopeptidase 3 | Extracellular Space | peptidase |
| POSTN | periostin | Extracellular Space | other |
| RECK | reversion inducing cysteine rich protein with kazal motifs | Plasma Membrane | other |
| SERPINA3 | serpin family A member 3 | Extracellular Space | other |
| TNC | tenascin C | Extracellular Space | other |
| VCAM1 | vascular cell adhesion molecule 1 | Plasma Membrane | transmembrane receptor |

The effect of differential gene expression induced by LMW-DS in neurons was analyzed. In the motor neurons the same metallopeptidase-dependent pathways could be responsible for the cell detachment seen in the Schwann cells, see Table 11.

TABLE 11

Molecules of the pathway regulating cell movement and attachment in motor neurons

| Symbol | Entrez Gene Name | Location | Type(s) |
| --- | --- | --- | --- |
| ADAM11 | ADAM metallopeptidase domain 11 | Plasma Membrane | peptidase |
| ADAM19 | ADAM metallopeptidase domain 19 | Plasma Membrane | peptidase |
| ADAMTS7 | ADAM metallopeptidase with thrombospondin type 1 motif 7 | Extracellular Space | peptidase |
| ADORA1 | adenosine A1 receptor | Plasma Membrane | G-protein coupled receptor |
| AGT | angiotensinogen | Extracellular Space | growth factor |
| APP | amyloid beta precursor protein | Plasma Membrane | other |
| CD44 | CD44 molecule (Indian blood group) | Plasma Membrane | other |
| F2R | coagulation factor II thrombin receptor | Plasma Membrane | G-protein coupled receptor |
| FAS | Fas cell surface death receptor | Plasma Membrane | transmembrane receptor |
| FGF2 | fibroblast growth factor 2 | Extracellular Space | growth factor |
| FN1 | fibronectin 1 | Extracellular Space | enzyme |
| HBEGF | heparin binding EGF like growth factor | Extracellular Space | growth factor |
| ITGAM | integrin subunit alpha M | Plasma Membrane | transmembrane receptor |
| JUN | Jun proto-oncogene, AP-1 transcription factor subunit | Nucleus | transcription regulator |
| KDR | kinase insert domain receptor | Plasma Membrane | kinase |
| MMP15 | matrix metallopeptidase 15 | Extracellular Space | peptidase |
| MMP17 | matrix metallopeptidase 17 | Extracellular Space | peptidase |
| NREP | neuronal regeneration related protein | Cytoplasm | other |
| PLAT | plasminogen activator, tissue type | Extracellular Space | peptidase |
| PPIA | peptidylprolyl isomerase A | Cytoplasm | enzyme |
| PSEN1 | presenilin 1 | Plasma Membrane | peptidase |
| SDC1 | syndecan 1 | Plasma Membrane | enzyme |
| SERPINE2 | serpin family E member 2 | Extracellular Space | other |
| SNAP23 | synaptosome associated protein 23 | Plasma Membrane | transporter |
| STX12 | syntaxin 12 | Cytoplasm | other |
| TIMP3 | TIMP metallopeptidase inhibitor 3 | Extracellular Space | other |
| TIMP4 | TIMP metallopeptidase inhibitor 4 | Extracellular Space | other |
| TPSAB1/TPSB2 | tryptase alpha/beta 1 | Extracellular Space | peptidase |

However, none of the MMP-related genes were found to be differentially expressed in the cortical neurons.

This finding led to the re-assessment of all molecular interactions that affect cell attachment and adhesion related molecules and their effect on cellular attachment in the four different cultures. The full list of the 217 attachment-related molecules (197 genes and 20 drugs) are presented below:

ACE2, ACP1, ADAM15, ADGRB1, ADGRE2, ADIPOQ, AG490, AMBN, ANGPT1, ANTXR1, ARAP3, ARMS2, batimastat, BCAM, BCAP31, BCAR1, benzyloxycarbonyl-Leu-Leu-Leu-aldehyde, BMP2, BMP4, BTC, C1QBP, $Ca^{2+}$, CA9, CADM1, CALR, calyculin A, caspase, CBL, CD209, CD36, CD44, CD46, CDH13, cerivastatin, chloramphenicol, chondroitin sulfate, CLEC4M, colchicine, Collagen type I, Collagen(s), COMP, CRK, CRP, CSF1, CSF2RB, CTGF, curcumin, CXCL12, cyclic AMP, DAB2, DAG1, DCN, DDR1, desferriexochelin 772SM, DOCK2, DSG2, DSG4, durapatite, Efna, EFNA1, EFNB, EFNB1, EGF, EGFR, EGR1, ELN, ENG, EP300, Eph Receptor, EPHA8, EPHB1, eptifibatide, ethylenediaminetetraacetic acid, ETS1, F11R, F3, FBLN5, FBN1, Fc receptor, FCN2, FERMT2, FES, FGF2, FGFR1, Fibrin, FN1, Focal adhesion kinase, FSH, FUT3, FUT6, FUT7, FYN, HACD1, heparin, Histone h3, Histone h4, HRAS, HSPG2, HTN1, hyaluronic acid, hydrocortisone, hydrogen peroxide, ICAM1, ICAM2, IGF1R, IgG, Igg3, IL1, IL1B, IL6, ILK, Integrin, Integrin alpha 4 beta 1, Integrina, IPO9, ITGA1, ITGA2, ITGA3, ITGA5, ITGA6, ITGB1, ITGB2, ITGB3, ITGB5, JAK2, Jnk, KP-SD-1, LAMC1, Laminin, Laminin1, levothyroxine, LGALS3, LIF, lipopolysaccharide, LOX, LRP1, LRPAP1, MAD1L1, mannose, MAPK7, MBL2, MERTK, metronidazole, MGAT5, MMP2, $Mn^{2+}$, NCK, NEDD9, NRG1, okadaic acid, OLR1, P38 MAPK, PDGF BB, phosphatidylinositol, PKM, platelet activating factor, PLD1, PLG, PMP22, PODXL, POSTN, PRKCD, PTAFR, PTEN, PTGER2, PTK2, PTK2B, PTN, PTPN11, PTPRZ1, pyrrolidine dithiocarbamate, Rac, RALB, RANBP9, RHOA, RHOB, RPSA, SDC3, SELE, Selectin, SELL, SEMA3A, simvastatin, SIRPA, SPARC, sphingosine-1-phosphate, SPI1, SPP1, SPRY2, SRC, STARD13, SWAP70, TEK, TFPI, TFPI2, TGFA, TGFB1, TGFBI, TGM2, THBS2, THY1, thyroid hormone, TIMP2, tirofiban, TLN1, TLN2, TNF, TP63, tretinoin, VAV1, VCAM1, VCAN, Vegf, VHL, VTN, VWF, and WRR-086.

Of the 197 genes regulating cell attachment none are differentially regulated by LMW-DS in HUVECs. In the Schwann cell cultures the 17 molecules differentially expressed lead to an overall slightly increased attachment. However, in the neurons the expression patterns lead to significant inhibition of cellular attachment in these cells.

The results explain the cell-type-specific effects of LMW-DS on cell adhesion. The findings are also relevant for an anti-scarring effect of LMW-DS (see Example 5) by reducing the signals of tissue fibrosis and adhesion of immune cells.

Upstream Regulator Pathways Affected by LMW-DS

In Schwann cells, the upstream regulator analysis revealed that LMW-DS modulated the effect of several growth factors by either increasing their activation or reducing their inhibition in the system as shown in Table 12.

TABLE 12

Upstream regulator comparison in Schwann cells

| Analysis | Upstream regulator | Predicted activation state relative D2 control | Activation z-score | p-value of overlap |
| --- | --- | --- | --- | --- |
| D2 control | ANGPT2 | | 1.062 | 0.003 |
| D2 LMW-DS treatment | | Activated | 1.283 | 0.00373 |
| D2 control | BMP2 | | 0.674 | 0.0126 |
| D2 LMW-DS treatment | | Activated | 1.395 | 0.00326 |
| D2 control | BMP4 | | −0.272 | 0.00253 |
| D2 LMW-DS treatment | | Activated | 0.927 | 0.000663 |
| D2 control | BMP7 | | 1.45 | 0.0346 |
| D2 LMW-DS treatment | | Activated | 1.86 | 0.0225 |
| D2 control | EGF | | −0.015 | 0.0000927 |
| D2 LMW-DS treatment | | Activated | 2.059 | 0.00735 |
| D2 control | FGF2 | | 1.366 | 0.0000142 |
| D2 LMW-DS treatment | | Activated | 2.37 | 0.000395 |
| D2 control | GDF2 | | 1.556 | 0.000299 |
| D2 LMW-DS treatment | | Activated | 2.561 | 0.000106 |
| D2 control | HGF | | −0.823 | 0.0114 |
| D2 LMW-DS treatment | | Activated | 1.432 | 0.0161 |
| D2 control | IGF1 | | 0.365 | 0.00883 |
| D2 LMW-DS treatment | | Activated | 1.332 | 0.0132 |
| D2 control | NRG1 | | 1.073 | 0.0473 |
| D2 LMW-DS treatment | | Activated | 1.768 | 0.143 |
| D2 control | NRTN | | | 0.0118 |
| D2 LMW-DS treatment | | Activated | 0.958 | 0.0149 |
| D2 control | PGF | | 0 | 0.00185 |
| D2 LMW-DS treatment | | Activated | 0.254 | 0.00871 |
| D2 control | TGFβ1 | | −1.239 | 0.0000354 |
| D2 LMW-DS treatment | | Less inhibited | 1.05 | 0.0000691 |
| D2 control | VEGFA | | 1.909 | 0.00981 |
| D2 LMW-DS treatment | | Activated | 3.4 | 0.00186 |
| D2 control | WISP2 | | −1.067 | 0.0323 |
| D2 LMW-DS treatment | | Less inhibited | −0.896 | 0.0349 |

In HUVECs the number of growth factors whose effect was enhanced by LMW-DS was relatively smaller but still highly significant, see Table 13.

TABLE 13

Upstream regulator comparison in HUVECs

| Analysis | Upstream regulator | Predicted activation state relative D2 control | Activation z-score | p-value of overlap |
| --- | --- | --- | --- | --- |
| D2 control | HGF | | 2.602 | 0.0000181 |
| D2 LMW-DS treatment | | Activated relative to control | 3.194 | 0.00000793 |
| D2 control | TGFβ1 | | 0.682 | 0.00328 |
| D2 LMW-DS treatment | | Activated relative to control | 1.429 | 0.0338 |
| D2 control | VEGF | | 3.113 | 2.78E-08 |
| D2 LMW-DS treatment | | Activated relative to control | 3.432 | 6.33E-09 |

In the motor neurons the upstream regulator analysis revealed that LMW-DS affected the effect of several growth factors either increasing their activation or reducing the inhibitions present in the system as shown in Table 14.

TABLE 14

Upstream regulator comparison in motor neurons

| Analysis | Upstream regulator | Predicted activation state relative D2 control | Activation z-score |
| --- | --- | --- | --- |
| D0 to D2 control | AGT | Activated | 2.292 |
| D0 to LMW-DS treatment | | Activated | 2.631 |
| D0 to D2 control | BMP4 | | 0.798 |
| D0 to LMW-DS treatment | | More activated relative to control | 0.972 |
| D0 to D2 control | BMP6 | | −0.269 |
| D0 to LMW-DS treatment | | More activated relative to control | 0.13 |
| D0 to D2 control | BMP7 | | −0.862 |
| D0 to LMW-DS treatment | | More activated relative to control | 1.092 |
| D0 to D2 control | INHA | | 2.292 |
| D0 to LMW-DS treatment | | More activated relative to control | 0.588 |

In cortical neurones in normal culture conditions most growth factor dependent pathways were significantly activated by the normal culture medium. In most instances this activation was not altered by LMW-DS. However, LMW-DS activated molecules that are the downstream effector of GDF7 indicating that the effect of this growth factor was enhanced by LMW-DS. As GDF7 is a powerful differentiation factor for neurons, and the additional activation of these growth factors, to the activation of BDNF and NT3, provide a good explanation for the enhanced differentiation of these cells in culture.

Discussion

The normal culture conditions for HUVECs mimics the environment following tissue hypoxia and reperfusion, containing a high nutrient content and growth factors also supplemented with heparin. The LMW-DS-treated cultures mimicked the effect of LMW-DS added after 24 hours of hypoxia and reperfusion. The real life scenario this relates to is that of angiogenesis following ischemic conditions, such as stroke.

In Schwann cells, the control cultures, with high nutrient content and glucose, recapitulate the activation of Schwann cells. The LMW-DS-treated cultures mimicked the effect of LMW-DS added after 24 hours of glial activation. The real life scenario that this recapitulates is glial activation following damage to the nervous system, such as following TBI.

The normal culture conditions for the neurons, both motor neurons and cortical neurons, with high nutrient content and growth factors mimic the environment during normal neuronal differentiation. The only negative effect in these cultures is the oxidative stress the cells suffer. The real life scenario this relates to is the degenerative conditions driven by oxidative stress in the presence of ample growth and differentiation factors. This corresponds to an early stage of a neurodegenerative disease or condition where oxidative stress plays a privotal role.

It is clear from the cell types that the molecular effects seen in Schwann cells and in HUVECs support a role for LMW-DS in protection against apoptosis; induction of angiogenesis; increased migration and movement of cells; increased cell viability and survival; and induction of cellular differentiation. The analysis of pivotal molecular pathways indicated that in neurons LMW-DS will reduce the effect of oxidative stress on mitochondria and will reduce neurodegeneration-related molecules, such as amyloid-β and Lewy bodies.

Accordingly, the results from the HUVEC cell model indicates that LMW-DS can protect against cell damage and promotes the development of new blood vessels in injured or diseased tissue, such as following stroke. The results from the Schwann cells indicate that LMW-DS can protect against cell loss in a diseased or damaged nervous system, such as due to TBI or a neurodegenerative disease.

The analysis of pivotal molecular pathways indicated that in Schwann cells LMW-DS reduced the effect of oxidative stress on mitochondria and increased the uptake of glutamate. The results in Schwann cells indicate that LMW-DS can protect against cell loss that occurs due to oxidative stress and glutamate excitotoxicity in the diseased or damaged nervous system, which is of relevance in, for instance, neurodegenerative diseases and TBI.

Of particular importance, LMW-DS increased the glutamate uptake in glia cells, as presented by Schwann cells. However, LMW-DS did not alter the production of glutamate by neurons. This is important since glutamate is needed for LTP, learning and memory. Thus, it is beneficial that LMW-DS did not alter production of glutamate by neurons since this glutamate is needed for the normal neurotransmission in the above mentioned processed. However, the increased levels of glutamate released from damaged or dying cells will be effectively taken up by surrounding glial cells due to the effects of LMW-DS. Thus, the activation of glutamate transporters in the glial cells caused by LMW-DS effectively removed the glutamate released by the damaged or dying neurons from the neural cleft. This in turn prevented the glutamate from exerting its excitotoxicity and thereby damaging further neurons. Accordingly, LMW-DS induced the uptake of the potentially harmful neurotoxic amounts of glutamate by the glial cells.

The results in the neurons therefore confirm the potential therapeutic usefulness of LMW-DS in neurodegenerative diseases, disorders and conditions by reducing secondary tissue damage due to oxidative stress, promoting repair, and reducing degeneration-related protein accumulation.

Taken together the results support the role of LMW-DS in protection against apoptosis in general and protection against neuronal cell death in particular, induction of angiogenesis, increased migration and movement of cells, increased cell viability and survival, induction of cellular differentiation, reduction of the effects of oxidative stress, reduction of glutamate excitotoxicity and reduction of the production of degeneration-related protein products, such as amyloid-β and Lewy bodies.

Cell adhesion was affected mainly in neurons and Schwann cells, where LMW-DS promoted cell detachment and movement. In HUVECs, cell adhesion was not affected. The effect on cell adhesion was mainly due to the expression of metalloproteinase-type enzymes, but the modulation of other adhesion molecules contributed to this effect as well.

This finding would also explain an anti-scarring effect of LMW-DS as seen in Example 5. The result suggests that the anti-scarring effect seen in Example 5 is mediated by LMW-DS activating degrading enzymes that help tissue remodeling and block the fibrogenic (scarring) signals in damaged tissues.

Scarring as a pathological reaction is driven by TGFβ. TGFβ induces a large interconnected network of 171 molecules causing adhesion of immune cells, activation of cells, cell movement, aggregation of cells, fibrosis and induction of TGFβ. Administration of LMW-DS totally abolished the TGFβ-induced effect in adhesion of immune cells, activation of cells, aggregation of cells, fibrosis and self-activation of TGFβ. These inactivating effects of LMW-DS on the molecular networks driven by TGFβ in Schwann cells are also seen even when TGFβ is activated, i.e., even in the presence of excessive TGFβ.

The effects revealed by the gene expression data support the phenotypic changes seen in Example 1 with regard to cell attachment, as well as on differentiation and cell survival.

These studies therefore confirm the potential therapeutic usefulness of LMW-DS in post-ischemic states, by promoting revascularisation, reducing secondary tissue damage, and promoting repair, and for neurodegenerative diseases, disorders and conditions, where it could promote neuronal survival, differentiation and ultimately repair.

The analysis of the upstream regulators of the genes regulated by LMW-DS indicated that LMW-DS enhanced the effect of existing growth factors on cells, similar to the effect of heparin. A hypothesis is that LMW-DS binds to the growth factor molecules and facilitates binding to their receptors.

This hypothesis is also supported by the observation that the LMW-DS-induced differential gene expression in HUVECs, where the normal CM already contains heparin, was relatively smaller than in the Schwann cells where the normal CM did not contain heparin.

This mechanism of action also explains why LMW-DS is effective in the acute stage of TBI as seen in Example 3, when growth factors are present, but less effective at later stage when the initial repair attempt has already diminished.

Thus, it could be possible that at least some of the therapeutic effects of LMW-DS depends on existing repair mechanisms, which are amplified by it. In such a case, it is generally recommended that in any neurodegenerative condition LMW-DS is given in the early stage of the disease or condition when there is enough repair potential in the tissue.

By protecting cell metabolism, LMW-DS may be a useful protective treatment in many degenerative conditions where cells are progressively lost due to ischemic, oxidative or traumatic damage. Non-limiting, but illustrative, examples of such degenerative conditions include stroke, ALS, MS, dementia, TBI, SCI, retinal damage, AD, etc. LMW-DS may help those damaged tissues to recover some lost function as it enhances the residual intrinsic repair mechanisms.

The anti-scarring actions of LMW-DS indicate a potential use to treat fibroproliferative (scarring) conditions. These include, for instance, glaucoma, proliferative vitreoretinopathy, SAH, brain and spinal trauma injuries, invasive surgical procedures, surgical adhesions, rotator cuff injuries, burns, reconstructive surgery, ulcerative conditions (diabetes), etc. The experimental results support the role of LMW-DS in both preventing the development of fibroproliferative (scarring) conditions and resolving already established fibrotic scars in such fibroproliferative (scarring) conditions.

Example 5

The present experiment investigated the effect of LMW-DS on trabecular meshwork (TM) scarring on glaucomatous eyes Materials and Methods Study Design Glaucoma was induced in adult male Sprague Dawley rats by repeat twice weekly intracameral (IC) injections of transforming growth factor-β (TGF-β) to increase intraocular pressure (IOP). Sustained increases in IOP (after two weeks) leads to death of retinal ganglion cells (30-40%). LMW-DS was administered at 15 mg/kg by daily subcutaneous injection from the start of the experiment to assess RGC protection compared to controls.

Group 1 n=12 rats; 24 eyes IOP-FIC TGF-β (twice weekly for 28 days) between day 0 and day 28+ daily subcutaneous administration of dextran sulfate from day 14 to day 28.

Group 2 n=8 rats; 16 eyes IOP+IC TGF-β (twice weekly for 28 days) between day 0 and day 28+ daily subcutaneous administration of vehicle (saline) from day 14 to day 28.

Group 3 n=8 rats; 8 eyes IOP+intact (uninjured eye) and 8 eyes IOP+IC PBS daily for 28 days.

Measured End-Points

IOP twice weekly throughout study from day 0 to day 28;
Immunohistochemistry for counting retinal ganglion cell (RGC) that are immunoreactive for brain-specific homeobox/POU domain protein 3A (Brn3a) at day 28 (RGC survival);
Immunohistochemistry for laminin and fibronectin to evaluate scarring in the trabecular meshwork at day 28 in Groups 1 and 2;

Anterior segment and optical coherence tomography (OCT) imaging at day 28 to examine the angle and the thickness of the retinal nerve fiber layer comprising RGC axons; and Body weight at day 28.

Animals and Surgery

Sixteen 8 to 10 week-old male 175-200 g Sprague Dawley rats (Charles River, Kent, UK), housed with free access to food and water under a 12 h dark/light cycle, were used for these experiments. Surgery was performed at the Biomedical Services Unit at the University of Birmingham in accordance with the Home Office guidelines set out in the 1986 Animal Act (UK) and the ARVO Statement for the Use of Animals in Ophthalmic and Vision Research. All ocular surgical procedures and IOP measurements were completed under inhalational anesthesia using 2-5% isofluorane/95% 02 (National Vet Supplies, Stoke, UK) at a flow rate of 1.5 l/min. The post-operative welfare of all rats was monitored closely.

At day 0, one self-sealing incision was made through the cornea into the anterior chamber of both eyes using a 15° disposable blade enabling repeated, twice a week (bi-weekly), 3.5 µl IC injections (every Monday and Thursday) through the tunnel generated using self-made disposable sterile glass micropipettes (Harvard Apparatus, Kent, UK) for 28 days of active human recombinant TGF-β1 (5 ng/µl; Peprotech, London, UK).

Tissue Preparation for Immunohistochemistry (IHC)

Rats were killed by exposure to increasing concentrations of $CO_2$ and transcardially perfused with 100 ml of phosphate-buffered saline (PBS) to wash out blood before further perfusion with 100 ml 4% paraformaldehyde (PFA) in PBS at pH 7.4. Dissected eyes for IHC were post-fixed by immersion in 4% PFA in PBS for 2 h at 4° C. before cryoprotection by immersion in increasing concentrations of sucrose solutions (PBS with 10%, 20% and 30% sucrose; all from Sigma, Poole, UK) for 24 h each at 4° C. then embedded in optimal cutting temperature embedding medium (Thermo Shandon, Runcorn, UK) in peel-away mold containers (Agar Scientific, Essex, UK). Eyes immersed in optimal cutting temperature embedding medium were rapidly frozen in crushed dry ice before storage at −80° C. and later sectioned in the parasagittal plane through the optic nerve head at −22° C. using a Bright cryostat microtome (Bright, Huntingdon, UK) at a thickness of 15 µm. Sections were mounted on positively charged glass slides (Superfrost plus; Fisher Scientific, Pittsburgh, USA), left for 2 h to dry at 37° C. and stored at −20° C.

Immunohistochemistry

Frozen sections were left to thaw for 30 min before 3×5 min washing in PBS followed by a 20 min permeabilization with 0.1% Triton X-100 (Sigma). Sections were blocked for 30 min in 0.5% bovine serum albumin (BSA) and 0.3% Tween-20 (all from Sigma) in PBS and were incubated overnight in primary antibody (Table 11) before washing 3×5 min in PBS and incubating for 1 h at room temperature (RT; 20-25° C.) with secondary antibody (Table 11). Sections were then washed 3×5 min in PBS and mounted in Vectorshield mounting medium containing 4',6-diamidino-2-phenylindole (DAPI) (Vector Laboratories). Control tissue sections incubated with secondary antibody alone were all negatively stained (not shown).

TABLE 11

Antibodies used in immunohistochemistry

| Antigen | Dilution | Supplier | Catalogue No. | To identify |
|---|---|---|---|---|
| Laminin | 1:200 | Sigma | L9393 | TM fibrosis |
| Fibronectin | 1:200 | Sigma | F3648 | TM fibrosis |
| Goat Anti-mouse IgG Alexa Fluor 594 | 1:400 | Molecular Probes | A-11032 | Secondary IgG for ED1 primary antibody |
| Goat Anti-rabbit IgG, Alexa Fluor 488 | 1:400 | Molecular Probes | A-21206 | Secondary IgG for rabbit primary antibodies |

Quantification of Immunohistochemistry

After immunofluorescence staining, sections were viewed on a Zeiss Axioplan 2 epi-fluorescent microscope (Carl Zeiss Ltd) and images captured using the same exposure times for each antibody using a Zeiss AxioCam HRc. IHC was quantified according to the methods previously described (Hill et al., Decorin reduces intraocular pressure and retinal ganglion cell loss in rodents through fibrolysis of the scarred trabecular meshwork. *Invest Ophthalmol Vis Sci.* 2015, 56(6): 3743-3757). Briefly, the region of interest used for quantitation of TM fibrosis was defined by a quadrant of the same prescribed size for all eyes/treatments within the TM, and ECM deposition was quantified within this defined quadrant of the TM and the % immunofluorescent pixels above a standardized background threshold calculated using ImageJ software (National Institutes of Health, USA). For each antibody, the threshold level of brightness in the area of the TM was set using intact untreated eye sections to define the reference level for test group analysis of pixel intensity. Images were assigned randomized numbers to ensure blinding of treatment groups during quantification by the assessor.

For quantification of RGC in retinal sections, $RPBMS^+$/$DAPI^+$ RGC were counted in 15 µm thick parasagittal sections of retina from a 250 µm linear portion from the ganglion cell layer at either side of the optic nerve. Four retinal sections from each eye in the control and treatment groups were quantified. Images were assigned randomized numbers to ensure blinding of treatment groups during quantification by the assessor.

Statistics

All statistical analyses were performed using SPSS 20 (IBM, USA). Normal distribution tests were carried out to determine the most appropriate statistical analysis to compare treatments. Statistical significance was determined at p<0.05. TM fibrosis were tested for significant differences using Student t test or 1-way ANOVA for >2 Group comparisons±SEM and are given in the text or displayed graphically as mean±SEM.

Results

Figure 20:
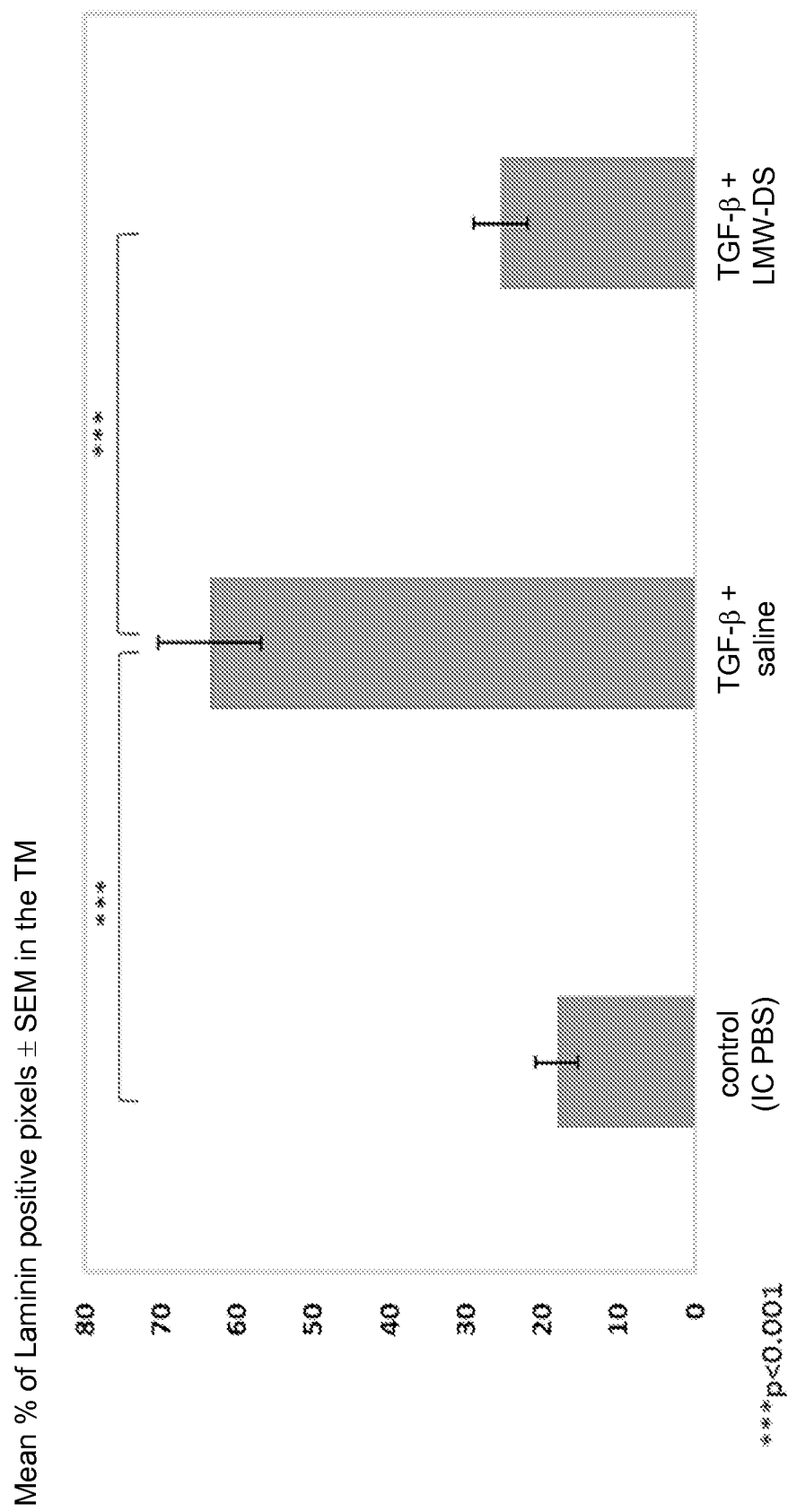
FIG. 20 is a diagram illustrating changes in laminin immunoreactivity in the angle in subjects suffering from primary open-angle glaucoma (POAG) and treated with saline control or LMW-DS.
Figure 21:
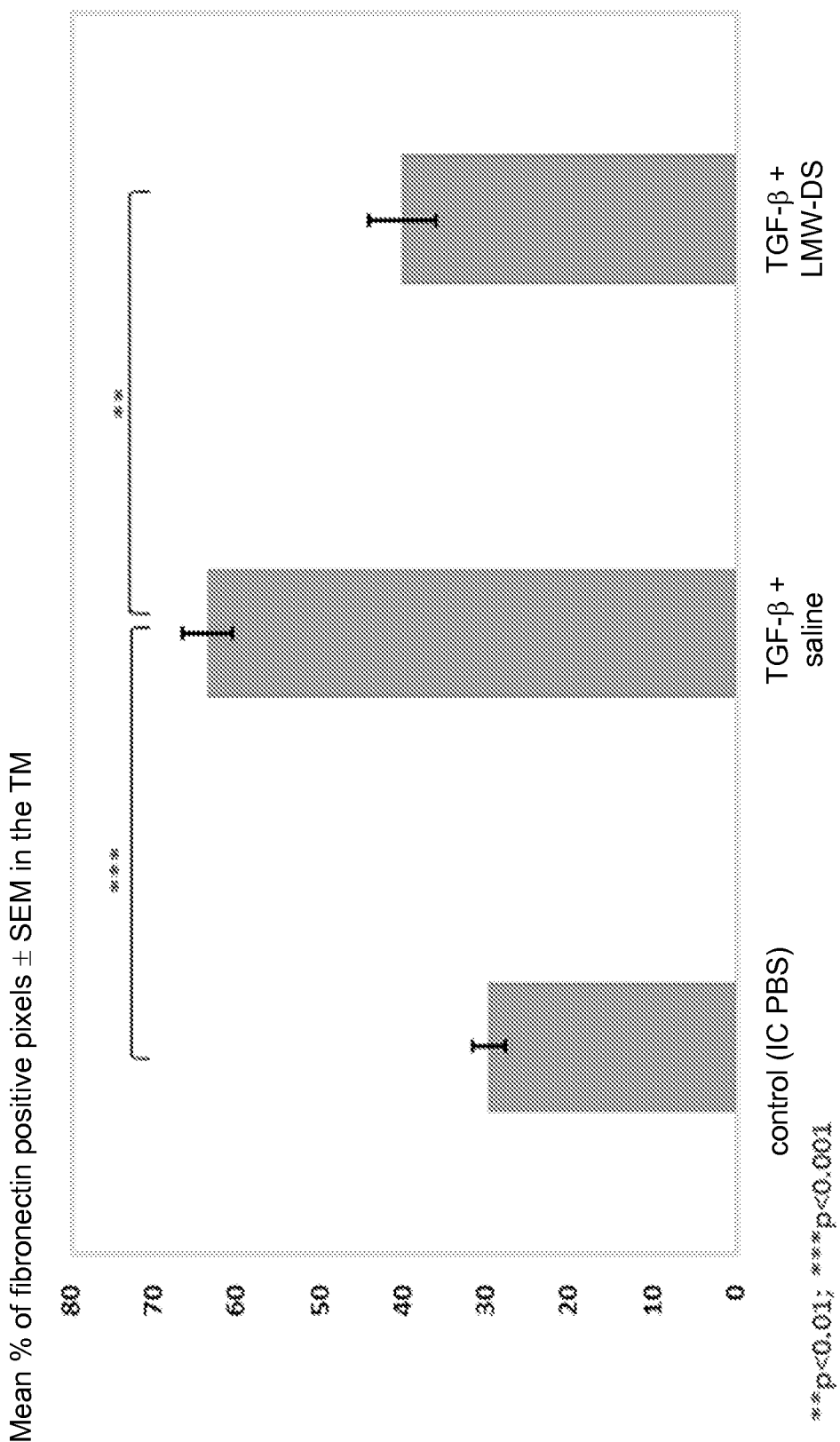
FIG. 21 is a diagram illustrating changes in fibronectin immunoreactivity in the angle in subjects suffering from POAG and treated with saline control or LMW-DS.

LMW-DS treatment significantly attenuated TM scarring, as evidenced by significantly reduced (P<0.001 laminin; P<0.01 fibronectin) levels of immunoreactive laminin (FIG. 20) and fibronectin (FIG. 21) in the angle.

Discussions

LMW-DS treatment induced dissolution of established TM scar elements as levels of laminin and fibronectin were significantly lower in the angle of dextran sulfate treated rats. This anti-scarring effect of LMW-DS thereby indicates that the drug can be used to dissolve already established scars and thereby enable a tissue remodeling and wound healing in, for instance fibrotic conditions.

Example 6

Alzheimer's disease (AD) is devastating for patients and their families as well as being a major burden upon the health care system requiring substantial economic resources. Little therapeutic benefit can be offered patients with current strategies trying to give patients small and often transient improvements in their symptoms but many fail to benefit at all. Disease modifying drugs would transform treatment and likely penetrate the market deeply.

A pathological characteristic of AD is the presence of senile plaques that are composed of β-amyloid protein. The β-amyloid protein oligomerizes to negatively impact physiological neurotransmission as well as forming neurotoxic complexes. Part of the detrimental action of oligomeric β-amyloid protein is mediated via a protein-protein interaction with cellular prion protein (PrP). Hence pharmacological strategies that inhibit this protein-protein interaction possess potential as disease modifying therapeutics.

The current study investigated the ability of LMW-DS to inhibit the protein-protein interaction between oligomeric β-amyloid and $PrP^c$ in an attempt to reveal therapeutic disease modifying potential to treat AD.

Material and Methods

Chemicals and Antibodies

Streptavidin HRP was from BioLegend; β-amyloid-(1-42)-biotin was from Innovagen; normal human cellular prion protein (PrP) was from Merck; TMB was from eBioscience; 1,1,1,3,3,3-hexafluoro-2-propanol (HFIP) was from Sigma; anti-amyloid β antibody clone 6E10 was from BioLegend; anti-mouse HRP was from Cell Signaling; dextran sulphate sodium salt (DSSS) with an average M.W.>500,000 Da was from Sigma; dextran (M.W. 450,000-650,000 Da) was from Sigma; Maxisorp plates were from Sigma.

Preparation of Amyloid-β Oligomers

Oligomerization of β-amyloid was optimized based on previous methods (Stine et al., Methods Mol. Biol. 2011, 670: 13-32; Aimi et al., J Neurochem. 2015, 134: 611-617). Briefly amyloid-β was dissolved in HFIP to a final concentration of 1.0 mM, subject to protected sonication and the HFIP carefully evaporated. Arising peptide films were stored at −20° C. in a sealed container. Prior to use, the peptide films were slowly dissolved in DMSO to a final concentration of 5.0 mM and subject to protected sonication for 10 minutes. To prepare oligomers, the DMSO solution was diluted in ice-cold DMEM medium to a final concentration of 100 µM and incubated 37° C. (β-amyloid-biotin) for 16 hours. To prepare monomers, the DMSO solution was diluted in ice-cold 18 MOhm water to a final concentration of 100 µM and used immediately.

Identification of Amyloid-β Monomers and Oligomers

Preparations optimized to generate monomers or oligomers of amyloid-β were solubilized in non-reducing gel sample buffer containing 5% SDS. Proteins were run on a 15% Bis-Tris gel using non-reducing MES running buffer. Gels were transferred to PVDF, blocked in 10% non-fat milk, before incubation with anti-amyloid-β antibody overnight at 4° C. and developed with anti-mouse HRP followed by ECL and exposed to film.

ELISA Method to Quantify the Protein-Protein Interaction Between Oligomeric Amyloid-β and $PrP^c$ $PrP^c$ was diluted to 10× the coating amount (in 100 µl; final amount of 500 ng $PrP^c$ per well) in carbonate coating buffer and applied to Maxisorp plates. Plates were then sealed and left overnight at 4° C. Coated plates were carefully washed in PBS-Tween 20 and blocked with 2% BSA in PBS. Plates were washed and 100 µl of oligomeric amyloid-β-biotin peptide preparation (final concentration 200 nM) carefully mixed with test compound before adding to each well. Plates were incubated for 60 minutes at room temperature, washed and treated with streptavidin-HRP and after further washes the color was developed using TMB (reaction stopped with 2N $H_2SO_4$). Absorbance was read at 450 nm within 30 minutes.

All conditions were performed in triplicate. Amyloid-β-biotin binding to $PrP^c$ was calculated as described by Aimi et al., J Neurochem. 2015, 134: 611-617.

Curve Fitting

Quantitative pharmacological analysis was performed by iterative curve fitting to a floating four parameter logistic equation.

Results

Production of Amyloid-β Monomers and Oligomers

Figure 22:
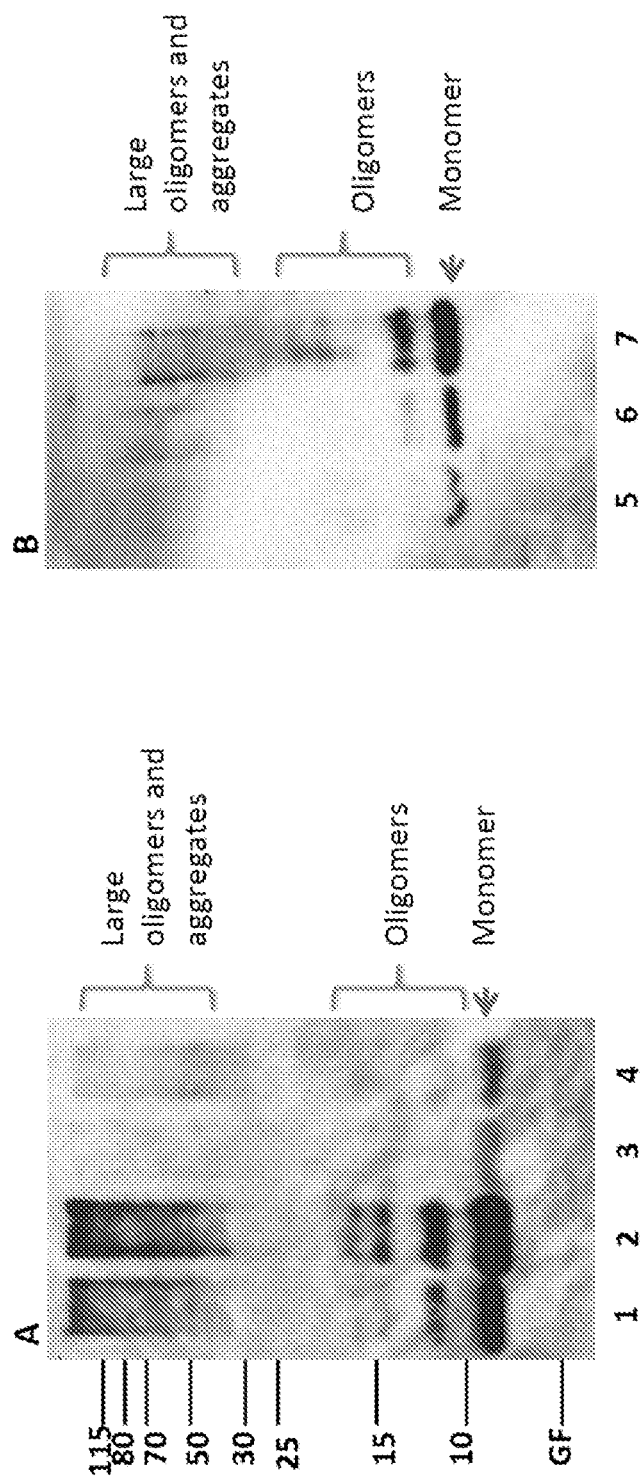
FIG. 22 illustrates amyloid-β monomer and oligomer preparation. Preparations of oligomers (lanes 1, 2, 5-7) or monomers (lanes 3 and 4) of amyloid-β (1-42) (A) or amyloid-β-biotin (B). The gels were loaded with 50 pmoles (lane 5), 100 pmoles (lanes 1, 3 and 6) or 200 pmoles (lanes 2, 4 and 7) of the respective 20 peptide preparation. Proteins on the arising Western blot were immuno-labelled with anti-amyloid-β. Predicted oligomers and the molecular weight markers are indicated.

Amyloid-β monomers and oligomers were prepared via an optimized protocol and resulted in successful oligomerization to a greater apparent efficiency (FIG. 22) compared to the results described by Aimi et al., J Neurochem. 2015, 134: 611-617.

Optimization of an ELISA Methodology for Quantitative Assessment of the Protein-Protein Interaction Between Oligomeric Amyloidβ and PrPc The methodology reported by Aimi et al., J Neurochem. 2015, 134: 611-617 did not specify the amount of protein to be coated per well on the ELISA plate but implied 50 ng of $PrP^c$ per well. However when this amount was coated onto the plate, no specific binding signal was evident with oligomeric amyloid-β. The experiment was repeated using a more effective coating buffer but still no signal was evident. The lack of a signal and the known theoretical maximum binding capacity of Maxisorp plates (600-650 ng/cm$^2$) indicated that the coating levels were sub-optimal. Therefore a range of $PrP^c$ coating levels was evaluated; at 250 ng $PrP^c$ per well, a relatively small signal with oligomeric amyloid-β was apparent, whilst a more robust and reproducible signal was evident at a coating level of 500 ng $PrP^c$ per well. This coating amount is in accord with the published literature (Beringe et al., Brain. 2003, 126: 2065-2073 used 500 ng/well; Nakato et al., J Immunol. 2012, 189: 1540-1544 used 250 ng/well, and Souan et al., Eur J Immunol. 2001, 31: 2338-2346 used 1.0 µg/well of various prion protein constructs).

Figure 23:
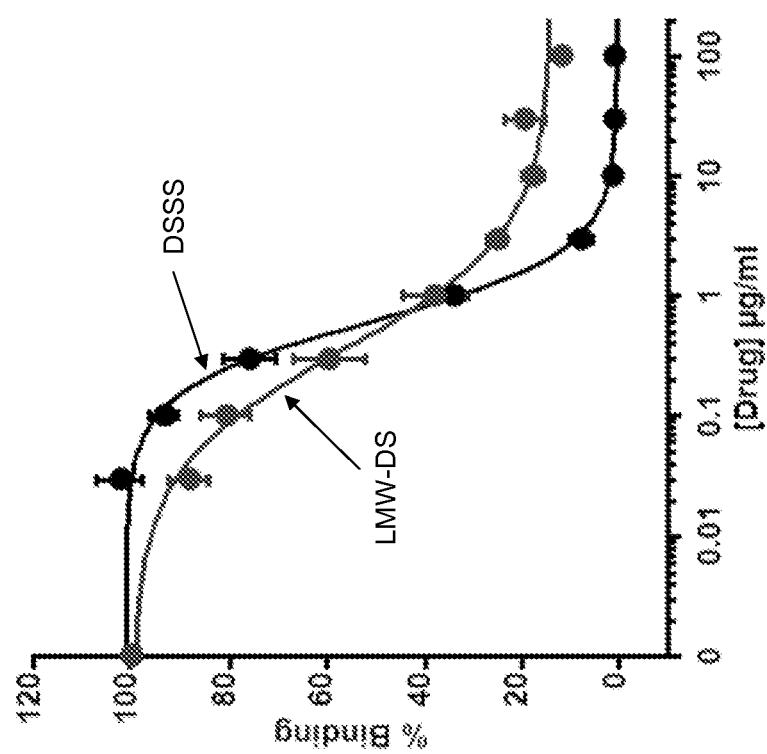
FIG. 23 illustrates dextran sulfate sodium salt (DSSS) and LMW-DS competition for the protein-protein interaction between amyloid-β and $PrP^c$.

Ability of DSSS and LMW-DS to Compete with the Protein-Protein Interaction Between Oligomeric Amyloid-β and $PrP^c$ DSSS competed for the protein-protein interaction between oligomeric amyloid-β and $PrP^c$ in a concentration dependent manner as did LMW-DS (FIG. 23; Table 12). Quantitative pharmacological analysis indicated that LMW-DS displayed comparable overall affinity to DSSS yet apparent differences in the side-by-side levels of competable binding and Hill coefficients suggest a differential interaction between the two compounds (FIG. 23; Table 12). In contrast to DSSS and LMW-DS, dextran failed to compete appreciably for the protein-protein interaction between oligomeric amyloid-β and PrP$^c$.

TABLE 12

Quantitative pharmacological analysis of ability to compete for protein-protein interaction between amyloid-β and PrP$^c$

| Compound | Competable binding (%) | IC$_{50}$ (µg/mL) | Hill coefficient |
|---|---|---|---|
| DSSS | 101 ± 2 | 0.62 ± 0.07 | 1.51 ± 0.06 |
| LMW-DS | 85 ± 4 | 0.42 ± 0.16 | 1.00 ± 0.21 |

Discussion

High-molecular weight dextran sulfate (DSSS) has previously been reported to compete with the protein-protein interaction between oligomeric amyloid-β and PrP$^c$ with effective concentrations in the low µg/ml range (Aimi et al., J Neurochem. 2015, 134: 611-617). In the present study, optimization of the methodology resulted in the generation of an apparent greater proportion of oligomeric amyloid-β relative to the study of Aimi et al. The optimization of the protein-protein interaction ELISA resulted in a greater degree of specific protein-protein interaction; the greater dynamic range of competition facilitated quantitative pharmacological analysis of the interaction by competing compounds. The present study therefore represents an improvement over the study reported by Aimi et al.

DSSS and LMW-DS displayed comparable affinity to compete for the protein-protein interaction between oligomeric amyloid-β and PrP$^c$, yielding IC$_{50}$ values of 0.62±0.07 and 0.42±0.16 µg/mL, respectively. Hill analysis of the nature of the competition indicated that LMW-DS displayed shallower competition curves in comparison to the relatively high Hill coefficients associated with DSSS, which provides evidence for a differential pharmacological action between DSSS and LMW-DS.

LMW-DS thereby competes for the protein-protein interaction between oligomeric amyloid-β and PrP$^c$ and can thereby be used to prevent or at least inhibit this protein-protein interaction. This effect as seen with LMW-DS has potentials in diseases and disorders involving protein-protein interaction between oligomeric amyloid-β and PrP$^c$, such as AD.

Example 7

The aim of this study was to evaluate the potential neuroprotective effects of LMW-DS on biochemical, molecular and histo-anatomical damages produced by the experimental model of closed-head diffuse severe TBI (sTBI) in the rat. In the present study, results were obtained through HPLC analyses of low molecular weight metabolites representative of energy metabolism, oxidative/nitrosative stress, antioxidants and free amino acids in cerebral tissue extracts of treated animals.

Materials and Methods

Induction of sTBI and Drug Administration Protocol

Male Wistar rats (n=160) of 300-350 g body weight were used in this study. They were fed with standard laboratory diet and water ad libitum in a controlled environment.

As the accepted anesthetic mixture, animals received 35 mg/kg b.w. ketamine and 0.25 mg/kg body weight midazolam by intramuscular injection. Diffuse sTBI was induced according to the "weight drop" impact acceleration model set up by Marmarou et al. J. Neurosurg. 1994, 80: 291-300. This model causes diffuse axonal injury and it is able to reproduce the physical and mechanical characteristics of the diffuse TBI in humans.

Severe TBI was induced by dropping a 450 g weight from 2 meters height onto the rat head protected by a helmet (metal disk previously fixed on the skull using dental cement) in order to uniformly distribute the mechanical force to the brain. Rats were placed prone on a bed of specific polyurethane foam inserted in a special container; this foam dissipates the major part of the potential energy (deriving from the mechanical forces) and prevents any rebound of the animal after the impact that could produce spinal damages.

Rats suffering from skull fracture, seizures, nasal bleeding, or did not survive the impact, were excluded from the study. After 2 or 7 days from TBI induction, rats were anesthetized again and then immediately sacrificed. These time points are coincident with the worst biochemical derangement (2 days) or, in the case of a mildly injured brain, with a full metabolic recovery (7 days).

The drug treatment consisted in a subcutaneous injection of 0.5 ml of LMW-DS (Tikomed) and administered at 3 different concentrations (1, 5 and 15 mg/kg body weight), according to the schematic protocol described below.

Sham-operated animals underwent the same procedure of anesthesia but TBI and were used as the control group.

Experimental Design

Rats used in this study were divided in 4 groups in order to carry out a study on the efficacy of three different concentrations of LMW-DS at two different times post TBI. As subsequently specified, in each group there were animals subjected to a specific treatment for metabolic analyses and other animals intended to histo-morphological studies, according to the procedures described below.

Group-1

Controls (n=12) dedicated to the biochemical evaluation. Four additional animals were used for the histo-morphological studies. Total rats in this group: n=16

Group-2

Rats subjected to sTBI with no pharmacological treatment were divided into the following subgroups:
1. 12 animals subjected to sTBI and sacrificed after 2 days post-TBI
2. 12 animals subjected to sTBI and sacrificed after 7 days post-TBI Four additional rats to each subgroup were used for the histo-morphological studies. Total rats in this group: n=32.

Group-3

Rats subjected to sTBI and receiving a single administration of LMW-DS after 30 minutes post-TBI, with sacrifice at 2 days post-TBI. Animals were divided in the following subgroups:
1. 12 animals subjected to sTBI and treated with 1 mg/kg b.w. LMW-DS
2. 12 animals subjected to sTBI and treated with 5 mg/kg b.w. LMW-DS
3. 12 animals subjected to sTBI and treated with 15 mg/kg b.w. LMW-DS Four additional rats to each subgroup were used for the histo-morphological studies. Total rats in this group: n=48.

Group-4

Rats subjected to sTBI and receiving a single administration of LMW-DS after 30 minutes post-TBI, with sacrifice at 7 days post-TBI. Animals were divided in the following subgroups:
1. 12 animals subjected to sTBI and treated with 1 mg/kg b.w. LMW-DS 2. 12 animals subjected to sTBI and treated with 5 mg/kg b.w. LMW-DS
3. 12 animals subjected to sTBI and treated with 15 mg/kg b.w. LMW-DS Four additional rats to each subgroup were used for the histo-morphological studies. Total rats in this group: n=48.

Group-5

Rats (n=12) subjected to sTBI and receiving repeated administrations of the maximal dose of LMW-DS (15 mg/kg b.w.) after 30 minutes, 3 days and 5 days post-TBI, with sacrifice at 7 days post-TBI. Four additional rats were used for the histo-morphological studies. Total rats in this group: n=16

Cerebral Tissue Processing for Biochemical and Gene Expression Analyses

To minimize metabolite loss, an in vivo craniectomy was performed in all animals during anesthesia. The rat skull was carefully removed, the brain was exposed, sharply cut along the sagittal fissure and the two hemispheres were separated. The hemispheres dedicated to biochemical analyses were freeze-clamped by aluminum tongues pre-cooled in liquid nitrogen and then immersed in liquid nitrogen. The freeze-clamping procedure was introduced to accelerate freezing of the tissue, thus minimizing potential metabolite loss.

The remaining hemispheres, dedicated to molecular biology analyses, were placed in 5-10 volumes of RNAlater® Solution (Invitrogen Life Technologies), a RNA stabilization solution that stabilize and protect RNA from degradation. Brain samples were stored at 4° C. overnight to allow the solution completely penetrate tissue.

Tissue homogenization for metabolite analyses was effected as described below. After the wet weight (w.w.) determination, the frozen hemispheres were placed into 7 ml of ice-cold, nitrogen-saturated, precipitating solution (1:10 w/v) composed by $CH_3CN+10$ mM $KH_2PO_4$, pH 7.40, (3:1; v:v), and the homogenization was performed using an Ultra-Turrax homogenizer set at 24,000 rpm/min (Janke & Kunkel, Staufen, Germany). After centrifugation at 20,690×g, for 10 min at 4° C., the clear supernatants were saved, pellets were supplemented with an aliquot of 10 mM $KH_2PO_4$ and homogenized again as described above and saved overnight at −20° C. in order to obtain a complete recovery of aqueous phase from tissue. A second centrifugation was performed (20,690×g, for 10 min at 4° C.) and supernatants combined with those previously obtained were extracted by vigorous agitation with a double volume of HPLC-grade $CHCl_3$ and centrifuged as above. The upper aqueous phases (containing water-soluble low-molecular weight compounds) were collected, subjected to chloroform washings for two more times (this procedure allowed the removal of all the organic solvent and of any lipid soluble compound from the buffered tissue extracts), adjusted in volumes with 10 mM $KH_2PO_4$, pH 7.40, to have ultimately aqueous 10% tissue homogenates and saved at −80° C. until assayed.

HPLC Analysis of Energy Metabolites, Antioxidants and Oxidative/Nitrosative Stress Biomarkers Aliquots of each deproteinized tissue sample were filtered through a 0.45 μm HV Millipore filter and loaded (200 μl) onto a Hypersil C-18, 250×4.6 mm, 5 μm particle size column, provided with its own guard column (Thermo Fisher Scientific, Rodano, Milan, Italy) and connected to an HPLC apparatus consisting of a Surveyor System (Thermo Fisher Scientific, Rodano, Milan, Italy) with a highly sensitive diode array detector (equipped with a 5 cm light path flow cell) and set up between 200 and 300 nm wavelength. Data acquisition and analysis were performed by a PC using the ChromQuest® software package provided by the HPLC manufacturer.

Metabolites (listed below) related to tissue energy state, mitochondrial function antioxidants and representative of oxidative/nitrosative stress were separated, in a single chromatographic run, according to slight modifications of existing ion-pairing HPLC methods formerly (Lazzarino et al., Anal Biochem. 2003, 322: 51-59; Tavazzi et al., Clin Biochem. 2005, 38: 997-1008). Assignment and calculations of the compounds of interest in chromatographic runs of tissue extracts were carried out at the proper wavelengths (206, 234 and 260 nm) by comparing retention times, absorption spectra and areas of peaks with those of peaks of chromatographic runs of freshly-prepared ultra-pure standard mixtures with known concentrations.

List of compounds: Cytosine, Creatinine, Uracil, Beta-Pseudouridine, Cytidine, Hypoxanthine, Guanine, Xanthine, CDP-Choline, Ascorbic Acid, Uridine, Nitrite ($NO_2$), reduced glutathione (GSH), Inosine, Uric Acid, Guanosine, CMP, Malondialdehyde (MDA), Nitrate ($NO_3$), UMP, $NAD^+$, ADO, IMP, GMP, UDP-glucose (UDP-Glc), UDP-galactose (UDP-Gal), UDP-N-acetyl-glucosamine (UDP-GlcNac), UDP-N-acetyl-galactosamine (UDP-GalNac), AMP, GDP-glucose, UDP, GDP, $NADP^+$, ADP-Ribose, CTP, ADP, UTP, GTP, NADH, ATP, NADPH, Malonyl-CoA, Coenzyme A (CoA-SH), Acetyl-CoA, N-acetylaspartate (NAA).

HPLC Analysis of Free Amino Acids and Amino Group Containing Compounds

The simultaneous determination of primary free amino acids (FAA) and amino group containing compounds (AGCC) (listed below) was performed using the precolumn derivatization of the sample with a mixture of OPA and MPA, as described in (Amorini et al., J Cell Mol Med. 2017, 21(3): 530-542; Amorino et al., Mol Cell Biochem. 2012, 359: 205-216). Briefly, the derivatization mixture composed by 25 mmol/l OPA, 1% MPA, 237.5 mmol/l sodium borate, pH 9.8 was prepared daily and placed in the autosampler. The automated precolumn derivatization of the samples (15 μl) with OPA-MPA was carried out at 24° C. and 25 μl of the derivatized mixture were loaded onto the HPLC column (Hypersil C-18, 250×4.6 mm, 5 μm particle size, thermostated at 21° C.) for the subsequent chromatographic separation. In order to quantify correctly Glutamate, deproteinized brain extracts were diluted 20 times with HPLC-grade $H_2O$ prior to the derivatization procedure and subsequent injection. Separation of OPA-AA and OPA-AGCC was carried out at a flow rate of 1.2 ml/min using two mobile phases (mobile phase A=24 mmol/l $CH_3COONa$+24 mmol/l $Na_2HPO_4$+1% tetrahydrofurane+0.1% trifluoroacetic acid, pH 6.5; mobile phase B=40% $CH_3OH$+30 $CH_3CN$+30% $H_2O$), using an appropriate step gradient.

Assignment and calculation of the OPA-AA and OPA-AGCC in chromatographic runs of whole brain extracts were carried out at 338 nm wavelengths by comparing retention times and areas of peaks with those of peaks of chromatographic runs of freshly-prepared ultra-pure standard mixtures with known concentrations.

List of FAA and AGCC compounds: aspartate (ASP), glutamate (GLU), asparagine (ASN), serine (SER), glutamine (GLN), histidine (HIS), glycine (GLY), threonine (THR), citrulline (CITR), arginine (ARG), alanine (ALA), taurine (TAU), γ-aminobutyrric acid (GABA), tyrosine (TYR), S-adenosylhomocysteine (SAH), L-cystathionine (L-Cystat), valine (VAL), methionine (MET), tryptophane (TRP), phenylalanine (PHE), isoleucine (ILE), leucine (LEU), ornithine (ORN), lysine (LYS).

Brain Tissue Processing for Histo-Morphological Analyses

After adequate anesthesia rats were transcardially perfused as described in (Di Pietro et al., Sci Rep. 2017, 7(1): 9189). Briefly, a thoracotomy was performed and a heparin solution was administered into the portal vein to avoid blood coagulation during all the operation. Afterwards, a right atrial incision was carried out and the perfusion needle was advanced into the ascending aorta. Perfusion was performed with 100 ml of Phosphate Buffer Solution (PBS) at pH 7.4 in order to wash out blood before further perfusion with 100 ml 4% paraformaldehyde (PFA) in PBS solution at pH 7.4. After rapid removal from the skull, each brain was post fixed by immersion in 4% PFA in PBS solution for 2 hours at 4° C. Cryoprotection was obtained by immersing the whole brain in PBS enriched with increasing sucrose solutions (10%, 20%, and 30%) for 24 hours at 4° C., then implanted in optimal cutting temperature embedding medium (OCT) (Thermo Shandon, Runcorn, UK) in peel-away mould containers (Agar Scientific, Essex, UK). Brain immersed in OCT were rapidly frozen in crushed dry ice before storage at −80° C.

Statistical Analysis

Differences across groups were estimated by the Student's t-test. Only two-tailed p-values of less than 0.05 were considered statistically significant.

Results

Summary of Biochemical Data Recorded at 2 Days Post sTBI

Effects of Increasing Doses of LMW-DS on Brain Energy Metabolism Measured

Table 13 summarizes values referring to phosphorylated high-energy purine and pyrimidine compounds. It is particularly evident the depletion of triphosphate nucleotides (ATP, GTP, UTP and CTP) caused by sTBI, that was accompanied by an increase in ADP and in the N-acetylated derivatives of UDP-glucose (UDP-GlcNac) and UDP-galactose (UDP-GalNac).

At this time post injury, treatment with LMW-DS was only partly effective in improving cell energy metabolism: Significantly higher values of high energy phosphates (ATP, GTP, and CTP) were recorded with all the three dosages of the drug tested. No effects were seen on the concentrations of UTP and ADP. It is worth recalling that 48 hours post TBI in rats represents a critical time point for brain metabolism, coincident with maximal alterations of mitochondrial functions including changes in the mitochondrial quality control. In this experimental model of TBI, this time point could be considered a sort of "turning point" at which recovery or no recovery of cerebral metabolism is defined.

TABLE 13

Concentrations of energy metabolites (phosphorylated purines and pyrimidines) measured in deproteinized brain homogenates of rats sacrificed at 2 days post-sTBI, without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only) | LMW-DS 1 | LMW-DS 5 | LMW-DS 15 |
|---|---|---|---|---|---|
| CMP | 13.52 ± 3.44 | 34.85 ± 7.11 | 29.39 ± 6.00 | *28.94 ± 5.91* | *25.61 ± 5.23* |
| UMP | 82.30 ± 9.82 | 151.45 ± 20.92 | 148.04 ± 20.45 | *97.98 ± 13.53* | 147.53 ± 20.38 |
| IMP | 51.57 ± 4.610 | 55.06 ± 10.36 | <u>45.97 ± 8.65</u> | *33.19 ± 6.25* | *68.95 ± 12.98* |
| GMP | 82.81 ± 7.821 | 186.08 ± 23.36 | 205.06 ± 25.74 | *167.44 ± 8.47* | 178.88 ± 22.46 |
| UDP-Glc | 51.00 ± 10.89 | 48.87 ± 7.24 | 45.14 ± 6.68 | *28.60 ± 4.23* | 43.41 ± 06.43 |
| UDP-Gal | 131.00 ± 13.26 | 127.11 ± 10.61 | 118.50 ± 9.89 | 116.42 ± 9.72 | *116.34 ± 9.71* |
| UDP-GlcNac | 88.77 ± 19.55 | 102.34 ± 9.32 | 96.62 ± 8.80 | *140.58 ± 12.80* | 108.74 ± 9.90 |
| UDP-GalNac | 38.82 ± 9.83 | 22.10 ± 3.26 | 21.24 ± 3.13 | 20.75 ± 3.06 | 22.37 ± 3.30 |
| GDP Glucose | 85.35 ± 12.76 | 89.05 ± 39.68 | 65.66 ± 41.61 | 83.81 ± 37.35 | 84.24 ± 37.54 |
| AMP | 43.59 ± 9.90 | 65.13 ± 41.27 | 62.04 ± 7.46 | 67.03 ± 11.85 | 66.26 ± 10.74 |
| UDP | 23.94 ± 6.75 | 64.40 ± 6.60 | *83.06 ± 8.52* | *70.93 ± 7.27* | 80.00 ± 8.20 |
| GDP | 57.40 ± 14.06 | 167.28 ± 23.11 | *189.85 ± 26.23* | 183.27 ± 25.32 | 194.61 ± 26.88 |
| ADP-Ribose | 12.69 ± 1.43 | 13.85 ± 2.78 | *25.69 ± 5.16* | *21.65 ± 4.35* | 23.06 ± 4.63 |
| CTP | 41.85 ± 10.32 | 28.32 ± 5.73 | 33.01 ± 7.63 | <u>*37.72 ± 7.63*</u> | *37.53 ± 7.59* |
| ADP | 222.67 ± 30.99 | 297.53 ± 25.59 | *333.90 ± 28.72* | 364.92 ± 31.39 | 346.37 ± 29.79 |
| UTP | 152.64 ± 17.39 | 100.79 ± 15.83 | 104.07 ± 16.34 | <u>*142.82 ± 22.43*</u> | 108.21 ± 16.99 |
| GTP | 569.00 ± 45.32 | 202.19 ± 21.33 | *169.98 ± 17.93* | 180.01 ± 18.99 | 179.07 ± 18.89 |
| ATP | 2390.14 ± 213.98 | 1330.60 ± 77.96 | *1696.96 ± 99.43* | *1683.87 ± 98.66* | *1556.54 ± 91.20* |

In Tables 13-31, bold indicates significantly different from controls (p<0.05); bold underlined indicates significantly different from TBI (p<0.05); and bold italic indicates significantly different from both controls and TBI (p<0.05).

Effects of Increasing Doses of LMW-DS on Nicotinic Coenzymes

Values of oxidized ($NAD^+$ and $NADP^+$) and reduced (NADH and NADPH) nicotinic coenzymes are summarized in Table 14. This Table 14 also reports the calculated, adimensional values of the NAD/NADH ratio which is suitable to evaluate how much metabolism is dependent on glycolysis or on mitochondrial oxidative phosphorylation.

As previously observed herein, sTBI caused decrease of $NAD^+$, $NADP^+$ and of the NAD/NADH ratio. At this time point, treatment with LMW-DS was effective only at the maximal dose tested (15 mg/kg b.w.) that produced significant protection of the nicotinic coenzyme pool and avoid the metabolic switch towards glycolysis, thereby indirectly suggesting overall better mitochondrial functions.

TABLE 14

Concentrations of nicotinic coenzymes measured in deproteinized brain homogenates of rats sacrificed at 2 days post-sTBI, without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w. The $NAD^+$/NADH ratio is adimensional.

| Compound | Controls | TBI only | LMW-DS 1 | LMW-DS 5 | LMW-DS 15 |
|---|---|---|---|---|---|
| $NAD^+$ | 485.74 ± 37.06 | 379.70 ± 64.64 | 325.87 ± 55.47 | 376.85 ± 64.15 | 475.32 ± 80.91 |
| NADH | 13.57 ± 1.94 | 12.45 ± 1.82 | 9.42 ± 1.38 | 10.37 ± 1.19 | 10.83 ± 1.58 |
| $NADP^+$ | 23.17 ± 4.58 | 17.68 ± 4.04 | 11.79 ± 2.70 | 11.86 ± 2.71 | 17.75 ± 4.06 |
| NADPH | 8.51 ± 0.71 | 7.94 ± 0.66 | 13.07 ± 1.09 | 37.48 ± 3.11 | 8.93 ± 0.74 |
| $NAD^+$/NADH | 36.47 ± 5.46 | 34.99 ± 6.05 | 33.91 ± 9.32 | 36.61 ± 6.09 | 44.40 ± 7.67 |

Effects of Increasing Doses of LMW-DS on CoA-SH Derivatives

Table 15 reports data referring to free CoA-SH and CoA-SH derivatives. Particularly Acetyl-CoA is a crucial compound for mitochondrial metabolism allowing correct functioning of the tricarboxylic acid cycle (TCA cycle), thus ensuring continuous electron supply for the electron transfer chain (ETC). TCA is the major cell cycle for the generation of reduced coenzymes (NADH and $FADH_2$) which, by transferring their electrons to mitochondrial complexes I and II, respectively, are the fuel for ETC and oxidative metabolism. All compounds, particularly Acetyl-CoA, are significantly affected by sTBI. A partial rescue of this compound was observed when 5 or 15 mg/kg b.w. LWM-DS was administered to animals 30 minutes post injury.

TABLE 15

Concentrations of free CoA-SH and CoA-SH derivatives (Acetyl-CoA and Malonyl-CoA) measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| Malonyl-CoA | 15.02 ± 2.38 | 11.82 ± 2.50 | 19.06 ± 4.04 | 35.58 ± 7.54 | 28.73 ± 6.09 |
| CoA-SH | 26.31 ± 3.86 | 21.00 ± 2.32 | 9.42 ± 1.04 | 7.46 ± 0.82 | 9.35 ± 1.03 |
| Acetyl-CoA | 36.97 ± 5.43 | 28.32 ± 3.29 | 27.74 ± 3.23 | 34.85 ± 4.05 | 32.38 ± 3.77 |

Effects of Increasing Doses of LMW-DS on Antioxidants and Oxidative/Nitrosative Stress Biomarkers Table 16 shows the concentrations of the main water-soluble brain antioxidants (ascorbic acid and GSH) and of biomarkers of oxidative (MDA) and nitrosative stress ($—NO_2^-$ and $—NO_3^-$). Malondialdehyde (MDA) originates from decomposition of unsaturated fatty acids of membrane phospholipids as a consequence of ROS-mediated lipid peroxidation. Nitrites ($—NO_2^-$) and nitrates ($—NO_3^-$) are stable end products of nitric oxide (NO) metabolism which, under pathological conditions, is generated in excess by an inducible form of nitric oxide synthase (iNOS) and gives raise to reactive nitrogen species (RNS) through the reaction with ROS:

At two days post impact, 25 to 45% decrease in both water-soluble antioxidants occurred in rats experiencing sTBI. Consequent increase in signatures of oxidative/nitrosative stress was also recorded. Administration of LWM-DS significantly ameliorated the concentrations of both ascorbic acid and reduced glutathione (GSH) with evident decrease of cerebral tissue nitrites and nitrates. These effects were more remarkable when 15 mg kg/b.w. where used.

TABLE 15

Concentrations of antioxidants and oxidative/nitrosative stress biomarkers measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| ASCORBIC ACID | 3315.38 ± 351.59 | 2577.87 ± 148.36 | 2567.35 ± 147.76 | 2626.68 ± 151.17 | 2783.04 ± 160.17 |
| GSH | 3521.63 ± 275.04 | 1972.14 ± 287.59 | 2337.06 ± 340.81 | 2067.79 ± 301.54 | 2418.94 ± 352.75 |

TABLE 15-continued

Concentrations of antioxidants and oxidative/nitrosative stress biomarkers measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| MDA | 0.85 ± 0.26 | 27.30 ± 4.45 | *44.00 ± 7.17* | 32.73 ± 5.33 | 18.28 ± 2.98 |
| NO$_2$ | 142.93 ± 28.19 | 232.31 ± 27.99 | 158.36 ± 19.08 | 218.12 ± 26.28 | *72.29 ± 8.71* |
| NO$_3$ | 169.51 ± 20.79 | 266.82 ± 58.06 | *99.16 ± 21.58* | 148.41 ± 32.30 | *56.50 ± 12.30* |

Effects of Increasing Doses of LMW-DS on De-Phosphorylated Purines and Pyrimidines The majority of the compounds reported in Table 16 originate from the degradation pathways of purine and pyrimidine nucleotides and are indirectly connected to cell energy metabolism. Rats receiving sTBI had higher cerebral concentrations of all these compounds, but CDP-choline, most of which were positively affected by the drug administration.

TABLE 16

Concentrations of de-phosphorylated purines and pyrimidines measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| CYTOSINE | 14.14 ± 3.38 | 20.19 ± 2.47 | 13.47 ± 1.65 | 13.65 ± 1.67 | 13.57 ± 1.66 |
| CREATININE | 17.12 ± 2.49 | 31.08 ± 5.79 | 17.66 ± 3.29 | *10.22 ± 1.90* | *11.77 ± 2.19* |
| URACIL | 10.91 ± 2.27 | 15.64 ± 3.06 | 17.18 ± 3.36 | 17.83 ± 3.48 | 15.55 ± 3.04 |
| β-PSEUDOURIDINE | 6.89 ± 1.27 | 8.51 ± 1.71 | *11.64 ± 2.3* | *10.41 ± 2.09* | 7.84 ± 1.57 |
| CYTIDINE | 12.76 ± 2.59 | 10.07 ± 1.82 | 13.79 ± 2.49 | *7.47 ± 1.35* | 11.46 ± 2.07 |
| HYPOXANTHINE | 7.57 ± 0.93 | 15.22 ± 2.49 | *4.02 ± 0.66* | *4.18 ± 0.68* | 6.82 ± 1.12 |
| GUANINE | 3.34 ± 0.88 | 5.11 ± 1.28 | *1.62 ± 0.41* | *1.68 ± 0.42* | *1.61 ± 0.40* |
| XANTHINE | 7.61 ± 1.39 | 15.82 ± 1.64 | *13.79 ± 1.43* | 6.71 ± 0.70 | *13.87 ± 1.44* |
| CDP choline | 7.97 ± 1.370 | 8.23 ± 1.23 | 8.23 ± 1.22 | *5.16 ± 0.77* | 87.55 ± 15.41 |
| URIDINE | 64.08 ± 14.14 | 131.59 ± 23.17 | *79.93 ± 14.07* | 117.21 ± 20.64 | 7.07 ± 1.05 |
| INOSINE | 89.43 ± 15.04 | 134.31 ± 17.51 | *113.85 ± 14.84* | *114.89 ± 14.98* | 142.91 ± 18.63 |
| URIC ACID | 3.36 ± 0.64 | 37.73 ± 7.74 | *52.42 ± 10.75* | *11.22 ± 2.30* | *26.00 ± 5.33* |
| GUANOSINE | 21.10 ± 5.56 | 19.69 ± 3.27 | *16.46 ± 2.73* | *30.97 ± 5.15* | 24.35 ± 4.05 |
| ADENOSINE | 46.71 ± 7.39 | 68.07 ± 16.30 | 68.91 ± 16.50 | 92.58 ± 22.16 | 53.25 ± 12.75 |

Effects of Increasing Doses of LMW-DS on N-Acetylaspartate (NAA)

NAA is the most abundant N-acetylated amino acid of the mammalian brain, with concentrations almost equaling those of the neurotransmitter glutamate in humans. Notwithstanding the biological role of NM has not yet been fully elucidated, we have clearly showed, in both preclinical and clinical studies, that TBI decreases NAA concentrations and that its time course changes following head injury mirrors those of ATP. Particularly, we found that sTBI causes an irreversible modification in NAA homeostasis, that NM is a good surrogate marker of brain energy metabolism and that decrease and recovery of NM levels are much slower than symptom clearance in post-concussed athletes. Hence, NAA has a particular relevance in studies on TBI.

Figure 24:
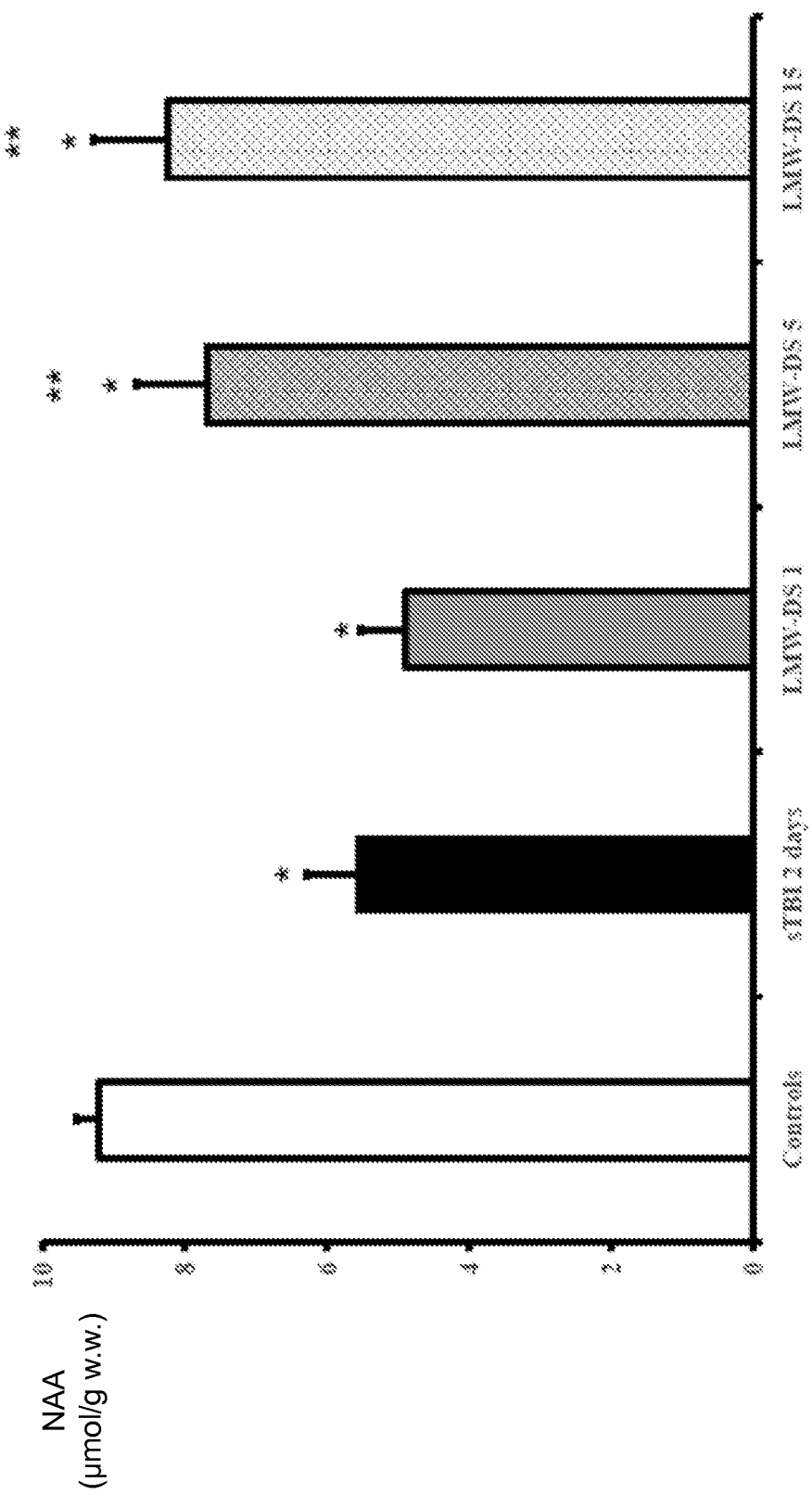
FIG. 24 illustrates concentrations of NAA measured in deproteinized brain homogenates of rats sacrificed at 2 days post-TBI without and with a single administration of increasing doses of LWM-DS (1, 5 and 15 mg/kg b.w.), performed 30 minutes after trauma induction. Controls are represented by sham-operated animals. Values are the mean of 12 animals. Standard deviations are represented by vertical bars. *significantly different from controls, $p<0.01$. **significantly different from sTBI 2 days, $p<0.01$.

Decrease by 40% in whole brain NM was observed in sTBI rats (FIG. 24) at two days post impact. LMW-DS produced beneficial effects on NM concentrations when administered at 5 or 15 mg/kg b.w. Although significantly lower than controls, NAA in rats administered with either one of the two drug dosages was significantly higher than values found in sTBI rats, with highest NM levels found in rats receiving the highest dose of LMW-DS.

Effects of Increasing Doses of LMW-DS on Free Amino Acids Involved in Neurotransmission Compounds listed in Table 17 are amino acids directly (GLU, GABA) of indirectly (GLN, ASP, ASN, GLY, SER, THR, ALA) involved in neurotransmission. Particularly, GLU is the main excitatory amino acid, counteracted in its action by GABA. Excitotoxicity of GLU is modulated by SER, GLY, THR and ALA and it is linked to the function of the GLU-GLN cycle involving neurons and astrocytes. As shown in a previous study (16), we here found that most of these amino acids increased in sTBI rats at two days post injury. Treating animals with a single administration of LMW-DS was partly effective when the drug was subcutaneously infused at 5 or 15 mg/kg b.w. In most cases, values of the different compounds were significantly better than those found in the group of untreated sTBI animals but not than those of controls.

TABLE 17

Concentrations of free amino acids with neurotransmitter functions measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| ASP | 2.88 ± 0.88 | 4.55 ± 0.63 | 4.17 ± 0.99 | 4.15 ± 0.95 | 3.05 ± 0.42 |
| GLU | 9.92 ± 0.83 | 12.88 ± 0.60 | 12.05 ± 0.91 | 11.93 ± 0.55 | 11.79 ± 0.55 |
| ASN | 0.10 ± 0.03 | 0.14 ± 0.02 | 0.13 ± 0.02 | 0.17 ± 0.03 | 0.17 ± 0.03 |
| SER | 0.64 ± 0.17 | 0.82 ± 0.07 | 0.91 ± 0.07 | 0.91 ± 0.07 | 0.76 ± 0.06 |
| GLN | 3.89 ± 0.87 | 4.34 ± 0.42 | 4.37 ± 0.59 | 4.55 ± 0.44 | 4.21 ± 0.51 |
| GLY | 0.78 ± 0.13 | 1.38 ± 0.27 | 1.35 ± 0.26 | 1.43 ± 0.28 | 1.18 ± 0.23 |
| THR | 0.69 ± 0.18 | 0.76 ± 0.16 | 0.70 ± 0.15 | 0.77 ± 0.17 | 0.61 ± 0.13 |
| ALA | 0.41 ± 0.11 | 0.58 ± 0.06 | 0.76 ± 0.08 | 0.79 ± 0.08 | 0.68 ± 0.07 |
| GABA | 1.36 ± 0.22 | 1.93 ± 0.17 | 1.87 ± 0.17 | 1.99 ± 0.18 | 1.58 ± 0.14 |

Effects of Increasing Doses of LMW-DS on Free Amino Acids Involved in the Methyl Cycle Free amino acids reported in Table 18 are involved either in the so called methyl cycle, regulating the homeostasis of compounds acting as methyl donors in cell metabolism, or in the formation of cysteine, the sole amino acid having a free —SH group. Severe head trauma caused significant changes in the main actors of this important metabolic pathway. Restoration of methionine was accomplished by LWM-DS at any dose tested. Drug treatment was partly effective in normalizing the other amino acids. Comments to changes in L-Cystathionine (L-Cystat) will be given in the corresponding Table at 7 days post impact.

TABLE 18

Concentrations of free amino acids involved in the methyl cycle and homeostasis of –SH groups measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 ( | LMW-DS 15 |
|---|---|---|---|---|---|
| SAH | 0.03 ± 0.01 | 0.07 ± 0.01 | 0.07 ± 0.02 | 0.07 ± 0.02 | 0.06 ± 0.02 |
| L-Cystat | 0.15 ± 0.03 | 0.31 ± 0.06 | 0.25 ± 0.05 | 0.31 ± 0.06 | 0.41 ± 0.08 |
| MET | 0.03 ± 0.01 | 0.02 ± 0.01 | 0.04 ± 0.01 | 0.05 ± 0.01 | 0.03 ± 0.01 |

Effects of Increasing Doses of LMW-DS on Free Amino Acids Involved in the Generation of Nitric Oxide (NO)

Table 19 illustrates concentrations of the free amino acids directly involved in the generation of NO, in the reaction catalyzed by nitric oxide synthases (NOS), a family of enzymes existing in three isoforms: endothelial NOS (eNOS), neuronal NOS (nNOS), inducible NOS (iNOS). The last isoform (iNOS) is the one involved in nitrosative stress. Nitric oxide is generated through a complex reaction in which arginine (ARG) donates a nitrogen atom undergoing a partial oxidation and forming citrulline (CITR) and NO. Animals at 2 days post sTBI showed concomitant decrease in ARG and increase in CITR, in line with data showing increase in the stable NO end products nitrites and nitrates (Table 15). Administration of LMW-DS was particularly effective when the 15 mg/kg b.w. dose was used.

TABLE 19

Concentrations of free amino acids involved in nitric oxide formation measured in deproteinized brain homogenates of rats sacrificed at 2 days post-TBI without and with lo increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| CITR | 0.03 ± 0.01 | 0.03 ± 0.01 | 0.01 ± 0.01 | 0.02 ± 0.01 | 0.01 ± 0.01 |
| ARG | 0.17 ± 0.03 | 0.11 ± 0.03 | 0.13 ± 0.03 | 0.13 ± 0.03 | 0.16 ± 0.04 |
| ORN | 0.02 ± 0.01 | 0.02 ± 0.01 | 0.02 ± 0.01 | 0.01 ± 0.01 | 0.02 ± 0.01 |

Effects of Increasing Doses of LMW-DS on Long-Chain Free Amino Acids

The free amino acids reported in Table 20 represents a source of carbon skeleton useful to generate α-ketoacids that cells use to replenish the TCA cycle. Among these compounds, only isoleucine (ILE) was significantly affected by sTBI and restored in rats receiving drug treatment.

TABLE 20

Concentrations of long chain free amino acids measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| VAL | 0.07 ± 0.02 | 0.06 ± 0.03 | 0.07 ± 0.03 | 0.08 ± 0.03 | 0.06 ± 0.03 |
| ILE | 0.03 ± 0.01 | 0.05 ± 0.01 | 0.13 ± 0.03 | *0.10 ± 0.02* | *0.06 ± 0.01* |
| LEU | 0.04 ± 0.01 | 0.04 ± 0.01 | *0.09 ± 0.02* | *0.10 ± 0.02* | 0.04 ± 0.01 |
| LYS | 0.23 ± 0.03 | 0.28 ± 0.10 | 0.29 ± 0.11 | 0.37 ± 0.14 | 0.32 ± 0.12 |

Effects of Increasing Doses of LMW-DS on Free Amino Acids Acting as Osmolytes and Aromatic Free Amino Acids Results summarized in Table 21 clearly show that sTBI caused the increase in the concentrations of all these free amino acids. Particularly, the increase in taurine (TAU) may suggest the attempt to counteract cell edema by increasing the levels of one of the most important brain osmolyte. Differently, increase in aromatic free amino acids may suggest reduced biosynthesis of the neurotransmitters serotonin (formed from tryptophan) and dopamine (generated from the biotransformation of phenylalanine first and tyrosine then). No remarkable effects of LMW-DS administration were observed at this time point after impact.

TABLE 21

Concentrations of free amino acids acting as osmolytes and aromatic free amino acids measured in deproteinized brain homogenates of rats sacrificed at 2 days post-TBI without and with a single administration of increasing doses of LWM-DS (1, 5 and 15 mg/kg b.w.), performed 30 minutes after brain trauma induction. Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 |
|---|---|---|---|---|---|
| TAU | 3.82 ± 0.61 | 4.84 ± 0.46 | 4.98 ± 0.47 | 5.15 ± 0.49 | 4.59 ± 0.43 |
| HYS | 0.05 ± 0.01 | 0.06 ± 0.01 | *0.08 ± 0.01* | *0.11 ± 0.02* | *0.10 ± 0.01* |
| TYR | 0.13 ± 0.03 | 0.17 ± 0.03 | 0.18 ± 0.03 | 0.20 ± 0.03 | 0.17 ± 0.03 |
| TRP | 0.01 ± 0.01 | 0.02 ± 0.01 | 0.02 ± 0.01 | 0.03 ± 0.01 | *0.04 ± 0.01* |
| PHE | 0.03 ± 0.01 | 0.05 ± 0.01 | *0.07 ± 0.03* | *0.07 ± 0.03* | *0.06 ± 0.01* |

Summary of Biochemical Data Recorded at 7 Days Post sTBI

Effects of Increasing Doses of LMW-DS on Brain Energy Metabolism Measured

Table 22 summarizes values referring to phosphorylated high-energy purine and pyrimidine compounds. It is particularly evident the no amelioration of the depletion of triphosphate nucleotides (ATP, GTP, UTP and CTP) was observed at 7 days post sTBI. Concomitant increase in AMP and ADP was accompanied by significant changes in the concentrations of UDP derivatives (UDP-Glc, UDP-Gal, UDP-GlcNac and UDP-GalNac). In general, it should be underlined that longer times post injury were often characterized by worsening of the biochemical, metabolic, molecular alterations induced by sTBI.

At this time post injury, treatment with LMW-DS produced a general improvement of cerebral energy metabolism, more evident when drug administration dose was higher than 1 mg/kg b. w. Although differences with controls were recorded even in rats receiving repeat administration of 15 mg kg/b. w. LWM-DS, significantly higher values of nucleotide triphosphates were found in drug treated animals. Of particular relevance is the progressive recovery of the calculated, adimensional value of the ATP/ADP ratio (which is considered as a good indicator of the mitochondrial phosphorylating capacity) that progressively increased by increasing the dose of drug administered to sTBI animals.

TABLE 22

Concentrations of energy metabolites (phosphorylated purines and pyrimidines) measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS5 | LMW-DS 15 | LMW-DS 15-R |
|---|---|---|---|---|---|---|
| CMP | 13.52 ± 3.44 | 30.98 ± 3.18 | 25.41 ± 10.81 | 55.67 ± 22.97 | 47.10 ± 20.04 | 31.21 ± 13.28 |
| UMP | 82.30 ± 9.82 | 139.70 ± 27.06 | 103.06 ± 19.96 | 167.18 ± 32.39 | 181.82 ± 35.22 | 107.66 ± 20.86 |
| IMP | 51.57 ± 4.61 | 110.07 ± 28.19 | 80.16 ± 20.53 | 68.72 ± 17.60 | 74.70 ± 19.13 | 141.84 ± 36.32 |
| GMP | 82.81 ± 7.82 | 164.41 ± 77.81 | 113.06 ± 53.51 | 101.42 ± 48.00 | 41.55 ± 19.66 | 61.86 ± 29.28 |
| UDP-Glc | 51.00 ± 10.89 | 39.28 ± 7.98 | 63.19 ± 12.84 | 58.10 ± 11.81 | 62.97 ± 12.80 | 61.37 ± 12.47 |
| UDP-Gal | 131.00 ± 13.26 | 112.58 ± 7.74 | 130.20 ± 8.95 | 132.66 ± 9.12 | 137.57 ± 9.46 | 135.15 ± 9.29 |
| UDP-GlcNac | 88.77 ± 19.55 | 134.24 ± 46.44 | 85.36 ± 29.53 | 85.14 ± 29.45 | 67.47 ± 23.34 | 86.42 ± 29.89 |
| UDP-GalNac | 38.82 ± 9.83 | 13.08 ± 3.75 | 15.85 ± 4.54 | 17.37 ± 4.98 | 17.91 ± 5.13 | 16.50 ± 4.73 |
| GDP Glucose | 85.35 ± 12.76 | 90.43 ± 10.58 | 112.22 ± 13.13 | 104.76 ± 12.25 | 101.65 ± 11.89 | 106.42 ± 12.45 |
| AMP | 43.59 ± 9.90 | 55.86 ± 4.39 | 43.13 ± 3.39 | 59.50 ± 4.68 | 50.50 ± 3.97 | 43.12 ± 3.39 |
| UDP | 23.94 ± 6.75 | 45.30 ± 6.37 | 38.59 ± 5.43 | 44.19 ± 6.22 | 37.91 ± 5.33 | 37.12 ± 5.22 |
| GDP | 57.40 ± 14.06 | 112.05 ± 12.80 | 121.72 ± 13.91 | 126.82 ± 14.49 | 122.07 ± 13.95 | 109.06 ± 12.46 |
| ADP-Ribose | 12.69 ± 1.43 | 22.64 ± 5.68 | 7.95 ± 1.99 | 6.76 ± 1.70 | 19.21 ± 4.82 | 13.23 ± 3.32 |
| CTP | 41.85 ± 10.32 | 34.12 ± 9.03 | 81.75 ± 31.55 | 79.08 ± 14.54 | 96.44 ± 25.54 | 92.67 ± 16.27 |
| ADP | 222.67 ± 30.99 | 302.60 ± 40.30 | 286.78 ± 38.19 | 289.27 ± 38.52 | 276.83 ± 36.87 | 260.32 ± 34.67 |
| UTP | 152.64 ± 17.39 | 108.55 ± 19.01 | 179.75 ± 31.48 | 175.02 ± 30.65 | 127.42 ± 22.32 | 133.72 ± 23.42 |
| GTP | 569.00 ± 45.32 | 375.24 ± 34.12 | 438.65 ± 39.88 | 453.86 ± 41.27 | 479.98 ± 43.64 | 466.06 ± 42.38 |
| ATP | 2390.14 ± 213.98 | 1561.36 ± 125.60 | 1792.01 ± 144.16 | 1730.92 ± 139.24 | 1846.63 ± 148.55 | 1971.17 ± 158.57 |
| APT/ADP | 10.99 ± 2.21 | 5.23 ± 0.66 | 6.12 ± 0.78 | 6.28 ± 0.80 | 6.76 ± 0.86 | 7.67 ± 0.97 |

Figure 25:
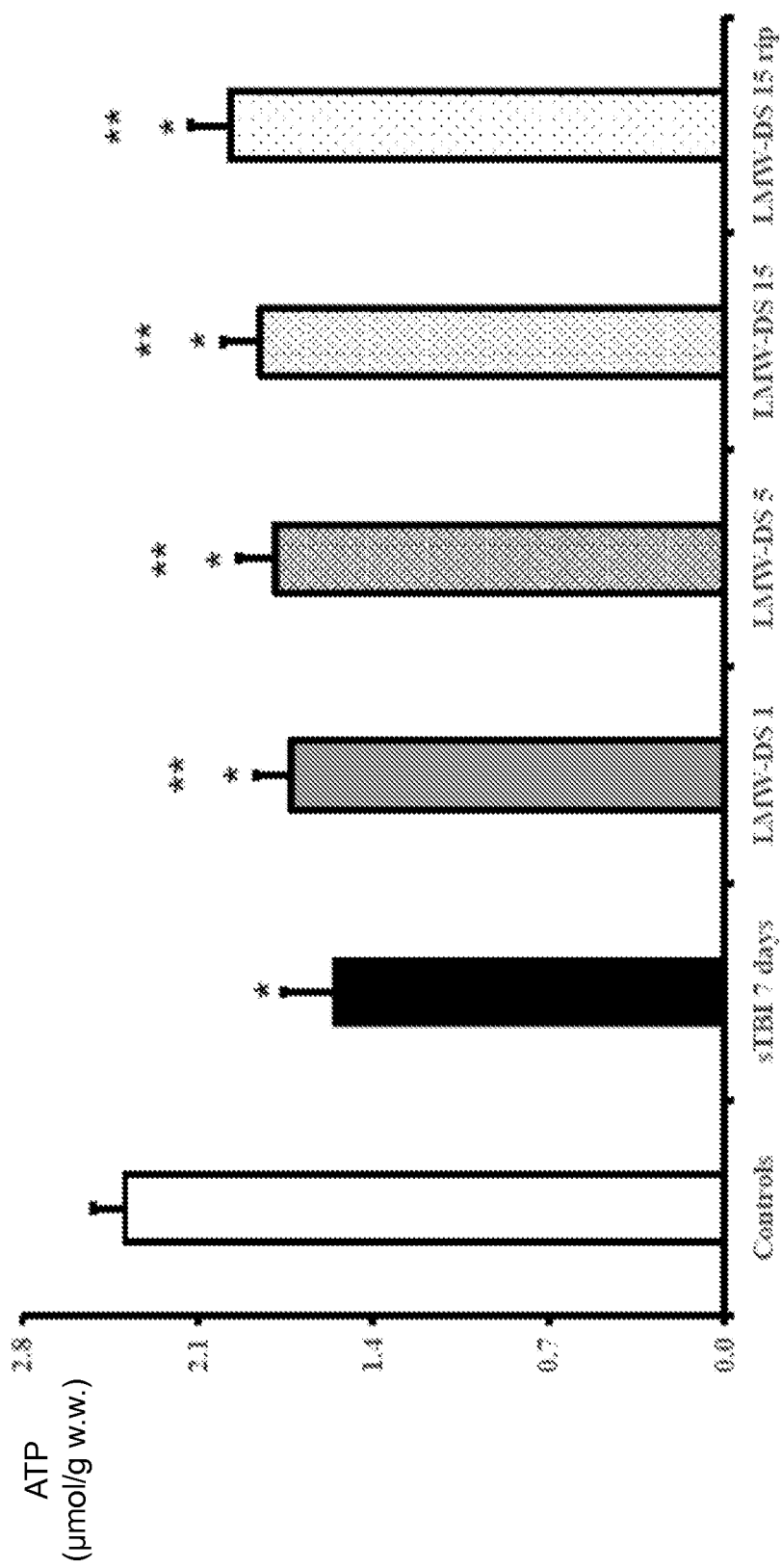
FIG. 25 illustrates concentrations of ATP measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean of 12 animals. Standard deviations are represented by vertical bars. *significantly different from controls, $p<0.01$. **significantly different from sTBI 2 days, $p<0.01$.

To better show that drug effects were related to the drug dosage, we graphically reported in FIG. 25 results concerning ATP. It is possible to observe that ATP increase was somehow related to the dosage administered and that drug administration produced significant increases of the most important high energy phosphate at any dose tested.

Effects of Increasing Doses of LMW-DS on Nicotinic Coenzymes

Values of oxidized (NAD+ and NADP+) and reduced (NADH and NADPH) nicotinic coenzymes are summarized in Table 23. Table 23 also reports the calculated, adimensional value of the NAD/NADH ratio which is suitable to evaluate how much metabolism is dependent on glycolysis or on mitochondrial oxidative phosphorylation.

As formerly observed, profound decrease of nicotinic coenzymes and of the NAD/NADH ratio was recorded in sTBI rats at 7 days post injury. With the exclusion of the lowest dose, treatment with LMW-DS produced significant improvement of the concentrations of nicotinic coenzymes. Particularly, single and repeat administration of 15 mg/kg b.w. LMW-DS were able to normalize NAD+ level and to restore the correct NAD/NADH ratio determined in control animals.

TABLE 23

Concentrations of nicotinic coenzymes measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| NAD+ | 485.74 ± 37.06 | 249.37 ± 35.32 | 268.14 ± 37.97 | 293.36 ± 41.55 | 491.52 ± 69.61 | 401.73 ± 56.89 |
| NADH | 13.57 ± 1.94 | 8.98 ± 1.55 | 8.20 ± 1.41 | 8.83 ± 1.26 | 11.65 ± 1.63 | 11.05 ± 1.52 |
| NADP+ | 23.17 ± 4.58 | 11.69 ± 4.29 | 39.94 ± 14.65 | 24.45 ± 8.97 | 23.75 ± 8.72 | 16.56 ± 6.08 |

TABLE 23-continued

Concentrations of nicotinic coenzymes measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| NADPH | 8.51 ± 0.71 | 10.66 ± 2.48 | *18.91 ± 4.39* | 12.30 ± 2.86 | *6.66 ± 1.55* | 11.21 ± 2.60 |
| NAD$^+$/ADH | 36.47 ± 5.46 | 27.51 ± 5.83 | 33.91 ± 9.32 | <u>33.90 ± 7.19</u> | *42.51 ± 5.26* | <u>37.47 ± 9.46</u> |

Effects of Increasing Doses of LMW-DS on CoA-SH Derivatives

Table 24 reports data referring to free CoA-SH and CoA-SH derivatives. Remarkable positive effects of the administration of 5 or 15 mg/kg b.w. (this dose both as a single and repeat administration) were detected both for CoA-SH and Acetyl-CoA, suggesting much more favorable metabolic conditions for the functioning of the TCA cycle.

TABLE 24

Concentrations of free CoA-SH and CoA-SH derivatives (Acetyl-CoA and Malonyl-CoA) measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| Malonyl-CoA | 15.02 ± 2.38 | 13.01 ± 2.35 | *5.43 ± 0.98* | *6.02 ± 1.09* | *7.98 ± 1.44* | 12.56 ± 2.27 |
| CoA-SH | 26.31 ± 3.86 | 26.44 ± 3.39 | 38.50 ± 4.94 | 51.86 ± 6.66 | 64.93 ± 8.33 | 45.76 ± 5.87 |
| Acetyl-CoA | 36.97 ± 5.43 | 18.28 ± 3.11 | 27.05 ± 4.61 | 22.87 ± 3.89 | <u>38.60 ± 6.57</u> | <u>37.91 ± 6.46</u> |

Effects of Increasing Doses of LMW-DS on Antioxidants and Oxidative/Nitrosative Stress Biomarkers Table 25 shows the concentrations of the main water-soluble brain antioxidants (ascorbic acid and GSH) and of biomarkers of oxidative (MDA) and nitrosative stress (—NO$_2^-$ and —NO$_3^-$). At 7 days post impact, no recovery in the concentrations of both water-soluble antioxidants occurred in rats experiencing sTBI. Remarkably high levels of signatures of oxidative/nitrosative stress were also recorded. The effects of the administration of the highest single and repeat dose of LWM-DS were particularly beneficial to rescue the concentrations of both ascorbic acid and reduced glutathione (GSH) with evident decrease of cerebral tissue nitrites and nitrates. These effects were also significant when 5 mg kg/b.w. where used.

TABLE 25

Concentrations of antioxidants and oxidative/nitrosative stress biomarkers measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| ASCORBIC ACID | 3315.38 ± 351.59 | 2251.89 ± 271.20 | 2177.22 ± 262.21 | 2195.87 ± 264.45 | *2853.35 ± 343.64* | *2617.09 ± 315.18* |
| GSH | 3521.63 ± 275.04 | 1752.50 ± 231.01 | 1627.30 ± 214.51 | 2412.17 ± 317.97 | *2390.89 ± 315.16* | *2342.03 ± 308.72* |
| MDA | 0.85 ± 0.26 | 10.70 ± 1.77 | 32.98 ± 5.44 | 17.78 ± 2.94 | *6.23 ± 1.03* | *4.09 ± 0.67* |

TABLE 25-continued

Concentrations of antioxidants and oxidative/nitrosative stress biomarkers measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| $NO_2$ | 142.93 ± 18.19 | 241.72 ± 52.37 | 93.04 ± 20.16 | 59.61 ± 12.91 | 110.72 ± 23.99 | 130.69 ± 28.31 |
| $NO_3$ | 169.51 ± 20.79 | 315.71 ± 53.92 | 153.62 ± 26.24 | 234.45 ± 40.05 | 161.99 ± 27.67 | 271.69 ± 46.41 |

Figure 26:
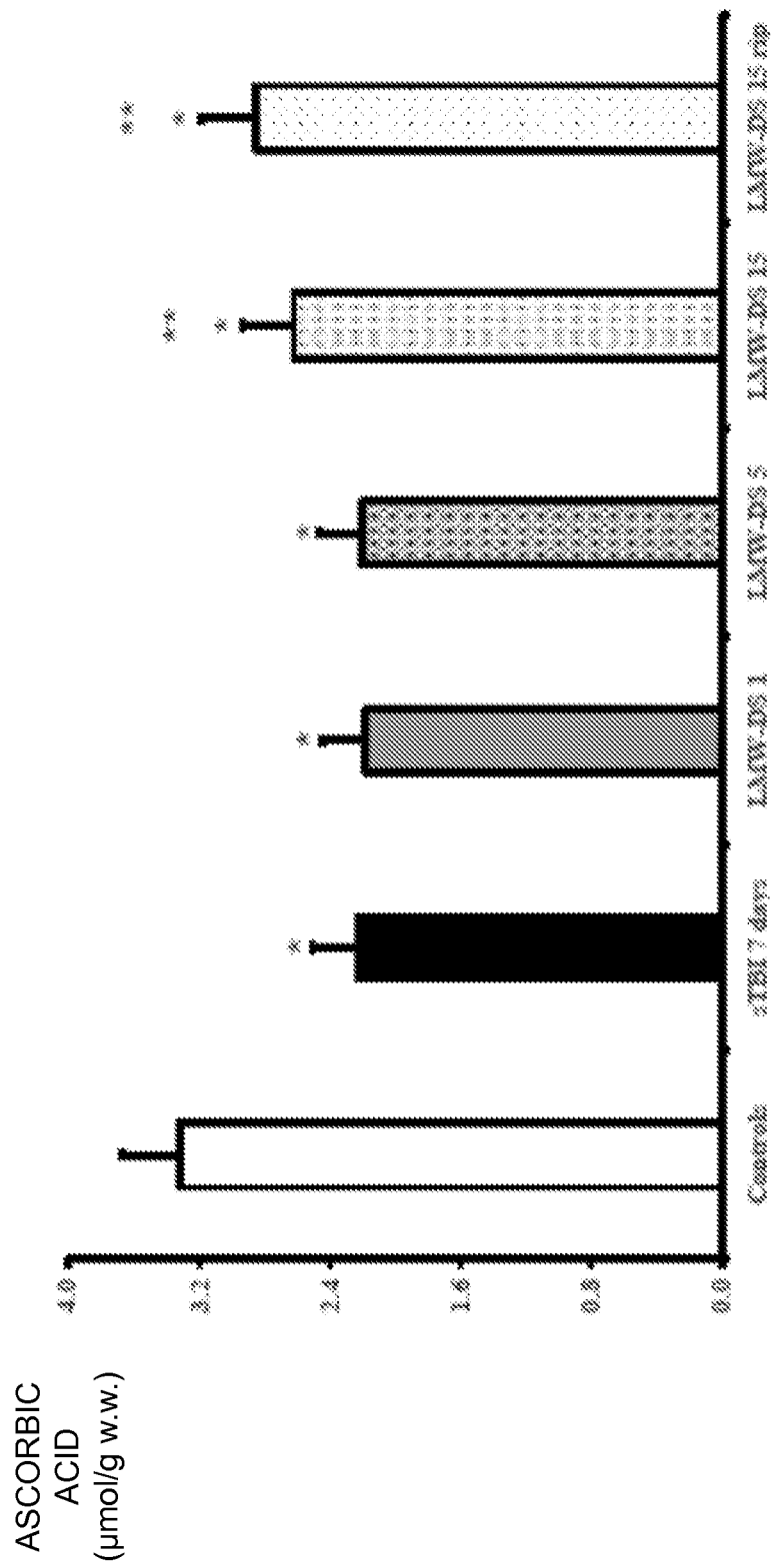
FIG. 26 illustrates concentrations of ascorbic acid measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean of 12 animals. Standard deviations are represented by vertical bars. *significantly different from controls, $p<0.01$. **significantly different from sTBI 2 days, $p<0.01$.
Figure 27:
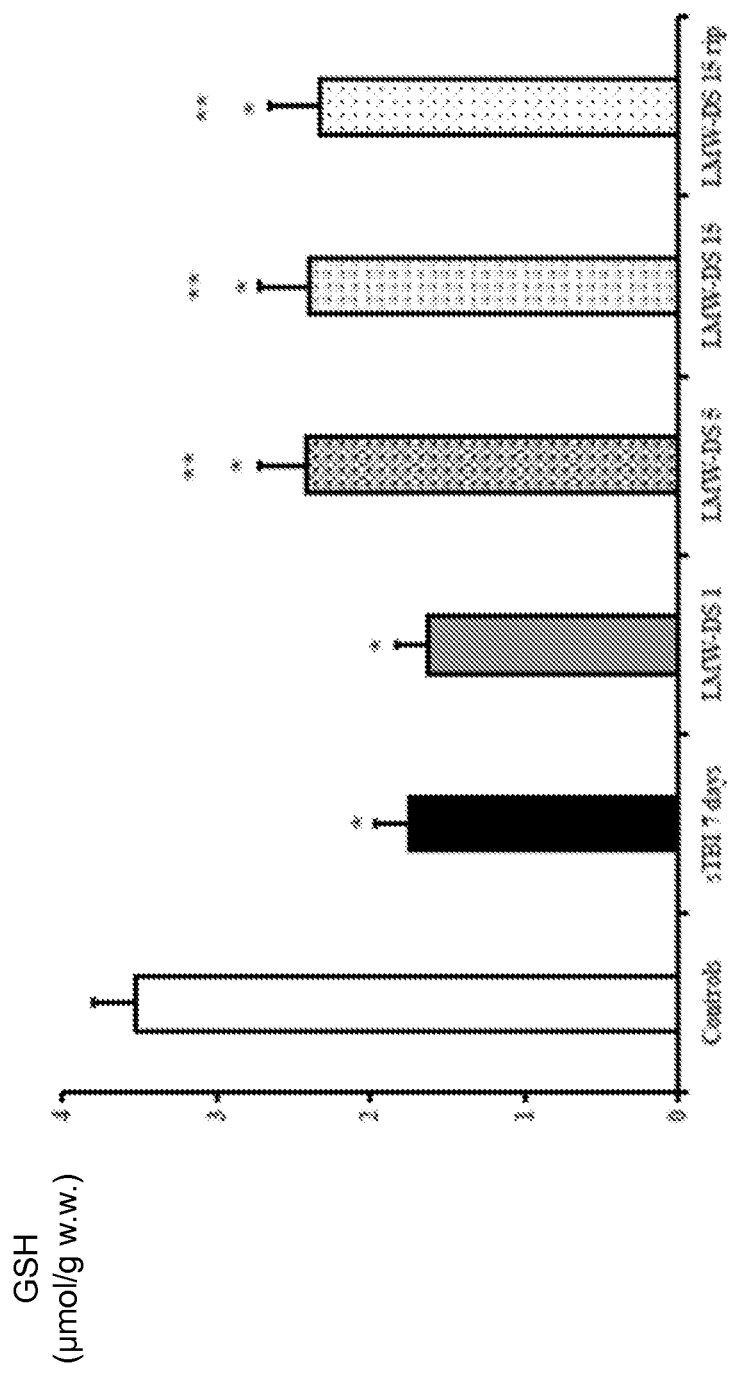
FIG. 27 illustrates concentrations of glutathione (GSH) measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean of 12 animals. Standard deviations are represented by vertical bars. *significantly different from controls, $p<0.01$. **significantly different from sTBI 2 days, $p<0.01$.

To better appreciate that drug effects were related to the drug dosage, we graphically reported in FIGS. 26 and 27 results concerning Ascorbic acid and GSH.

Effects of Increasing Doses of LMW-DS on De-Phosphorylated Purines and Pyrimidines A further worsening in the majority of the compounds reported in Table 26, originating from the degradation pathways of purine and pyrimidine nucleotides and indirectly connected to cell energy metabolism, were observed in rats receiving sTBI at 7 days post injury. Most of these compounds were positively affected by the drug administration.

TABLE 26

Concentrations of de-phosphorylated purines and pyrimidines measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| CYTOSINE | 14.14 ± 3.38 | 21.43 ± 4.60 | 16.03 ± 3.44 | 12.67 ± 2.72 | 13.87 ± 2.98 | 8.76 ± 1.88 |
| CREATININE | 17.12 ± 2.49 | 7.68 ± 1.36 | 6.57 ± 1.16 | 5.48 ± 0.97 | 5.23 ± 0.92 | 9.07 ± 1.60 |
| URACIL | 10.91 ± 2.27 | 22.71 ± 4.67 | 14.78 ± 3.04 | 18.34 ± 3.77 | 15.92 ± 3.27 | 24.13 ± 4.96 |
| β-PSEUDOURIDINE | 6.89 ± 1.27 | 23.36 ± 4.33 | 14.00 ± 2.60 | 17.51 ± 3.25 | 63.77 ± 11.83 | 16.72 ± 3.10 |
| CYTIDINE | 12.76 ± 2.59 | 29.68 ± 10.44 | 29.67 ± 10.44 | 26.51 ± 9.33 | 33.06 ± 11.63 | 72.85 ± 25.63 |
| HYPDXANTHINE | 7.57 ± 0.93 | 24.66 ± 7.18 | 16.97 ± 4.94 | 13.45 ± 3.91 | 10.21 ± 2.97 | 4.10 ± 1.19 |
| GUANINE | 3.34 ± 0.87 | 5.21 ± 2.22 | 6.86 ± 2.92 | 7.92 ± 3.37 | 5.27 ± 2.24 | 3.32 ± 1.41 |
| XANTHINE | 7.61 ± 1.39 | 13.58 ± 3.84 | 12.53 ± 3.54 | 14.33 ± 4.05 | 12.71 ± 3.60 | 11.24 ± 3.18 |
| CDP choline | 7.97 ± 1.37 | 7.90 ± 2.54 | 6.26 ± 2.01 | 10.37 ± 3.33 | 10.06 ± 3.23 | 11.72 ± 3.76 |
| URIDINE | 64.08 ± 14.14 | 84.44 ± 20.01 | 110.17 ± 26.11 | 134.60 ± 31.89 | 134.04 ± 31.76 | 97.21 ± 23.03 |
| INOSINE | 89.43 ± 15.04 | 139.98 ± 15.70 | 124.27 ± 13.94 | 196.61 ± 22.06 | 104.41 ± 11.72 | 139.26 ± 15.62 |
| URIC ACID | 3.36 ± 0.64 | 25.06 ± 5.96 | 7.13 ± 1.70 | 17.26 ± 4.11 | 8.60 ± 2.05 | 7.80 ± 1.86 |
| GUANOSINE | 21.10 ± 5.56 | 31.85 ± 6.64 | 19.11 ± 3.98 | 33.42 ± 6.96 | 20.91 ± 4.36 | 19.66 ± 4.10 |
| ADENOSINE | 46.71 ± 7.39 | 46.71 ± 7.39 | 26.08 ± 19.31 | 22.24 ± 16.47 | 55.95 ± 41.44 | 40.84 ± 30.25 |

Effects of Increasing Doses of LMW-DS on N-Acetylaspartate (NAA)

Figure 28:
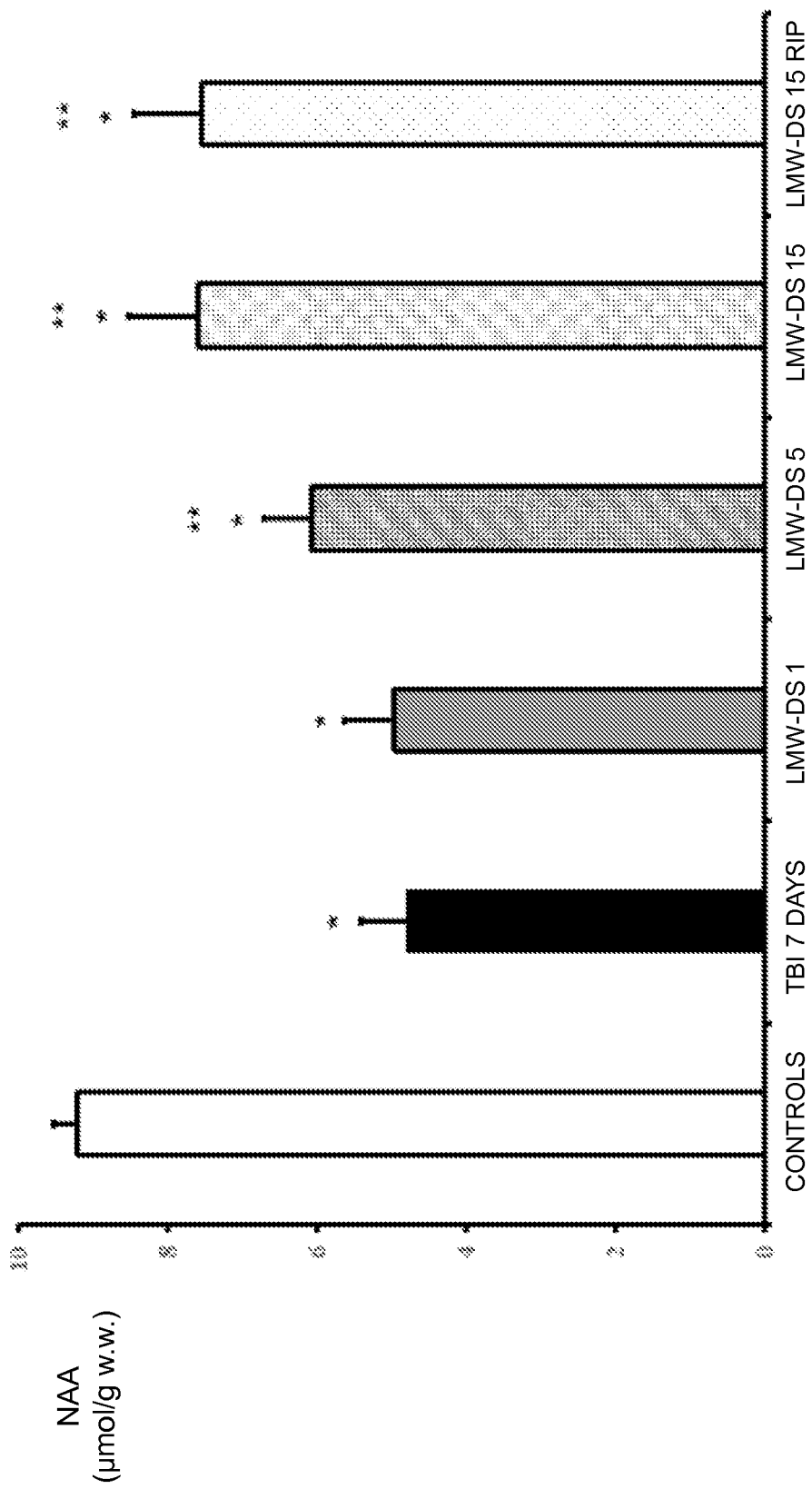
FIG. 28 illustrates concentrations of NAA measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean of 12 animals. Standard deviations are represented by vertical bars. *significantly different from controls, $p<0.01$. **significantly different from sTBI 2 days, $p<0.01$.

As previously mentioned, sTBI causes an irreversible modification in NAA homeostasis. Even in this study, we found that at 7 days post sTBI whole brain NAA was about 50% lower than that measured in control rats, see FIG. 28. Interestingly, a dose dependent increase in NAA was detected in rats receiving increasing doses of single LMW-DS or repeat administrations of the maximal dose tested.

Effects of Increasing Doses of LMW-DS on Free Amino Acids Involved in Neurotransmission Compounds listed in Table 27 are amino acids directly (GLU, GABA) of indirectly (GLN, ASP, AASN, GLY, SER, THR, ALA) involved in neurotransmission. Most of these amino acids had still higher in sTBI rats at 7 days post injury when compared with controls. It is evident from this Table that administration of LMW-DS was effective particularly when the drug was subcutaneously infused at 15 mg/kg b.w., either in a single or in repeat administrations. Particularly relevant is the normalization of GLU, thus indicating that LMW-DS is capable to abolish excitotoxicity cause by excess GLU release after sTBI.

TABLE 27

Concentrations of free amino acids with neurotransmitter functions measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| ASP | 2.88 ± 0.88 | 4.14 ± 0.75 | 4.17 ± 0.67 | 3.63 ± 0.59 | *2.29 ± 0.37* | 2.42 ± 0.39 |
| GLU | 9.92 ± 0.83 | 12.26 ± 1.03 | 12.14 ± 1.02 | 11.82 ± 0.99 | 10.25 ± 0.86 | *10.78 ± 0.91* |
| ASN | 0.10 ± 0.03 | 0.10 ± 0.02 | 0.10 ± 0.02 | 0.10 ± 0.02 | 0.10 ± 0.02 | 0.10 ± 0.02 |
| SER | 0.64 ± 0.17 | 1.04 ± 0.18 | 0.92 ± 0.16 | *0.83 ± 0.14* | 0.76 ± 0.12 | *0.79 ± 0.13* |
| GLN | 3.89 ± 0.87 | 3.97 ± 0.41 | 4.10 ± 0.42 | 3.86 ± 0.40 | 3.73 ± 0.38 | 3.88 ± 0.40 |
| GLY | 0.78 ± 0.13 | 0.91 ± 0.17 | 0.98 ± 0.20 | 0.88 ± 0.15 | 0.78 ± 0.12 | 0.78 ± 0.10 |
| THR | 0.69 ± 0.18 | 0.76 ± 0.10 | 0.71 ± 0.12 | 0.71 ± 0.15 | 0.72 ± 0.14 | 0.77 ± 0.14 |
| ALA | 0.41 ± 0.11 | 0.51 ± 0.05 | *0.57 ± 0.06* | 0.44 ± 0.05 | 0.38 ± 0.04 | 0.47 ± 0.05 |
| GABA | 1.36 ± 0.22 | 1.78 ± 0.18 | 1.73 ± 0.18 | *1.63 ± 0.17* | 1.43 ± 0.15 | 1.38 ± 0.14 |

Effects of Increasing Doses of LMW-DS on Free Amino Acids Involved in the Methyl Cycle As shown in Table 28, levels of free amino acids involved either in the so called methyl cycle or in the formation of cysteine, were still different in sTBI rats at 7 days post impact, when compared to corresponding values of controls. Increase in MET was observed in animals receiving the highest dose of LWM-DS (both as single or as repeat administrations). As already observed at 2 days post injury, these drug levels produced a significant increase in L-Cystathionine (L-Cystat). Since this compound is an intermediate in the generation of cysteine (CYS), it is conceivable to hypothesize that increase in L-Cystat may produce a consequent increase in CYS. It is worth recalling that determination of CYS requires a specific additional HPLC assay with additional derivatization with F-MOC, a fluorescent compound that reacts with secondary amine and with CYS.

TABLE 28

Concentrations of free amino acids involved in the methyl cycle and homeostasis of —SH groups measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| SAH | 0.03 ± 0.01 | 0.05 ± 0.01 | 0.04 ± 0.01 | *0.04 ± 0.01* | 0.04 ± 0.01 | 0.04 ± 0.04 |
| L-Cystat | 0.15 ± 0.03 | 0.23 ± 0.04 | 0.24 ± 0.04 | 0.26 ± 0.04 | 0.25 ± 0.04 | *0.44 ± 0.07* |
| MET | 0.03 ± 0.01 | 0.03 ± 0.01 | 0.03 ± 0.01 | 0.04 ± 0.01 | 0.04 ± 0.01 | 0.05 ± 0.01 |

Effects of Increasing Doses of LMW-DS on Free Amino Acids Involved in the Generation of Nitric Oxide (NO)

Table 29 illustrates concentrations of the free amino acids directly involved in the generation of NO. Animals at 7 days post sTBI showed still concomitant decrease in ARG and increase in CITR, in line with data showing increase in the stable NO end products nitrites and nitrates (Table 15). Administration of LMW-DS was particularly effective when 5 or 15 mg/kg b.w. (single and repeat) were used.

TABLE 29

Concentrations of free amino acids involved in nitric oxide formation measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| CITR | 0.03 ± 0.01 | 0.04 ± 0.02 | 0.03 ± 0.01 | 0.03 ± 0.01 | 0.03 ± 0.01 | 0.03 ± 0.01 |
| ARG  | 0.17 ± 0.03 | 0.13 ± 0.02 | 0.13 ± 0.02 | 0.15 ± 0.02 | 0.14 ± 0.02 | *0.19 ± 0.02* |
| ORN  | 0.02 ± 0.01 | 0.01 ± 0.01 | 0.01 ± 0.01 | *0.01 ± 0.01* | *0.01 ± 0.01* | *0.02 ± 0.01* |

Effects of Increasing Doses of LMW-DS on Long-Chain Free Amino Acids

The free amino acids reported in Table 30, representing a source of carbon skeleton useful to generate a-ketoacids that cells use to replenish the TCA cycle, were practically normal at 7 days post sTBI and any other group of animals treated with the drug of interest.

TABLE 30

Concentrations of long chain free amino acids measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmoL/g w.w.

| Compound | Controls | TBI only | LMW-DS 1 | LMW-DS 5 | LMW-DS 15 | LMW-DS 15-R |
|---|---|---|---|---|---|---|
| VAL | 0.07 ± 0.02 | 0.07 ± 0.01 | 0.08 ± 0.01 | 0.08 ± 0.01 | *0.10 ± 0.01* | 0.07 ± 0.01 |
| ILE | 0.03 ± 0.01 | 0.03 ± 0.01 | 0.04 ± 0.01 | *0.05 ± 0.01* | *0.07 ± 0.01* | 0.03 ± 0.01 |
| LEU | 0.04 ± 0.01 | 0.04 ± 0.01 | *0.05 ± 0.01* | *0.05 ± 0.01* | *0.07 ± 0.01* | 0.04 ± 0.01 |
| LYS | 0.23 ± 0.03 | 0.19 ± 0.03 | 0.19 ± 0.06 | 0.21 ± 0.04 | 0.21 ± 0.05 | 0.23 ± 0.07 |

Effects of Increasing Doses of LMW-DS on Free Amino Acids Acting as Osmolytes and Aromatic Free Amino Acids Results summarized in Table 31 clearly show that sTBI caused the increase in the concentrations of taurine (TAU) at 7 days after injury. LMW-DS administration normalized TAU concentrations and caused the increase in aromatic amino acids.

TABLE 31

Concentrations of free amino acids acting as osmolytes and aromatic free amino acids measured in deproteinized brain homogenates of rats sacrificed at 7 days post-sTBI, without and with administration of increasing doses of LWM-DS (single administration of 1, 5 and 15 mg/kg b.w. and repeated administration of 15 mg/kg b.w.). Controls are represented by sham-operated animals. Values are the mean ± S.D. of 12 animals in each group and are expressed as nmol/g w.w.

| Compound | Controls | TBI only | LMW-DS 1 | LMW-DS 5 | LMW-DS 15 | LMW-DS 15-R |
|---|---|---|---|---|---|---|
| HYS | 0.05 ± 0.01 | 0.06 ± 0.01 | 0.06 ± 0.01 | 0.06 ± 0.01 | 0.06 ± 0.01 | 0.06 ± 0.01 |
| TAU | 3.82 ± 0.61 | 4.36 ± 0.56 | 4.02 ± 0.51 | 3.51 ± 0.44 | 3.38 ± 0.44 | 3.47 ± 0.44 |
| TYR | 0.13 ± 0.03 | 0.14 ± 0.02 | 0.13 ± 0.02 | 0.13 ± 0.02 | 0.14 ± 0.02 | 0.14 ± 0.02 |
| TRP | 0.02 ± 0.01 | 0.02 ± 0.01 | *0.01 ± 0.01* | 0.02 ± 0.01 | *0.03 ± 0.01* | *0.03 ± 0.01* |
| PHE | 0.03 ± 0.01 | 0.04 ± 0.01 | *0.05 ± 0.01* | *0.06 ± 0.01* | *0.07 ± 0.01* | *0.05 ± 0.01* |

Discussion

TBI is one of the most common neurodegenerative diseases and represents the leading cause of death under 45 years of age in Western countries. Its incidence is on the rise and by 2020 the World Health Organization estimates that TBI will be the largest cause of disability worldwide. Depending on the severity of the symptoms related to TBI (evaluated by the Glasgow Coma Scale), it is possible to identify three different types of TBI: mild TBI (mTBI), moderate TBI and severe TBI (sTBI). It has been calculated that the ratio in the occurrence of mTBI to sTBI is approximately 22 to 1. Unfortunately, the consequences of a TBI are often invalidating and possibly leading to permanent or temporary impairment of cognitive, physical and psychosocial functions, with an associated diminished or altered state of consciousness. Thus, patients are affected in some important aspects, primarily the ability to be independent, to correctly work and to maintain social relationships.

TBI is considered a complicated pathological process consisting of a primary insult (the impact force acting on the brain tissue) directly inducing a scarcely predictable secondary insult characterized by a cascade of biochemical, metabolic and molecular changes causing profound mitochondrial malfunctioning in cerebral cells. The severity of the damage depends on the impact force acting on the cerebral tissue; in fact, this event induces a stretching of axonal and neuronal fibers, triggering the biochemical and molecular events, which are not simultaneous with the insurgence of clinical symptoms.

To date, there are no satisfying pharmacological treatments capable to decrease mortality and improve recovery of TBI patients. Putative pharmacological treatments are generally tested in their ability to interfere with the neurometabolic cascade triggered by the primary insult, such as the biochemical and molecular alterations occurring to the cerebral tissue metabolism, as well as the vascular and hematic flow changes strictly correlated with tissue damages.

Previous studies have demonstrated a significant correlation between the severity of TBI and energy deficit associated with the increase rate of the anaerobic metabolism, mitochondrial dysfunction, increase production of reactive oxygen (ROS) and nitrogen species (RNS) and enhance in excitatory amino acid release. Moreover, N-acetylated amino acid N-acetylaspartate (NAA) is a reliable surrogate biomarker useful to monitor in vivo the state of the energetic metabolism. Indeed, since mitochondrial NAA biosynthesis has a high indirect energy expenditure, changes in NAA intracerebral concentration are closely related to changes in homeostasis of some parameters related to energy metabolism (ATP, GTP, ADP, AMP, Acetyl-CoA, CoA-SH and NAD+) and to mitochondrial phosphorylating capacity (ATP/ADP).

The study conducted to evaluate the effects of increasing doses of LMW-DS on a large panel of brain metabolites in rats experiencing sTBI at different times post injury evidenced that the administration of this compound produces a general amelioration of cerebral metabolism.

LMW-DS was effective in restoring mitochondrial related energy metabolism, profoundly imbalanced in sTBI animals with no treatment, with positive effects on the concentration of triphosphates purine and pyrimidine nucleotides. Particularly, ATP levels, at 7 days post impact, were only 16% lower than the value of controls, whilst in sTBI rats a 35% decrease was found (Table 21 and FIG. 25). Remarkably, NAA concentration in animals treated with LMW-DS at the same time point was only 16% lower than the value of controls, whilst sTBI animals showed 48% lower values of this compound. This finding once again strongly confirms the strict connection between the homeostasis of NAA and correct mitochondrial energy metabolism, and underlines the importance of pharmacological interventions capable to act positively on mitochondrial functioning.

The general amelioration of brain metabolism produced by LMW-DS administration also involved nicotinic coenzymes and metabolism of free CoA-SH and CoA-SH derivatives. This implies that drug treated animals, notwithstanding submitted to sTBI, had quasi-normal coenzymes to ensure correct oxido-reductive reactions and to allow a good functioning of the TCA cycle.

The aforementioned improvement of brain metabolism certainly contributed to the other remarkable drug effect, i.e., the abolishment of GLU excitotoxicity. Additionally, the drug affected sulphur-containing amino acids. Possibly, this effect might be related to the drug molecule that contains S atoms. Increasing the bioavailability of this atom might have produced a net increase in the biosynthesis of these amino acids, one of them (MET) is crucial in the methylation reaction and in the so called methyl cycle.

Further positive effects recorded in this study were the increase in antioxidants and the decrease of biochemical signatures of oxidative/nitrosative stress in sTBI rats receiving administration of LMW-DS. Even this phenomenon might well be connected with the normalization of mitochondrial functions, since dysfunctional mitochondria are the main intracellular source of both ROS and RNS. Of relevance is that the effects of LMW-DS were more evident at 7 than at 2 days post sTBI. This strongly suggest that the general amelioration of brain metabolism caused by the drug administration is not a transitory phenomenon. Also, it is worth underlining that, under the present experimental conditions, drug effects are often related to the dose administered, even though the repeat administration of 15 mg/kg b.w. was often similar to the single administration of the same dosage. That is, it was not always advantageous to repeat the administration of the drug.

This contradictory result might have the following explanation: 1) it is well known that sTBI induces breakdown of the blood brain barrier (BBB); 2) it is possible that uptake by the brain tissue of LMW-DS is highly favored during period of BBB alterations/breakdown; 3) if the hypothesis in point 2) is correct, then the administration performed at 30 minutes post injury might had occurred when BBB was still open/altered; 4) if the hypotheses of points 2) and 3) are correct, then the administration early post injury, when BBB is still open/altered, might have facilitated the passage of the compound within the cerebral compartment, allowing the drug to elicit its beneficial effects on brain metabolism and functions, including normalization of the BBB; 5) if what reported in point 4) is correct, it means that the administration of 15 mg/kg b.w. of LMW-DS at 30 minutes post sTBI in addition to start brain metabolism normalization, also caused the closure of the BBB so that the second (at 3 days) and the third (at 5 days) drug administrations occurred under unfavorable condition for a further significant passage within the brain compartment, thus limiting the possibility to obtain additional effects with a repeat drug administration protocol.

Example 8

In this study LMW-DS was characterized by profiling in the BioMAP® Diversity PLUS panel. The BioMAP® panel consists of human primary cell-based systems designed to model different aspects of the human body in an in vitro format. The 12 systems in the BioMAP® Diversity PLUS panel (Table 32) allow test agent characterization in an unbiased way across a broad set of systems modeling various human disease states. The BioMA®P systems are constructed with one or more primary cell types from healthy human donors, with stimuli, such as cytokines or growth factors, added to capture relevant signaling networks that naturally occur in human tissue or pathological conditions. Vascular biology is modeled in both a Th1 (3C system) and a Th2 (4H system) inflammatory environment, as well as in a Th1 inflammatory state specific to arterial smooth muscle cells (CASM3C system). Additional systems recapitulate aspects of the systemic immune response including monocyte-driven Th1 inflammation (LPS system) or T cell stimulation (SAg system), chronic Th1 inflammation driven by macrophage activation (IMphg system) and the T cell-dependent activation of B cells that occurs in germinal centers (BT system). The BE3C system (Th1) and the BF4T system (Th2) represent airway inflammation of the lung, while the MyoF system models myofibroblast-lung tissue remodeling. Lastly, skin biology is addressed in the KF3CT system modeling Th1 cutaneous inflammation and the HDF3CGF system modeling wound healing.

Each test agent generates a signature BioMAP® profile that is created from the changes in protein biomarker readouts within individual system environments. Biomarker readouts (7-17 per system) are selected for therapeutic and biological relevance, are predictive for disease outcomes or specific drug effects and are validated using agents with known mechanism of action (MoA). Each readout is measured quantitatively by immune-based methods that detect protein, e.g., ELISA, or functional assays that measure proliferation and viability. BioMAP® readouts are diverse and include cell surface receptors, cytokines, chemokines, matrix molecules and enzymes. In total, the BioMAP® Diversity PLUS panel contains 148 biomarker readouts that capture biological changes that occur within the physiological context of the particular BioMAP® system.

Materials and Methods

Four concentrations of LMW-DS (150 nM, 440 nM, 1.3 µM, 4 µM) were investigated in the BioMAP® Diversity PLUS panel by Eurofins.

Methods for Diversity PLUS

Human primary cells in BioMAP systems are used at early passage (passage 4 or earlier) to minimize adaptation to cell culture conditions and preserve physiological signaling responses. All cells are from a pool of multiple donors (n=2-6), commercially purchased and handled according to the recommendations of the manufacturers. Human blood derived $CD14^+$ monocytes are differentiated into macrophages in vitro before being added to the /Mphg system. Abbreviations are used as follows: Human umbilical vein endothelial cells (HUVEC), Peripheral blood mononuclear cells (PBMC), Human neonatal dermal fibroblasts (HDFn), B cell receptor (BCR), T cell receptor (TCR) and Toll-like receptor (TLR).

Cell types and stimuli used in each system are as follows: 3C system [HUVEC+(IL-1β, TNFα and IFNγ)], 4H system [HUVEC+(IL-4 and histamine)], LPS system [PBMC and HUVEC+LPS (TLR4 ligand)], SAg system [PBMC and HUVEC+TCR ligands], BT system [$CD19^+$ B cells and PBMC+(a-IgM and TCR ligands)], BF4T system [bronchial epithelial cells and HDFn+(TNFα and IL-4)], BE3C system [bronchial epithelial cells+(IL-1β, TNFα and IFNγ)], CASM3C system [coronary artery smooth muscle cells+(IL-1β, TNFα and IFNγ)], HDF3CGF system [HDFn+(IL-1β, TNFα, IFNγ, EGF, bFGF and PDGF-BB)], KF3CT system [keratinocytes and HDFn+(IL-1β, TNFα, IFNγ and TGFβ)], MyoF system [differentiated lung myofibroblasts+(TNFα and TGFβ)] and /Mphg system [HUVEC and M1 macrophages+Zymosan (TLR2 ligand)].

Systems are derived from either single cell types or co-culture systems. Adherent cell types are cultured in 96 or 384-well plates until confluence, followed by the addition of PBMC (SAg and LPS systems). The BT system consists of CD19+ B cells co-cultured with PBMC and stimulated with a BCR activator and low levels of TCR stimulation. Test agents prepared in either DMSO (small molecules; final concentration 0.1%) or PBS (biologics) are added at the indicated concentrations 1-hr before stimulation, and remain in culture for 24-hrs or as otherwise indicated (48-hrs, MyoF system; 72-hrs, BT system (soluble readouts); 168-hrs, BT system (secreted IgG)). Each plate contains drug controls (e.g., legacy control test agent colchicine at 1.1 µM), negative controls (e.g., non-stimulated conditions) and vehicle controls (e.g., 0.1% DMSO) appropriate for each system. Direct ELISA is used to measure biomarker levels of cell-associated and cell membrane targets. Soluble factors from supernatants are quantified using either HTRF® detection, bead-based multiplex immunoassay or capture ELISA. Overt adverse effects of test agents on cell proliferation and viability (cytotoxicity) are detected by sulforhodamine B (SRB) staining, for adherent cells, and alamarBlue® reduction for cells in suspension. For proliferation assays, individual cell types are cultured at subconfluence and measured at time points optimized for each system (48-hrs: 3C and CASM3C systems; 72-hrs: BT and HDF3CGF systems; 96-hrs: SAg system). Cytotoxicity for adherent cells is measured by SRB (24-hrs: 3C, 4H, LPS, SAg, BF4T, BE3C, CASM3C, HDF3CGF, KF3CT, and /Mphg systems; 48-hrs: MyoF system), and by alamarBlue staining for cells in suspension (24-hrs: SAg system; 42-hrs: BT system) at the time points indicated.

Data Analysis

Biomarker measurements in a test agent-treated sample are divided by the average of control samples (at least 6 vehicle controls from the same plate) to generate a ratio that is then $\log_{10}$ transformed. Significance prediction envelopes are calculated using historical vehicle control data at a 95% confidence interval.

Profile Analysis

Biomarker activities are annotated when 2 or more consecutive concentrations change in the same direction relative to vehicle controls, are outside of the significance envelope and have at least one concentration with an effect size>20% ($|\log_{10}$ ratio$|>0.1$). Biomarker key activities are described as modulated if these activities increase in some systems, but decrease in others. Cytotoxic conditions are noted when total protein levels decrease by more than 50% ($\log_{10}$ ratio of SRB or alamarBlue levels<–0.3) and are indicated by a thin black arrow above the X-axis. A compound is considered to have broad cytotoxicity when cytotoxicity is detected in 3 or more systems. Concentrations of test agents with detectable broad cytotoxicity are excluded from biomarker activity annotation and downstream benchmarking, similarity search and cluster analysis. Antiproliferative effects are defined by an SRB or alamarBlue $\log_{10}$ ratio value <–0.1 from cells plated at a lower density and are indicated by grey arrows above the X-axis. Cytotoxicity and antiproliferative arrows only require one concentration to meet the indicated threshold for profile annotation.

Benchmark Analysis

Common biomarker readouts are annotated when the readout for both profiles is outside of the significance envelope with an effect size >20% in the same direction. Differentiating biomarkers are annotated when one profile has a readout outside of the significance envelope with an effect size >20%, and the readout for the other profile is either inside the envelope or in the opposite direction. Unless specified, the top non-cytotoxic concentration of both the test agent and benchmark agent are included in the benchmark overlay analysis.

Similarity Analysis

Common biomarker readouts are annotated when the readout for both profiles is outside of the significance envelope with an effect size >20% in the same direction. Concentrations of test agents that have 3 or more detectable systems with cytotoxicity are excluded from similarity analysis. Concentrations of test agents that have 1-2 systems with detectable cytotoxicity will be included in the similarity search analysis, along with an overlay of the database match with the top concentration of the test agent. This will be followed by an additional overlay of the next highest concentration of the test agent containing no systems with detectable cytotoxicity and the respective database match. To determine the extent of similarity between BioMAP® profiles of compounds run in the Diversity PLUS panel, we have developed a custom similarity metric (BioMAP Z-Standard) that is a combinatorial approach that has improved performance in mechanism classification of reference agents compared to other measures tested (including Pearson's and Spearman's correlation coefficients). This approach more effectively accounts for variations in the number of data points, systems, active biomarker readouts and the amplitude of biomarker readout changes that are characteristic features of BioMAP® profiles. A Pearson's correlation coefficient (r) is first generated to measure the linear association between two profiles that is based on the similarity in the direction and magnitude of the relationship. Since the Pearson's correlation can be influenced by the magnitude of any biomarker activity, a per-system weighted average Tanimoto metric is used as a filter to account for underrepresentation of less robust systems. The Tanimoto metric does not consider the amplitude of biomarker activity, but addresses whether the identity and number of readouts are in common on a weighted, per system basis. A real-value Tanimoto metric is calculated first by normalizing each profile to the unit vector $$\left(e.g., A = \frac{A}{\|A\|}\right)$$

and then applying the following formula:

$$\frac{A \cdot B}{\|A\| + \|B\| - A \cdot B},$$

where A and B are the 2 profile vectors. Then, it is incorporated into a system weighted-averaged real-value Tanimoto metric in this calculation:

$$\frac{\Sigma W_i \cdot T_i}{\Sigma W_i}.$$

The calculation uses the real-value Tanimoto score for each $i^{th}$ system (T1) and the weight of each $i^{th}$ system (W). W is calculated for each system in the following formula:

$$\frac{1}{1 + \exp(-100 \times ())/lr - 0.09},$$

where lr is the largest absolute value of the ratios from the 2 profiles being compared. Based on the optimal performance of reference compounds, profiles are identified as having mechanistically relevant similarity if the Pearson's correlation coefficient (r) 0.7. Finally, a Fisher r-to-z-transformation is used to calculate a z-score to convert a short tail distribution into a normal distribution as follows:

$$z = 0.5 \log_{10} \frac{1+r}{1-r}.$$

Then the BioMAP® Z-Standard, which adjusts for the number of common readouts (CR), is generated according to the following formula: Z-Standard=z·$\sqrt{CR-3}$. A larger BioMAP® Z-Standard value corresponds to a higher confidence level, and this is the metric used to rank similarity results.

Cluster Analysis

Cluster analysis (function similarity map) uses the results of pairwise correlation analysis to project the "proximity" of agent profiles from multi-dimensional space into two dimensions. Functional clustering of the agent profiles generated during this analysis uses Pearson correlation values for pairwise comparisons of the profiles for each agent at each concentration, and then subjects the pairwise correlation data to multidimensional scaling. Profiles that are similar with a Pearson's correlation coefficient (r) 0.7 are connected by lines. Agents that do not cluster with one another are interpreted as mechanistically distinct. This analysis is performed for projects with 3 or more agents tested. Cytotoxic concentrations are excluded from cluster analysis.

Mechanism HeatMAP Analysis

Mechanism HeatMAP analysis provides a visualization of the test compound and 19 consensus mechanisms allowing comparison of biomarker activities across all compound concentrations and consensus mechanisms. The synthetic consensus profiles used in the Mechanism HeatMAP analysis are representative BioMAP® profiles of the average of multiple compounds from structurally distinct chemical classes. Profiles were calculated by averaging the values for each biomarker endpoint for all profiles selected (multiple agents at different concentrations) to build the consensus mechanism profile. Biomarker activities are colored in the heatmap for consensus mechanisms and compounds when they have expression relative to vehicle controls outside of the significance envelope. Red represents increased protein expression, blue represents decreased expression and white indicates levels that were unchanged or within filtering conditions. Darker shades of color represent greater change in biomarker activity relative to vehicle control. The Mechanism HeatMAP was prepared using R and the gplots package for R.

Assay Acceptance Criteria

A BioMAP® assay includes the multi-parameter data sets generated by the BioMAP® platform for agents tested in the systems that make up the Diversity PLUS panel. Assays contain drug controls (e.g., legacy control test agent colchicine), negative controls (e.g., non-stimulated conditions), and vehicle controls (e.g., DMSO) appropriate for each system. BioMAP® assays are plate-based, and data acceptance criteria depend on both plate performance (% CV of vehicle control wells) and system performance across historical controls for that system. The QA/QC Pearson Test is performed by first establishing the 1% false negative Pearson cutoff from the reference dataset of historical positive controls. The process iterates through every profile of system biomarker readouts in the positive control reference dataset, calculating Pearson values between each profile and the mean of the remaining profiles in the dataset. The overall number of Pearson values used to determine the 1% false negative cutoff is the total number of profiles present in the reference dataset. The Pearson value at the one percentile of all values calculated is the 1% false negative Pearson cutoff. A system will pass if the Pearson value between the experimental plate's negative control or drug control profile and the mean of the historical control profiles in the reference dataset exceeds this 1% false negative Pearson cutoff. Overall assays are accepted when each individual system passes the Pearson test and 95% of all project plates have % CV<20%.

Results

The BioMAP® Diversity PLUS panel contained 12 individual BioMAP human primary cell-based co-culture system as shown in Table 32.

TABLE 32

BioMAP ® Diversity PLUS panel

| System name | Disease/Tissue relevance | Human cell types | Biomarker readouts |
|---|---|---|---|
| 3C | Cardiovascular Disease, Chronic Inflammation | Venular endothelial cells | CCL2/MCP-1, CD106/VCAM-1, CD141/Thrombomodulin, CD142/Tissue Factor, CD54/ICAM-1, CD62E/E-Selectin, CD87/uPAR, CXCL8/IL-8, CXCL9/MIG, HLA-DR, Proliferation, SRB |
| 4H | Allergy, Asthma, Autoimmunity | Venular endothelial cells | CCL2/MCP-1, CCL26/Eotaxin-3, CD106/VCAM-1, CD62P/P-Selectin, CD87/uPAR, SRB, VEGFR2 |
| BE3C | COPD, Lung Inflammation | Bronchial epithelial cells | CD54/ICAM-1 , CD87/uPAR, CXCL10/IP-10, CXCL11/I-TAC, CXCL8/IL-8, CXCL9/MIG, EGFR, HLA-DR, IL-1 α, Keratin 8/18, MMP-1, MMP-9, PAI-I, SRB, tPA, uPA |
| BF4T | Allergy, Asthma, Fibrosis, Lung Inflammation | Bronchial epithelial cells+ Dermal fibroblasts | CCL2/MCP-1, CCL26/Eotaxin-3, CD106/VCAM-1, CD54/ICAM-1, CD90, CXCL8/IL-8, IL-1 α, Keratin 8/18, MMP-1, MMP-3, MMP-9, PAI-I, SRB, tPA, uPA |
| BT | Allergy, Asthma, Autoimmunity, Oncology | B cells+ Peripheral blood mononuclear cells | B cell Proliferation, PBMC Cytotoxicity, Secreted IgG, sIL-17A, sIL-17F, sIL-2, sIL-6, sTNF-α |
| CASM3C | Cardiovascular Inflammation, Restenosis | Coronary artery smooth muscle cells | CCL24/MCP-1, CD106/VCAM-1, CD141/Thrombomodulin, CD142/Tissue Factor, CD87/uPAR, CXCL8/IL-8, CXCL9/MIG, HLA-DR, IL-6, LDLR, M-CSF, PAI-I, Proliferation, Serum Amyloid A, SRB |
| HDF3CGF | Chronic Inflammation, Fibrosis | Dermal fibroblasts | CCL2/MCP-1, CD106/VCAM-1, CD54/ICAM-1, Collagen I, Collagen III, CXCL10/IP-10, CXCL11/I-TAC, CXCL8/IL-8, CXCL9/MIG, EGFR, M-CSF, MMP-I, PAI-I, Proliferation_72hr, SRB, TIMP-1, TIMP-2 |
| KF3CT | Dermatitis, Psoriasis | Dermal fibroblasts+ Keratinocytes | CCL2/MCP-1 , CD54/ICAM-1, CXCL10/IP-10, CXCL8/IL-8, CXCL9/MIG, IL-1 α, MMP-9, PAI-I, SRB, TIMP-2, uPA |
| LPS | Cardiovascular Disease, Chronic Inflammation | Peripheral blood mononuclear cells+ Venular endothelial cells | CCL2/MCP-1, CD106/VCAM-1, CD141/Thrombomodulin, CD142/Tissue Factor, CD40, CD62E/E-Selectin, CD69, CXCL8/IL-8, IL-1 α, M-CSF, sPGE2, SRB, sTNF-α |
| MyoF | Chronic Inflammation, Fibrosis, Matrix Remodeling, Wound Healing | Lung fibroblasts | bFGF, CD106/VCAM-1, Collagen I, Collagen III, Collagen V. CXCL8/IL-8, Decorin, MMP-1, PAI-I, SRB, TMP-I, α-SM Actin |
| SAg | Autoimmune Disease, Chronic Inflammation | Peripheral blood mononuclear cells+ Venular endothelial cells | CCL2/MCP-1, CD38, CD40, CD62E/E-Selectin, CD69, CXCL8/IL-8, CXCL9/MIG, PBMC Cytotoxicity, Proliferation, SRB |
| /Mphg | Cardiovascular Disease, Chronic Inflammation, Restenosis | Macrophages+ Venular endothelial cells | CCL2/MCP-1, CCL3/MIP-1 α, CD106/VCAM-I, CD40, CD62E/E-Selectin, CD69, CXCL8/IL8, IL-1 α, M-CSF, sIL-10, SRB, SRB-Mphg |

Biomarker activities were annotated when two or more consecutive concentrations changed in the same direction relative to vehicle controls, were outside of the 95% significance envelope, and had at least one concentration with an effect size >20% (|log$_{10}$ ratio|>0.1). Biomarker key activities were described as modulated if these activities increased in some systems, but decreased in others.

LMW-DS was active with 25 annotated readouts. LMW-DS was not cytotoxic for any of the human primary cells at the concentrations tested in this study. LMW-DS mediated changes in key biomarker activities included inflammation-related activities in the form of decreased vascular cell adhesion molecule 1 (VCAM-1), monocyte chemoattractant protein-1 (MCP-1), soluble tumor necrosis factor alpha (sTNFα), interferon-inducible T cell alpha chemoattractant (I-TAC), monokine induced by gamma interferon (MIG), and interferon gamma-induced protein 10 (IP-10) and increased Eotaxin 3 (Eot3), and interleukin 8 (IL-8). LMW-DS also had immunomodulatory activities in the form of decreased secreted immunoglobulin G (sIgG) and macrophage colony-stimulating factor (M-CSF) and increased soluble IL-17A (sIL-17A), and cluster of differentiation 69 (CD69). LMW-DS also showed tissue remodeling activities in the form of increased matrix metalloproteinase-1 (MMP-1), plasminogen activator inhibitor-1 (PAI-1), urokinase plasminogen activator receptor (uPAR) and epidermal growth factor receptor (EGFR), and hemostasis-related activities in the form of increased thrombomodulin (TM). Table 33 summaries the effects of LMW-DS on the 12 different human primary cells in the BioMAP® Diversity PLUS panel.

TABLE 33

Summary of BioMAP® Diversity PLUS results

| Cell system | Increased biomarker activity | Decreased biomarker activity |
|---|---|---|
| 3C | IL-8 | |
| 4H | uPAR | |
| LPS | IL-8 | sTNFα |
| SAg | IL-8 | |
| BT | sIL-17A | sIgG, sIL-17F |
| BF4T | Eot3 | |
| BE3C | | |
| CASM3C | TM | VCAM-1, MIG |
| HDF3CGF | EGFR, MMP-1, PAI-1 | VCAM-1, IP-10, ITAC, MIG, M-CSF MCP-1 |
| KF3CT | IL-8 | |
| MyoF | IL-8 | |
| /Mphg | IL-8, CD69 | |

The BioMAP® Reference Database contains >4,500 BioMAP® profiles of bioactive agents (biologics, approved drugs, chemicals and experimental agents) and can be used to classify and identify the most similar profiles.

In an unsupervised search for mathematically similar compound profiles from the BioMAP® Reference Database, LMW-DS (4 M) is most similar to clexane (30 μg/ml) (Pearson's correlation coefficient, r=0.701). Clexane (enoxaparin sodium) is a low molecular weight heparin that is an anticoagulant used to treat deep vein thrombosis (DVT). There are five common activities that are annotated within the following systems: BT (sIgG, sIL-17A), CASM3C (MIG), and HDF3CGF (VCAM-1, IP-10).

Discussion

In study LMW-DS was characterized by profiling in the BioMAP® Diversity PLUS panel of human primary cell-based assays modeling complex tissue and disease biology of organs (vasculature, immune system, skin, lung) and general tissue biology. The BioMAP® Diversity PLUS panel evaluated the biological impact of LMW-DS in conditions that preserve the complex crosstalk and feedback mechanisms that are relevant to in vivo outcomes.

LMW-DS was active and noncytotoxic at the concentrations tested in this study. LMW-DS was modestly and selectively antiproliferative to human primary endothelial cells at the top concentration only (4 μM). LMW-DS profiles had 25 annotated readouts indicating modulation of immune and inflammation-related readouts as well as matrix related biomarkers. Specific activities included decreased inflammation-related VCAM-1, MCP-1, sTNFα, I-TAC, MIG, and IP-10 as well as increased IL-8. Modestly increased Eotaxin-3 was observed in the BF4T system at the lower concentrations only. Immunomodulatory activities included decreased sIgG and IL-17A and IL-17F in the BT system, but without any antiproliferative effects on B cells. Decreased M-CSF and increased CD69 were also identified. LMW-DS also modulated tissue remodeling biomarkers including increased MMP-1, PAI-1, uPAR, EGFR, and the hemostasis-related TM. Key inflammation biomarkers including MIG, VCAM, IP-10 and ITAC were decreased over all tested concentrations in the CASM3C and HDF3CGF systems, while an increase in the chemotactic factor IL-8 was noted in multiple systems. Together these data indicate that LMW-DS plays a role in regulating immune activation and/or immune resolution responses in the context of inflammation and wound healing biology.

The modulations of the inflammatory markers indicate utility of LMW-DS in treating multiple chronic and acute inflammatory conditions and diseases including inflammatory components, such as ALS.

Initially after injury, the innate/proinflammatory response and selected components of the acquired immune response are up-regulated to maintain a defense against foreign pathogens, clear tissue debris present at the injury site, and orchestrate tissue remodeling, cell proliferation and angiogenic processes associated with the wound response. However, for proper wound healing to progress, this initial inflammatory response has to be regulated or shut down so as to allow for the reestablishment of matrix, recellularization and tissue remodeling. Such immune resolving activities were induced by LMW-DS, including activation of MMP-1, PAR-1 and uPAR, indicating an induced immune resolution having utility in treating tissue damaged by trauma, including neurotrauma, which otherwise would result in deleterious fibrosis formation.

LMW-DS modulated a lot of biomarker activities in the HDF3CGF system but merely IL-8 in the MyoF system. Both systems include fibroblasts but HDF3CGF models wound healing and matrix remodeling in connection with such wound healing, whereas MyoF is more a fibrosis model of collagen deposition. The results thereby indicate that LMW-DS had immunomodulatory and tissue remodeling activities but without inducing undesired collagen fibrosis, which could result in deleterious fibrosis deposition.

In conclusion, LMW-DS seems to normalize and resolve the inflammation present in tissue after trauma or a disease and these results are thereby consistent with the effects of LMW-DS seen in foregoing Examples.

Example 9

The aim of this Example was to determine the neuroprotective effects of different doses of LMW-DS (1, 5 and 15 mg/kg) in sTBI using gene expression studies followed by functional analysis of the differentially regulated genes.

Materials and Methods

Induction of sTBI and Drug Administration Protocol

The experimental protocol used in this study was approved by the Ethical Committee of the Catholic University of Rome, according to international standards and guidelines for animal care. Male Wistar rats of 300-350 g body weight were fed with standard laboratory diet and water ad libitum in a controlled environment. As the anesthetic mixture, the animals received 35 mg/kg b.w. ketamine and 0.25 mg/kg body weight midazolam by i.p. injection. Severe traumatic brain injury (sTBI) was induced by dropping a 450 g weight from 2 m height on to the rat head that had been protected by a metal disk previously fixed on the skull, according to the "weight drop" impact acceleration model (Marmarou et al., A new model of diffuse brain injury in rats. Part I: Pathophysiology and biomechanics. *J Neurosurg*. 1994; 80: 291-300). Rats that suffered from skull fracture, seizures, nasal bleeding, or did not survive the impacts, were excluded from the study. At the end of each period of treatment, rats were anesthetized again and then immediately sacrificed.

Test Compound

LMW-DS (Tikomed AB) was provided at a stock concentration of 20 mg/ml and was kept in a temperature-monitored refrigerator at 4° C. LMW-DS aliquots were diluted to the appropriate dosing concentration in sterile saline prior to delivery of a single subcutaneous injection.

Acute Phase—1

Three doses of LMW-DS were administered subcutaneously 30 minutes post-TBI. The animals were sacrificed at 2 days post-TBI. The animals were divided into the following subgroups:

1. n=4 animals subjected to sTBI and receiving a subcutaneous injection of 0.5 ml of LMW-DS at a concentration of 15 mg/kg 2. n=4 animals subjected to sTBI and receiving a subcutaneous injection of 0.5 ml of LMW-DS at a concentration of 5 mg/kg 3. n=4 animals subjected to sTBI and receiving a subcutaneous injection of 0.5 ml of LMW-DS at a concentration of 1 mg/kg Acute Phase—2

Three doses of LMW-DS were administered subcutaneously 30 minutes post-TBI. The animals were sacrificed at 7 days post-TBI. The animals were divided into the following subgroups:

4. n=4 animals subjected to sTBI and receiving a subcutaneous injection of 0.5 ml of LMW-DS at a concentration of 15 mg/kg 5. n=4 animals subjected to sTBI and receiving a subcutaneous injection of 0.5 ml of LMW-DS at a concentration of 5 mg/kg 6. n=4 animals subjected to sTBI and receiving a subcutaneous injection of 0.5 ml of LMW-DS at a concentration of 1 mg/kg 7. n=4 animals subjected to sTBI and receiving three repeated subcutaneous injections of 0.5 ml of LMW-DS at a concentration of 15 mg/kg sTBI—No Treatment 8. n=4 animals subjected to sTBI only and sacrificed at 2 days post-TBI 9. n=4 animals subjected to sTBI only and sacrificed at 7 days post-TBI Sham Operated (Healthy Control)

10. n=4 animals receiving anesthesia only.

Cerebral Tissue Processing

An in vivo craniectomy was performed on all animals during anesthesia. After carefully removing the rat's skull, the brain was exposed and removed with a surgical spatula and quickly dropped in RNALater and preserved at 4° C. for further processing.

RNA Extraction and Array Analysis

RNA extraction and array processing was carried out by SourceBioscience. The arrays used were the Agilent Rat expression arrays.

Statistical Analysis

Statistical analysis was performed to quantitate the effect of sTBI on the brain in this model. The follow-on analyses looked at the effects of LMW-DS in this model using different iterations and algorithms.

Statistical analysis was carried out using the Metaboanalyst software package. Gene expression changes of 10% with a $p<0.05$ were regarded as significant.

Results

Differential gene expression seen 2 days after sTBI

Within 2 days of sTBI the brain gene expression changes significantly with a relatively small number of genes (221) up and downregulated.

The administration of 1 mg/kg LMW-DS within 30 minutes after injury altered the TBI-specific gene expression in 372 genes, the administration of 5 mg/kg LMW-DS within 30 minutes after TBI altered the TBI-specific gene expression in 702 genes and the administration of 15 mg/kg within 30 minutes after TBI alters the TBI-specific gene expression in 247 genes within 2 days of sTBI.

The LMW-DS treated animals differed from the healthy controls in the expression of 209 genes (1 mg/kg LMW-DS), 258 genes (5 mg/kg LMW-DS) and 47 genes (15 mg/kg LMW-DS).

Differential Gene Expression Seen 7 Days after sTBI

Within 7 days of sTBI the brain gene expression changes significantly with a large number of genes (2739) up and downregulated.

The administration of 1 mg/kg LMW-DS within 30 minutes after injury altered the TBI-specific gene expression in 3602 genes, the administration of 5 mg/kg LMW-DS within 30 minutes after TBI altered the TBI-specific gene expression in 3852 genes and the administration of 15 mg/kg within 30 minutes after TBI alters the TBI-specific gene expression in 3901 genes within 7 days of sTBI.

The LMW-DS treated animals differed from the healthy controls in the expression of 282 genes (1 mg/kg LMW-DS), 398 genes (5 mg/kg LMW-DS) and 158 genes (15 mg/kg LMW-DS). The LMW-DS treated animals (3 repeated doses of 15 mg/kg LMW-DS) differed from the healthy controls in the expression of 234 genes.

Comparison Analysis of Expression Changes Seen with LMW-DS

The comparison of the significantly affected genes in different statistical iterations provided information on how LMW-DS changed the TBI induced gene expression.

The comparison for 2 days post-TBI indicated that from the 221 genes deregulated by TBI (2 days) only 22 (10%), 51 (23%) and 19 (8.5%) remained deregulated relative to healthy control animals when 1 mg/kg, 5 mg/kg and 15 mg/kg LMW-DS was given, respectively.

The comparison for 7 days post-TBI indicated that from the 2741 genes deregulated by TBI (7 days) only 124 (4.5%), 169 (6.1%) and 85 (3.1%) remained deregulated relative to healthy control animals when 1 mg/kg, 5 mg/kg and 15 mg/kg LMW-DS was given, respectively. The remaining number of deregulated genes relative healthy animals for the 3 repeated doses of 15 mg/kg LMW-DS relative to healthy control animals were 116 (4.25%).

Pathway Analysis and Mechanistic Studies

Pathway analysis of the differentially regulated genes was carried out using the Ingenuity pathway analysis package. The analysis was performed with special reference to pathways and molecular processes and diseases associated with neurodegenerative disease, including dementia, Alzheimer's disease, ALS, TBI and stroke, and with scarring and fibrosis, including glaucoma and normal pressure hydrocephalus (NPH) after subarachnoid haemorrhage.

Although the effects induced by TBI within 2 days were relatively small, the alterations in many neurodegeneration and scaring-related canonical pathways were significant. Most of these pathway alterations were counteracted by LMW-DS given within 30 minutes of the TBI (Table 34 and 35). Similar to the pathways, the number of significantly affected molecular processes and diseases within 2 days of TBI was modest. However, the effect of TBI was mostly abolished by LMW-DS given 30 minutes after the injury (Table 36 and 37).

TABLE 34

Canonical pathways affected by TBI after 2 days and the effects of LMW-DS relative to control (p values and z scores)

| Ingenuity Canonical Pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS |
|---|---|---|---|---|---|---|
| Dendritic Cell Maturation | 10.5 | 33.6 | −1 | * | | |
| Role of NFAT in Regulation of the Immune Response | 5.53 | 15.1 | −0.447 | 0.378 | | |
| Osteoarthritis Pathway | 17.6 | 43.2 | 0.447 | −1.342 | −2.646 | |
| Role of NFAT in Cardiac Hypertrophy | 18.1 | 16.1 | 0.447 | | −1.63 | |
| NF-κb Signaling | 8.97 | 36.4 | 0.447 | | −2 | |
| Ephrin B Signaling | 3 | 4 | 1 | | | |
| RhoA Signaling | | 2.58 | 1 | | | |
| Endothelin-1 Signaling | 12.2 | 14.1 | 1.633 | * | | |
| IL-1 Signaling | 3.22 | 7.14 | 2 | −1 | | |
| Axonal Guidance Signaling | 11 | 17.3 | * | | | |
| CREB Signaling in Neurons | 17.8 | 3.94 | * | | | |
| Phospholipase C Signaling | 4.22 | 11.6 | * | | | |
| Role of Osteoblasts, Osteoclasts and Chondrocytes in Rheumatoid Arthritis | 8.77 | 47.7 | * | | | |
| Thrombin Signaling | 3.11 | 10.2 | * | | | |
| Hepatic Fibrosis/Hepatic Stellate Cell Activation | 15.1 | 68.7 | * | | | |
| Fcγ Receptor-mediated Phagocytosis in Macrophages and Monocytes | 7.62 | 6.87 | * | | | |
| VDR/RXR Activation | 4.65 | 10.2 | * | | | |
| Role of Wnt/GSK-3β Signaling in the Pathogenesis of Influenza | | | * | | | |
| Calcium-induced T Lymphocyte Apoptosis | 3.2 | 4.29 | * | | | |
| Antioxidant Action of Vitamin C | 6.6 | 8.13 | * | | | |
| Phospholipases | | 1.76 | * | | | |
| Cdc42 Signaling | | 1.97 | * | | | |
| Role of Pattern Recognition Receptors in Recognition of Bacteria and Viruses | 11.6 | 28.6 | * | | | |
| Hepatic Cholestasis | 12.5 | 24.6 | * | | | |
| Neuroprotective Role of THOP1 in Alzheimer's Disease | 7.23 | 1.73 | * | | | |
| Type I Diabetes Mellitus Signaling | 6.73 | 24.6 | * | | | |
| Nur77 Signaling in T Lymphocytes | 1.41 | 3.45 | * | | | |
| Cytotoxic T Lymphocyte-mediated Apoptosis of Target Cells | 2.73 | 2.21 | * | | | |
| Th2 Pathway | 5.34 | 28.9 | * | | | |
| Toll-like Receptor Signaling | 4.77 | 16.8 | * | | | |
| Choline Biosynthesis III | | 1.33 | * | | | |
| DNA Methylation and Transcriptional Repression Signaling | | | * | | | |
| T Helper Cell Differentiation | 4.27 | 28.4 | * | | | |
| Role of Cytokines in Mediating Communication between Immune Cells | 3.44 | 17.2 | * | | | |

TABLE 34-continued

Canonical pathways affected by TBI after 2 days and the effects of LMW-DS relative to control (p values and z scores)

| Ingenuity Canonical Pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS |
|---|---|---|---|---|---|---|
| iCOS-iCOSL Signaling in T Helper Cells | 3.52 | 17.3 | * | | | |
| Allograft Rejection Signaling | | 5.54 | * | | | |
| Autoimmune Thyroid Disease Signaling | | 8.75 | * | | | |
| Graft-versus-Host Disease Signaling | 1.8 | 6.77 | * | | | |
| Communication between Innate and Adaptive Immune Cells | 4.99 | 14.2 | * | | | |
| Crosstalk between Dendritic Cells and Natural Killer Cells | 5.34 | 14.8 | * | | | |
| Systemic Lupus Erythematosus Signaling | 9.46 | 13.3 | * | | | |
| Altered T Cell and B Cell Signaling in Rheumatoid Arthritis | 4.04 | 22.5 | * | | | |
| Role of Hypercytokinemia/hyperchemokinemia in the Pathogenesis of Influenza | 5.07 | 10.7 | * | | | |
| OX40 Signaling Pathway | 1.86 | 3.25 | * | | | |
| Hematopoiesis from Pluripotent Stem Cells | 3.84 | 12.4 | * | | | |
| Antigen Presentation Pathway | 1.69 | 1.29 | * | | | |
| Adrenomedullin Signaling pathway | 10.4 | | * | * | −2.236 | |

* ambiguous effect

TABLE 35

Canonical pathways affected by TBI after 2 days and the effects of LMW-DS

| Ingenuity Canonical Pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS |
|---|---|---|---|---|---|---|
| Dendritic Cell Maturation | sign affected | sign affected | Inhibited | * | | |
| Role of NFAT in Regulation of the Immune Response | sign affected | sign affected | Inhibited | Activated | | |
| Osteoarthritis Pathway | sign affected | sign affected | Activated | Inhibited | Inhibited | |
| Role of NFAT in Cardiac Hypertrophy | sign affected | sign affected | Activated | | Inhibited | |
| NF-κ13 Signaling | sign affected | sign affected | Activated | | Inhibited | |
| Ephrin B Signaling | | sign affected | Activated | | | |
| RhoA Signaling affected | | sign affected | Activated | | | |
| Endothelin-1 Signaling | sign affected | sign affected | Activated | * | | |
| IL-1 Signaling | sign affected | sign affected | Activated | Inhibited | | |
| Axonal Guidance sign affected Signaling | sign affected | sign affected | * | | | |
| CREB Signaling in sign affected Neurons | sign affected | sign affected | * | | | |
| Phospholipase C sign affected Signaling | sign affected | sign affected | * | | | |

TABLE 35-continued

Canonical pathways affected by TBI after 2 days and the effects of LMW-DS

| Ingenuity Canonical Pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS |
|---|---|---|---|---|---|---|
| Role of Osteoblasts, Osteoclasts and Chondrocytes in Rheumatoid Arthritis | sign affected | sign affected | * | | | |
| Thrombin Signaling | sign affected | sign affected | * | | | |
| Hepatic Fibrosis/Hepatic Stellate Cell Activation | sign affected | sign affected | * | | | |
| Fcγ Receptor-mediated Phagocytosis in Macrophages and Monocytes | sign affected | sign affected | * | | | |
| VDR/RXR Activation | sign affected | sign affected | * | | | |
| Role of WM/GSK-3-62 Signaling in the Pathogenesis of Influenza | | | * | | | |
| Calcium-induced T Lymphocyte Apoptosis | sign affected | sign affected | * | | | |
| Antioxidant Action of Vitamin C | sign affected | sign affected | * | | | |
| Phospholipases | | sign affected | * | | | |
| Cdc42 Signaling | | sign affected | * | | | |
| Role of Pattern Recognition Receptors in Recognition of Bacteria and Viruses | sign affected | sign affected | * | | | |
| Hepatic Cholestasis | sign affected | sign affected | * | | | |
| Neuroprotective Role of THOP1 in Alzheimer's Disease | sign affected | sign affected | * | | | |
| Type I Diabetes Mellitus Signaling | sign affected | sign affected | * | | | |
| Nur77 Signaling in T Lymphocytes | sign affected | sign affected | * | | | |
| Cytotoxic T Lymphocyte-mediated Apoptosis of Target Cells | sign affected | sign affected | * | | | |
| Th2 Pathway affected | sign affected | sign affected | * | | | |
| Toll-like Receptor Signaling sign | sign affected | sign affected | * | | | |
| Choline Biosynthesis III | | sign affected | * | | | |
| DNA Methylation and Transcriptional Repression Signaling | | | * | | | |
| T Helper Cell Differentiation | sign affected | sign affected | * | | | |
| Role of Cytokines in Mediating Communication between Immune Cells | sign affected | sign affected | * | | | |
| iCOS-iCOSL Signaling in T Helper Cells | sign affected | sign affected | * | | | |
| Allograft Rejection Signaling | | sign affected | * | | | |
| Autoimmune Thyroid Disease Signaling | | sign affected | * | | | |
| Graft-versus-Host Disease Signaling | sign affected | sign affected | * | | | |
| Communication between Innate and Adaptive Immune Cells | sign affected | sign affected | * | | | |
| Crosstalk between Dendritic Cells and Natural Killer Cells | sign affected | sign affected | * | | | |
| Systemic Lupus Erythematosus Signaling | sign affected | sign affected | * | | | |

TABLE 35-continued

Canonical pathways affected by TBI after 2 days and the effects of LMW-DS

| Ingenuity Canonical Pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS |
|---|---|---|---|---|---|---|
| Altered T Cell and B Cell Signaling in Rheumatoid Arthritis | sign affected | sign affected | * | | | |
| Role of Hypercytokinemia/ hyperchemokinemia in the Pathogenesis of Influenza | sign affected | sign affected | * | | | |
| OX40 Signaling Pathway | sign affected | sign affected | * | | | |
| Hematopoiesis from Pluripotent Stem Cells | sign affected | sign affected | * | | | |
| Antigen Presentation Pathway | sign affected | sign affected | * | | | |
| Adrenomedullin Signaling pathway | sign affected | | * | * | Inhibited | |

* ambiguous effect

TABLE 36

Diseases and molecular functions affected by TBI after 2 days and the effects of LMW-DS (p values and z scores)

| Diseases of functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS |
|---|---|---|---|---|---|---|
| MAPKKK cascade | | | −2.236 | | | |
| Apoptosis of tumor cell lines | 4.41E−93 | 5.28E−155 | −2.077 | | | 0.09 |
| Abdominal carcinoma | | | −1.98 | −1.715 | −2.631 | |
| Carcinoma | | | −1.941 | −0.127 | −2.071 | |
| Synthesis of cyclic AMP | | | −1.794 | | | |
| Cell death of tumor cell lines | 3.79E−88 | 5.76E−159 | −1.705 | | −1.947 | |
| Survival of organism | 1.39E−73 | 3.6E−208 | −1.599 | −0.095 | | |
| Paired-pulse facilitation | | | −1.4 | | | |
| Resorption of bone | | | −1.353 | | −0.478 | |
| Proliferation of hematopoietic progenitor cells | | | −1.331 | | −2.951 | |
| Epithelial neoplasm | | | −1.223 | | −1.393 | |
| Cytostasis of tumor cell lines | | | −1.2 | | | |
| Self- renewal of cells | | | −1.199 | | | |
| Digestive system cancer | | | −1.131 | | −2.221 | |
| Cell proliferation of leukocyte cell lines | | | −1.083 | | −2.754 | |
| Paired-pulse facilitation of synapse | | | −1 | | | |
| Osteoclastogenesis of bone cells | | | −1 | | | |
| Development of connective tissue cells | | 1.1E−76 | −0.973 | −0.332 | | |
| Binding of tumor cell lines | | 2.44E−75 | −0.957 | 2.397 | | |
| T cell development | | 4.12E−88 | −0.928 | | | |
| Tumorigenesis of tissue | | | −0.885 | | | |
| Growth of lymphoid organ | | | −0.881 | | | |
| Lymphopoiesis | | 5.45E−106 | −0.874 | 0.583 | −3.105 | |
| Lymphocyte homeostasis | | 6.36E−90 | −0.855 | | −2.94 | |
| Hypersensitive reaction | | 1.77E−82 | −0.832 | | | |
| Behavior | 7.65E−146 | | −0.793 | 1.334 | −2.009 | −0.139 |
| Proliferation of bone marrow cell lines | | | −0.762 | | | |
| Necrosis | 3.13E−153 | 1.37E−251 | −0.719 | −0.361 | −1.503 | −0.477 |
| Proliferation of blood cells | 4.3E−57 | 4.19E−154 | −0.687 | −1.083 | | |
| Feeding | | | −0.668 | | −0.895 | |
| Digestive organ tumor | | | −0.666 | −0.604 | −1.149 | |
| Non-hematologic malignant neoplasm | | | −0.63 | −0.243 | | |
| Analgesia | | | −0.587 | | | |
| Abdominal cancer | | | −0.57 | −1.538 | −2.553 | |

TABLE 36-continued

Diseases and molecular functions affected by TBI after 2 days and the effects of LMW-DS
(p values and z scores)

| Diseases of functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS |
|---|---|---|---|---|---|---|
| Differentiation of T lymphocytes | | | −0.568 | | | |
| Proliferation of lymphatic system cells | 4.71E−58 | 2.05E−141 | −0.559 | −1.112 | | |
| Proliferation of thymocytes | | | −0.555 | | | |
| Cell movement of tumor cells | | | −0.555 | | | |
| Protein kinase cascade | | | −0.412 | | | |
| Hepatic injury | 2.69E−66 | | −0.339 | | | |
| Leukopoiesis | | 4.76E−137 | −0.296 | 1.185 | −3.549 | |
| Development of hematopoietic progenitor cells | | | −0.295 | | | |
| Regeneration of neurons | | | −0.277 | | | |
| Quantity of neuroglia | | | −0.277 | | −1.446 | |
| Experimentally-induced arthritis | | | −0.262 | −0.816 | | |
| Proliferation of lymphocytes | 2.25E−52 | 1.05E−119 | −0.244 | −0.852 | | |
| Differentiation of hematopoietic progenitor cells | | | −0.223 | 0.487 | | |
| Cell proliferation of T lymphocytes | | 6.09E−108 | −0.211 | −1.097 | | |
| Place preference | | | −0.192 | | | |
| Non-hematological solid tumor | | | −0.167 | | | |
| Adhesion of tumor cell lines | | | −0.093 | 2.074 | | |
| Inflammation of joint | 3.04E−121 | 4.99E−137 | −0.079 | −0.053 | | |
| Rheumatic Disease | 1.08E−145 | 7.12E−183 | −0.079 | −0.053 | | |
| Hematopoiesis of bone marrow cells | | | −0.07 | | | |
| Hematologic cancer | 1.05E−92 | 2.16E−115 | −0.063 | | −1.067 | |
| Thrombus | | | −0.042 | 1 | | |
| Apoptosis | 7.51E−135 | 1.07E−244 | −0.011 | −0.337 | 0.601 | −0.502 |
| Non-melanoma solid tumor | | | −0.001 | | −1.249 | |
| Formation of osteoclasts | | | Ambiguous effect | | | |
| Atelectasis | | | * | | | |
| Quantity of osteoblasts | | | * | | | |
| Development of hematopoietic system | | 8.45E−77 | 0.026 | | | |
| Quantity of lymphocytes | | 7.81E−128 | 0.042 | | −0.943 | |
| Cell death of blood cells | 5.88E−70 | 3.48E−151 | 0.045 | 1.082 | | |
| Development of cytoplasm | | | 0.066 | | | |
| Hematopoiesis of hematopoietic progenitor cells | | | 0.083 | | | |
| Cell death of leukemia cell lines | | | 0.084 | | | |
| Concentration of prostaglandin | | | 0.119 | −0.911 | | |
| Polyarthritis | | | 0.133 | | | |
| Cell death | 6.48E−155 | 3.74E−254 | 0.142 | −0.793 | 0.051 | −0.141 |
| Memory deficits | | | 0.152 | | | |
| Differentiation of adipocytes | | | 0.168 | | | |
| Interaction of lymphocytes | | | 0.186 | | | |
| Binding of lymphocytes | | | 0.186 | | | |
| Cellular homeostasis | 1.04E−117 | 1.56E−154 | 0.202 | 0.19 | −3.19 | |
| Incidence of tumor | | | 0.21 | −1.131 | −0.731 | |
| Quantity of lymphatic system cells | | 1.35E−136 | 0.219 | −0.701 | | |
| Cell death of immune cells | 4.29E−72 | 1.75E−147 | 0.225 | 1.001 | −1 | |
| Locomotion | 1.34E−66 | | 0.239 | −0.039 | | |
| Hematopoiesis of bone marrow | | | 0.265 | | | |
| Differentiation of connective tissue cells | 1.6E−52 | 3.39E−143 | 0.278 | 0.73 | | |
| Cell death of antigen presenting cells | | | 0.306 | | −0.62 | |
| Differentiation of osteoclasts | | | 0.339 | −0.223 | | |
| Lymphatic system tumor | 4.79E−88 | | 0.339 | | | |
| Neoplasia of leukocytes | 5.5E−88 | 1.29E−149 | 0.339 | | −0.48 | |
| Lymphoid cancer | 1.85E−77 | 1.81E−114 | 0.339 | | | |
| Lymphocytic neoplasm | 2.2E−82 | 4.25E−139 | 0.339 | | −0.48 | |

TABLE 36-continued

Diseases and molecular functions affected by TBI after 2 days and the effects of LMW-DS (p values and z scores)

| Diseases of functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS |
|---|---|---|---|---|---|---|
| Lymphocytic cancer | 3.97E−73 | | 0.339 | | −0.48 | |
| Lymphoproliferative disorder | 2.49E−83 | 1.95E−104 | 0.339 | | −0.48 | |
| Release of Ca2+ | | | 0.342 | | | |
| Interaction of mononuclear leukocytes | | | 0.343 | 1.626 | | |
| Binding of mononuclear leukocytes | | | 0.343 | | | |
| Concentration of fatty acid | | | 0.395 | | | |
| Edema | 2.05E−71 | 6.78E−82 | 0.447 | | 3.386 | |
| Quantity of osteoclasts | | | 0.447 | | | |
| Quantity of epithelial tissue | | | 0.447 | | −0.028 | |
| Differentiation of bone cells | | 1.39E−102 | 0.463 | −0.341 | | |
| Malignant solid tumor | | | 0.475 | −0.562 | −1.492 | |
| Chemotaxis of tumor cell lines | | | 0.495 | | | |
| Quantity of amino acids | | | 0.516 | | | |
| Quantity of bone cells | | | 0.537 | | | |
| Quantity of mononuclear leukocytes | | 1.1E−133 | 0.539 | | | |
| Formation of reactive oxygen species | | | 0.555 | | | |
| Quantity of blood cells | 8.73E−61 | 1.92E−184 | 0.62 | −1.479 | | −0.34 |
| Quantity of connective tissue cells | | 3.02E−74 | 0.622 | 0.637 | | |
| Abdominal neoplasm | | | 0.628 | −0.154 | −0.927 | |
| Release of metal | | | 0.647 | | | |
| Angiogenesis of extraembryonic tissue | | | 0.689 | | | |
| Development of extraembryonic tissue | | | 0.689 | | | |
| Hematopoietic neoplasm | 2.37E−95 | | 0.692 | | | |
| Quantity of connective tissue | | 4.84E−113 | 0.702 | | | |
| Concentration of eicosanoid | | | 0.734 | | | |
| Binding of breast cancer cell lines | | | 0.747 | | | |
| Damage of liver | 7.95E−76 | 4.11E−168 | 0.784 | | | |
| Quantity of leukocytes | 7.27E−55 | 1.75E−172 | 0.803 | −1.163 | | |
| Size of body | | | 0.813 | −4.771 | | |
| Cell movement of breast cancer cell lines | | 1.15E−73 | 0.836 | | | |
| Formation of muscle cells | | | 0.842 | | | |
| Migration of breast cell lines | | | 0.849 | | | |
| Vascularization | | 1.92E−105 | 0.881 | | | |
| Vasculogenesis | 3.63E−68 | 6.72E−185 | 0.894 | | −2.274 | |
| Release of prostaglandin E2 | | | 0.911 | | | |
| Cell proliferation of lymphoma cell lines | | | 0.97 | | | |
| Aggregation of blood cells | | | 0.976 | | | |
| Activation of endothelial cells | | | 1 | | | |
| Cell movement of cervical cancer cell lines | | | 1.009 | | | |
| Cell survival | 1.22E−94 | 4.03E−184 | 1.01 | | | |
| Attachment of cells | | | 1.041 | | | |
| Inflammation of organ | 1.21E−228 | * | 1.041 | −1.295 | | |
| Transcription of DNA | | | 1.044 | | | |
| Metastasis of carcinoma cell lines | | | 1.067 | | | |
| Fusion of muscle cells | | | 1.091 | | | |
| Aggregation of cells | | 1.14E−83 | 1.104 | | | |
| Formation of muscle | | | 1.107 | | | |
| Vascularization of eye | | | 1.109 | | | |
| Differentiation of muscle cell lines | | | 1.117 | | | |
| Quantity of cells | 2.72E−102 | 2.87E−233 | 1.121 | −0.765 | −3.092 | −0.797 |
| Quantity of bone | | | 1.159 | −1.985 | | |
| Cell movement of breast cell lines | | | 1.172 | | | |
| Activation of T lymphocytes | | | 1.193 | | | |
| Activation of lymphocytes | | | 1.221 | −1.158 | | |
| Activation of blood cells | 1.69E−56 | 3.43E−146 | 1.258 | 0.086 | | |
| Quantity of phagocytes | | 4.3E−140 | 1.289 | −2.061 | | |

TABLE 36-continued

Diseases and molecular functions affected by TBI after 2 days and the effects of LMW-DS
(p values and z scores)

| Diseases of functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS |
|---|---|---|---|---|---|---|
| Aggregation of blood platelets | | | 1.299 | | | |
| Development of vasculature | 1.8E−77 | 1.84E−221 | 1.299 | | −1.534 | |
| Solid tumor | | | 1.31 | −0.186 | | |
| Extracranial solid tumor | | | 1.311 | 0.056 | −0.992 | |
| Cancer | | | 1.318 | | | |
| Activation of leukocytes | 2.75E−57 | 5.84E−135 | 1.325 | 0.086 | | |
| G1 phase of tumor cell lines | | | 1.342 | | | |
| Myelopoiesis of bone marrow | | | 1.342 | | | |
| Cell-mediated response | | | 1.387 | | | |
| Interaction of protein | | | 1.4 | | | |
| Chemotaxis | | 4.9E−120 | 1.425 | | −3.642 | |
| Cell movement of epithelial cell lines | | | 1.446 | | | |
| Fusion of cells | | | 1.446 | | | |
| G1/S phase transition | | | 1.455 | | | |
| Apoptosis of muscle cells | | 2.49E−119 | 1.467 | 0.041 | | |
| Pelvic tumor | 1.81E−59 | | 1.491 | −0.651 | | |
| Transcription of RNA | | 2.71E−75 | 1.519 | −2.488 | | |
| Transcription | | 3.3E−92 | 1.537 | | | |
| G1 phase | | 6.31E−76 | 1.609 | | | |
| Migration of brain cells | | | 1.616 | | | |
| Activation of cells | 3.66E−78 | 6.43E−190 | 1.629 | 0.836 | | |
| Proliferation of leukemia cell lines | | 5.94E−78 | 1.662 | | | |
| Migration of neurons | | | 1.676 | | | |
| Neovascularization of eye | | | 1.677 | | | |
| Apoptosis of stem cells | | | 1.686 | | | |
| Leukocyte migration | 1.46E−79 | 3.36E−205 | 1.694 | 1.296 | −2.163 | |
| Expression of RNA | | 5.44E−90 | 1.78 | | | |
| Necrosis of muscle | 3.34E−54 | 1.37E−133 | 1.792 | | | |
| Cell movement of tumor cell lines | 1.17E−69 | 1.12E−156 | 1.812 | | −2.078 | |
| Interphase | | 1.99E−94 | 1.823 | | | |
| Growth of tumor | 2.27E−68 | 2.81E−193 | 1.937 | | −1.233 | |
| Genital tumor | 1.07E−52 | | 1.981 | 0.13 | | |
| Attachment of tumor cell lines | | | 1.982 | | | |
| Adipogenesis of connective tissue | | | 1.982 | | | |
| Quantity of IL-6 in blood | | | 1.982 | | | |
| Quantity of TNF in blood | | | 2 | | | |
| Inflammation of body cavity | 6.8E−184 | * | 2.004 | −1.757 | | |
| Inflammation of absolute anatomical region | 1.33E−208 | * | 2.016 | −1.359 | | |
| Cell movement | 1.08E−108 | 5.26E−246 | 2.142 | 1.948 | −3.723 | |
| Metabolism of hormone | | | 2.185 | | −1.632 | |
| Synthesis of hormone | | | 2.185 | 0.977 | −1.632 | |
| Migration of cells | 6.76E−103 | 4.26E−241 | 2.188 | 2.093 | −3.087 | |
| Cell movement of vascular smooth muscle cells | | | 2.213 | −0.588 | | |
| Inflammatory response | 2.02E−74 | 9.77E−181 | 2.246 | 1.159 | | |
| Secretion of molecule | 1.66E−75 | | 2.281 | | 1.634 | |
| Cell movement of muscle cells | | 6.73E−75 | 2.393 | −0.26 | | |
| Transport of molecule | 1.58E−117 | | 2.597 | 2.421 | 0.248 | |

* ambiguous effect

TABLE 37

Diseases and molecular functions affected by TBI after 2 days and the effects of LMW-DS

| Diseases or functions annotation | Diseases and functions affected in dementia and neurodegeneration (p value) | Diseases and functions affected in fibrosis and scarring (p value) | Effect TBI | TBI + 1 mg/kg LMW-DS | TBI + 5 mg/kg LMW-DS | TBI + 15 mg/kg LMW-DS |
|---|---|---|---|---|---|---|
| MAPKKK cascade | | | Inhibited | | | |
| Apoptosis of tumor cell lines | 4.41E−93 | 5.28E−155 | Inhibited | | | Activated |
| Abdominal carcinoma | | | Inhibited | Inhibited | Inhibited | |
| Carcinoma | | | Inhibited | Inhibited | Inhibited | |
| Synthesis of cyclic AMP | | | Inhibited | | | |
| Cell death of tumor cell lines | 3.79E−88 | 5.76E−159 | Inhibited | | Inhibited | |
| Survival of organism | 1.39E−73 | 3.6E−208 | Inhibited | Inhibited | | |
| Paired-pulse facilitation | | | Inhibited | | | |
| Resorption of bone | | | Inhibited | | Inhibited | |
| Proliferation of hematopoietic progenitor cells | | | Inhibited | | Inhibited | |
| Epithelial neoplasm | | | Inhibited | | Inhibited | |
| Cytostasis of tumor cell lines | | | Inhibited | | | |
| Self-renewal of cells | | | Inhibited | | | |
| Digestive system cancer | | | Inhibited | | Inhibited | |
| Cell proliferation of leukocyte cell lines | | | Inhibited | | Inhibited | |
| Paired-pulse facilitation of synapse | | | Inhibited | | | |
| Osteoclastogenesis of bone cells | | | Inhibited | | | |
| Development of connective tissue cells | | 1.1E−76 | Inhibited | Inhibited | | |
| Binding of tumor cell lines | | 2.44E−75 | Inhibited | Activated | | |
| T cell development | | 4.12E−88 | Inhibited | | | |
| Tumorigenesis of tissue | | | Inhibited | | | |
| Growth of lymphoid organ | | | Inhibited | | | |
| Lymphopoiesis | | 5.45E−106 | Inhibited | Activated | Inhibited | |
| Lymphocyte homeostasis | | 6.36E−90 | Inhibited | | Inhibited | |
| Hypersensitive reaction | | 1.77E−82 | Inhibited | | | |
| Behavior | 7.65E−146 | | Inhibited | Activated | Inhibited | Inhibited |
| Proliferation of bone marrow cell lines | | | Inhibited | | | |
| Necrosis | 3.13E−153 | 1.37E−251 | Inhibited | Inhibited | Inhibited | Inhibited |
| Proliferation of blood cells | 4.3E−57 | 4.19E−154 | Inhibited | Inhibited | | |
| Feeding | | | Inhibited | | Inhibited | |
| Digestive organ tumor | | | Inhibited | Inhibited | Inhibited | |
| Non-hematologic malignant neoplasm | | | Inhibited | Inhibited | | |
| Analgesia | | | Inhibited | | | |
| Abdominal cancer | | | Inhibited | Inhibited | Inhibited | |
| Differentiation of T lymphocytes | | | Inhibited | | | |
| Proliferation of lymphatic system cells | 4.71E−58 | 2.05E−141 | Inhibited | Inhibited | | |
| Proliferation of thymocytes | | | Inhibited | | | |
| Cell movement of tumor cells | | | Inhibited | | | |
| Protein kinase cascade | | | Inhibited | | | |
| Hepatic injury | 2.69E−66 | | Inhibited | | | |
| Leukopoiesis | | 4.76E−137 | Inhibited | Activated | Inhibited | |
| Development of hematopoietic progenitor cells | | | Inhibited | | | |
| Regeneration of neurons | | | Inhibited | | | |
| Quantity of neuroglia | | | Inhibited | | Inhibited | |
| Experimentally-induced arthritis | | | Inhibited | Inhibited | | |
| Proliferation of lymphocytes | 2.25E−52 | 1.05E−119 | Inhibited | Inhibited | | |

TABLE 37-continued

Diseases and molecular functions affected by TBI after 2 days and the effects of LMW-DS

| Diseases or functions annotation | Diseases and functions affected in dementia and neurodegeneration (p value) | Diseases and functions affected in fibrosis and scarring (p value) | Effect TBI | TBI + 1 mg/kg LMW-DS | TBI + 5 mg/kg LMW-DS | TBI + 15 mg/kg LMW-DS |
|---|---|---|---|---|---|---|
| Differentiation of hematopoietic progenitor cells | | | Inhibited | Activated | | |
| Cell proliferation of T lymphocytes | | 6.09E−108 | Inhibited | Inhibited | | |
| Place preference | | | Inhibited | | | |
| Non-hematological solid tumor | | | Inhibited | | | |
| Adhesion of tumor cell lines | | | Inhibited | Activated | | |
| Inflammation of joint | 3.04E−121 | 4.99E−137 | Inhibited | Inhibited | | |
| Rheumatic Disease | 1.08E−145 | 7.12E−183 | Inhibited | Inhibited | | |
| Hematopoiesis of bone marrow cells | | | Inhibited | | | |
| Hematologic cancer | 1.05E−92 | 2.16E−115 | Inhibited | | Inhibited | |
| Thrombus | | | Inhibited | Activated | | |
| Apoptosis | 7.51E−135 | 1.07E−244 | Inhibited | Inhibited | Activated | Inhibited |
| Non-melanoma solid tumor | | | Inhibited | | Inhibited | |
| Formation of osteoclasts | | | | | | |
| Atelectasis | | | | | | |
| Quantity of osteoblasts | | | | | | |
| Development of hematopoietic system | | 8.45E−77 | Activated | | | |
| Quantity of lymphocytes | | 7.81E−128 | Activated | | | Inhibited |
| Cell death of blood cells | 5.88E−70 | 3.48E−151 | Activated | Activated | | |
| Development of cytoplasm | | | Activated | | | |
| Hematopoiesis of hematopoietic progenitor cells | | | Activated | | | |
| Cell death of leukemia cell lines | | | Activated | | | |
| Concentration of prostaglandin | | | Activated | | Inhibited | |
| Polyarthritis | | | Activated | | | |
| Cell death | 6.48E−155 | 3.74E−254 | Activated | Inhibited | Activated | Inhibited |
| Memory deficits | | | Activated | | | |
| Differentiation of adipocytes | | | Activated | | | |
| Interaction of lymphocytes | | | Activated | | | |
| Binding of lymphocytes | | | Activated | | | |
| Cellular homeostasis | 1.04E−117 | 1.56E−154 | Activated | Activated | Inhibited | |
| Incidence of tumor | | | Activated | Inhibited | Inhibited | |
| Quantity of lymphatic system cells | | 1.35E−136 | Activated | Inhibited | | |
| Cell death of immune cells | 4.29E−72 | 1.75E−147 | Activated | Activated | Inhibited | |
| Locomotion | 1.34E−66 | | Activated | | Inhibited | |
| Hematopoiesis of bone marrow | | | Activated | | | |
| Differentiation of connective tissue cells | 1.6E−52 | 3.39E−143 | Activated | Activated | | |
| Cell death of antigen presenting cells | | | Activated | | Inhibited | |
| Differentiation of osteoclasts | | | Activated | Inhibited | | |
| Lymphatic system tumor | 4.79E−88 | | Activated | | | |
| Neoplasia of leukocytes | 5.5E−88 | 1.29E−149 | Activated | | Inhibited | |
| Lymphoid cancer | 1.85E−77 | 1.81E−114 | Activated | | | |
| Lymphocytic neoplasm | 2.2E−82 | 4.25E−139 | Activated | | Inhibited | |
| Lymphocytic cancer | 3.97E−73 | | Activated | | Inhibited | |
| Lymphoproliferative disorder | 2.49E−83 | 1.95E−104 | Activated | | Inhibited | |
| Release of Ca$^{2+}$ | | | Activated | | | |
| Interaction of mononuclear leukocytes | | | Activated | Activated | | |

TABLE 37-continued

Diseases and molecular functions affected by TBI after 2 days and the effects of LMW-DS

| Diseases or functions annotation | Diseases and functions affected in dementia and neurodegeneration (p value) | Diseases and functions affected in fibrosis and scarring (p value) | Effect TBI | TBI + 1 mg/kg LMW-DS | TBI + 5 mg/kg LMW-DS | TBI + 15 mg/kg LMW-DS |
|---|---|---|---|---|---|---|
| Binding of mononuclear leukocytes | | | Activated | | | |
| Concentration of fatty acid | | | Activated | | | |
| Edema | 2.05E−71 | 6.78E−82 | Activated | | Activated | |
| Quantity of osteoclasts | | | Activated | | | |
| Quantity of epithelial tissue | | | Activated | | Inhibited | |
| Differentiation of bone cells | | 1.39E−102 | Activated | Inhibited | | |
| Malignant solid tumor | | | Activated | Inhibited | Inhibited | |
| Chemotaxis of tumor cell lines | | | Activated | | | |
| Quantity of amino acids | | | Activated | | | |
| Quantity of bone cells | | | Activated | | | |
| Quantity of mononuclear leukocytes | | 1.1E−133 | Activated | | | |
| Formation of reactive oxygen species | | | Activated | | | |
| Quantity of blood cells | 8.73E−61 | 1.92E−184 | Activated | Inhibited | | Inhibited |
| Quantity of connective tissue cells | | 3.02E−74 | Activated | Activated | | |
| Abdominal neoplasm | | | Activated | Inhibited | Inhibited | |
| Release of metal | | | Activated | | | |
| Angiogenesis of extraembryonic tissue | | | Activated | | | |
| Development of extraembryonic tissue | | | Activated | | | |
| Hematopoietic neoplasm | 2.37E−95 | | Activated | | | |
| Quantity of connective tissue | | 4.84E−113 | Activated | | | |
| Concentration of eicosanoid | | | Activated | | | |
| Binding of breast cancer cell lines | | | Activated | | | |
| Damage of liver | 7.95E−76 | 4.11E−168 | Activated | | | |
| Quantity of leukocytes | 7.27E−55 | 1.75E−172 | Activated | Inhibited | | |
| Size of body | | | Activated | | Inhibited | |
| Cell movement of breast cancer cell lines | | 1.15E−73 | Activated | | | |
| Formation of muscle cells | | | Activated | | | |
| Migration of breast cell lines | | | Activated | | | |
| Vascularization | | 1.92E−105 | Activated | | | |
| Vasculogenesis | 3.63E−68 | 6.72E−185 | Activated | | Inhibited | |
| Release of prostaglandin E2 | | | Activated | | | |
| Cell proliferation of lymphoma cell lines | | | Activated | | | |
| Aggregation of blood cells | | | Activated | | | |
| Activation of endothelial cells | | | Activated | | | |
| Cell movement of cervical cancer cell lines | | | Activated | | | |
| Cell survival | 1.22E−94 | 4.03E−184 | Activated | | | |
| Attachment of cells | | | Activated | | | |
| Inflammation of organ | 1.21E−228 | * | Activated | Inhibited | | |
| Transcription of DNA | | | Activated | | | |
| Metastasis of carcinoma cell lines | | | Activated | | | |
| Fusion of muscle cells | | | Activated | | | |
| Aggregation of cells | | 1.14E−83 | Activated | | | |
| Formation of muscle | | | Activated | | | |
| Vascularization of eye | | | Activated | | | |
| Differentiation of muscle cell lines | | | Activated | | | |

TABLE 37-continued

Diseases and molecular functions affected by TBI after 2 days and the effects of LMW-DS

| Diseases or functions annotation | Diseases and functions affected in dementia and neurodegeneration (p value) | Diseases and functions affected in fibrosis and scarring (p value) | Effect TBI | TBI + 1 mg/kg LMW-DS | TBI + 5 mg/kg LMW-DS | TBI + 15 mg/kg LMW-DS |
|---|---|---|---|---|---|---|
| Quantity of cells | 2.72E−102 | 2.87E−233 | Activated | Inhibited | Inhibited | Inhibited |
| Quantity of bone | | | Activated | Inhibited | | |
| Cell movement of breast cell lines | | | Activated | | | |
| Activation of T lymphocytes | | | Activated | | | |
| Activation of lymphocytes | | | Activated | Inhibited | | |
| Activation of blood cells | 1.69E−56 | 3.43E−146 | Activated | Activated | | |
| Quantity of phagocytes | | 4.3E−140 | Activated | Inhibited | | |
| Aggregation of blood platelets | | | Activated | | | |
| Development of vasculature | 1.8E−77 | 1.84E−221 | Activated | | Inhibited | |
| Solid tumor | | | Activated | Inhibited | | |
| Extracranial solid tumor | | | Activated | Activated | Inhibited | |
| Cancer | | | Activated | | | |
| Activation of leukocytes | 2.75E−57 | 5.84E−135 | Activated | Activated | | |
| G1 phase of tumor cell lines | | | Activated | | | |
| Myelopoiesis of bone marrow | | | Activated | | | |
| Cell-mediated response | | | Activated | | | |
| Interaction of protein | | | Activated | | | |
| Chemotaxis | | 4.9E−120 | Activated | | Inhibited | |
| Cell movement of epithelial cell lines | | | Activated | | | |
| Fusion of cells | | | Activated | | | |
| G1/S phase transition | | | Activated | | | |
| Apoptosis of muscle cells | | 2.49E−119 | Activated | Activated | | |
| Pelvic tumor | 1.81E−59 | | Activated | Inhibited | | |
| Transcription of RNA | | 2.71E−75 | Activated | | Inhibited | |
| Transcription | | 3.3E−92 | Activated | | | |
| G1 phase | | 6.31E−76 | Activated | | | |
| Migration of brain cells | | | Activated | | | |
| Activation of cells | 3.66E−78 | 6.43E−190 | Activated | Activated | | |
| Proliferation of leukemia cell lines | | 5.94E−78 | Activated | | | |
| Migration of neurons | | | Activated | | | |
| Neovascularization of eye | | | Activated | | | |
| Apoptosis of stem cells | | | Activated | | | |
| Leukocyte migration | 1.46E−79 | 3.36E−205 | Activated | Activated | Inhibited | |
| Expression of RNA | | 5.44E−90 | Activated | | | |
| Necrosis of muscle | 3.34E−54 | 1.37E−133 | Activated | | | |
| Cell movement of tumor cell lines | 1.17E−69 | 1.12E−156 | Activated | | Inhibited | |
| Interphase | | 1.99E−94 | Activated | | | |
| Growth of tumor | 2.27E−68 | 2.81E−193 | Activated | | Inhibited | |
| Genital tumor | 1.07E−52 | | Activated | Activated | | |
| Attachment of tumor cell lines | | | Activated | | | |
| Adipogenesis of connective tissue | | | Activated | | | |
| Quantity of IL-6 in blood | | | Activated | | | |
| Quantity of TNF in blood | | | Activated | | | |
| Inflammation of body cavity | 6.8E−184 | * | Activated | Inhibited | | |
| Inflammation of absolute anatomical region | 1.33E−208 | * | Activated | Inhibited | | |
| Cell movement | 1.08E−108 | 5.26E−246 | Activated | Activated | Inhibited | |
| Metabolism of hormone | | | Activated | | Inhibited | |
| Synthesis of hormone | | | Activated | Activated | Inhibited | |
| Migration of cells | 6.76E−103 | 4.26E−241 | Activated | Activated | Inhibited | |
| Cell movement of vascular smooth muscle cells | | | Activated | Inhibited | | |

TABLE 37-continued

Diseases and molecular functions affected by TBI after 2 days and the effects of LMW-DS

| Diseases or functions annotation | Diseases and functions affected in dementia and neurodegeneration (p value) | Diseases and functions affected in fibrosis and scarring (p value) | Effect TBI | TBI + 1 mg/kg LMW-DS | TBI + 5 mg/kg LMW-DS | TBI + 15 mg/kg LMW-DS |
|---|---|---|---|---|---|---|
| Inflammatory response | 2.02E−74 | 9.77E−181 | Activated | Activated | | |
| Secretion of molecule | 1.66E−75 | | Activated | | Activated | |
| Cell movement of muscle cells | | 6.73E−75 | Activated | Inhibited | | |
| Transport of molecule | 1.58E−117 | | Activated | Activated | Activated | |

* ambiguous effect

The effects induced by TBI within 7 days were significant with a large number of genes deregulated. Consequently, the alterations in many neurodegeneration and scaring-related canonical pathways were significant. Most of these pathway alterations were counteracted by ILB given within 30 minutes of the TBI (Table 38 and 39). Similar to the pathways the number of significantly affected molecular processes and diseases within 7 days of TBI was large and the effects were significant. However, the effect of TBI was mostly abolished by LMW-DS given 30 minutes after the injury (Table 40 and 41).

TABLE 38

Canonical pathways affected by TBI after 7 days and the effects of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Axonal Guidance Signaling | 11 | 17.3 | * | | | | |
| CREB Signaling in Neurons | 17.8 | 3.94 | −3.703 | | | | |
| Opioid Signaling Pathway | 20.8 | | −3.048 | −0.447 | * | | 0.816 |
| Synaptic Long Term Depression | 13.7 | 4.67 | −4.061 | 1.342 | 1 | | 1.342 |
| Synaptic Long Term Potentiation | 14.3 | 3.49 | −3.479 | | | | |
| GNRH Signaling | 17.9 | 9.75 | −3.592 | | 2 | | |
| Molecular Mechanisms of Cancer | 14.6 | 32.2 | * | | | | |
| CXCR4 Signaling | 4.2 | 10.3 | −1.622 | | | | |
| Neuropathic Pain Signaling In Dorsal Horn Neurons | 16.9 | 3.31 | −3.55 | | | | * |
| Factors Promoting Cardiogenesis in Vertebrates | 4.56 | 12.6 | * | | | | |
| Cholecystokinin/Gastrin-mediated Signaling | 7.43 | 9.52 | −1.219 | | | | |
| Calcium Signaling | 33.2 | 6.28 | −3.781 | | | | |
| Osteoarthritis Pathway | 17.6 | 43.2 | −1.64 | | −1 | | |
| Epithelial Adherens Junction Signaling | 2.74 | 21.8 | * | | | | |
| Endothelin-1 Signaling | 12.2 | 14.1 | −1.155 | 1.342 | 1.633 | 1 | |
| Cardiac Hypertrophy Signaling | 14.6 | 19.9 | −2.828 | | 1 | | |
| Glutamate Receptor Signaling | 12.1 | | −2.53 | | | | |
| GPCR-Mediated Nutrient Sensing in Enteroendocrine Cells | 12.4 | | −2.121 | | | | |
| Actin Cytoskeleton Signaling | 1.66 | 12.5 | −3.286 | | | | |
| UVC-Induced MAPK Signaling | 6.23 | 8.51 | −1.147 | | | | |
| Dopamine-DARPP32 Feedback in cAMP Signaling | 16.2 | 2.58 | −2.611 | | | | |

TABLE 38-continued

Canonical pathways affected by TBI after 7 days and the effects of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Role of NFAT in Cardiac Hypertrophy | 18.1 | 16.1 | −3.244 | | * | | 0.447 |
| Phospholipase C Signaling | 4.22 | 11.6 | −2.534 | | 1 | 2 | |
| Role of Macrophages, Fibroblasts and Endothelial Cells in Rheumatoid Arthritis | 14.2 | 53.2 | * | | | | |
| Role of Osteoblasts, Osteoclasts and Chondrocytes in Rheumatoid Arthritis | 8.77 | 47.7 | * | | | | |
| Agrin Interactions at Neuromuscular Junction | 4.16 | 6.61 | −2.4 | | | | |
| Aldosterone Signaling in Epithelial Cells | 4.23 | 3.44 | −2.335 | | | | |
| Protein Kinase A Signaling | 6.1 | 8.04 | −1.386 | | −1.342 | | |
| PTEN Signaling | 9.31 | 28.9 | 2.828 | | | | |
| Gap Junction Signaling | 13.4 | 21.8 | * | | | | |
| G Beta Gamma Signaling | 14.7 | 5.48 | −3.413 | 1 | | | 2.236 |
| Wnt/β-catenin Signaling | | 8.18 | 0.686 | | −1 | | |
| Thrombin Signaling | 3.11 | 10.2 | −2 | | | | |
| Glioblastoma Multiform Signaling | 3.92 | 16.4 | −1.48 | | | | |
| Corticotropin Releasing Hormone Signaling | 18.1 | 7.67 | −1.414 | | | | |
| Tec Kinase Signaling | 4.92 | 17.4 | −1.257 | | | | |
| nNOS Signaling in Neurons | 13 | 3.94 | −1.89 | | | | |
| Cellular Effects of Sildenafil (Viagra) | 6.22 | 2.54 | * | | | | |
| IL-8 Signaling | 9.79 | 34.7 | −1.982 | | 2.646 | | |
| Ephrin Receptor Signaling | 4.59 | 8.64 | −4.004 | | | | 2.236 |
| Basal Cell Carcinoma Signaling | | 3.44 | 0 | | | | |
| Colorectal Cancer Metastasis Signaling | 10.2 | 38.4 | −1.155 | | −0.378 | | |
| PPARα/RXRα Activation | 8.12 | 16.4 | 2.335 | | * | | |
| Neuregulin Signaling | 6.88 | 10.7 | −2.558 | | | | |
| Hepatic Fibrosis/Hepatic Stellate Cell Activation | 15.1 | 68.7 | * | | | | |
| Ephrin B Signaling | | 4 | −2.668 | | | | |
| GP6 Signaling Pathway | 1.86 | | −2.959 | | | | |
| Regulation of the Epithelial-Mesenchymal Transition Pathway | 3.69 | 30 | * | | | | |
| UVA-Induced MAPK Signaling | 6.66 | 9.44 | −2.683 | | | | |
| Signaling by Rho Family GTPases | 2.29 | 8.92 | −2.412 | | 1 | | 1 |
| Pyridoxal 5'-phosphate Salvage Pathway | 4.9 | | −1.789 | | | | |
| Huntington's Disease Signaling | 20.9 | 6.68 | −2.121 | | | | |
| ErbB Signaling | 6.54 | 14.8 | −2.887 | | | | |
| α-Adrenergic Signaling | 5.91 | 1.99 | −2.357 | | | | |
| Fcγ Receptor-mediated Phagocytosis in Macrophages and Monocytes | 7.62 | 6.87 | 0.6 | | 2.236 | | |
| Natural Killer Cell Signaling | 4.39 | 5.95 | * | | | | |

TABLE 38-continued

Canonical pathways affected by TBI after 7 days and the effects of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Renin-Angiotensin Signaling | 13.2 | 18.9 | −2.646 | | | | |
| RhoGDI Signaling | | 2.14 | 1.976 | | | | |
| GPCR-Mediated Integration of Enteroendocrine Signaling Exemplified by an L Cell | 4.53 | | 0.218 | | | | |
| HGF Signaling | 7.48 | 17.4 | −3.138 | | | | |
| Gaq Signaling | 12.2 | 15.2 | −2.401 | | | | |
| 14-3-3-mediated Signaling | 12.2 | 23.7 | −1.134 | | | | |
| P2Y Purigenic Receptor Signaling Pathway | 7.16 | 7.78 | −2.191 | | | | |
| G-Protein Coupled Receptor Signaling | 22.1 | 18.1 | * | | | | |
| PCP pathway | | 2.56 | −0.243 | | | | |
| Thyroid Cancer Signaling | 9.4 | 7.72 | * | | | | |
| Melatonin Signaling | 8.59 | | −0.471 | | | | |
| Mouse Embryonic Stem Cell Pluripotency | 1.35 | 17.9 | −2.502 | | | | |
| IL-3 Signaling | 4.09 | 16.8 | −2.711 | | | | |
| Integrin Signaling | 1.36 | 12.4 | −2.846 | | | | |
| Androgen Signaling | 12.2 | 2.95 | −2.065 | | | | |
| Nitric Oxide Signaling in the Cardiovascular System | 11.7 | 12.9 | −3 | | | | |
| Paxillin Signaling | 1.56 | 10.6 | −3.578 | | | | |
| Fc Epsilon RI Signaling | 5.05 | 15.7 | −0.756 | | | | −1 |
| NGF Signaling | 9.02 | 14.7 | −3.024 | | | | |
| Adrenomedullin signaling pathway | 10.4 | | −2.03 | −1 | −0.632 | * | −0.378 |
| Semaphorin Signaling in Neurons | | 1.33 | * | | | | |
| FLT3 Signaling in Hematopoietic Progenitor Cells | 1.8 | 14.4 | −3.128 | | | | * |
| fMLP Signaling in Neutrophils | 3.74 | 14.3 | −2.502 | | | | |
| Phagosome Formation | 5.65 | 6.16 | * | | | | |
| Ovarian Cancer Signaling | 6.42 | 21.1 | −3.606 | | | | |
| VDR/RXR Activation | 4.65 | 10.2 | 1.069 | | * | | |
| Leukocyte Extravasation Signaling | 6.36 | 19.7 | −2.92 | | 1.342 | | |
| D-myo-inositol (1,4,5)-Trisphosphate Biosynthesis | | | −0.632 | | | | |
| Salvage Pathways of Pyrimidine Ribonucleotides | 3.02 | | −1.46 | | | | |
| Writ/Ca+ pathway | 4.79 | 1.59 | −1.698 | | | | |
| Role of NANOG in Mammalian Embryonic Stem Cell Pluripotency | | 17 | −3.051 | | | | |
| Virus Entry via Endocytic Pathways | 3.75 | 11 | * | | | | |
| Type II Diabetes Mellitus Signaling | 19 | 16.1 | −0.894 | | | | |
| Rac Signaling | 2.62 | 13.5 | −4.426 | | | | |
| CCR3 Signaling in Eosinophils | 3.08 | 10.5 | −2.558 | | | | |
| cAMP-mediated signaling | 15.8 | 10 | −2.722 | | −2 | 1 | |
| Notch Signaling | 3.05 | | −0.378 | | | | |
| HER-2 Signaling in Breast Cancer | 3.27 | 13.1 | * | | | | |

TABLE 38-continued

Canonical pathways affected by TBI after 7 days and the effects
of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Caveolar-mediated Endocytosis Signaling | 1.96 | 5.58 | * | | | | |
| CCR5 Signaling in Macrophages | 16.3 | 4.77 | 0 | | | | |
| Sperm Motility | 4.03 | 1.76 | −1.961 | | | | |
| Regulation of Actin-based Motility by Rho | | 2.14 | −0.218 | | | | |
| Adipogenesis pathway | 4.87 | 13.9 | * | | | | |
| Growth Hormone Signaling | 6.85 | 9.43 | −2.065 | | | | |
| B Cell Receptor Signaling | 9.59 | 28.2 | −3.212 | | | | −0.447 |
| PI3K Signaling in B Lymphocytes | 7.67 | 20.4 | −2.887 | | 1.89 | | |
| Role of Tissue Factor in Cancer | 5.6 | 27.1 | * | | | | |
| Human Embryonic Stem Cell Pluripotency | 3.32 | 19.9 | * | | | | |
| TGF-β Signaling | 2.26 | 24.2 | −1.886 | | | | |
| Erythropoietin Signaling | 4.67 | 16.7 | * | | | | |
| Antiproliferative Role of Somatostatin Receptor 2 | | 8.4 | −3.207 | | | | |
| ERK/MAPK Signaling | 5.66 | 12.8 | −3.667 | | 1 | | |
| p70S6K Signaling | 6.22 | 11.9 | −3.024 | | | | |
| CNTF Signaling | | 13.2 | −3.638 | | | | |
| GDNF Family Ligand-Receptor Interactions | 3.68 | 9.29 | −2.183 | | | | |
| BMP signaling pathway | 5.09 | 17.7 | −2.183 | | | | |
| Role of NFAT in Regulation of the Immune Response | 5.53 | 15.1 | −2.921 | 0.816 | 2.53 | | 2.236 |
| Neuroinflammation Signaling Pathway | 54.8 | | −1.809 | | 1.941 | | |
| Germ Cell-Sertoli Cell Junction Signaling | 3.63 | 23.6 | * | | | | |
| Glioma Signaling | 6.44 | 18.2 | −3.13 | | | | |
| Netrin Signaling | 14.4 | 2.95 | * | | | | |
| Role of Wnt/GSK-3β Signaling in the Pathogenesis of Influenza | | | 0.577 | | | | |
| Production of Nitric Oxide and Reactive Oxygen Species in Macrophages | 13.7 | 27.7 | −1 | | 2.236 | | |
| Cardiac β-adrenergic Signaling | 3.77 | | −1.886 | | | | |
| Calcium-induced T Lymphocyte Apoptosis | 3.2 | 4.29 | −1.069 | | | | |
| UVB-Induced MAPK Signaling | 7.17 | 9.71 | −1.5 | | | | |
| ErbB4 Signaling | 3.93 | 8.87 | −2.183 | | | | |
| Gαs Signaling | 8.77 | 3.53 | −1.964 | | | | |
| RAR Activation | 6.66 | 8.92 | * | | | | |
| 1D-myo-inositol Hexakisphosphate Biosynthesis II (Mammalian) | | | −1.134 | | | | |
| Acute Myeloid Leukemia Signaling | 2.95 | 14.1 | −1.964 | | | | |
| Relaxin Signaling | 3.61 | 10.1 | −3.3 | | | | |
| NF-κB Activation by Viruses | 3.27 | 15.1 | −3.13 | | | | |
| Telomere Extension by Telomerase | | | * | | | | |
| Superpathway of Inositol Phosphate Compounds | | 2.44 | −2.655 | | | | 2 |

TABLE 38-continued

Canonical pathways affected by TBI after 7 days and the effects
of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| PAK Signaling | 1.8 | 11.5 | −2.4 | | | | |
| GABA Receptor Signaling | 30.6 | | * | | | | |
| IL-4 Signaling | 3.7 | 11.8 | * | | | | |
| Prolactin Signaling | 4.56 | 12.3 | −2.357 | | | | |
| Phenylalanine Degradation I (Aerobic) | | | * | | | | |
| ILK Signaling | 6.57 | 24.1 | −1.567 | | 1.89 | | |
| Thrombopoietin Signaling | 6.39 | 10.3 | −2.5 | | | | |
| STAT3 Pathway | 9.57 | 25.5 | −2.4 | | * | | |
| Parkinson's Signaling | 7.06 | 1.7 | * | | | | |
| SAPK/JNK Signaling | 2.17 | 7.22 | −1.706 | | | | |
| NRF2-mediated Oxidative Stress Response | 8.95 | 10.5 | −1.4 | | | | |
| Melanocyte Development and Pigmentation Signaling | 2.8 | 7.64 | −3.13 | | | | |
| RhoA Signaling | | 2.58 | −1.043 | | | | |
| FcγRIIB Signaling in B Lymphocytes | 11.9 | 8.78 | −1.265 | | | | |
| eNOS Signaling | 29 | 9.79 | −1.961 | | | | |
| FAK Signaling | 1.82 | 14.4 | * | | | | |
| Serotonin Receptor Signaling | 9.58 | | * | | | | |
| PEDF Signaling | 6.56 | 25.5 | −2.524 | | | | |
| VEGF Family Ligand-Receptor Interactions | 4.77 | 13.3 | −2.357 | | | | |
| Breast Cancer Regulation by Stathmin1 | 5.84 | 11 | * | | | | |
| D-myo-inositol-5-phosphate Metabolism | | | −1.671 | | | | |
| IL-10 Signaling | 6.55 | 23.3 | * | | | | |
| IL-15 Signaling | 3.78 | 25 | * | | | | |
| Sertoli Cell-Sertoli Cell Junction Signaling | 5.76 | 21.6 | * | | | | |
| JAK/Stat Signaling | 2.4 | 20.2 | −2.828 | | | | |
| Apoptosis Signaling | 13 | 13.8 | 2.524 | | | | |
| PDGF Signaling | 6.67 | 20.4 | −3.441 | | | | |
| Non-Small Cell Lung Cancer Signaling | 3.49 | 13.7 | −2.324 | | | | |
| D-myo-inositol (1,4,5)-trisphosphate Degradation | | | 0 | | | | |
| Gαi Signaling | 9.38 | 9.83 | −1.964 | | | | |
| Glutamate Dependent Acid Resistance | 2 | | * | | | | |
| PKCθ Signaling in T Lymphocytes | 10.7 | 17.3 | −2.558 | | 2 | | |
| Role of IL-17F in Allergic Inflammatory Airway Diseases | 4.79 | 11.7 | −2.53 | | | | |
| Amyotrophic Lateral Sclerosis Signaling | 28.1 | 13.5 | −1.886 | | | | |
| TWEAK Signaling | 5 | 4.46 | −0.333 | | | | |
| Sphingosine-1-phosphate Signaling | 5.14 | 7.9 | −0.426 | | | | |
| Superpathway of D-myo-inositol (1,4,5)-trisphosphate Metabolism | 1.37 | | −0.378 | | | | |
| Mechanisms of Viral Exit from Host Cells | 5.27 | | * | | | | |
| CDK5 Signaling | 8.38 | 3.35 | −2.524 | | | | |
| IL-1 Signaling | 3.22 | 7.14 | −1.069 | 1 | | | * |
| D-myo-inositol (1,3,4)-trisphosphate Biosynthesis | | | −0.816 | | | | |

TABLE 38-continued

Canonical pathways affected by TBI after 7 days and the effects of LMW-DS relative to control (p values and z scores)

| Ingenuity canonical pathways | Canonical pathways affected in dementia and neurodegenerative disease (p value) | Canonical pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Leptin Signaling in Obesity | 5.34 | 4.55 | −1.89 | | | | |
| Acute Phase Response Signaling | 18.7 | 37.8 | −1.877 | | 1.89 | | −0.447 |
| Pancreatic Adenocarcinoma Signaling | 9.68 | 35.1 | −1.606 | | | | |
| LPS-stimulated MAPK Signaling | 7.31 | 18.4 | −1.886 | | | | |
| Cancer Drug Resistance By Drug Efflux | 5.87 | 11 | * | | | | |
| Calcium Transport I | | | 0 | | | | |
| Antioxidant Action of Vitamin C | 6.6 | 8.13 | 0.229 | | | | |
| Phospholipases | | 1.76 | −0.277 | | | | |
| 3-phosphoinositide Degradation | | | −2.117 | | | | 2 |
| Urea Cycle | | 1.44 | * | | | | |
| Regulation of Cellular Mechanics by Calpain Protease | 1.3 | 8.67 | −1.667 | | | | |
| Angiopoietin Signaling | 2.01 | 12 | −3.051 | | | | |
| Role of MAPK Signaling in the Pathogenesis of Influenza | 4.53 | 13.7 | * | | | | |
| IL-6 Signaling | 7.42 | 32.4 | −2.711 | | 1 | | * |
| ERK5 Signaling | 3.67 | 6.1 | −2.673 | −2 | −0.447 | | |
| GM-CSF Signaling | 3.32 | 25.7 | −3.606 | | | | |
| Oncostatin M Signaling | 2.22 | 15.3 | −2.333 | | | | |
| Circadian Rhythm Signaling | 4.89 | | * | | | | |
| Inhibition of Angiogenesis by TSP1 | 10.7 | 12.7 | 1.134 | | | | |
| 3-phosphoinositide Biosynthesis | | 3.42 | −2.828 | | | | |
| Tyrosine Biosynthesis IV | | | * | | | | |
| Dendritic Cell Maturation | 10.5 | 33.6 | −0.557 | | 1.897 | | |
| Glycoaminoglycan-protein Linkage Region Biosynthesis | | | * | | | | |
| NF-κB Signaling | 8.97 | 36.4 | −2.921 | −0.447 | * | | 0.447 |
| RAN Signaling | | | * | | | | |
| Macropinocytosis Signaling | 5.53 | 15 | −1.941 | | | | |
| PPAR Signaling | 3.53 | 20.5 | 1.886 | | −1.342 | | |
| nNOS Signaling in Skeletal Muscle Cells | 15.4 | 1.44 | * | | | | |
| HMGB1 Signaling | 8.48 | 38.7 | −1.46 | | 1.134 | | |
| Actin Nucleation by ARP-WASP Complex | | 2.98 | −1.155 | | | | |
| Insulin Receptor Signaling | 5.78 | 8.97 | −1.877 | | | | |
| mTOR Signaling | 2.43 | 6.06 | −1.89 | 1 | | | |

* ambiguous effect

TABLE 39

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Axonal Guidance Signaling | 11 | 17.3 | * | | | | |
| CREB Signaling in Neurons | 17.8 | 3.94 | Inhibited | | | | |
| Opioid Signaling Pathway | 20.8 | | Inhibited | Inhibited | * | | Activated |
| Synaptic Long Term Depression | 13.7 | 4.67 | Inhibited | Activated | Activated | | Activated |
| Synaptic Long Term Potentiation | 14.3 | 3.49 | Inhibited | | | | |
| GNRH Signaling | 17.9 | 9.75 | Inhibited | | Activated | | |
| Molecular Mechanisms of Cancer | 14.6 | 32.2 | * | | | | |
| CXCR4 Signaling | 4.2 | 10.3 | Inhibited | | | | |
| Neuropathic Pain Signaling In Dorsal Horn Neurons | 16.9 | 3.31 | Inhibited | | | | * |
| Factors Promoting Cardiogenesis in Vertebrates | 4.56 | 12.6 | * | | | | |
| Cholecystokinin/Gastrin-mediated Signaling | 7.43 | 9.52 | Inhibited | | | | |
| Calcium Signaling | 33.2 | 6.28 | Inhibited | | | | |
| Osteoarthritis Pathway | 17.6 | 43.2 | Inhibited | | Inhibited | | |
| Epithelial Adherens Junction Signaling | 2.74 | 21.8 | * | | | | |
| Endothelin-1 Signaling | 12.2 | 14.1 | Inhibited | Activated | Activated | Activated | |
| Cardiac Hypertrophy Signaling | 14.6 | 19.9 | Inhibited | | Activated | | |
| Glutamate Receptor Signaling | 12.1 | | Inhibited | | | | |
| GPCR-Mediated Nutrient Sensing in Enteroendocrine Cells | 12.4 | | Inhibited | | | | |
| Actin Cytoskeleton Signaling | 1.66 | 12.5 | Inhibited | | | | |
| UVC-Induced MAPK Signaling | 6.23 | 8.51 | Inhibited | | | | |
| Dopamine-DARPP32 Feedback in cAMP Signaling | 16.2 | 2.58 | Inhibited | | | | |
| Role of NFAT in Cardiac Hypertrophy | 18.1 | 16.1 | Inhibited | | * | | Activated |
| Phospholipase C Signaling | 4.22 | 11.6 | Inhibited | | Activated | Activated | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Role of Macrophages, Fibroblasts and Endothelial Cells in Rheumatoid Arthritis | 14.2 | 53.2 | * | | | | |
| Role of Osteoblasts, Osteoclasts and Chondrocytes in Rheumatoid Arthritis | 8.77 | 47.7 | * | | | | |
| Agrin Interactions at Neuromuscular Junction | 4.16 | 6.61 | Inhibited | | | | |
| Aldosterone Signaling in Epithelial Cells | 4.23 | 3.44 | Inhibited | | | | |
| Protein Kinase A Signaling | 6.1 | 8.04 | Inhibited | | Inhibited | | |
| PTEN Signaling | 9.31 | 28.9 | Activated | | | | |
| Gap Junction Signaling | 13.4 | 21.8 | * | | | | |
| G Beta Gamma Signaling | 14.7 | 5.48 | Inhibited | Activated | | | Activated |
| Wnt/β-catenin Signaling | | 8.18 | Activated | | Inhibited | | |
| Thrombin Signaling | 3.11 | 10.2 | Inhibited | | | | |
| Glioblastoma Multiform Signaling | 3.92 | 16.4 | Inhibited | | | | |
| Corticotropin Releasing Hormone Signaling | 18.1 | 7.67 | Inhibited | | | | |
| Tec Kinase Signaling | 4.92 | 17.4 | Inhibited | | | | |
| nNOS Signaling in Neurons | 13 | 3.94 | Inhibited | | | | |
| Cellular Effects of Sildenafil (Viagra) | 6.22 | 2.54 | * | | | | |
| IL-8 Signaling | 9.79 | 34.7 | Inhibited | | Activated | | |
| Ephrin Receptor Signaling | 4.59 | 8.64 | Inhibited | | | | Activated |
| Basal Cell Carcinoma Signaling | | 3.44 | | | | | |
| Colorectal Cancer Metastasis Signaling | 10.2 | 38.4 | Inhibited | | Inhibited | | |
| PPARα/RXRα Activation | 8.12 | 16.4 | Activated | | * | | |
| Neuregulin Signaling | 6.88 | 10.7 | Inhibited | | | | |
| Hepatic Fibrosis/ Hepatic Stellate Cell Activation | 15.1 | 68.7 | * | | | | |
| Ephrin B Signaling | | 4 | Inhibited | | | | |
| GP6 Signaling Pathway | 1.86 | | Inhibited | | | | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Regulation of the Epithelial-Mesenchymal Transition Pathway | 3.69 | 30 | * | | | | |
| UVA-Induced MAPK Signaling | 6.66 | 9.44 | Inhibited | | | | |
| Signaling by Rho Family GTPases | 2.29 | 8.92 | Inhibited | | Activated | | Activated |
| Pyridoxal 5'-phosphate Salvage Pathway | 4.9 | | Inhibited | | | | |
| Huntington's Disease Signaling | 20.9 | 6.68 | Inhibited | | | | |
| ErbB Signaling | 6.54 | 14.8 | Inhibited | | | | |
| α-Adrenergic Signaling | 5.91 | 1.99 | Inhibited | | | | |
| Fcγ Receptor-mediated Phagocytosis in Macrophages and Monocytes | 7.62 | 6.87 | Activated | | Activated | | |
| Natural Killer Cell Signaling | 4.39 | 5.95 | * | | | | |
| Renin-Angiotensin Signaling | 13.2 | 18.9 | Inhibited | | | | |
| RhoGDI Signaling | | 2.14 | Activated | | | | |
| GPCR-Mediated Integration of Enteroendocrine Signaling Exemplified by an L Cell | 4.53 | | Activated | | | | |
| HGF Signaling | 7.48 | 17.4 | Inhibited | | | | |
| Gaq Signaling | 12.2 | 15.2 | Inhibited | | | | |
| 14-3-3-mediated Signaling | 12.2 | 23.7 | Inhibited | | | | |
| P2Y Purigenic Receptor Signaling Pathway | 7.16 | 7.78 | Inhibited | | | | |
| G-Protein Coupled Receptor Signaling | 22.1 | 18.1 | * | | | | |
| PCP pathway | | 2.56 | Inhibited | | | | |
| Thyroid Cancer Signaling | 9.4 | 7.72 | * | | | | |
| Melatonin Signaling | 8.59 | | Inhibited | | | | |
| Mouse Embryonic Stem Cell Pluripotency | 1.35 | 17.9 | Inhibited | | | | |
| IL-3 Signaling | 4.09 | 16.8 | Inhibited | | | | |
| Integrin Signaling | 1.36 | 12.4 | Inhibited | | | | |
| Androgen Signaling | 12.2 | 2.95 | Inhibited | | | | |
| Nitric Oxide Signaling in the Cardiovascular System | 11.7 | 12.9 | Inhibited | | | | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Paxillin Signaling | 1.56 | 10.6 | Inhibited | | | | |
| Fc Epsilon RI Signaling | 5.05 | 15.7 | Inhibited | | | | Inhibited |
| NGF Signaling | 9.02 | 14.7 | Inhibited | | | | |
| Adrenomedullin signaling pathway | 10.4 | | Inhibited | Inhibited | Inhibited | * | Inhibited |
| Semaphorin Signaling in Neurons | | 1.33 | * | | | | |
| FLT3 Signaling in Hematopoietic Progenitor Cells | 1.8 | 14.4 | Inhibited | | | | * |
| fMLP Signaling in Neutrophils | 3.74 | 14.3 | Inhibited | | | | |
| Phagosome Formation | 5.65 | 6.16 | * | | | | |
| Ovarian Cancer Signaling | 6.42 | 21.1 | Inhibited | | | | |
| VDR/RXR Activation | 4.65 | 10.2 | Activated | | * | | |
| Leukocyte Extravasation Signaling | 6.36 | 19.7 | Inhibited | | Activated | | |
| D-myo-inositol (1,4,5)-Trisphosphate Biosynthesis | | | Inhibited | | | | |
| Salvage Pathways of Pyrimidine Ribonucleotides | 3.02 | | Inhibited | | | | |
| Wnt/Ca+ pathway | 4.79 | 1.59 | Inhibited | | | | |
| Role of NANOG in Mammalian Embryonic Stem Cell Pluripotency | | 17 | Inhibited | | | | |
| Virus Entry via Endocytic Pathways | 3.75 | 11 | * | | | | |
| Type II Diabetes Mellitus Signaling | 19 | 16.1 | Inhibited | | | | |
| Rac Signaling | 2.62 | 13.5 | Inhibited | | | | |
| CCR3 Signaling in Eosinophils | 3.08 | 10.5 | Inhibited | | | | |
| cAMP-mediated signaling | 15.8 | 10 | Inhibited | Inhibited | Activated | | |
| Notch Signaling | 3.05 | | Inhibited | | | | |
| HER-2 Signaling in Breast Cancer | 3.27 | 13.1 | * | | | | |
| Caveolar-mediated Endocytosis Signaling | 1.96 | 5.58 | * | | | | |
| CCR5 Signaling in Macrophages | 16.3 | 4.77 | | | | | |
| Sperm Motility | 4.03 | 1.76 | Inhibited | | | | |
| Regulation of Actin-based Motility by Rho | | 2.14 | Inhibited | | | | |
| Adipogenesis pathway | 4.87 | 13.9 | * | | | | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Growth Hormone Signaling | 6.85 | 9.43 | Inhibited | | | | |
| B Cell Receptor Signaling | 9.59 | 28.2 | Inhibited | | | | Inhibited |
| PI3K Signaling in B Lymphocytes | 7.67 | 20.4 | Inhibited | | Activated | | |
| Role of Tissue Factor in Cancer | 5.6 | 27.1 | * | | | | |
| Human Embryonic Stem Cell Pluripotency | 3.32 | 19.9 | * | | | | |
| TGF-β Signaling | 2.26 | 24.2 | Inhibited | | | | |
| Erythropoietin Signaling | 4.67 | 16.7 | * | | | | |
| Antiproliferative Role of Somatostatin Receptor 2 | | 8.4 | Inhibited | | | | |
| ERK/MAPK Signaling | 5.66 | 12.8 | Inhibited | | Activated | | |
| p70S6K Signaling | 6.22 | 11.9 | Inhibited | | | | |
| CNTF Signaling | | 13.2 | Inhibited | | | | |
| GDNF Family Ligand-Receptor Interactions | 3.68 | 9.29 | Inhibited | | | | |
| BMP signaling pathway | 5.09 | 17.7 | Inhibited | | | | |
| Role of NFAT in Regulation of the Immune Response | 5.53 | 15.1 | Inhibited | Activated | Activated | | Activated |
| Neuroinflammation Signaling Pathway | 54.8 | | Inhibited | | Activated | | |
| Germ Cell-Sertoli Cell Junction Signaling | 3.63 | 23.6 | * | | | | |
| Glioma Signaling | 6.44 | 18.2 | Inhibited | | | | |
| Netrin Signaling | 14.4 | 2.95 | * | | | | |
| Role of WM/GSK-3β Signaling in the Pathogenesis of Influenza | | | Activated | | | | |
| Production of Nitric Oxide and Reactive Oxygen Species in Macrophages | 13.7 | 27.7 | Inhibited | | Activated | | |
| Cardiac β-adrenergic Signaling | 3.77 | | Inhibited | | | | |
| Calcium-induced T Lymphocyte Apoptosis | 3.2 | 4.29 | Inhibited | | | | |
| UVB-Induced MAPK Signaling | 7.17 | 9.71 | Inhibited | | | | |
| ErbB4 Signaling | 3.93 | 8.87 | Inhibited | | | | |
| Gas Signaling | 8.77 | 3.53 | Inhibited | | | | |
| RAR Activation | 6.66 | 8.92 | * | | | | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| 1D-myo-inositol Hexakisphosphate Biosynthesis II (Mammalian) | | | Inhibited | | | | |
| Acute Myeloid Leukemia Signaling | 2.95 | 14.1 | Inhibited | | | | |
| Relaxin Signaling | 3.61 | 10.1 | Inhibited | | | | |
| NF-κB Activation by Viruses | 3.27 | 15.1 | Inhibited | | | | |
| Telomere Extension by Telomerase | | | * | | | | |
| Superpathway of Inositol Phosphate Compounds | | 2.44 | Inhibited | | | | Activated |
| PAK Signaling | 1.8 | 11.5 | Inhibited | | | | |
| GABA Receptor Signaling | 30.6 | | * | | | | |
| IL-4 Signaling | 3.7 | 11.8 | * | | | | |
| Prolactin Signaling | 4.56 | 12.3 | Inhibited | | | | |
| Phenylalanine Degradation I (Aerobic) | | | * | | | | |
| ILK Signaling | 6.57 | 24.1 | Inhibited | Activated | | | |
| Thrombopoietin Signaling | 6.39 | 10.3 | Inhibited | | | | |
| STAT3 Pathway | 9.57 | 25.5 | Inhibited | | * | | |
| Parkinson's Signaling | 7.06 | 1.7 | * | | | | |
| SAPK/JNK Signaling | 2.17 | 7.22 | Inhibited | | | | |
| NRF2-mediated Oxidative Stress Response | 8.95 | 10.5 | Inhibited | | | | |
| Melanocyte Development and Pigmentation Signaling | 2.8 | 7.64 | Inhibited | | | | |
| RhoA Signaling | | 2.58 | Inhibited | | | | |
| FcγRIIB Signaling in B Lymphocytes | 11.9 | 8.78 | Inhibited | | | | |
| eNOS Signaling | 29 | 9.79 | Inhibited | | | | |
| FAK Signaling | 1.82 | 14.4 | * | | | | |
| Serotonin Receptor Signaling | 9.58 | | * | | | | |
| PEDF Signaling | 6.56 | 25.5 | Inhibited | | | | |
| VEGF Family Ligand-Receptor Interactions | 4.77 | 13.3 | Inhibited | | | | |
| Breast Cancer Regulation by Stathmin1 | 5.84 | 11 | * | | | | |
| D-myo-inositol-5-phosphate Metabolism | | | Inhibited | | | | |
| IL-10 Signaling | 6.55 | 23.3 | * | | | | |
| IL-15 Signaling | 3.78 | 25 | * | | | | |
| Sertoli Cell-Sertoli Cell Junction Signaling | 5.76 | 21.6 | * | | | | |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| JAK/Stat Signaling | 2.4 | 20.2 | Inhibited | | | | |
| Apoptosis Signaling | 13 | 13.8 | Activated | | | | |
| PDGF Signaling | 6.67 | 20.4 | Inhibited | | | | |
| Non-Small Cell Lung Cancer Signaling | 3.49 | 13.7 | Inhibited | | | | |
| D-myo-inositol (1,4,5)-trisphosphate Degradation | | | | | | | |
| Gai Signaling | 9.38 | 9.83 | Inhibited | | | | |
| Glutamate Dependent Acid Resistance | 2 | | * | | | | |
| PKCθ Signaling in T Lymphocytes | 10.7 | 17.3 | Inhibited | | Activated | | |
| Role of IL-17F in Allergic Inflammatory Airway Diseases | 4.79 | 11.7 | Inhibited | | | | |
| Amyotrophic Lateral Sclerosis Signaling | 28.1 | 13.5 | Inhibited | | | | |
| TWEAK Signaling | 5 | 4.46 | Inhibited | | | | |
| Sphingosine-1-phosphate Signaling | 5.14 | 7.9 | Inhibited | | | | |
| Superpathway of D-myo-inositol (1,4,5)-trisphosphate Metabolism | 1.37 | | Inhibited | | | | |
| Mechanisms of Viral Exit from Host Cells | 5.27 | | * | | | | |
| CDK5 Signaling | 8.38 | 3.35 | Inhibited | | | | |
| IL-1 Signaling | 3.22 | 7.14 | Inhibited | | Activated | | * |
| D-myo-inositol (1,3,4)-trisphosphate Biosynthesis | | | Inhibited | | | | |
| Leptin Signaling in Obesity | 5.34 | 4.55 | Inhibited | | | | |
| Acute Phase Response Signaling | 18.7 | 37.8 | Inhibited | | Activated | | Inhibited |
| Pancreatic Adenocarcinoma Signaling | 9.68 | 35.1 | Inhibited | | | | |
| LPS-stimulated MAPK Signaling | 7.31 | 18.4 | Inhibited | | | | |
| Cancer Drug Resistance By Drug Efflux | 5.87 | 11 | * | | | | |
| Calcium Transport I | | | | | | | |
| Antioxidant Action of Vitamin C | 6.6 | 8.13 | Activated | | | | |
| Phospholipases | | 1.76 | Inhibited | | | | |
| 3-phosphoinositide Degradation | | | Inhibited | | | | Activated |

TABLE 39-continued

Canonical pathways affected by TBI after 7 days and the effects of LMW-DS

| Ingenuity canonical pathways | Canonical pathways affected in dementia and neurodegenerative disease (p value) | Canonical Pathways affected in scar formation and fibrosis (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Urea Cycle | | 1.44 | * | | | | |
| Regulation of Cellular Mechanics by Calpain Protease | 1.3 | 8.67 | Inhibited | | | | |
| Angiopoietin Signaling | 2.01 | 12 | Inhibited | | | | |
| Role of MAPK Signaling in the Pathogenesis of Influenza | 4.53 | 13.7 | * | | | | |
| IL-6 Signaling | 7.42 | 32.4 | Inhibited | | Activated | | * |
| ERK5 Signaling | 3.67 | 6.1 | Inhibited | Inhibited | Inhibited | | |
| GM-CSF Signaling | 3.32 | 25.7 | Inhibited | | | | |
| Oncostatin M Signaling | 2.22 | 15.3 | Inhibited | | | | |
| Circadian Rhythm Signaling | 4.89 | | * | | | | |
| Inhibition of Angiogenesis by TSP1 | 10.7 | 12.7 | Activated | | | | |
| 3-phosphoinositide Biosynthesis | | 3.42 | Inhibited | | | | |
| Tyrosine Biosynthesis IV | | | * | | | | |
| Dendritic Cell Maturation | 10.5 | 33.6 | Inhibited | | Activated | | |
| Glycoaminoglycan-protein Linkage Region Biosynthesis | | | * | | | | |
| NF-κB Signaling | 8.97 | 36.4 | Inhibited * | Inhibited | * | | Activated |
| RAN Signaling | | | | | | | |
| Macropinocytosis Signaling | 5.53 | 15 | Inhibited | | | | |
| PPAR Signaling | 3.53 | 20.5 | Activated | | Inhibited | | |
| nNOS Signaling in Skeletal Muscle Cells | 15.4 | 1.44 | * | | | | |
| HMGB1 Signaling | 8.48 | 38.7 | Inhibited | | Activated | | |
| Actin Nucleation by ARP-WASP Complex | | 2.98 | Inhibited | | | | |
| Insulin Receptor Signaling | 5.78 | 8.97 | Inhibited | | | | |
| mTOR Signaling | 2.43 | 6.06 | Inhibited | | Activated | | |

TABLE 40

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Cell movement | 1.1E-108 | 5.3E-246 | -6.524 | -1.01 | 2.297 | | 0.154 |
| Size of body | | | -6.2 | | 0.748 | | 0.67 |

TABLE 40-continued

Diseases and molecular functions affected by TBI after
7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Organization of cytoskeleton | 1.61E−68 | 3.76E−76 | −5.922 | | 2.174 | | 1.922 |
| Migration of cells | 6.8E−103 | 4.3E−241 | −5.885 | | 2.659 | | 0.271 |
| Organization of cytoplasm | 4.68E−69 | 7.6E−74 | −5.875 | | | | 1.922 |
| Cell survival | 1.22E−94 | 4E−184 | −5.807 | | 1.966 | | |
| Formation of cellular protrusions | 2.84E−52 | | −5.739 | | | | 1.183 |
| Development of neurons | 7.82E−63 | | −5.726 | | 1.106 | | 0.688 |
| Quantity of cells | 2.7E−102 | 2.9E−233 | −5.577 | | 0.634 | 0.991 | 0.493 |
| Microtubule dynamics | 2.4E−63 | | −5.549 | | 1.82 | | 1.962 |
| Cell viability | 9.14E−94 | 1E−176 | −5.42 | −1.584 | 1.879 | | |
| Cell viability of tumor cell lines | 7.56E−63 | 1.1E−114 | −5.022 | | 0.991 | | |
| Developmental process of synapse | | | −4.97 | −0.152 | | | 0.849 |
| Development of gap junctions | | | −4.826 | | | | 0.849 |
| Formation of plasma membrane | | | −4.725 | −0.152 | | | |
| Cell-cell contact | | | −4.682 | | | | 1.504 |
| Assembly of intercellular junctions | | | −4.584 | | | | |
| Formation of intercellular junctions | | | −4.329 | | | | 0.391 |
| Morphogenesis of neurons | 4.16E−54 | | −4.318 | | | | 0.205 |
| Neuritogenesis | 2.04E−53 | | −4.318 | | | | |
| Invasion of cells | 1.26E−64 | 1.1E−148 | −4.317 | | 1.32 | | |
| Homing of cells | | 2E−126 | −4.314 | | | | |
| Chemotaxis | | 4.9E−120 | −4.232 | | 1.873 | | |
| Angiogenesis | 6.89E−75 | 1E−210 | −4.219 | | 0.294 | | |
| Development of vasculature | 1.8E−77 | 1.8E−221 | −4.218 | | 0.295 | | |
| Collapse of growth cone | | | −4.145 | | | | |
| Cell movement of tumor cell lines | 1.17E−69 | 1.1E−156 | −4.06 | | 1.492 | | |
| Vasculogenesis | 3.63E−68 | 6.7E−185 | −3.982 | | 0.507 | | |
| Neurotransmission | 3.7E−100 | | −3.909 | | | | 1.214 |
| Cell movement of endothelial cells | | 2.38E−86 | −3.817 | | 2.084 | | |
| Transactivation of RNA | | | −3.66 | | | | |
| Transactivation | | | −3.651 | | | | |
| Long-term potentiation | 6.19E−76 | | −3.624 | | | | |
| Transcription | | 3.3E−92 | −3.459 | | 1.317 | 0.747 | |
| Transcription of RNA | | 2.71E−75 | −3.445 | | 1.221 | 0.517 | |
| Synaptic transmission of cells | | | −3.371 | | | | |
| Plasticity of synapse | | | −3.364 | | | | |
| Potentiation of synapse | 1.58E−77 | | −3.319 | | | | |
| Migration of endothelial cells | | 1.18E−81 | −3.312 | | 2.16 | | |
| Synaptic transmission | 8.3E−97 | | −3.304 | | | | |
| Long-term potentiation of brain | | | −3.278 | | | | |
| Migration of tumor cell lines | 9.34E−62 | 5.5E−134 | −3.236 | | | | |
| Quantity of neurons | 1.57E−59 | | −3.147 | | | | |
| Quantity of nervous tissue | 4.93E−60 | | −3.126 | | | | |
| Development of genitourinary system | | 1.77E−77 | −3.125 | | −0.336 | | |
| Long-term potentiation of cerebral cortex | | | −3.102 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Cellular homeostasis | 1E−117 | 1.6E−154 | −3.087 | | 1.615 | | |
| Expression of RNA | | 5.44E−90 | −3.057 | | 1.797 | | |
| Growth of connective tissue | | 4.3E−157 | −3.055 | | −0.324 | | |
| Non-hematologic malignant neoplasm | | | −2.986 | | −0.243 | | −0.223 |
| Synaptic transmission of nervous tissue | | | −2.963 | | | | |
| Shape change of neurites | | | −2.953 | | | | |
| Branching of neurites | | | −2.881 | | | | |
| Transcription of DNA | | | −2.793 | | | | |
| Long-term potentiation of hippocampus | | | −2.789 | | | | |
| Behavior | 7.7E−146 | | −2.715 | | | | |
| Development of body trunk | | 7.2E−188 | −2.709 | | 1.09 | | |
| Cognition | 9.8E−112 | | −2.679 | | | | |
| Branching of neurons | | | −2.669 | | | | |
| Learning | 1.2E−108 | | −2.66 | | | | 0.469 |
| Sprouting | 6.17E−59 | | −2.655 | | | | |
| Branching of cells | 8.41E−54 | | −2.65 | | | | 0.397 |
| Coordination | | | −2.648 | | | | |
| Potentiation of hippocampus | | | −2.611 | | | | |
| Long-term memory | | | −2.571 | | | | |
| Differentiation of neurons | | | −2.556 | | | | |
| Cell movement of blood cells | 2.64E−79 | 2.3E−210 | −2.533 | | | | |
| Leukocyte migration | 1.46E−79 | 3.4E−205 | −2.532 | | 3.062 | 2.365 | |
| Shape change of neurons | | | −2.531 | | | | |
| Dendritic growth/branching | | | −2.491 | | | | −0.169 |
| Memory | 1.31E−83 | | −2.473 | | | | |
| Carcinoma | | | −2.446 | | −0.403 | 1.067 | −0.358 |
| Genitourinary adenocarcinoma | | | −2.425 | | | | |
| Formation of brain | | | −2.415 | | | | |
| Growth of tumor | 2.27E−68 | 2.8E−193 | −2.369 | | 2.295 | | |
| Growth of organism | | 5.6E−102 | −2.364 | | | | |
| Synthesis of lipid | 1.14E−78 | 5.59E−92 | −2.355 | 0.033 | 1.937 | | |
| Respiratory system development | | | −2.335 | | | | |
| Differentiation of osteoblasts | | | −2.329 | | | | |
| Conditioning | | | −2.324 | | | | |
| Proliferation of neuronal cells | 4.49E−61 | | −2.298 | | | | |
| Male genital neoplasm | | | −2.296 | | | | |
| Synaptic depression | | | −2.292 | | | | |
| Development of epithelial tissue | 8.97E−54 | 4.4E−109 | −2.287 | | 0.262 | | |
| Density of neurons | | | −2.27 | | | | |
| Proliferation of connective tissue cells | | 4.7E−152 | −2.237 | | −0.747 | | |
| Formation of lung | | | −2.236 | | | | |
| Prostatic carcinoma | | | −2.219 | | | | |
| Formation of rhombencephalon | | | −2.212 | | | | |
| Innervation | | | −2.204 | | | | |
| Guidance of axons | | | −2.194 | | | | |
| Genitourinary carcinoma | | | −2.191 | | 1.131 | | |
| Discomfort | 4.2E−181 | | −2.184 | | | | |
| Metabolism of hormone | | | −2.158 | −1.066 | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Cell movement of neurons | | | −2.143 | | | | |
| Long term depression | | | −2.107 | | | | |
| Differentiation of osteoblastic-lineage cells | | | −2.093 | | | | |
| Outgrowth of cells | 2.39E−58 | | −2.085 | | | | |
| Malignant solid tumor | | | −2.079 | | 0.423 | | |
| Non-hematological solid tumor | | | −2.073 | | 0.021 | | −0.913 |
| Growth of neurites | 5.41E−59 | | −2.054 | | | | |
| Transport of molecule | 1.6E−117 | | −2.045 | | 1.854 | | 1.143 |
| Formation of hippocampus | | | −2.042 | | | | |
| Prostatic tumor | | | −2.02 | | | | |
| Formation of muscle | | | −2.01 | | | | |
| Genital tumor | 1.07E−52 | | −2.009 | | 0.305 | | |
| Fibrogenesis | | | −1.986 | | | | |
| Prostatic adenocarcinoma | | | −1.982 | | | | |
| Adenocarcinoma | | | −1.939 | | −0.155 | | −0.944 |
| Transport of K+ | | | −1.912 | | | | |
| Abdominal cancer | | | −1.902 | −2.426 | −0.474 | | −2.015 |
| Cardiogenesis | | 2.07E−92 | −1.895 | | | | |
| Malignant neoplasm of retroperitoneum | | | −1.889 | | | | |
| Development of central nervous system cells | | | −1.886 | | | | |
| Development of reproductive system | | | −1.882 | | | | |
| Epithelial neoplasm | | | −1.877 | −1.313 | | 0.775 | −0.999 |
| Malignant neoplasm of male genital organ | | | −1.864 | | | | |
| Development of head | | | −1.851 | | 1.213 | | |
| Development of body axis | | | −1.851 | | 1.213 | | |
| Patterning of rhombencephalon | | | −1.835 | | | | |
| Axonogenesis | | | −1.798 | | | | |
| Tumorigenesis of tissue | | | −1.785 | −0.998 | −0.832 | 0.918 | −1.333 |
| Synthesis of nitric oxide | 2.05E−53 | 1.3E−98 | −1.752 | | | | |
| Melanoma | | | −1.723 | | | | |
| Outgrowth of neurites | 5.63E−52 | | −1.714 | | | | |
| Urinary tract cancer | 6.04E−53 | | −1.698 | | | | |
| Abdominal adenocarcinoma | | | −1.687 | | 0.73 | | |
| Transport of ion | | | −1.687 | | | | 1.109 |
| Hyperalgesia | 1.56E−55 | | −1.679 | | | | |
| Development of cerebral cortex | | | −1.661 | | | | |
| Dyskinesia | 3.5E−136 | | −1.657 | | | | |
| Proliferation of smooth muscle cells | | 5.2E−120 | −1.64 | | | | |
| Differentiation of connective tissue cells | 1.6E−52 | 3.4E−143 | −1.635 | −0.349 | 0.769 | | −0.011 |
| Prostate cancer | | | −1.628 | | | | |
| Muscle contraction | | | −1.623 | | | | |
| Pelvic tumor | 1.81E−59 | | −1.62 | −1.214 | 0.445 | | |
| Transport of metal ion | | | −1.609 | | | | |
| Formation of filaments | | | −1.578 | | | | |
| Genital tract cancer | | | −1.575 | | | | |
| Neoplasia of epithelial cells | | | −1.555 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Transport of cation | | | −1.55 | | | | |
| Quantity of connective tissue | | 4.8E−113 | −1.546 | | 0.609 | | |
| Differentiation of nervous system | | | −1.543 | | | | |
| Migration of neurons | | | −1.538 | | | | |
| Transport of metal | | | −1.527 | | | | 1 |
| Upper gastrointestinal tract cancer | | | −1.501 | | | | |
| Malignant genitourinary solid tumor | 5.22E−63 | | −1.497 | −0.537 | 0.346 | | |
| Development of central nervous system | | | −1.481 | | | | |
| Differentiation of bone | | 3.9E−104 | −1.458 | | 1.012 | | |
| Proliferation of muscle cells | 1.11E−56 | 1.8E−148 | −1.458 | | | | |
| Formation of dendrites | | | −1.436 | | | | |
| Development of cytoplasm | | | −1.435 | | | | |
| Spatial learning | | | −1.431 | | | | |
| Disorder of basal ganglia | 6.6E−167 | | −1.423 | | | | |
| Cued conditioning | | | −1.414 | | | | |
| Formation of cytoskeleton | | | −1.408 | | | | |
| Transport of inorganic cation | | | −1.402 | | | | |
| Neurological signs | 2.6E−167 | | −1.359 | | | | |
| Development of genital tumor | | | −1.353 | | | | |
| Pelvic cancer | 1.1E−54 | | −1.328 | | | | |
| Central nervous system cancer | 2.25E−65 | 1.15E−85 | −1.321 | | | | |
| Cell cycle progression | | 3.6E−129 | −1.3 | | 1.58 | | |
| Heart rate | | 3.1E−76 | −1.29 | | | | |
| Action potential of neurons | | | −1.279 | | | | |
| Action potential of cells | | | −1.279 | | | | |
| Phosphorylation of protein | | | −1.272 | | | | |
| Abdominal carcinoma | | | −1.258 | −1.987 | −0.831 | | |
| Digestive system cancer | | | −1.241 | −1.96 | −1.792 | | −1.513 |
| Squamous-cell carcinoma | | | −1.234 | | | | |
| Formation of forebrain | | | −1.212 | | | | |
| Formation of telencephalon | | | −1.212 | | | | |
| Hyperesthesia | 2.75E−59 | | −1.204 | | | | |
| Differentiation of bone cells | | 1.4E−102 | −1.199 | −1.799 | 0.85 | 0.903 | −0.237 |
| Cancer of secretory structure | 3.5E−54 | | −1.193 | | 0.64 | | |
| Pancreatic ductal carcinoma | | | −1.177 | | | | |
| Pancreatic ductal adenocarcinoma | | | −1.177 | | | | |
| Pancreatic adenocarcinoma | | | −1.177 | | | | |
| Quantity of metal ion | 2.5E−56 | | −1.165 | | | | |
| Organization of actin cytoskeleton | | | −1.164 | | | | |
| Development of carcinoma | | | −1.158 | | 0.152 | | |
| B-cell non-Hodgkin lymphoma | | | −1.154 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Formation of actin stress fibers | | | −1.139 | | | | |
| Mature B-cell neoplasm | 6.27E−65 | | −1.131 | | | | |
| Glioblastoma | 3.36E−56 | | −1.103 | | | | |
| Pancreatic cancer | | | −1.089 | | | | |
| Sensory disorders | 7.43E−58 | | −1.063 | | | | |
| Development of gastrointestinal tract | | | −1.062 | | | | |
| Quantity of metal | 8.53E−63 | 1.99E−81 | −1.061 | 0.415 | | | |
| Cell movement of myeloid cells | 8.57E−58 | 1.3E−173 | −1.047 | | 3.907 | 1.197 | |
| Function of muscle | | 6.94E−87 | −1.043 | | | | |
| Cancer | | | −1.035 | | 0.905 | 1.705 | |
| Formation of actin filaments | | | −1.028 | | | | |
| Head and neck carcinoma | | | −1.026 | | | | |
| Excitatory postsynaptic potential | | | −1 | | | | |
| Progressive neurological disorder | 6.6E−215 | | −0.963 | | | | |
| Development of adenocarcinoma | | | −0.952 | | | | |
| Cancer of cells | 7.6E−56 | 1.17E−97 | −0.927 | | 0.742 | | |
| Concentration of hormone | | | −0.917 | −0.32 | | | 0.825 |
| Genitourinary tumor | 6.65E−66 | | −0.908 | | 1.388 | 1.746 | |
| Abdominal neoplasm | | | −0.871 | | 0.061 | −0.272 | −1.116 |
| Spatial memory | | | −0.869 | | | | |
| Urinary tract tumor | 8.53E−58 | 3.28E−74 | −0.863 | | | | |
| Head and neck cancer | | | −0.86 | | −1.154 | | |
| Upper gastrointestinal carcinoma | | | −0.849 | | | | |
| Extraadrenal retroperitoneal tumor | | | −0.821 | | | | |
| Secretion of molecule | 1.66E−75 | | −0.8 | | 1.386 | | |
| Astrocytoma | | | −0.786 | | | | |
| Gonadal tumor | | | −0.732 | | | | |
| Quantity of carbohydrate | 3.84E−52 | 2.39E−87 | −0.732 | 0.49 | | | −0.017 |
| Ductal carcinoma | | | −0.728 | | | | |
| Development of digestive system | | | −0.724 | | | | |
| Tumorigenesis of reproductive tract | | | −0.713 | | | | |
| Development of connective tissue cells | | 1.1E−76 | −0.712 | −0.005 | 1.638 | 0.766 | −0.005 |
| Neoplasia of cells | 1.65E−64 | 4.1E−103 | −0.704 | | 0.474 | | |
| Non-melanoma solid tumor | | | −0.698 | | 0.01 | 1.121 | −1.478 |
| Ovarian tumor | | | −0.668 | | | | |
| Growth of epithelial tissue | 3.1E−59 | 7.7E−164 | −0.65 | | −1.58 | | |
| Pancreatic carcinoma | | | −0.649 | | | | |
| Fear | | | −0.637 | | | | |
| Quantity of $Ca^{2+}$ | 1.96E−55 | | −0.627 | −0.11 | | 0.224 | |
| Lung cancer | 1.74E−74 | 1.33E−95 | −0.602 | | | | |
| Ossification of bone | | | −0.588 | | | | |
| Abnormality of cerebral cortex | | | −0.524 | | | | |
| Function of smooth muscle | | | −0.516 | | | | |
| Female genital neoplasm | | | −0.502 | | | | |
| Emotional behavior | 1.13E−57 | | −0.502 | | | | |
| Solid tumor | | | −0.473 | | 1.29 | 0.992 | |
| Malignant connective or soft tissue neoplasm | | 3.28E−97 | −0.471 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Liver tumor | | | −0.451 | −1.91 | | | |
| Respiratory system tumor | 4.27E−70 | 2.31E−95 | −0.451 | | | | |
| Cognitive impairment | 7.8E−118 | | −0.428 | | | | |
| Thoracic cancer | 5.97E−75 | 6.2E−100 | −0.425 | | | | |
| Glioma | 2.96E−58 | | −0.416 | | | | |
| Central nervous system tumor | 4.16E−69 | 7.45E−77 | −0.411 | | | | |
| Central nervous system solid tumor | 9.68E−69 | 1.55E−76 | −0.411 | | | | |
| Liquid tumor | 3.25E−66 | 1.21E−82 | −0.398 | | | | |
| Skin carcinoma | | | −0.391 | | | | |
| Leukemic tumor | 4.28E−54 | | −0.379 | | | | |
| Gastrointestinal tract cancer | | | −0.377 | | | | |
| Abnormality of cerebrum | | | −0.365 | | | | |
| Concentration of lipid | 2.48E−87 | 6.3E−118 | −0.361 | | −0.575 | | −0.204 |
| Glioma cancer | 1.45E−57 | 5.12E−74 | −0.351 | | | | |
| Tumor in nervous system | 8.7E−72 | 3.4E−77 | −0.337 | | | | |
| Colon cancer | | | −0.314 | | | | |
| Upper gastrointestinal tract tumor | | | −0.295 | | | | |
| Hepatobiliary system cancer | | | −0.293 | | | | |
| Head and neck tumor | | | −0.269 | | −0.355 | | |
| Colorectal cancer | | | −0.251 | | | | |
| Liver cancer | | | −0.25 | | | | |
| Proliferation of epithelial cells | | 4.7E−125 | −0.219 | | −1.196 | | |
| Breast or pancreatic cancer | 1.55E−69 | | −0.211 | | −1.026 | | |
| Tumorigenesis of epithelial neoplasm | | | −0.168 | −1.981 | | 0.152 | |
| Development of colorectal tumor | | | −0.152 | | | | |
| Weight gain | 1.15E−72 | | −0.15 | 0.625 | | | |
| Quantity of steroid hormone | | | −0.127 | | | | |
| Lung carcinoma | 3.9E−61 | | −0.113 | | | | |
| B-cell lymphoproliferative disorder | | | −0.085 | | | | |
| B-cell neoplasm | 1.39E−70 | | −0.085 | | | | |
| B cell cancer | | | −0.085 | | | | |
| Lung tumor | 1.04E−78 | 8.1E−103 | −0.082 | | | | |
| Gastrointestinal carcinoma | | | −0.068 | | | | |
| Epileptic seizure | | | −0.054 | | | | |
| Endocrine gland tumor | | | −0.049 | | −0.067 | | |
| Oscillation of $Ca^{2+}$ | | | −0.035 | | | | |
| Tauopathy | 0 | 5.43E−89 | * | | | | |
| Extracranial solid tumor | | | 0.01 | | 0.369 | 1.474 | 0.529 |
| Development of sensory organ | | | 0.02 | | 0.669 | | |
| Malignant neoplasm of large intestine | | | 0.048 | | | | |
| Pancreatobiliary tumor | | | 0.052 | | | | |
| Secretion of neurotransmitter | | | 0.083 | | | | |
| Sarcoma | | 1.96E−92 | 0.083 | | | | |
| Connective tissue tumor | | 4.4E−105 | 0.086 | | | | |
| Epilepsy | 1.79E−93 | | 0.091 | | | | |
| Liver carcinoma | | | 0.101 | | | | |
| Cell death of brain | 6.8E−111 | | 0.108 | | | | |
| Thermoregulation | | | 0.122 | | | | |
| Pancreatic tumor | | | 0.125 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Skin tumor | | | 0.148 | | −2.396 | | |
| Thoracic neoplasm | 2.34E−79 | 2.5E−108 | 0.173 | | | | |
| Development of respiratory system tumor | | | 0.174 | | | | |
| Necrosis of epithelial tissue | 4.75E−82 | 6.8E−155 | 0.183 | | 1.674 | | |
| Cell death of central nervous system cells | 3E−107 | | 0.185 | | | | |
| B-cell lymphoma | | | 0.19 | | | | |
| Cell death of tumor cell lines | 3.79E−88 | 5.8E−159 | 0.215 | | −0.811 | 0.178 | |
| Digestive organ tumor | | | 0.227 | −1.396 | −1.348 | | −1.481 |
| Connective or soft tissue tumor | | 1.2E−119 | 0.231 | | | | |
| Formation of eye | | | 0.251 | | 1.664 | | |
| Neuronal cell death | 9.9E−137 | 4.87E−88 | 0.254 | | | | |
| Stomach tumor | | | 0.275 | | | | |
| Growth of axons | | | 0.275 | | | | |
| Disorder of pregnancy | | | 0.29 | | | | |
| Breast or colorectal cancer | 6.1E−55 | | 0.33 | | −1.953 | | |
| Sensory system development | | | 0.335 | | −0.307 | | |
| Development of lung tumor | | | 0.347 | | | | |
| Cell death of brain cells | 7.5E−108 | | 0.349 | | | | |
| Neurodegeneration of cerebral cortex | | | 0.385 | | | | |
| Anxiety | | | 0.388 | | | | |
| Breast carcinoma | | | 0.418 | | | | |
| Obesity | 5.6E−152 | | 0.419 | | 0.493 | | 2.18 |
| Development of intestinal tumor | | | 0.44 | | | | |
| Development of malignant tumor | | | 0.455 | −1.326 | | −0.774 | |
| Lung adenocarcinoma | | | 0.468 | | | | |
| Skin cancer | | | 0.488 | | | | |
| Non-small cell lung carcinoma | 1.09E−56 | | 0.493 | | | | |
| Movement Disorders | 2E−227 | | 0.536 | | | | |
| Diffuse lymphoma | | | 0.555 | | | | |
| Gastric lesion | | | 0.565 | | | | |
| Occlusion of artery | 3E−152 | 3.2E−178 | 0.586 | | | | |
| Non-Hodgkin lymphoma | | | 0.621 | | | | |
| Locomotion | 1.34E−66 | | 0.697 | | | | |
| Breast or ovarian carcinoma | | | 0.73 | | | | |
| Breast cancer | 2.25E−70 | 2.2E−134 | 0.73 | | | | |
| Glucose metabolism disorder | 1.4E−184 | 1.4E−170 | 0.75 | | 0.439 | | |
| Incidence of tumor | | | 0.782 | −1.614 | | −0.865 | |
| Atherosclerosis | 9.5E−131 | 2.8E−174 | 0.783 | | | | |
| Amyloidosis | 0 | 1.46E−91 | 0.812 | | | | |
| Liver lesion | | 1.4E−110 | 0.833 | | | | |
| Mood Disorders | 2.4E−173 | | 0.836 | | | | |
| Depressive disorder | 9.7E−162 | | 0.836 | | | | |
| Lymphohematopoietic cancer | 1.28E−94 | 6.2E−121 | 0.845 | | | | |
| Paired-pulse facilitation | | | 0.852 | | | | |
| Lymphoreticular neoplasm | 6.38E−75 | | 0.856 | | −1.224 | | |
| Colon tumor | | | 0.864 | | | | |
| Apoptosis of tumor cell lines | 4.41E−93 | 5.3E−155 | 0.867 | | −0.941 | 0.783 | |
| Cell death of epithelial cells | 4.48E−69 | 3E−123 | 0.886 | | 1.993 | | |

TABLE 40-continued

Diseases and molecular functions affected by TBI after
7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Vaso-occlusion | 6.2E−151 | 2.9E−179 | 0.909 | 1.264 | | | |
| Subcutaneous tumor | | | 0.911 | | | | |
| Colorectal tumor | | | 0.93 | | | | |
| Occlusion of blood vessel | 1.7E−152 | 3.4E−180 | 0.969 | | | | |
| Lymphatic system tumor | 4.79E−88 | | 0.977 | | −0.956 | | |
| Breast or ovarian cancer | 7.8E−65 | 4.6E−113 | 1.011 | | −1.953 | | |
| Hypertrophy | 1.65E−56 | 2.6E−219 | 1.011 | | | | |
| Hematologic cancer | 1.05E−92 | 2.2E−115 | 1.074 | −1.067 | −1.725 | | −2.216 |
| Large intestine neoplasm | | | 1.126 | −1.192 | | | |
| Lymphoid cancer | 1.85E−77 | 1.8E−114 | 1.127 | | −0.956 | | |
| Hypertension | 4.14E−89 | | 1.128 | | | | |
| Gastrointestinal adenocarcinoma | | | 1.181 | | | | |
| Frequency of tumor | | | 1.228 | −2.128 | | −1.519 | |
| Lymphohematopoietic neoplasia | 1E−96 | 6.2E−133 | 1.232 | | | | |
| Skin lesion | | | 1.234 | | −0.111 | | 0.532 |
| Neck neoplasm | | | 1.257 | | | | |
| Mammary tumor | 3.35E−72 | 5.2E−153 | 1.261 | | | | |
| Motor dysfunction or movement disorder | 7.7E−228 | | 1.269 | | | | |
| Gastrointestinal tumor | | | 1.279 | −1.029 | −1.215 | | −1.284 |
| Hematologic cancer of cells | 2.64E−71 | 4E−144 | 1.314 | | −1.486 | | |
| Disorder of blood pressure | 3.79E−97 | | 1.325 | | | | |
| Hematopoietic neoplasm | 2.37E−95 | | 1.338 | −0.686 | −1.002 | | −2.027 |
| Seizure disorder | 3E−118 | | 1.343 | | | | 1.376 |
| Seizures | 1.01E−97 | | 1.362 | | | | |
| Necrosis | 3.1E−153 | 1.4E−251 | 1.376 | | 0.228 | 0.213 | |
| Peripheral vascular disease | 5.7E−170 | | 1.389 | | 1 | | |
| Lymphoproliferative disorder | 2.49E−83 | 2E−104 | 1.435 | | −1.727 | | |
| Neoplasia of leukocytes | 5.5E−88 | 1.3E−149 | 1.44 | | −1.486 | | |
| Intestinal tumor | | | 1.486 | | −1.09 | | |
| Lymphocytic cancer | 3.97E−73 | | 1.569 | | −1.486 | | |
| Lymphocytic neoplasm | 2.2E−82 | 4.3E−139 | 1.569 | | −1.486 | | |
| Cell death of muscle cells | 1.7E−54 | 9.9E−127 | 1.829 | | | | |
| Renal impairment | 4.4E−100 | 3.2E−101 | 1.835 | | 0.555 | | |
| Failure of kidney | 4.17E−85 | 4.4E−107 | 1.835 | | 0.555 | | |
| Cerebrovascular dysfunction | 1.3E−186 | | 1.845 | | | | |
| Lymphoma | 4.3E−54 | 1E−143 | 1.896 | | −1.224 | | |
| Development of digestive organ tumor | | | 1.909 | | | | |
| Cell death of muscle | | 1.7E−134 | 1.921 | | | | |
| Necrosis of muscle | 3.34E−54 | 1.4E−133 | 1.921 | | | | |
| Neurodegeneration | 3.46E−85 | | 2.046 | | | | |
| Abnormality of heart ventricle | 1.36E−63 | 7.5E−128 | 2.157 | | | | |
| Development of benign tumor | 2.1E−59 | | 2.423 | | | | |
| Benign Tumors | 3.71E−75 | | 2.493 | | | | |
| Benign lesion | 9.74E−87 | | 2.695 | | | | |
| Cell death | 6.5E−155 | 3.7E−254 | 3.326 | | 0.791 | −1.269 | |
| Apoptosis | 7.5E−135 | 1.1E−244 | 3.418 | | −0.676 | −0.256 | |
| Hyperactive behavior | | | 4.022 | | | | |
| Bleeding | 7.55E−94 | 2.5E−102 | 4.287 | | −2.118 | | |
| Neonatal death | | | 6.487 | | | | |
| Perinatal death | | | 8.086 | | | | |

TABLE 40-continued

Diseases and molecular functions affected by TBI after 7 days and the effects of LMW-DS (p values and z scores)

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeated dose LMW-DS |
|---|---|---|---|---|---|---|---|
| Morbidity or mortality | 4.8E−108 | 2.3E−216 | 11.646 | | −2.848 | | |
| Organismal death | 2E−109 | 3.5E−213 | 11.962 | | −2.885 | | |

TABLE 41

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Cell movement | 1.1E−108 | 5.3E−246 | Inhibited | Inhibited | Activated | | Activated |
| Size of body | | | Inhibited | | Activated | | Activated |
| Organization of cytoskeleton | 1.61E−68 | 3.76E−76 | Inhibited | | Activated | | Activated |
| Migration of cells | 6.8E−103 | 4.3E−241 | Inhibited | | Activated | | Activated |
| Organization of cytoplasm | 4.68E−69 | 7.6E−74 | Inhibited | | | | Activated |
| Cell survival | 1.22E−94 | 4E−184 | Inhibited | | Activated | | |
| Formation of cellular protrusions | 2.84E−52 | | Inhibited | | | | Activated |
| Development of neurons | 7.82E−63 | | Inhibited | | Activated | | Activated |
| Quantity of cells | 2.7E−102 | 2.9E−233 | Inhibited | | Activated | Activated | Activated |
| Microtubule dynamics | 2.4E−63 | | Inhibited | | Activated | | Activated |
| Cell viability | 9.14E−94 | 1E−176 | Inhibited | Inhibited | Activated | | |
| Cell viability of tumor cell lines | 7.56E−63 | 1.1E−114 | Inhibited | | Activated | | |
| Developmental process of synapse | | | Inhibited | Inhibited | | | Activated |
| Development of gap junctions | | | Inhibited | | | | Activated |
| Formation of plasma membrane | | | Inhibited | Inhibited | | | |
| Cell-cell contact | | | Inhibited | | | | Activated |
| Assembly of intercellular junctions | | | Inhibited | | | | |
| Formation of intercellular junctions | | | Inhibited | | | | Activated |
| Morphogenesis of neurons | 4.16E−54 | | Inhibited | | | | Activated |
| Neuritogenesis | 2.04E−53 | | Inhibited | | | | |
| Invasion of cells | 1.26E−64 | 1.1E−148 | Inhibited | | Activated | | |
| Homing of cells | | 2E−126 | Inhibited | | | | |
| Chemotaxis | | 4.9E−120 | Inhibited | | Activated | | |
| Angiogenesis | 6.89E−75 | 1E−210 | Inhibited | | Activated | | |
| Development of vasculature | 1.8E−77 | 1.8E−221 | Inhibited | | Activated | | |
| Collapse of growth cone | | | Inhibited | | | | |
| Cell movement of tumor cell lines | 1.17E−69 | 1.1E−156 | Inhibited | | Activated | | |
| Vasculogenesis | 3.63E−68 | 6.7E−185 | Inhibited | | Activated | | |
| Neurotransmission | 3.7E−100 | | Inhibited | | | | Activated |
| Cell movement of endothelial cells | | 2.38E−86 | Inhibited | | Activated | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Transactivation of RNA | | | Inhibited | | | | |
| Transactivation | | | Inhibited | | | | |
| Long-term potentiation | 6.19E−76 | | Inhibited | | | | |
| Transcription | | 3.3E−92 | Inhibited | | Activated | Activated | |
| Transcription of RNA | | 2.71E−75 | Inhibited | | Activated | Activated | |
| Synaptic transmission of cells | | | Inhibited | | | | |
| Plasticity of synapse | | | Inhibited | | | | |
| Potentiation of synapse | 1.58E−77 | | Inhibited | | | | |
| Migration of endothelial cells | | 1.18E−81 | Inhibited | | Activated | | |
| Synaptic transmission | 8.3E−97 | | Inhibited | | | | |
| Long-term potentiation of brain | | | Inhibited | | | | |
| Migration of tumor cell lines | 9.34E−62 | 5.5E−134 | Inhibited | | | | |
| Quantity of neurons | 1.57E−59 | | Inhibited | | | | |
| Quantity of nervous tissue | 4.93E−60 | | Inhibited | | | | |
| Development of genitourinary system | | 1.77E−77 | Inhibited | | Inhibited | | |
| Long-term potentiation of cerebral cortex | | | Inhibited | | | | |
| Cellular homeostasis | 1E−117 | 1.6E−154 | Inhibited | | Activated | | |
| Expression of RNA | | 5.44E−90 | Inhibited | | Activated | | |
| Growth of connective tissue | | 4.3E−157 | Inhibited | | Inhibited | | |
| Nonhematologic malignant neoplasm | | | Inhibited | | Inhibited | | Inhibited |
| Synaptic transmission of nervous tissue | | | Inhibited | | | | |
| Shape change of neurites | | | Inhibited | | | | |
| Branching of neurites | | | Inhibited | | | | |
| Transcription of DNA | | | Inhibited | | | | |
| Long-term potentiation of hippocampus | | | Inhibited | | | | |
| Behavior | 7.7E−146 | | Inhibited | | | | |
| Development of body trunk | | 7.2E−188 | Inhibited | | Activated | | |
| Cognition | 9.8E−112 | | Inhibited | | | | |
| Branching of neurons | | | Inhibited | | | | |
| Learning | 1.2E−108 | | Inhibited | | | | Activated |
| Sprouting | 6.17E−59 | | Inhibited | | | | |
| Branching of cells | 8.41E−54 | | Inhibited | | | | Activated |
| Coordination | | | Inhibited | | | | |
| Potentiation of hippocampus | | | Inhibited | | | | |
| Long-term memory | | | Inhibited | | | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Differentiation of neurons | | | Inhibited | | | | |
| Cell movement of blood cells | 2.64E−79 | 2.3E−210 | Inhibited | | | | |
| Leukocyte migration | 1.46E−79 | 3.4E−205 | Inhibited | | Activated | Activated | |
| Shape change of neurons | | | Inhibited | | | | |
| Dendritic growth/branching | | | Inhibited | | | | Inhibited |
| Memory | 1.31E−83 | | Inhibited | | | | |
| Carcinoma | | | Inhibited | | Inhibited | Activated | Inhibited |
| Genitourinary adenocarcinoma | | | Inhibited | | | | |
| Formation of brain | | | Inhibited | | | | |
| Growth of tumor | 2.27E−68 | 2.8E−193 | Inhibited | | Activated | | |
| Growth of organism | | 5.6E−102 | Inhibited | | | | |
| Synthesis of lipid | 1.14E−78 | 5.59E−92 | Inhibited | Activated | Activated | | |
| Respiratory system development | | | Inhibited | | | | |
| Differentiation of osteoblasts | | | Inhibited | | | | |
| Conditioning | | | Inhibited | | | | |
| Proliferation of neuronal cells | 4.49E−61 | | Inhibited | | | | |
| Male genital neoplasm | | | Inhibited | | | | |
| Synaptic depression | | | Inhibited | | | | |
| Development of epithelial tissue | 8.97E−54 | 4.4E−109 | Inhibited | | Activated | | |
| Density of neurons | | | Inhibited | | | | |
| Proliferation of connective tissue cells | | 4.7E−152 | Inhibited | | Inhibited | | |
| Formation of lung | | | Inhibited | | | | |
| Prostatic carcinoma | | | Inhibited | | | | |
| Formation of rhombencephalon | | | Inhibited | | | | |
| Innervation | | | Inhibited | | | | |
| Guidance of axons | | | Inhibited | | | | |
| Genitourinary carcinoma | | | Inhibited | | Activated | | |
| Discomfort | 4.2E−181 | | Inhibited | | | | |
| Metabolism of hormone | | | Inhibited | Inhibited | | | |
| Cell movement of neurons | | | Inhibited | | | | |
| Long term depression | | | Inhibited | | | | |
| Differentiation of osteoblastic-lineage cells | | | Inhibited | | | | |
| Outgrowth of cells | 2.39E−58 | | Inhibited | | | | |
| Malignant solid tumor | | | Inhibited | | Activated | | |
| Non-hematological solid tumor | | | Inhibited | | Activated | | Inhibited |
| Growth of neurites | 5.41E−59 | | Inhibited | | | | |
| Transport of molecule | 1.6E−117 | | Inhibited | | Activated | | Activated |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Formation of hippocampus | | | Inhibited | | | | |
| Prostatic tumor | | | Inhibited | | | | |
| Formation of muscle | | | Inhibited | | | | |
| Genital tumor | 1.07E-52 | | Inhibited | | Activated | | |
| Fibrogenesis | | | Inhibited | | | | |
| Prostatic adenocarcinoma | | | Inhibited | | | | |
| Adenocarcinoma | | | Inhibited | | Inhibited | | Inhibited |
| Transport of K$^+$ | | | Inhibited | | | | |
| Abdominal cancer | | | Inhibited | Inhibited | Inhibited | | Inhibited |
| Cardiogenesis | | 2.07E-92 | Inhibited | | | | |
| Malignant neoplasm of retroperitoneum | | | Inhibited | | | | |
| Development of central nervous system cells | | | Inhibited | | | | |
| Development of reproductive system | | | Inhibited | | | | |
| Epithelial neoplasm | | | Inhibited | Inhibited | | Activated | Inhibited |
| Malignant neoplasm of male genital organ | | | Inhibited | | | | |
| Development of head | | | Inhibited | | Activated | | |
| Development of body axis | | | Inhibited | | Activated | | |
| Patterning of rhombencephalon | | | Inhibited | | | | |
| Axonogenesis | | | Inhibited | | | | |
| Tumorigenesis of tissue | | | Inhibited | Inhibited | Inhibited | Activated | Inhibited |
| Synthesis of nitric oxide | 2.05E-53 | 1.3E-98 | Inhibited | | | | |
| Melanoma | | | Inhibited | | | | |
| Outgrowth of neurites | 5.63E-52 | | Inhibited | | | | |
| Urinary tract cancer | 6.04E-53 | | Inhibited | | | | |
| Abdominal adenocarcinoma | | | Inhibited | | Activated | | |
| Transport of ion | | | Inhibited | | | | Activated |
| Hyperalgesia | 1.56E-55 | | Inhibited | | | | |
| Development of cerebral cortex | | | Inhibited | | | | |
| Dyskinesia | 3.5E-136 | | Inhibited | | | | |
| Proliferation of smooth muscle cells | | 5.2E-120 | Inhibited | | | | |
| Differentiation of connective tissue cells | 1.6E-52 | 3.4E-143 | Inhibited | Inhibited | Activated | | Inhibited |
| Prostate cancer | | | Inhibited | | | | |
| Muscle contraction | | | Inhibited | | | | |
| Pelvic tumor | 1.81E-59 | | Inhibited | Inhibited | Activated | | |
| Transport of metal ion | | | Inhibited | | | | |
| Formation of filaments | | | Inhibited | | | | |
| Genital tract cancer | | | Inhibited | | | | |
| Neoplasia of epithelial cells | | | Inhibited | | | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Transport of cation | | | Inhibited | | | | |
| Quantity of connective tissue | | 4.8E−113 | Inhibited | | Activated | | |
| Differentiation of nervous system | | | Inhibited | | | | |
| Migration of neurons | | | Inhibited | | | | |
| Transport of metal | | | Inhibited | | | | Activated |
| Upper gastrointestinal tract cancer | | | Inhibited | | | | |
| Malignant genitourinary solid tumor | 5.22E−63 | | Inhibited | Inhibited | Activated | | |
| Development of central nervous system | | | Inhibited | | | | |
| Differentiation of bone | | 3.9E−104 | Inhibited | | Activated | | |
| Proliferation of muscle cells | 1.11E−56 | 1.8E−148 | Inhibited | | | | |
| Formation of dendrites | | | Inhibited | | | | |
| Development of cytoplasm | | | Inhibited | | | | |
| Spatial learning | | | Inhibited | | | | |
| Disorder of basal ganglia | 6.6E−167 | | Inhibited | | | | |
| Cued conditioning | | | Inhibited | | | | |
| Formation of cytoskeleton | | | Inhibited | | | | |
| Transport of inorganic cation | | | Inhibited | | | | |
| Neurological signs | 2.6E−167 | | Inhibited | | | | |
| Development of genital tumor | | | Inhibited | | | | |
| Pelvic cancer | 1.1E−54 | | Inhibited | | | | |
| Central nervous system cancer | 2.25E−65 | 1.15E−85 | Inhibited | | | | |
| Cell cycle progression | | 3.6E−129 | Inhibited | | Activated | | |
| Heart rate | | 3.1E−76 | Inhibited | | | | |
| Action potential of neurons | | | Inhibited | | | | |
| Action potential of cells | | | Inhibited | | | | |
| Phosphorylation of protein | | | Inhibited | | | | |
| Abdominal carcinoma | | | Inhibited | Inhibited | Inhibited | | |
| Digestive system cancer | | | Inhibited | Inhibited | Inhibited | | Inhibited |
| Squamous-cell carcinoma | | | Inhibited | | | | |
| Formation of forebrain | | | Inhibited | | | | |
| Formation of telencephalon | | | Inhibited | | | | |
| Hyperesthesia | 2.75E−59 | | Inhibited | | | | |
| Differentiation of bone cells | | 1.4E−102 | Inhibited | Inhibited | Activated | Activated | Inhibited |
| Cancer of secretory structure | 3.5E−54 | | Inhibited | | Activated | | |
| Pancreatic ductal carcinoma | | | Inhibited | | | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Pancreatic ductal adenocarcinoma | | | Inhibited | | | | |
| Pancreatic adenocarcinoma | | | Inhibited | | | | |
| Quantity of metal ion | 2.5E−56 | | Inhibited | | | | |
| Organization of actin cytoskeleton | | | Inhibited | | | | |
| Development of carcinoma | | | Inhibited | | | Activated | |
| B-cell non-Hodgkin lymphoma | | | Inhibited | | | | |
| Formation of actin stress fibers | | | Inhibited | | | | |
| Mature B-cell neoplasm | 6.27E−65 | | Inhibited | | | | |
| Glioblastoma | 3.36E−56 | | Inhibited | | | | |
| Pancreatic cancer | | | Inhibited | | | | |
| Sensory disorders | 7.43E−58 | | Inhibited | | | | |
| Development of gastrointestinal tract | | | Inhibited | | | | |
| Quantity of metal | 8.53E−63 | 1.99E−81 | Inhibited | Activated | | | |
| Cell movement of myeloid cells | 8.57E−58 | 1.3E−173 | Inhibited | | Activated | Activated | |
| Function of muscle | | 6.94E−87 | Inhibited | | | | |
| Cancer | | | Inhibited | | Activated | Activated | |
| Formation of actin filaments | | | Inhibited | | | | |
| Head and neck carcinoma | | | Inhibited | | | | |
| Excitatory postsynaptic potential | | | Inhibited | | | | |
| Progressive neurological disorder | 6.6E−215 | | Inhibited | | | | |
| Development of adenocarcinoma | | | Inhibited | | | | |
| Cancer of cells | 7.6E−56 | 1.17E−97 | Inhibited | | Activated | | |
| Concentration of hormone | | | Inhibited | Inhibited | | | Activated |
| Genitourinary tumor | 6.65E−66 | | Inhibited | | Activated | Activated | |
| Abdominal neoplasm | | | Inhibited | | Activated | Inhibited | Inhibited |
| Spatial memory | | | Inhibited | | | | |
| Urinary tract tumor | 8.53E−58 | 3.28E−74 | Inhibited | | | | |
| Head and neck cancer | | | Inhibited | | Inhibited | | |
| Upper gastrointestinal carcinoma | | | Inhibited | | | | |
| Extraadrenal retroperitoneal tumor | | | Inhibited | | | | |
| Secretion of molecule | 1.66E−75 | | Inhibited | | Activated | | |
| Astrocytoma | | | Inhibited | | | | |
| Gonadal tumor | | | Inhibited | | | | |
| Quantity of carbohydrate | 3.84E−52 | 2.39E−87 | Inhibited | Activated | | | Inhibited |
| Ductal carcinoma | | | Inhibited | | | | |
| Development of digestive system | | | Inhibited | | | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Tumorigenesis of reproductive tract | | | Inhibited | | | | |
| Development of connective tissue cells | | 1.1E−76 | Inhibited | Inhibited | Activated | Activated | Inhibited |
| Neoplasia of cells | 1.65E−64 | 4.1E−103 | Inhibited | | Activated | | |
| Non-melanoma solid tumor | | | Inhibited | | Activated | Activated | Inhibited |
| Ovarian tumor | | | Inhibited | | | | |
| Growth of epithelial tissue | 3.1E−59 | 7.7E−164 | Inhibited | | Inhibited | | |
| Pancreatic carcinoma | | | Inhibited | | | | |
| Fear | | | Inhibited | | | | |
| Quantity of $Ca^{2+}$ | 1.96E−55 | | Inhibited | Inhibited | | | Activated |
| Lung cancer | 1.74E−74 | 1.33E−95 | Inhibited | | | | |
| Ossification of bone | | | Inhibited | | | | |
| Abnormality of cerebral cortex | | | Inhibited | | | | |
| Function of smooth muscle | | | Inhibited | | | | |
| Female genital neoplasm | | | Inhibited | | | | |
| Emotional behavior | 1.13E−57 | | Inhibited | | | | |
| Solid tumor | | | Inhibited | | Activated | Activated | |
| Malignant connective or soft tissue neoplasm | | 3.28E−97 | Inhibited | | | | |
| Liver tumor | | | Inhibited | Inhibited | | | |
| Respiratory system tumor | 4.27E−70 | 2.31E−95 | Inhibited | | | | |
| Cognitive impairment | 7.8E−118 | | Inhibited | | | | |
| Thoracic cancer | 5.97E−75 | 6.2E−100 | Inhibited | | | | |
| Glioma | 2.96E−58 | | Inhibited | | | | |
| Central nervous system tumor | 4.16E−69 | 7.45E−77 | Inhibited | | | | |
| Central nervous system solid tumor | 9.68E−69 | 1.55E−76 | Inhibited | | | | |
| Liquid tumor | 3.25E−66 | 1.21E−82 | Inhibited | | | | |
| Skin carcinoma | | | Inhibited | | | | |
| Leukemic tumor | 4.28E−54 | | Inhibited | | | | |
| Gastrointestinal tract cancer | | | Inhibited | | | | |
| Abnormality of cerebrum | | | Inhibited | | | | |
| Concentration of lipid | 2.48E−87 | 6.3E−118 | Inhibited | | Inhibited | | Inhibited |
| Glioma cancer | 1.45E−57 | 5.12E−74 | Inhibited | | | | |
| Tumor in nervous system | 8.7E−72 | 3.4E−77 | Inhibited | | | | |
| Colon cancer | | | Inhibited | | | | |
| Upper gastrointestinal tract tumor | | | Inhibited | | | | |
| Hepatobiliary system cancer | | | Inhibited | | | | |
| Head and neck tumor | | | Inhibited | | Inhibited | | |
| Colorectal cancer | | | Inhibited | | | | |
| Liver cancer | | | Inhibited | | | | |
| Proliferation of epithelial cells | | 4.7E−125 | Inhibited | | Inhibited | | |
| Breast or pancreatic cancer | 1.55E−69 | | Inhibited | | Inhibited | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Tumorigenesis of epithelial neoplasm | | | Inhibited | Inhibited | | Activated | |
| Development of colorectal tumor | | | Inhibited | | | | |
| Weight gain | 1.15E−72 | | Inhibited | Activated | | | |
| Quantity of steroid hormone | | | Inhibited | | | | |
| Lung carcinoma | 3.9E−61 | | Inhibited | | | | |
| B-cell lymphoproliferative disorder | | | Inhibited | | | | |
| B-cell neoplasm | 1.39E−70 | | Inhibited | | | | |
| B cell cancer | | | Inhibited | | | | |
| Lung tumor | 1.04E−78 | 8.1E−103 | Inhibited | | | | |
| Gastrointestinal carcinoma | | | Inhibited | | | | |
| Epileptic seizure | | | Inhibited | | | | |
| Endocrine gland tumor | | | Inhibited | | Inhibited | | |
| Oscillation of $Ca^{2+}$ | | | Inhibited | | | | |
| Tauopathy | 0 | 5.43E−89 | * | | | | |
| Extracranial solid tumor | | | Activated | | Activated | Activated | Activated |
| Development of sensory organ | | | Activated | Activated | | | |
| Malignant neoplasm of large intestine | | | Activated | | | | |
| Pancreatobiliary tumor | | | Activated | | | | |
| Secretion of neurotransmitter | | | Activated | | | | |
| Sarcoma | | 1.96E−92 | Activated | | | | |
| Connective tissue tumor | | 4.4E−105 | Activated | | | | |
| Epilepsy | 1.79E−93 | | Activated | | | | |
| Liver carcinoma | | | Activated | | | | |
| Cell death of brain | 6.8E−111 | | Activated | | | | |
| Thermoregulation | | | Activated | | | | |
| Pancreatic tumor | | | Activated | | | | |
| Skin tumor | | | Activated | | Inhibited | | |
| Thoracic neoplasm | 2.34E−79 | 2.5E−108 | Activated | | | | |
| Development of respiratory system tumor | | | Activated | | | | |
| Necrosis of epithelial tissue | 4.75E−82 | 6.8E−155 | Activated | | Activated | | |
| Cell death of central nervous system cells | 3E−107 | | Activated | | | | |
| B-cell lymphoma | | | Activated | | | | |
| Cell death of tumor cell lines | 3.79E−88 | 5.8E−159 | Activated | | Inhibited | Activated | |
| Digestive organ tumor | | | Activated | Inhibited | Inhibited | | Inhibited |
| Connective or soft tissue tumor | | 1.2E−119 | Activated | | | | |
| Formation of eye | | | Activated | | Activated | | |
| Neuronal cell death | 9.9E−137 | 4.87E−88 | Activated | | | | |
| Stomach tumor | | | Activated | | | | |
| Growth of axons | | | Activated | | | | |
| Disorder of pregnancy | | | Activated | | | | |
| Breast or colorectal cancer | 6.1E−55 | | Activated | | Inhibited | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Sensory system development | | | Activated | | Inhibited | | |
| Development of lung tumor | | | Activated | | | | |
| Cell death of brain cells | 7.5E−108 | | Activated | | | | |
| Neurodegeneration of cerebral cortex | | | Activated | | | | |
| Anxiety | | | Activated | | | | |
| Breast carcinoma | | | Activated | | | | |
| Obesity | 5.6E−152 | | Activated | | Activated | | Activated |
| Development of intestinal tumor | | | Activated | | | | |
| Development of malignant tumor | | | Activated | Inhibited | | Inhibited | |
| Lung adenocarcinoma | | | Activated | | | | |
| Skin cancer | | | Activated | | | | |
| Non-small cell lung carcinoma | 1.09E−56 | | Activated | | | | |
| Movement Disorders | 2E−227 | | Activated | | | | |
| Diffuse lymphoma | | | Activated | | | | |
| Gastric lesion | | | Activated | | | | |
| Occlusion of artery | 3E−152 | 3.2E−178 | Activated | | | | |
| Non-Hodgkin lymphoma | | | Activated | | | | |
| Locomotion | 1.34E−66 | | Activated | | | | |
| Breast or ovarian carcinoma | | | Activated | | | | |
| Breast cancer | 2.25E−70 | 2.2E−134 | Activated | | | | |
| Glucose metabolism disorder | 1.4E−184 | 1.4E−170 | Activated | | Activated | | |
| Incidence of tumor | | | Activated | Inhibited | | Inhibited | |
| Atherosclerosis | 9.5E−131 | 2.8E−174 | Activated | | | | |
| Amyloidosis | 0 | 1.46E−91 | Activated | | | | |
| Liver lesion | | 1.4E−110 | Activated | | | | |
| Mood Disorders | 2.4E−173 | | Activated | | | | |
| Depressive disorder | 9.7E−162 | | Activated | | | | |
| Lymphohematopoietic cancer | 1.28E−94 | 6.2E−121 | Activated | | | | |
| Paired-pulse facilitation | | | Activated | | | | |
| Lymphoreticular neoplasm | 6.38E−75 | | Activated | | Inhibited | | |
| Colon tumor | | | Activated | | | | |
| Apoptosis of tumor cell lines | 4.41E−93 | 5.3E−155 | Activated | | Inhibited | Activated | |
| Cell death of epithelial cells | 4.48E−69 | 3E−123 | Activated | | Activated | | |
| Vaso-occlusion | 6.2E−151 | 2.9E−179 | Activated | Activated | | | |
| Subcutaneous tumor | | | Activated | | | | |
| Colorectal tumor | | | Activated | | | | |
| Occlusion of blood vessel | 1.7E−152 | 3.4E−180 | Activated | | | | |
| Lymphatic system tumor | 4.79E−88 | | Activated | | Inhibited | | |
| Breast or ovarian cancer | 7.8E−65 | 4.6E−113 | Activated | | Inhibited | | |
| Hypertrophy | 1.65E−56 | 2.6E−219 | Activated | | | | |
| Hematologic cancer | 1.05E−92 | 2.2E−115 | Activated | Inhibited | Inhibited | | Inhibited |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Large intestine neoplasm | | | Activated | Inhibited | | | |
| Lymphoid cancer | 1.85E−77 | 1.8E−114 | Activated | | Inhibited | | |
| Hypertension | 4.14E−89 | | Activated | | | | |
| Gastrointestinal adenocarcinoma | | | Activated | | | | |
| Frequency of tumor | | | Activated | Inhibited | | Inhibited | |
| Lymphohematopoietic neoplasia | 1E−96 | 6.2E−133 | Activated | | | | |
| Skin lesion | | | Activated | | Inhibited | | Activated |
| Neck neoplasm | | | Activated | | | | |
| Mammary tumor | 3.35E−72 | 5.2E−153 | Activated | | | | |
| Motor dysfunction or movement disorder | 7.7E−228 | | Activated | | | | |
| Gastrointestinal tumor | | | Activated | Inhibited | Inhibited | | Inhibited |
| Hematologic cancer of cells | 2.64E−71 | 4E−144 | Activated | | Inhibited | | |
| Disorder of blood pressure | 3.79E−97 | | Activated | | | | |
| Hematopoietic neoplasm | 2.37E−95 | | Activated | Inhibited | Inhibited | | Inhibited |
| Seizure disorder | 3E−118 | | Activated | | | | Activated |
| Seizures | 1.01E−97 | | Activated | | | | |
| Necrosis | 3.1E−153 | 1.4E−251 | Activated | | Activated | Activated | |
| Peripheral vascular disease | 5.7E−170 | | Activated | | Activated | | |
| Lymphoproliferative disorder | 2.49E−83 | 2E−104 | Activated | | Inhibited | | |
| Neoplasia of leukocytes | 5.5E−88 | 1.3E−149 | Activated | | Inhibited | | |
| Intestinal tumor | | | Activated | | Inhibited | | |
| Lymphocytic cancer | 3.97E−73 | | Activated | | Inhibited | | |
| Lymphocytic neoplasm | 2.2E−82 | 4.3E−139 | Activated | | Inhibited | | |
| Cell death of muscle cells | 1.7E−54 | 9.9E−127 | Activated | | | | |
| Renal impairment | 4.4E−100 | 3.2E−101 | Activated | | Activated | | |
| Failure of kidney | 4.17E−85 | 4.4E−107 | Activated | | Activated | | |
| Cerebrovascular dysfunction | 1.3E−186 | | Activated | | | | |
| Lymphoma | 4.3E−54 | 1E−143 | Activated | | Inhibited | | |
| Development of digestive organ tumor | | | Activated | | | | |
| Cell death of muscle | | 1.7E−134 | Activated | | | | |
| Necrosis of muscle | 3.34E−54 | 1.4E−133 | Activated | | | | |
| Neurodegeneration | 3.46E−85 | | Activated | | | | |
| Abnormality of heart ventricle | 1.36E−63 | 7.5E−128 | Activated | | | | |
| Development of benign tumor | 2.1E−59 | | Activated | | | | |
| Benign Tumors | 3.71E−75 | | Activated | | | | |
| Benign lesion | 9.74E−87 | | Activated | | | | |
| Cell death | 6.5E−155 | 3.7E−254 | Activated | | Activated | Inhibited | |
| Apoptosis | 7.5E−135 | 1.1E−244 | Activated | | Inhibited | Inhibited | |
| Hyperactive behavior | | | Activated | | | | |
| Bleeding | 7.55E−94 | 2.5E−102 | Activated | | Inhibited | | |
| Neonatal death | | | Activated | | | | |

TABLE 41-continued

Diseases and molecular functions affected by TBI after 7 days and the effects of LMW-DS

| Diseases or functions annotation | Diseases and functions affected in dementia and neurodegeneration (p value) | Diseases and functions affected in fibrosis and scarring (p value) | TBI | TBI + 1 mg/kg LMW-DS | TBI + 5 mg/kg LMW-DS | TBI + 15 mg/kg LMW-DS | TBI + 15 mg/kg repeat dose LMW-DS |
|---|---|---|---|---|---|---|---|
| Perinatal death | | | Activated | | | | |
| Morbidity or mortality | 4.8E−108 | 2.3E−216 | Activated | | Inhibited | | |
| Organismal death | 2E−109 | 3.5E−213 | Activated | | Inhibited | | |

* ambiguous effect

Discussion

LMW-DS was able to counteract and reverse the effects of TBI in most pathways and molecular process. The data indicated that LMW-DS was able to normalize tissue gene expression and function after TBI. The functions and pathways studied were highly relevant to neurodegenerative disease as well as fibrosis and scarring. From the results it was apparent that LMW-DS was able to affect these pathways in a beneficial way even when the disruption was severe.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible.

The invention claimed is:

1. A method for treating glutamate excitotoxicity in a subject suffering from amyotrophic lateral sclerosis (ALS) and exhibiting glutamate excitotoxicity, the method comprising administering dextran sulfate, or a pharmaceutically acceptable salt thereof, having a weight average molecular weight ($M_w$) equal to or below 10,000 Da to the subject suffering from ALS and exhibiting glutamate excitotoxicity to treat glutamate excitotoxicity in neurons of the subject.

2. The method according to claim 1, wherein the dextran sulfate, or the pharmaceutically acceptable salt thereof, has a number average molecular weight ($M_n$) as measured by nuclear magnetic resonance (NMR) spectroscopy within an interval of 1850 and 3500 Da.

3. A method for protecting neurons from oxidative stress in a subject suffering from amyotrophic lateral sclerosis (ALS) and exhibiting oxidative stress, the method comprising administering dextran sulfate, or a pharmaceutically acceptable salt thereof, having a weight average molecular weight ($M_w$) equal to or below 10,000 Da to the subject suffering from ALS and exhibiting oxidative stress to protect neurons from oxidative stress induced by ALS and causing mitochondrial dysfunction in the neurons.

4. The method according to claim 3, wherein the dextran sulfate, or the pharmaceutically acceptable salt thereof, has a number average molecular weight ($M_n$) as measured by nuclear magnetic resonance (NMR) spectroscopy within an interval of 1850 and 3500 Da.

5. A method for restoring metabolic hemostasis in a subject suffering from amyotrophic lateral sclerosis (ALS) and exhibiting impaired metabolic hemostasis, the method comprising administering dextran sulfate, or a pharmaceutically acceptable salt thereof, having a weight average molecular weight ($M_w$) equal to or below 10,000 Da to the subject suffering from ALS and exhibiting impaired metabolic hemostasis to restore metabolic hemostasis in neurons in the subject.

6. The method according to claim 5, wherein the dextran sulfate, or the pharmaceutically acceptable salt thereof, has a number average molecular weight ($M_n$) as measured by nuclear magnetic resonance (NMR) spectroscopy within an interval of 1850 and 3500 Da.

7. A method for treating neuroinflammation associated with amyotrophic lateral sclerosis (ALS), the method comprising administering dextran sulfate, or a pharmaceutically acceptable salt thereof, to a subject suffering from ALS and exhibiting neuroinflammation to treat the neuroinflammation, wherein the dextran sulfate, or the pharmaceutically acceptable salt thereof, has a number average molecular weight ($M_n$) as measured by nuclear magnetic resonance (NMR) spectroscopy within an interval of 1850 and 3500 Da.

8. A method for treating neuroinflammation, the method comprising administering dextran sulfate, or a pharmaceutically acceptable salt thereof, having a weight average molecular weight ($M_w$) equal to or below 10,000 Da to a subject suffering from neuroinflammation to treat the neuroinflammation.

9. The method according to claim 8, wherein the dextran sulfate, or the pharmaceutically acceptable salt thereof, has a number average molecular weight ($M_n$) as measured by nuclear magnetic resonance (NMR) spectroscopy within an interval of 1850 and 3500 Da.

10. The method according to claim 9, wherein the dextran sulfate, or the pharmaceutically acceptable salt thereof, has a $M_n$ as measured by NMR spectroscopy within an interval of 1850 and 2500 Da.

11. The method according to claim 10, wherein the dextran sulfate, or the pharmaceutically acceptable salt thereof, has a $M_n$ as measured by NMR spectroscopy within an interval of 1850 and 2300 Da.

12. The method according to claim 11, wherein the dextran sulfate, or the pharmaceutically acceptable salt thereof, has a $M_n$ as measured by NMR spectroscopy within an interval of 1850 and 2000 Da.

13. The method according to claim 8, wherein the dextran sulfate, or the pharmaceutically acceptable salt thereof, has an average sulfate number per glucose unit within an interval of 2.5 and 3.0.

14. The method according to claim 13, wherein the dextran sulfate, or the pharmaceutically acceptable salt thereof, has an average sulfate number per glucose unit within an interval of 2.5 and 2.8.

15. The method according to claim 14, wherein the dextran sulfate, or the pharmaceutically acceptable salt thereof, has an average sulfate number per glucose unit within an interval of 2.6 and 2.7.

16. The method according to claim 8, wherein the dextran sulfate, or the pharmaceutically acceptable salt thereof, has on average 5.1 glucose units and an average sulfate number per glucose unit of 2.6 to 2.7.

17. The method according to claim 8, wherein administering dextran sulfate, or the pharmaceutically acceptable salt thereof, comprises intravenously or subcutaneously administering dextran sulfate, or the pharmaceutically acceptable salt thereof, to the subject.

* * * * *